(12) United States Patent
Wiklander et al.

(10) Patent No.: US 11,236,143 B2
(45) Date of Patent: Feb. 1, 2022

(54) EXTRACELLULAR VESICLE COMPRISING A FUSION PROTEIN HAVING FC BINDING CAPACITY

(71) Applicant: Evox Therapeutics Ltd, Oxford (GB)

(72) Inventors: Oscar Wiklander, Solna (SE); André Görgens, Huddinge (SE); Dhanu Gupta, Huddinge (SE)

(73) Assignee: Evox Therapeutics Ltd, Oxford (GB)

(*) Notice: Subject to any disclaimer, the term of this patent is extended or adjusted under 35 U.S.C. 154(b) by 0 days.

(21) Appl. No.: 16/319,061

(22) PCT Filed: Jul. 21, 2017

(86) PCT No.: PCT/EP2017/068476
§ 371 (c)(1),
(2) Date: Jan. 18, 2019

(87) PCT Pub. No.: WO2018/015535
PCT Pub. Date: Jan. 25, 2018

(65) Prior Publication Data
US 2020/0109183 A1  Apr. 9, 2020

(30) Foreign Application Priority Data
Jul. 21, 2016 (GB) ..................... 1612643

(51) Int. Cl.
| | | |
|---|---|---|
| *C07K 14/705* | (2006.01) | |
| *A61K 47/69* | (2017.01) | |
| *A61K 47/64* | (2017.01) | |
| *A61K 9/127* | (2006.01) | |
| *A61K 47/24* | (2006.01) | |
| *C07K 14/47* | (2006.01) | |
| *A61K 38/00* | (2006.01) | |

(52) U.S. Cl.
CPC .......... *C07K 14/705* (2013.01); *A61K 9/1271* (2013.01); *A61K 47/24* (2013.01); *A61K 47/64* (2017.08); *A61K 47/6913* (2017.08); *C07K 14/47* (2013.01); *A61K 38/00* (2013.01); *C07K 2319/03* (2013.01); *C07K 2319/30* (2013.01); *C07K 2319/33* (2013.01)

(58) Field of Classification Search
CPC .. C07K 14/705; C07K 2319/30; C07K 16/00; C07K 14/47; C07K 2319/03; C07K 2319/33; C07K 14/31; C07K 14/315; C07K 14/7151; C07K 14/195; C07K 2319/705; A61K 47/6913; A61K 47/64; A61K 9/1271; A61K 47/24; A61K 38/00; A61K 39/44; A61K 47/6901; A61K 47/46; A61P 43/00; A61P 37/06; A61P 35/00; A61P 29/00
See application file for complete search history.

(56) References Cited

U.S. PATENT DOCUMENTS

| | | | |
|---|---|---|---|
| 10,538,570 B2 * | 1/2020 | Leonard | A61K 31/713 |
| 2010/0086490 A1 | 4/2010 | Alleman et al. | |
| 2010/0267846 A1 * | 10/2010 | Parton | A61K 9/1277 |
| | | | 514/773 |
| 2012/0207754 A1 | 8/2012 | Giacalone et al. | |

FOREIGN PATENT DOCUMENTS

| | | |
|---|---|---|
| WO | WO 99/59643 A2 | 11/1999 |
| WO | WO 2010/119256 A1 | 10/2010 |
| WO | WO 2013/084000 A2 | 6/2013 |
| WO | WO 2013/084001 A1 | 6/2013 |
| WO | WO 2014/168548 A2 | 10/2014 |
| WO | WO 2015/002956 A1 | 1/2015 |
| WO | WO 2015/058148 A1 | 4/2015 |

OTHER PUBLICATIONS

Stancovski et al., Proceedings of the National Academy of Science USA 88: 8691-8695 (Year: 1991).*
Wahberg et al., PNAS 100(6): 3185-3190 (Year: 2003).*
Nizard et al., FEBS Letters 433: 83-88 (Year: 1998).*
De Jong et al., Acc Chem Res 52: 1761-1770 (Year: 2019).*
Hung et al., J Biol Chemistry 290: 8166-8172 (Year: 2015).*
Chen et al. "Protein G-liposomal nanovesicles as universal reagents for immunoassays", Science Direct, Talanta, vol. 67, 2005, p. 205-211.
Fais S. et al. "Evidence-Based Clinical Use of Nanoscale Extracellular Vesicles in Nanomedicine", ACS NANO, vol. 10, No. 4, 2016, p. 3886-3899.
Kooijmans S. et al. " Display of GPI-anchored anti-EGFR nanobodies on extracellular vesicles promotes tumour cell targeting", Journal of Extracellular Vesicles, vol. 5, No. 1, 2016, p. 31053 (12 pages).
Nizard et al. "Anchoring antibodies to membranes using a diphtheria toxin T domain-ZZ fusion protein as a pH sensitive membrane anchor", FEBS Letters, vol. 433, 1998, p. 83-88.
Wiklander O. et al. "Extracellular vesicle in vivo biodistribution is determined by cell source, route of administration and targeting", Journal of Extracellular Vesicles, vol. 4, No. 1, 2015, p. 26316 (13 pages).

* cited by examiner

*Primary Examiner* — Phuong Huynh
(74) *Attorney, Agent, or Firm* — Cooley LLP; Matthew Pavao; Chun L. Yu

(57) ABSTRACT

The present invention pertains to extracellular vesicle (EV) therapeutics, wherein the EVs are coated with proteins containing Fc domains (such as antibodies) for i.a. targeting and therapeutic applications. The coating of EVs is achieved through inventive protein engineering of EV polypeptides. The present invention thus relates to methods for coating of EVs, EVs per se, as well as pharmaceutical compositions and medical applications of such EVs coated with Fc containing proteins.

12 Claims, 11 Drawing Sheets
Specification includes a Sequence Listing.

SEQUENCE LISTING

```
<160> NUMBER OF SEQ ID NOS: 83

<210> SEQ ID NO 1
<211> LENGTH: 227
<212> TYPE: PRT
<213> ORGANISM: Homo sapiens

<400> SEQUENCE: 1

Pro Val Lys Gly Gly Thr Lys Cys Ile Lys Tyr Leu Leu Phe Gly Phe
1               5                   10                  15

Asn Phe Ile Phe Trp Leu Ala Gly Ile Ala Val Leu Ala Ile Gly Leu
            20                  25                  30

Trp Leu Arg Phe Asp Ser Gln Thr Lys Ser Ile Phe Glu Gln Glu Thr
        35                  40                  45

Asn Asn Asn Asn Ser Ser Phe Tyr Thr Gly Val Tyr Ile Leu Ile Gly
    50                  55                  60

Ala Gly Ala Leu Met Met Leu Val Gly Phe Leu Gly Cys Cys Gly Ala
65                  70                  75                  80

Val Gln Glu Ser Gln Cys Met Leu Gly Leu Phe Phe Gly Phe Leu Leu
                85                  90                  95

Val Ile Phe Ala Ile Glu Ile Ala Ala Ala Ile Trp Gly Tyr Ser His
            100                 105                 110

Lys Asp Glu Val Ile Lys Glu Val Gln Glu Phe Tyr Lys Asp Thr Tyr
        115                 120                 125

Asn Lys Leu Lys Thr Lys Asp Glu Pro Gln Arg Glu Thr Leu Lys Ala
```

```
            130                 135                 140
Ile His Tyr Ala Leu Asn Cys Cys Gly Leu Ala Gly Gly Val Glu Gln
145                 150                 155                 160

Phe Ile Ser Asp Ile Cys Pro Lys Lys Asp Val Leu Glu Thr Phe Thr
                165                 170                 175

Val Lys Ser Cys Pro Asp Ala Ile Lys Glu Val Phe Asp Asn Lys Phe
                180                 185                 190

His Ile Ile Gly Ala Val Gly Ile Gly Ile Ala Val Val Met Ile Phe
                195                 200                 205

Gly Met Ile Phe Ser Met Ile Leu Cys Cys Ala Ile Arg Arg Asn Arg
                210                 215                 220

Glu Met Val
225

<210> SEQ ID NO 2
<211> LENGTH: 219
<212> TYPE: PRT
<213> ORGANISM: Homo sapiens

<400> SEQUENCE: 2

Met Gly Met Ser Ser Leu Lys Leu Leu Lys Tyr Val Leu Phe Phe Phe
1               5                   10                  15

Asn Leu Leu Phe Trp Ile Cys Gly Cys Cys Ile Leu Gly Phe Gly Ile
                20                  25                  30

Tyr Leu Leu Ile His Asn Asn Phe Gly Val Leu Phe His Asn Leu Pro
                35                  40                  45

Ser Leu Thr Leu Gly Asn Val Phe Val Ile Val Gly Ser Ile Ile Met
50                  55                  60

Val Val Ala Phe Leu Gly Cys Met Gly Ser Ile Lys Glu Asn Lys Cys
65                  70                  75                  80

Leu Leu Met Ser Phe Phe Ile Leu Leu Leu Ile Ile Leu Leu Ala Glu
                85                  90                  95

Val Thr Leu Ala Ile Leu Leu Phe Val Tyr Glu Gln Lys Leu Asn Glu
                100                 105                 110

Tyr Val Ala Lys Gly Leu Thr Asp Ser Ile His Arg Tyr His Ser Asp
                115                 120                 125

Asn Ser Thr Lys Ala Ala Trp Asp Ser Ile Gln Ser Phe Leu Gln Cys
130                 135                 140

Cys Gly Ile Asn Gly Thr Ser Asp Trp Thr Ser Gly Pro Pro Ala Ser
145                 150                 155                 160

Cys Pro Ser Asp Arg Lys Val Glu Gly Cys Tyr Ala Lys Ala Arg Leu
                165                 170                 175

Trp Phe His Ser Asn Phe Leu Tyr Ile Gly Ile Ile Thr Ile Cys Val
                180                 185                 190

Cys Val Ile Glu Val Leu Gly Met Ser Phe Ala Leu Thr Leu Asn Cys
                195                 200                 205

Gln Ile Asp Lys Thr Ser Gln Thr Ile Gly Leu
                210                 215

<210> SEQ ID NO 3
<211> LENGTH: 237
<212> TYPE: PRT
<213> ORGANISM: Homo sapiens

<400> SEQUENCE: 3

Ala Val Glu Gly Gly Met Lys Cys Val Lys Phe Leu Leu Tyr Val Leu
```

```
1               5                   10                  15
Leu Leu Ala Phe Cys Ala Cys Ala Val Gly Leu Ile Ala Val Gly Val
                20                  25                  30

Gly Ala Gln Leu Val Leu Ser Gln Thr Ile Ile Gln Gly Ala Thr Pro
            35                  40                  45

Gly Ser Leu Leu Pro Val Val Ile Ile Ala Val Gly Val Phe Leu Phe
        50                  55                  60

Leu Val Ala Phe Val Gly Cys Cys Gly Ala Cys Lys Glu Asn Tyr Cys
65                  70                  75                  80

Leu Met Ile Thr Phe Ala Ile Phe Leu Ser Leu Ile Met Leu Val Glu
                85                  90                  95

Val Ala Ala Ala Ile Ala Gly Tyr Val Phe Arg Asp Lys Val Met Ser
            100                 105                 110

Glu Phe Asn Asn Asn Phe Arg Gln Gln Met Glu Asn Tyr Pro Lys Asn
        115                 120                 125

Asn His Thr Ala Ser Ile Leu Asp Arg Met Gln Ala Asp Phe Lys Cys
    130                 135                 140

Cys Gly Ala Ala Asn Tyr Thr Asp Trp Glu Lys Ile Pro Ser Met Ser
145                 150                 155                 160

Lys Asn Arg Val Pro Asp Ser Cys Cys Ile Asn Val Thr Val Gly Cys
                165                 170                 175

Gly Ile Asn Phe Asn Glu Lys Ala Ile His Lys Glu Gly Cys Val Glu
            180                 185                 190

Lys Ile Gly Gly Trp Leu Arg Lys Asn Val Leu Val Val Ala Ala Ala
        195                 200                 205

Ala Leu Gly Ile Ala Phe Val Glu Val Leu Gly Ile Val Phe Ala Cys
    210                 215                 220

Cys Leu Val Lys Ser Ile Arg Ser Gly Tyr Glu Val Met
225                 230                 235

<210> SEQ ID NO 4
<211> LENGTH: 236
<212> TYPE: PRT
<213> ORGANISM: Homo sapiens

<400> SEQUENCE: 4

Met Gly Val Glu Gly Cys Thr Lys Cys Ile Lys Tyr Leu Leu Phe Val
1               5                   10                  15

Phe Asn Phe Val Phe Trp Leu Ala Gly Gly Val Ile Leu Gly Val Ala
                20                  25                  30

Leu Trp Leu Arg His Asp Pro Gln Thr Thr Asn Leu Leu Tyr Leu Glu
            35                  40                  45

Leu Gly Asp Lys Pro Ala Pro Asn Thr Phe Tyr Val Gly Ile Tyr Ile
        50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
            100                 105                 110

Phe Val Asn Lys Asp Gln Ile Ala Lys Asp Val Lys Gln Phe Tyr Asp
        115                 120                 125

Gln Ala Leu Gln Gln Ala Val Val Asp Asp Asp Ala Asn Asn Ala Lys
    130                 135                 140
```

-continued

Ala Val Val Lys Thr Phe His Glu Thr Leu Asp Cys Cys Gly Ser Ser
145                 150                 155                 160

Thr Leu Thr Ala Leu Thr Thr Ser Val Leu Lys Asn Asn Leu Cys Pro
            165                 170                 175

Ser Gly Ser Asn Ile Ile Ser Asn Leu Phe Lys Glu Asp Cys His Gln
        180                 185                 190

Lys Ile Asp Asp Leu Phe Ser Gly Lys Leu Tyr Leu Ile Gly Ile Ala
    195                 200                 205

Ala Ile Val Val Ala Val Ile Met Ile Phe Glu Met Ile Leu Ser Met
210                 215                 220

Val Leu Cys Cys Gly Ile Arg Asn Ser Ser Val Tyr
225                 230                 235

<210> SEQ ID NO 5
<211> LENGTH: 532
<212> TYPE: PRT
<213> ORGANISM: Homo sapiens

<400> SEQUENCE: 5

Met Ala Pro Ser Ser Pro Arg Pro Ala Leu Pro Ala Leu Leu Val Leu
1               5                   10                  15

Leu Gly Ala Leu Phe Pro Gly Pro Gly Asn Ala Gln Thr Ser Val Ser
            20                  25                  30

Pro Ser Lys Val Ile Leu Pro Arg Gly Gly Ser Val Leu Val Thr Cys
        35                  40                  45

Ser Thr Ser Cys Asp Gln Pro Lys Leu Leu Gly Ile Glu Thr Pro Leu
    50                  55                  60

Pro Lys Lys Glu Leu Leu Leu Pro Gly Asn Asn Arg Lys Val Tyr Glu
65                  70                  75                  80

Leu Ser Asn Val Gln Glu Asp Ser Gln Pro Met Cys Tyr Ser Asn Cys
                85                  90                  95

Pro Asp Gly Gln Ser Thr Ala Lys Thr Phe Leu Thr Val Tyr Trp Thr
            100                 105                 110

Pro Glu Arg Val Glu Leu Ala Pro Leu Pro Ser Trp Gln Pro Val Gly
        115                 120                 125

Lys Asn Leu Thr Leu Arg Cys Gln Val Glu Gly Gly Ala Pro Arg Ala
130                 135                 140

Asn Leu Thr Val Val Leu Leu Arg Gly Glu Lys Glu Leu Lys Arg Glu
145                 150                 155                 160

Pro Ala Val Gly Glu Pro Ala Glu Val Thr Thr Thr Val Leu Val Arg
                165                 170                 175

Arg Asp His His Gly Ala Asn Phe Ser Cys Arg Thr Glu Leu Asp Leu
            180                 185                 190

Arg Pro Gln Gly Leu Glu Leu Phe Glu Asn Thr Ser Ala Pro Tyr Gln
        195                 200                 205

Leu Gln Thr Phe Val Leu Pro Ala Thr Pro Pro Gln Leu Val Ser Pro
    210                 215                 220

Arg Val Leu Glu Val Asp Thr Gln Gly Thr Val Val Cys Ser Leu Asp
225                 230                 235                 240

Gly Leu Phe Pro Val Ser Glu Ala Gln Val His Leu Ala Leu Gly Asp
                245                 250                 255

Gln Arg Leu Asn Pro Thr Val Thr Tyr Gly Asn Asp Ser Phe Ser Ala
            260                 265                 270

Lys Ala Ser Val Ser Val Thr Ala Glu Asp Glu Gly Thr Gln Arg Leu
        275                 280                 285

Thr Cys Ala Val Ile Leu Gly Asn Gln Ser Gln Glu Thr Leu Gln Thr
            290                 295                 300

Val Thr Ile Tyr Ser Phe Pro Ala Pro Asn Val Ile Leu Thr Lys Pro
305                 310                 315                 320

Glu Val Ser Glu Gly Thr Glu Val Thr Val Lys Cys Glu Ala His Pro
                325                 330                 335

Arg Ala Lys Val Thr Leu Asn Gly Val Pro Ala Gln Pro Leu Gly Pro
            340                 345                 350

Arg Ala Gln Leu Leu Leu Lys Ala Thr Pro Glu Asp Asn Gly Arg Ser
        355                 360                 365

Phe Ser Cys Ser Ala Thr Leu Glu Val Ala Gly Gln Leu Ile His Lys
370                 375                 380

Asn Gln Thr Arg Glu Leu Arg Val Leu Tyr Gly Pro Arg Leu Asp Glu
385                 390                 395                 400

Arg Asp Cys Pro Gly Asn Trp Thr Trp Pro Glu Asn Ser Gln Gln Thr
                405                 410                 415

Pro Met Cys Gln Ala Trp Gly Asn Pro Leu Pro Glu Leu Lys Cys Leu
            420                 425                 430

Lys Asp Gly Thr Phe Pro Leu Pro Ile Gly Glu Ser Val Thr Val Thr
        435                 440                 445

Arg Asp Leu Glu Gly Thr Tyr Leu Cys Arg Ala Arg Ser Thr Gln Gly
450                 455                 460

Glu Val Thr Arg Lys Val Thr Val Asn Val Leu Ser Pro Arg Tyr Glu
465                 470                 475                 480

Ile Val Ile Ile Thr Val Val Ala Ala Val Ile Met Gly Thr Ala
                485                 490                 495

Gly Leu Ser Thr Tyr Leu Tyr Asn Arg Gln Arg Lys Ile Lys Lys Tyr
            500                 505                 510

Arg Leu Gln Gln Ala Gln Lys Gly Thr Pro Met Lys Pro Asn Thr Gln
        515                 520                 525

Ala Thr Pro Pro
    530

<210> SEQ ID NO 6
<211> LENGTH: 547
<212> TYPE: PRT
<213> ORGANISM: Homo sapiens

<400> SEQUENCE: 6

Met Ala Thr Met Val Pro Ser Val Leu Trp Pro Arg Ala Cys Trp Thr
1               5                   10                  15

Leu Leu Val Cys Cys Leu Leu Thr Pro Gly Val Gln Gly Gln Glu Phe
            20                  25                  30

Leu Leu Arg Val Glu Pro Gln Asn Pro Val Leu Ser Ala Gly Gly Ser
        35                  40                  45

Leu Phe Val Asn Cys Ser Thr Asp Cys Pro Ser Ser Glu Lys Ile Ala
    50                  55                  60

Leu Glu Thr Ser Leu Ser Lys Glu Leu Val Ala Ser Gly Met Gly Trp
65                  70                  75                  80

Ala Ala Phe Asn Leu Ser Asn Val Thr Gly Asn Ser Arg Ile Leu Cys
                85                  90                  95

Ser Val Tyr Cys Asn Gly Ser Gln Ile Thr Gly Ser Ser Asn Ile Thr
            100                 105                 110

Val Tyr Arg Leu Pro Glu Arg Val Glu Leu Ala Pro Leu Pro Pro Trp

```
            115                 120                 125
Gln Pro Val Gly Gln Asn Phe Thr Leu Arg Cys Gln Val Glu Asp Gly
    130                 135                 140

Ser Pro Arg Thr Ser Leu Thr Val Val Leu Arg Trp Glu Glu Glu
145                 150                 155                 160

Leu Ser Arg Gln Pro Ala Val Glu Glu Pro Ala Glu Val Thr Ala Thr
                165                 170                 175

Val Leu Ala Ser Arg Asp Asp His Gly Ala Pro Phe Ser Cys Arg Thr
            180                 185                 190

Glu Leu Asp Met Gln Pro Gln Gly Leu Gly Leu Phe Val Asn Thr Ser
            195                 200                 205

Ala Pro Arg Gln Leu Arg Thr Phe Val Leu Pro Val Thr Pro Pro Arg
        210                 215                 220

Leu Val Ala Pro Arg Phe Leu Glu Val Glu Thr Ser Trp Pro Val Asp
225                 230                 235                 240

Cys Thr Leu Asp Gly Leu Phe Pro Ala Ser Glu Ala Gln Val Tyr Leu
                245                 250                 255

Ala Leu Gly Asp Gln Met Leu Asn Ala Thr Val Met Asn His Gly Asp
            260                 265                 270

Thr Leu Thr Ala Thr Ala Thr Ala Thr Ala Arg Ala Asp Gln Glu Gly
        275                 280                 285

Ala Arg Glu Ile Val Cys Asn Val Thr Leu Gly Gly Glu Arg Arg Glu
290                 295                 300

Ala Arg Glu Asn Leu Thr Val Phe Ser Phe Leu Gly Pro Ile Val Asn
305                 310                 315                 320

Leu Ser Glu Pro Thr Ala His Glu Gly Ser Thr Val Thr Val Ser Cys
                325                 330                 335

Met Ala Gly Ala Arg Val Gln Val Thr Leu Asp Gly Val Pro Ala Ala
            340                 345                 350

Ala Pro Gly Gln Pro Ala Gln Leu Gln Leu Asn Ala Thr Glu Ser Asp
        355                 360                 365

Asp Gly Arg Ser Phe Phe Cys Ser Ala Thr Leu Glu Val Asp Gly Glu
    370                 375                 380

Phe Leu His Arg Asn Ser Ser Val Gln Leu Arg Val Leu Tyr Gly Pro
385                 390                 395                 400

Lys Ile Asp Arg Ala Thr Cys Pro Gln His Leu Lys Trp Lys Asp Lys
                405                 410                 415

Thr Arg His Val Leu Gln Cys Gln Ala Arg Gly Asn Pro Tyr Pro Glu
            420                 425                 430

Leu Arg Cys Leu Lys Glu Gly Ser Ser Arg Glu Val Pro Val Gly Ile
        435                 440                 445

Pro Phe Phe Val Asn Val Thr His Asn Gly Thr Tyr Gln Cys Gln Ala
    450                 455                 460

Ser Ser Ser Arg Gly Lys Tyr Thr Leu Val Val Val Met Asp Ile Glu
465                 470                 475                 480

Ala Gly Ser Ser His Phe Val Pro Val Phe Val Ala Val Leu Leu Thr
                485                 490                 495

Leu Gly Val Val Thr Ile Val Leu Ala Leu Met Tyr Val Phe Arg Glu
            500                 505                 510

His Gln Arg Ser Gly Ser Tyr His Val Arg Glu Glu Ser Thr Tyr Leu
        515                 520                 525

Pro Leu Thr Ser Met Gln Pro Thr Glu Ala Met Gly Glu Glu Pro Ser
    530                 535                 540
```

Arg Ala Glu
545

<210> SEQ ID NO 7
<211> LENGTH: 427
<212> TYPE: PRT
<213> ORGANISM: Homo sapiens

<400> SEQUENCE: 7

Met Phe Phe Thr Cys Gly Pro Asn Glu Ala Met Val Val Ser Gly Phe
1               5                   10                  15

Cys Arg Ser Pro Pro Val Met Val Ala Gly Gly Arg Val Phe Val Leu
            20                  25                  30

Pro Cys Ile Gln Gln Ile Gln Arg Ile Ser Leu Asn Thr Leu Thr Leu
        35                  40                  45

Asn Val Lys Ser Glu Lys Val Tyr Thr Arg His Gly Val Pro Ile Ser
    50                  55                  60

Val Thr Gly Ile Ala Gln Val Lys Ile Gln Gly Gln Asn Lys Glu Met
65                  70                  75                  80

Leu Ala Ala Ala Cys Gln Met Phe Leu Gly Lys Thr Glu Ala Glu Ile
                85                  90                  95

Ala His Ile Ala Leu Glu Thr Leu Glu Gly His Gln Arg Ala Ile Met
            100                 105                 110

Ala His Met Thr Val Glu Glu Ile Tyr Lys Asp Arg Gln Lys Phe Ser
        115                 120                 125

Glu Gln Val Phe Lys Val Ala Ser Ser Asp Leu Val Asn Met Gly Ile
    130                 135                 140

Ser Val Val Ser Tyr Thr Leu Lys Asp Ile His Asp Asp Gln Asp Tyr
145                 150                 155                 160

Leu His Ser Leu Gly Lys Ala Arg Thr Ala Gln Val Gln Lys Asp Ala
                165                 170                 175

Arg Ile Gly Glu Ala Glu Ala Lys Arg Asp Ala Gly Ile Arg Glu Ala
            180                 185                 190

Lys Ala Lys Gln Glu Lys Val Ser Ala Gln Tyr Leu Ser Glu Ile Glu
        195                 200                 205

Met Ala Lys Ala Gln Arg Asp Tyr Glu Leu Lys Lys Ala Ala Tyr Asp
    210                 215                 220

Ile Glu Val Asn Thr Arg Arg Ala Gln Ala Asp Leu Ala Tyr Gln Leu
225                 230                 235                 240

Gln Val Ala Lys Thr Lys Gln Gln Ile Glu Glu Gln Arg Val Gln Val
                245                 250                 255

Gln Val Val Glu Arg Ala Gln Gln Val Ala Val Gln Glu Gln Glu Ile
            260                 265                 270

Ala Arg Arg Glu Lys Glu Leu Glu Ala Arg Val Arg Lys Pro Ala Glu
        275                 280                 285

Ala Glu Arg Tyr Lys Leu Glu Arg Leu Ala Glu Ala Glu Lys Ser Gln
    290                 295                 300

Leu Ile Met Gln Ala Glu Ala Glu Ala Ala Ser Val Arg Met Arg Gly
305                 310                 315                 320

Glu Ala Glu Ala Phe Ala Ile Gly Ala Arg Ala Arg Ala Glu Ala Glu
                325                 330                 335

Gln Met Ala Lys Lys Ala Glu Ala Phe Gln Leu Tyr Gln Glu Ala Ala
            340                 345                 350

Gln Leu Asp Met Leu Leu Glu Lys Leu Pro Gln Val Ala Glu Glu Ile

```
            355                 360                 365
Ser Gly Pro Leu Thr Ser Ala Asn Lys Ile Thr Leu Val Ser Ser Gly
    370                 375                 380

Ser Gly Thr Met Gly Ala Ala Lys Val Thr Gly Glu Val Leu Asp Ile
385                 390                 395                 400

Leu Thr Arg Leu Pro Glu Ser Val Glu Arg Leu Thr Gly Val Ser Ile
                405                 410                 415

Ser Gln Val Asn His Lys Pro Leu Arg Thr Ala
            420                 425

<210> SEQ ID NO 8
<211> LENGTH: 427
<212> TYPE: PRT
<213> ORGANISM: Homo sapiens

<400> SEQUENCE: 8

Gly Asn Cys His Thr Val Gly Pro Asn Glu Ala Leu Val Val Ser Gly
1               5                   10                  15

Gly Cys Cys Gly Ser Asp Tyr Lys Gln Tyr Val Phe Gly Gly Trp Ala
            20                  25                  30

Trp Ala Trp Cys Ile Ser Asp Thr Gln Arg Ile Ser Leu Glu Ile
        35                  40                  45

Met Thr Leu Gln Pro Arg Cys Glu Asp Val Glu Thr Ala Glu Gly Val
50                  55                  60

Ala Leu Thr Val Thr Gly Val Ala Gln Val Lys Ile Met Thr Glu Lys
65                  70                  75                  80

Glu Leu Leu Ala Val Ala Cys Glu Gln Phe Leu Gly Lys Asn Val Gln
                85                  90                  95

Asp Ile Lys Asn Val Val Leu Gln Thr Leu Glu Gly His Leu Arg Ser
            100                 105                 110

Ile Leu Gly Thr Leu Thr Val Glu Gln Ile Tyr Gln Asp Arg Asp Gln
        115                 120                 125

Phe Ala Lys Leu Val Arg Glu Val Ala Ala Pro Asp Val Gly Arg Met
    130                 135                 140

Gly Ile Glu Ile Leu Ser Phe Thr Ile Lys Asp Val Tyr Asp Lys Val
145                 150                 155                 160

Asp Tyr Leu Ser Ser Leu Gly Lys Thr Gln Thr Ala Val Val Gln Arg
                165                 170                 175

Asp Ala Asp Ile Gly Val Ala Glu Ala Glu Arg Asp Ala Gly Ile Arg
            180                 185                 190

Glu Ala Glu Cys Lys Lys Glu Met Leu Asp Val Lys Phe Met Ala Asp
        195                 200                 205

Thr Lys Ile Ala Asp Ser Lys Arg Ala Phe Glu Leu Gln Lys Ser Ala
    210                 215                 220

Phe Ser Glu Glu Val Asn Ile Lys Thr Ala Glu Ala Gln Leu Ala Tyr
225                 230                 235                 240

Glu Leu Gln Gly Ala Arg Glu Gln Gln Lys Ile Arg Gln Glu Glu Ile
                245                 250                 255

Glu Ile Glu Val Val Gln Arg Lys Lys Gln Ile Ala Val Glu Ala Gln
            260                 265                 270

Glu Ile Leu Arg Thr Asp Lys Glu Leu Ile Ala Thr Val Arg Arg Pro
        275                 280                 285

Ala Glu Ala Glu Ala His Arg Ile Gln Gln Ile Ala Glu Gly Glu Lys
    290                 295                 300
```

```
Val Lys Gln Val Leu Leu Ala Gln Ala Glu Glu Lys Ile Arg Lys
305                 310                 315                 320

Ile Gly Glu Ala Glu Ala Val Ile Glu Ala Met Gly Lys Ala Glu
                325                 330                 335

Ala Glu Arg Met Lys Leu Lys Ala Glu Ala Tyr Gln Lys Tyr Gly Asp
            340                 345                 350

Ala Ala Lys Met Ala Leu Val Leu Glu Ala Leu Pro Gln Ile Ala Ala
                355                 360                 365

Lys Ile Ala Ala Pro Leu Thr Lys Val Asp Glu Ile Val Val Leu Ser
    370                 375                 380

Gly Asp Asn Ser Lys Val Thr Ser Glu Val Asn Arg Leu Leu Ala Glu
385                 390                 395                 400

Leu Pro Ala Ser Val His Ala Leu Thr Gly Val Asp Leu Ser Lys Ile
                405                 410                 415

Pro Leu Ile Lys Lys Ala Thr Gly Val Gln Val
                420                 425
```

<210> SEQ ID NO 9
<211> LENGTH: 1032
<212> TYPE: PRT
<213> ORGANISM: Homo sapiens

<400> SEQUENCE: 9

```
Met Ala Trp Glu Ala Arg Arg Glu Pro Gly Pro Arg Arg Ala Ala Val
1               5                   10                  15

Arg Glu Thr Val Met Leu Leu Leu Cys Leu Gly Val Pro Thr Gly Arg
                20                  25                  30

Pro Tyr Asn Val Asp Thr Glu Ser Ala Leu Leu Tyr Gln Gly Pro His
            35                  40                  45

Asn Thr Leu Phe Gly Tyr Ser Val Val Leu His Ser His Gly Ala Asn
    50                  55                  60

Arg Trp Leu Leu Val Gly Ala Pro Thr Ala Asn Trp Leu Ala Asn Ala
65                  70                  75                  80

Ser Val Ile Asn Pro Gly Ala Ile Tyr Arg Cys Arg Ile Gly Lys Asn
                85                  90                  95

Pro Gly Gln Thr Cys Glu Gln Leu Gln Leu Gly Ser Pro Asn Gly Glu
            100                 105                 110

Pro Cys Gly Lys Thr Cys Leu Glu Glu Arg Asp Asn Gln Trp Leu Gly
        115                 120                 125

Val Thr Leu Ser Arg Gln Pro Gly Glu Asn Gly Ser Ile Val Thr Cys
130                 135                 140

Gly His Arg Trp Lys Asn Ile Phe Tyr Ile Lys Asn Glu Asn Lys Leu
145                 150                 155                 160

Pro Thr Gly Gly Cys Tyr Gly Val Pro Pro Asp Leu Arg Thr Glu Leu
                165                 170                 175

Ser Lys Arg Ile Ala Pro Cys Tyr Gln Asp Tyr Val Lys Lys Phe Gly
            180                 185                 190

Glu Asn Phe Ala Ser Cys Gln Ala Gly Ile Ser Ser Phe Tyr Thr Lys
        195                 200                 205

Asp Leu Ile Val Met Gly Ala Pro Gly Ser Ser Tyr Trp Thr Gly Ser
    210                 215                 220

Leu Phe Val Tyr Asn Ile Thr Thr Asn Lys Tyr Lys Ala Phe Leu Asp
225                 230                 235                 240

Lys Gln Asn Gln Val Lys Phe Gly Ser Tyr Leu Gly Tyr Ser Val Gly
                245                 250                 255
```

```
Ala Gly His Phe Arg Ser Gln His Thr Thr Glu Val Val Gly Gly Ala
            260                 265                 270
Pro Gln His Glu Gln Ile Gly Lys Ala Tyr Ile Phe Ser Ile Asp Glu
            275                 280                 285
Lys Glu Leu Asn Ile Leu His Glu Met Lys Gly Lys Lys Leu Gly Ser
            290                 295                 300
Tyr Phe Gly Ala Ser Val Cys Ala Val Asp Leu Asn Ala Asp Gly Phe
305                 310                 315                 320
Ser Asp Leu Leu Val Gly Ala Pro Met Gln Ser Thr Ile Arg Glu Glu
            325                 330                 335
Gly Arg Val Phe Val Tyr Ile Asn Ser Gly Ser Gly Ala Val Met Asn
            340                 345                 350
Ala Met Glu Thr Asn Leu Val Gly Ser Asp Lys Tyr Ala Ala Arg Phe
            355                 360                 365
Gly Glu Ser Ile Val Asn Leu Gly Asp Ile Asp Asn Asp Gly Phe Glu
            370                 375                 380
Asp Val Ala Ile Gly Ala Pro Gln Glu Asp Asp Leu Gln Gly Ala Ile
385                 390                 395                 400
Tyr Ile Tyr Asn Gly Arg Ala Asp Gly Ile Ser Ser Thr Phe Ser Gln
            405                 410                 415
Arg Ile Glu Gly Leu Gln Ile Ser Lys Ser Leu Ser Met Phe Gly Gln
            420                 425                 430
Ser Ile Ser Gly Gln Ile Asp Ala Asp Asn Asn Gly Tyr Val Asp Val
            435                 440                 445
Ala Val Gly Ala Phe Arg Ser Asp Ser Ala Val Leu Leu Arg Thr Arg
            450                 455                 460
Pro Val Val Ile Val Asp Ala Ser Leu Ser His Pro Glu Ser Val Asn
465                 470                 475                 480
Arg Thr Lys Phe Asp Cys Val Glu Asn Gly Trp Pro Ser Val Cys Ile
            485                 490                 495
Asp Leu Thr Leu Cys Phe Ser Tyr Lys Gly Lys Glu Val Pro Gly Tyr
            500                 505                 510
Ile Val Leu Phe Tyr Asn Met Ser Leu Asp Val Asn Arg Lys Ala Glu
            515                 520                 525
Ser Pro Pro Arg Phe Tyr Phe Ser Ser Asn Gly Thr Ser Asp Val Ile
            530                 535                 540
Thr Gly Ser Ile Gln Val Ser Ser Arg Glu Ala Asn Cys Arg Thr His
545                 550                 555                 560
Gln Ala Phe Met Arg Lys Asp Val Arg Asp Ile Leu Thr Pro Ile Gln
            565                 570                 575
Ile Glu Ala Ala Tyr His Leu Gly Pro His Val Ile Ser Lys Arg Ser
            580                 585                 590
Thr Glu Glu Phe Pro Pro Leu Gln Pro Ile Leu Gln Gln Lys Lys Glu
            595                 600                 605
Lys Asp Ile Met Lys Lys Thr Ile Asn Phe Ala Arg Phe Cys Ala His
            610                 615                 620
Glu Asn Cys Ser Ala Asp Leu Gln Val Ser Ala Lys Ile Gly Phe Leu
625                 630                 635                 640
Lys Pro His Glu Asn Lys Thr Tyr Leu Ala Val Gly Ser Met Lys Thr
            645                 650                 655
Leu Met Leu Asn Val Ser Leu Phe Asn Ala Gly Asp Asp Ala Tyr Glu
            660                 665                 670
```

```
Thr Thr Leu His Val Lys Leu Pro Val Gly Leu Tyr Phe Ile Lys Ile
            675                 680                 685

Leu Glu Leu Glu Glu Lys Gln Ile Asn Cys Glu Val Thr Asp Asn Ser
        690                 695                 700

Gly Val Val Gln Leu Asp Cys Ser Ile Gly Tyr Ile Tyr Val Asp His
705                 710                 715                 720

Leu Ser Arg Ile Asp Ile Ser Phe Leu Leu Asp Val Ser Ser Leu Ser
                725                 730                 735

Arg Ala Glu Glu Asp Leu Ser Ile Thr Val His Ala Thr Cys Glu Asn
                740                 745                 750

Glu Glu Glu Met Asp Asn Leu Lys His Ser Arg Val Thr Val Ala Ile
            755                 760                 765

Pro Leu Lys Tyr Glu Val Lys Leu Thr Val His Gly Phe Val Asn Pro
        770                 775                 780

Thr Ser Phe Val Tyr Gly Ser Asn Asp Glu Asn Glu Pro Glu Thr Cys
785                 790                 795                 800

Met Val Glu Lys Met Asn Leu Thr Phe His Val Ile Asn Thr Gly Asn
                805                 810                 815

Ser Met Ala Pro Asn Val Ser Val Glu Ile Met Val Pro Asn Ser Phe
                820                 825                 830

Ser Pro Gln Thr Asp Lys Leu Phe Asn Ile Leu Asp Val Gln Thr Thr
            835                 840                 845

Thr Gly Glu Cys His Phe Glu Asn Tyr Gln Arg Val Cys Ala Leu Glu
        850                 855                 860

Gln Gln Lys Ser Ala Met Gln Thr Leu Lys Gly Ile Val Arg Phe Leu
865                 870                 875                 880

Ser Lys Thr Asp Lys Arg Leu Leu Tyr Cys Ile Lys Ala Asp Pro His
                885                 890                 895

Cys Leu Asn Phe Leu Cys Asn Phe Gly Lys Met Glu Ser Gly Lys Glu
                900                 905                 910

Ala Ser Val His Ile Gln Leu Glu Gly Arg Pro Ser Ile Leu Glu Met
            915                 920                 925

Asp Glu Thr Ser Ala Leu Lys Phe Glu Ile Arg Ala Thr Gly Phe Pro
930                 935                 940

Glu Pro Asn Pro Arg Val Ile Glu Leu Asn Lys Asp Glu Asn Val Ala
945                 950                 955                 960

His Val Leu Leu Glu Gly Leu His His Gln Arg Pro Lys Arg Tyr Phe
                965                 970                 975

Thr Ile Val Ile Ile Ser Ser Ser Leu Leu Leu Gly Leu Ile Val Leu
                980                 985                 990

Leu Leu Ile Ser Tyr Val Met Trp Lys Ala Gly Phe Phe Lys Arg Gln
            995                 1000                1005

Tyr Lys Ser Ile Leu Gln Glu Glu Asn Arg Arg Asp Ser Trp Ser
        1010                1015                1020

Tyr Ile Asn Ser Lys Ser Asn Asp Asp
        1025                1030

<210> SEQ ID NO 10
<211> LENGTH: 760
<212> TYPE: PRT
<213> ORGANISM: Homo sapiens

<400> SEQUENCE: 10

Met Met Asp Gln Ala Arg Ser Ala Phe Ser Asn Leu Phe Gly Gly Glu
1               5                   10                  15
```

```
Pro Leu Ser Tyr Thr Arg Phe Ser Leu Ala Arg Gln Val Asp Gly Asp
            20                  25                  30

Asn Ser His Val Glu Met Lys Leu Ala Val Asp Glu Glu Asn Ala
        35                  40                  45

Asp Asn Asn Thr Lys Ala Asn Val Thr Lys Pro Lys Arg Cys Ser Gly
50                  55                  60

Ser Ile Cys Tyr Gly Thr Ile Ala Val Ile Val Phe Phe Leu Ile Gly
65                  70                  75                  80

Phe Met Ile Gly Tyr Leu Gly Tyr Cys Lys Gly Val Glu Pro Lys Thr
                85                  90                  95

Glu Cys Glu Arg Leu Ala Gly Thr Glu Ser Pro Val Arg Glu Glu Pro
            100                 105                 110

Gly Glu Asp Phe Pro Ala Ala Arg Arg Leu Tyr Trp Asp Asp Leu Lys
            115                 120                 125

Arg Lys Leu Ser Glu Lys Leu Asp Ser Thr Asp Phe Thr Gly Thr Ile
        130                 135                 140

Lys Leu Leu Asn Glu Asn Ser Tyr Val Pro Arg Glu Ala Gly Ser Gln
145                 150                 155                 160

Lys Asp Glu Asn Leu Ala Leu Tyr Val Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Arg
        195                 200                 205

Leu Val Tyr Leu Val Glu Asn Pro Gly Gly Tyr Val Ala Tyr Ser Lys
        210                 215                 220

Ala Ala Thr Val Thr Gly Lys Leu Val His Ala Asn Phe Gly Thr Lys
225                 230                 235                 240

Lys Asp Phe Glu Asp Leu Tyr Thr Pro Val Asn Gly Ser Ile Val Ile
            245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Asn Ala Glu Leu Ser Phe Phe Gly His Ala His Leu Gly
        290                 295                 300

Thr Gly Asp Pro Tyr Thr Pro Gly Phe Pro Ser Phe Asn His Thr Gln
305                 310                 315                 320

Phe Pro Pro Ser Arg Ser Ser Gly Leu Pro Asn Ile Pro Val Gln Thr
            325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Arg Met Val Thr Ser
            355                 360                 365

Glu Ser Lys Asn Val Lys Leu Thr Val Ser Asn Val Leu Lys Glu Ile
        370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Gly Val Gly Thr Ala Leu Leu Leu Lys Leu Ala Gln Met
            420                 425                 430
```

```
Phe Ser Asp Met Val Leu Lys Asp Gly Phe Gln Pro Ser Arg Ser Ile
            435                 440                 445

Ile Phe Ala Ser Trp Ser Ala Gly Asp Phe Gly Ser Val Gly Ala Thr
450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
                500                 505                 510

Val Lys His Pro Val Thr Gly Gln Phe Leu Tyr Gln Asp Ser Asn Trp
            515                 520                 525

Ala Ser Lys Val Glu Lys Leu Thr Leu Asp Asn Ala Ala Phe Pro Phe
530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
595                 600                 605

Leu Asp Tyr Glu Arg Tyr Asn Ser Gln Leu Leu Ser Phe Val Arg Asp
            610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
675                 680                 685

Tyr Val Ser Pro Lys Glu Ser Pro Phe Arg His Val Phe Trp Gly Ser
            690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
755                 760
```

<210> SEQ ID NO 11
<211> LENGTH: 865
<212> TYPE: PRT
<213> ORGANISM: Homo sapiens

<400> SEQUENCE: 11

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
                20                  25                  30

Asn Tyr Glu Leu Pro Ala Thr Asn Tyr Glu Thr Gln Asp Ser His Lys
            35                  40                  45
```

-continued

```
Ala Gly Pro Ile Gly Ile Leu Phe Glu Leu Val His Ile Phe Leu Tyr
     50                  55                  60
Val Val Gln Pro Arg Asp Phe Pro Glu Asp Thr Leu Arg Lys Phe Leu
 65                  70                  75                  80
Gln Lys Ala Tyr Glu Ser Lys Ile Asp Tyr Asp Lys Pro Glu Thr Val
                 85                  90                  95
Ile Leu Gly Leu Lys Ile Val Tyr Tyr Glu Ala Gly Ile Ile Leu Cys
            100                 105                 110
Cys Val Leu Gly Leu Leu Phe Ile Ile Leu Met Pro Leu Val Gly Tyr
            115                 120                 125
Phe Phe Cys Met Cys Arg Cys Cys Asn Lys Cys Gly Gly Glu Met His
    130                 135                 140
Gln Arg Gln Lys Glu Asn Gly Pro Phe Leu Arg Lys Cys Phe Ala Ile
145                 150                 155                 160
Ser Leu Leu Val Ile Cys Ile Ile Ser Ile Gly Ile Phe Tyr Gly
                165                 170                 175
Phe Val Ala Asn His Gln Val Arg Thr Arg Ile Lys Arg Ser Arg Lys
                180                 185                 190
Leu Ala Asp Ser Asn Phe Lys Asp Leu Arg Thr Leu Leu Asn Glu Thr
            195                 200                 205
Pro Glu Gln Ile Lys Tyr Ile Leu Ala Gln Tyr Asn Thr Thr Lys Asp
            210                 215                 220
Lys Ala Phe Thr Asp Leu Asn Ser Ile Asn Ser Val Leu Gly Gly Gly
225                 230                 235                 240
Ile Leu Asp Arg Leu Arg Pro Asn Ile Ile Pro Val Leu Asp Glu Ile
                245                 250                 255
Lys Ser Met Ala Thr Ala Ile Lys Glu Thr Lys Glu Ala Leu Glu Asn
                260                 265                 270
Met Asn Ser Thr Leu Lys Ser Leu His Gln Gln Ser Thr Gln Leu Ser
            275                 280                 285
Ser Ser Leu Thr Ser Val Lys Thr Ser Leu Arg Ser Ser Leu Asn Asp
            290                 295                 300
Pro Leu Cys Leu Val His Pro Ser Ser Glu Thr Cys Asn Ser Ile Arg
305                 310                 315                 320
Leu Ser Leu Ser Gln Leu Asn Ser Asn Pro Glu Leu Arg Gln Leu Pro
                325                 330                 335
Pro Val Asp Ala Glu Leu Asp Asn Val Asn Asn Val Leu Arg Thr Asp
            340                 345                 350
Leu Asp Gly Leu Val Gln Gln Gly Tyr Gln Ser Leu Asn Asp Ile Pro
            355                 360                 365
Asp Arg Val Gln Arg Gln Thr Thr Thr Val Val Ala Gly Ile Lys Arg
    370                 375                 380
Val Leu Asn Ser Ile Gly Ser Asp Ile Asp Asn Val Thr Gln Arg Leu
385                 390                 395                 400
Pro Ile Gln Asp Ile Leu Ser Ala Phe Ser Val Tyr Val Asn Asn Thr
                405                 410                 415
Glu Ser Tyr Ile His Arg Asn Leu Pro Thr Leu Glu Glu Tyr Asp Ser
            420                 425                 430
Tyr Trp Trp Leu Gly Gly Leu Val Ile Cys Ser Leu Leu Thr Leu Ile
            435                 440                 445
Val Ile Phe Tyr Tyr Leu Gly Leu Leu Cys Gly Val Cys Gly Tyr Asp
    450                 455                 460
```

-continued

Arg His Ala Thr Pro Thr Arg Gly Cys Val Ser Asn Thr Gly Gly
465                 470                 475                 480

Val Phe Leu Met Val Gly Val Gly Leu Ser Phe Leu Phe Cys Trp Ile
            485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
            565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
            610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
            645                 650                 655

Lys Ala Asn Ser Leu Pro Pro Gly Asn Leu Arg Asn Ser Leu Lys Arg
            660                 665                 670

Asp Ala Gln Thr Ile Lys Thr Ile His Gln Gln Arg Val Leu Pro Ile
            675                 680                 685

Glu Gln Ser Leu Ser Thr Leu Tyr Gln Ser Val Lys Ile Leu Gln Arg
            690                 695                 700

Thr Gly Asn Gly Leu Leu Glu Arg Val Thr Arg Ile Leu Ala Ser Leu
705                 710                 715                 720

Asp Phe Ala Gln Asn Phe Ile Thr Asn Asn Thr Ser Ser Val Ile Ile
            725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
            755                 760                 765

Lys Pro Val Ala Thr Ala Leu Asp Thr Ala Val Asp Val Phe Leu Cys
770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
            805                 810                 815

Lys Tyr Tyr Arg Arg Met Asp Ser Glu Asp Val Tyr Asp Asp Val Glu
            820                 825                 830

Thr Ile Pro Met Lys Asn Met Glu Asn Gly Asn Asn Gly Tyr His Lys
            835                 840                 845

Asp His Val Tyr Gly Ile His Asn Pro Val Met Thr Ser Pro Ser Gln
            850                 855                 860

His
865

<210> SEQ ID NO 12
<211> LENGTH: 310
<212> TYPE: PRT
<213> ORGANISM: Homo sapiens

<400> SEQUENCE: 12

Met Arg Arg Ala Ala Leu Trp Leu Trp Leu Cys Ala Leu Ala Leu Ser
1               5                   10                  15

Leu Gln Pro Ala Leu Pro Gln Ile Val Ala Thr Asn Leu Pro Pro Glu
            20                  25                  30

Asp Gln Asp Gly Ser Gly Asp Ser Asp Asn Phe Ser Gly Ser Gly
        35                  40                  45

Ala Gly Ala Leu Gln Asp Ile Thr Leu Ser Gln Gln Thr Pro Ser Thr
50                  55                  60

Trp Lys Asp Thr Gln Leu Leu Thr Ala Ile Pro Thr Ser Pro Glu Pro
65                  70                  75                  80

Thr Gly Leu Glu Ala Thr Ala Ala Ser Thr Ser Thr Leu Pro Ala Gly
                85                  90                  95

Glu Gly Pro Lys Glu Gly Glu Ala Val Val Leu Pro Glu Val Glu Pro
            100                 105                 110

Gly Leu Thr Ala Arg Glu Gln Glu Ala Thr Pro Arg Pro Arg Glu Thr
        115                 120                 125

Thr Gln Leu Pro Thr Thr His Leu Ala Ser Thr Thr Ala Thr Thr
130                 135                 140

Ala Gln Glu Pro Ala Thr Ser His Pro His Arg Asp Met Gln Pro Gly
145                 150                 155                 160

His His Glu Thr Ser Thr Pro Ala Gly Pro Ser Gln Ala Asp Leu His
                165                 170                 175

Thr Pro His Thr Glu Asp Gly Gly Pro Ser Ala Thr Glu Arg Ala Ala
            180                 185                 190

Glu Asp Gly Ala Ser Ser Gln Leu Pro Ala Ala Glu Gly Ser Gly Glu
        195                 200                 205

Gln Asp Phe Thr Phe Glu Thr Ser Gly Glu Asn Thr Ala Val Val Ala
210                 215                 220

Val Glu Pro Asp Arg Arg Asn Gln Ser Pro Val Asp Gln Gly Ala Thr
225                 230                 235                 240

Gly Ala Ser Gln Gly Leu Leu Asp Arg Lys Glu Val Leu Gly Gly Val
                245                 250                 255

Ile Ala Gly Gly Leu Val Gly Leu Ile Phe Ala Val Cys Leu Val Gly
            260                 265                 270

Phe Met Leu Tyr Arg Met Lys Lys Lys Asp Glu Gly Ser Tyr Ser Leu
        275                 280                 285

Glu Glu Pro Lys Gln Ala Asn Gly Gly Ala Tyr Gln Lys Pro Thr Lys
290                 295                 300

Gln Glu Glu Phe Tyr Ala
305             310

<210> SEQ ID NO 13
<211> LENGTH: 150
<212> TYPE: PRT
<213> ORGANISM: Homo sapiens

<400> SEQUENCE: 13

Met Tyr Gly Lys Ile Ile Phe Val Leu Leu Leu Ser Glu Ile Val Ser
1               5                   10                  15

Ile Ser Ala Ser Ser Thr Thr Gly Val Ala Met His Thr Ser Thr Ser

```
                20                  25                  30
Ser Ser Val Thr Lys Ser Tyr Ile Ser Ser Gln Thr Asn Asp Thr His
            35                  40                  45

Lys Arg Asp Thr Tyr Ala Ala Thr Pro Arg Ala His Glu Val Ser Glu
     50                  55                  60

Ile Ser Val Arg Thr Val Tyr Pro Pro Glu Glu Thr Gly Glu Arg
 65                  70                  75                  80

Val Gln Leu Ala His His Phe Ser Glu Pro Glu Ile Thr Leu Ile Ile
                    85                  90                  95

Phe Gly Val Met Ala Gly Val Ile Gly Thr Ile Leu Leu Ile Ser Tyr
                100                 105                 110

Gly Ile Arg Arg Leu Ile Lys Lys Ser Pro Ser Asp Val Lys Pro Leu
            115                 120                 125

Pro Ser Pro Asp Thr Asp Val Pro Leu Ser Ser Val Glu Ile Glu Asn
    130                 135                 140

Pro Glu Thr Ser Asp Gln
145                 150

<210> SEQ ID NO 14
<211> LENGTH: 867
<212> TYPE: PRT
<213> ORGANISM: Homo sapiens

<400> SEQUENCE: 14

Ala Thr Phe Ile Ser Val Gln Leu Lys Lys Thr Ser Glu Val Asp Leu
 1               5                  10                  15

Ala Lys Pro Leu Val Lys Phe Ile Gln Gln Thr Tyr Pro Ser Gly Gly
             20                  25                  30

Glu Glu Gln Ala Gln Tyr Cys Arg Ala Ala Glu Glu Leu Ser Lys Leu
         35                  40                  45

Arg Arg Ala Ala Val Gly Arg Pro Leu Asp Lys His Glu Gly Ala Leu
     50                  55                  60

Glu Thr Leu Leu Arg Tyr Tyr Asp Gln Ile Cys Ser Ile Glu Pro Lys
 65                  70                  75                  80

Phe Pro Phe Ser Glu Asn Gln Ile Cys Leu Thr Phe Thr Trp Lys Asp
                 85                  90                  95

Ala Phe Asp Lys Gly Ser Leu Phe Gly Gly Ser Val Lys Leu Ala Leu
            100                 105                 110

Ala Ser Leu Gly Tyr Glu Lys Ser Cys Val Leu Phe Asn Cys Ala Ala
        115                 120                 125

Leu Ala Ser Gln Ile Ala Ala Glu Gln Asn Leu Asp Asn Asp Glu Gly
    130                 135                 140

Leu Lys Ile Ala Ala Lys His Tyr Gln Phe Ala Ser Gly Ala Phe Leu
145                 150                 155                 160

His Ile Lys Glu Thr Val Leu Ser Ala Leu Ser Arg Glu Pro Thr Val
                165                 170                 175

Asp Ile Ser Pro Asp Thr Val Gly Thr Leu Ser Leu Ile Met Leu Ala
            180                 185                 190

Gln Ala Gln Glu Val Phe Phe Leu Lys Ala Thr Arg Asp Lys Met Lys
        195                 200                 205

Asp Ala Ile Ile Ala Lys Leu Ala Asn Gln Ala Ala Asp Tyr Phe Gly
    210                 215                 220

Asp Ala Phe Lys Gln Cys Gln Tyr Lys Asp Thr Leu Pro Lys Glu Val
225                 230                 235                 240
```

```
Phe Pro Val Leu Ala Ala Lys His Cys Ile Met Gln Ala Asn Ala Glu
                245                 250                 255
Tyr His Gln Ser Ile Leu Ala Lys Gln Gln Lys Lys Phe Gly Glu Glu
                260                 265                 270
Ile Ala Arg Leu Gln His Ala Ala Glu Leu Ile Lys Thr Val Ala Ser
                275                 280                 285
Arg Tyr Asp Glu Tyr Val Asn Val Lys Asp Phe Ser Asp Lys Ile Asn
                290                 295                 300
Arg Ala Leu Ala Ala Lys Lys Asp Asn Asp Phe Ile Tyr His Asp
305                 310                 315                 320
Arg Val Pro Asp Leu Lys Asp Leu Asp Pro Ile Gly Lys Ala Thr Leu
                325                 330                 335
Val Lys Ser Thr Pro Val Asn Val Pro Ile Ser Gln Lys Phe Thr Asp
                340                 345                 350
Leu Phe Glu Lys Met Val Pro Val Ser Val Gln Gln Ser Leu Ala Ala
                355                 360                 365
Tyr Asn Gln Arg Lys Ala Asp Leu Val Asn Arg Ser Ile Ala Gln Met
                370                 375                 380
Arg Glu Ala Thr Thr Leu Ala Asn Gly Val Leu Ala Ser Leu Asn Leu
385                 390                 395                 400
Pro Ala Ala Ile Glu Asp Val Ser Gly Asp Thr Val Pro Gln Ser Ile
                405                 410                 415
Leu Thr Lys Ser Arg Ser Val Ile Glu Gln Gly Gly Ile Gln Thr Val
                420                 425                 430
Asp Gln Leu Ile Lys Glu Leu Pro Glu Leu Leu Gln Arg Asn Arg Glu
                435                 440                 445
Ile Leu Asp Glu Ser Leu Arg Leu Leu Asp Glu Glu Ala Thr Asp
                450                 455                 460
Asn Asp Leu Arg Ala Lys Phe Lys Glu Arg Trp Gln Arg Thr Pro Ser
465                 470                 475                 480
Asn Glu Leu Tyr Lys Pro Leu Arg Ala Glu Gly Thr Asn Phe Arg Thr
                485                 490                 495
Val Leu Asp Lys Ala Val Gln Ala Asp Gly Gln Val Lys Glu Cys Tyr
                500                 505                 510
Gln Ser His Arg Asp Thr Ile Val Leu Leu Cys Lys Pro Glu Pro Glu
                515                 520                 525
Leu Asn Ala Ala Ile Pro Ser Ala Asn Pro Ala Lys Thr Met Gln Gly
                530                 535                 540
Ser Glu Val Val Asn Val Leu Lys Ser Leu Leu Ser Asn Leu Asp Glu
545                 550                 555                 560
Val Lys Lys Glu Arg Glu Gly Leu Glu Asn Asp Leu Lys Ser Val Asn
                565                 570                 575
Phe Asp Met Thr Ser Lys Phe Leu Thr Ala Leu Ala Gln Asp Gly Val
                580                 585                 590
Ile Asn Glu Glu Ala Leu Ser Val Thr Glu Leu Asp Arg Val Tyr Gly
                595                 600                 605
Gly Leu Thr Thr Lys Val Gln Glu Ser Leu Lys Lys Gln Glu Gly Leu
                610                 615                 620
Leu Lys Asn Ile Gln Val Ser His Gln Glu Phe Ser Lys Met Lys Gln
625                 630                 635                 640
Ser Asn Asn Glu Ala Asn Leu Arg Glu Val Leu Lys Asn Leu Ala
                645                 650                 655
Thr Ala Tyr Asp Asn Phe Val Glu Leu Val Ala Asn Leu Lys Glu Gly
```

```
                    660                 665                 670
Thr Lys Phe Tyr Asn Glu Leu Thr Glu Ile Leu Val Arg Phe Gln Asn
            675                 680                 685

Lys Cys Ser Asp Ile Val Phe Ala Arg Lys Thr Glu Arg Asp Glu Leu
        690                 695                 700

Leu Lys Asp Leu Gln Gln Ser Ile Ala Arg Glu Pro Ser Ala Pro Ser
705                 710                 715                 720

Ile Pro Thr Pro Ala Tyr Gln Ser Ser Pro Ala Gly Gly His Ala Pro
                725                 730                 735

Thr Pro Pro Thr Pro Ala Pro Arg Thr Met Pro Pro Thr Lys Pro Gln
            740                 745                 750

Pro Pro Ala Arg Pro Pro Pro Val Leu Pro Ala Asn Arg Ala Pro
        755                 760                 765

Ser Ala Thr Ala Pro Ser Pro Val Gly Ala Gly Thr Ala Ala Pro Ala
770                 775                 780

Pro Ser Gln Thr Pro Gly Ser Ala Pro Pro Gln Ala Gln Gly Pro
785                 790                 795                 800

Pro Tyr Pro Thr Tyr Pro Gly Tyr Pro Gly Tyr Cys Gln Met Pro Met
                805                 810                 815

Pro Met Gly Tyr Asn Pro Tyr Ala Tyr Gly Gln Tyr Asn Met Pro Tyr
            820                 825                 830

Pro Pro Val Tyr His Gln Ser Pro Gly Gln Ala Pro Tyr Pro Gly Pro
        835                 840                 845

Gln Gln Pro Ser Tyr Pro Phe Pro Gln Pro Pro Gln Gln Ser Tyr Tyr
    850                 855                 860

Pro Gln Gln
865

<210> SEQ ID NO 15
<211> LENGTH: 297
<212> TYPE: PRT
<213> ORGANISM: Homo sapiens

<400> SEQUENCE: 15

Ser Leu Tyr Pro Ser Leu Glu Asp Leu Lys Val Asp Lys Val Ile Gln
1               5                   10                  15

Ala Gln Thr Ala Phe Ser Ala Asn Pro Ala Asn Pro Ala Ile Leu Ser
            20                  25                  30

Glu Ala Ser Ala Pro Ile Pro His Asp Gly Asn Leu Tyr Pro Arg Leu
        35                  40                  45

Tyr Pro Glu Leu Ser Gln Tyr Met Gly Leu Ser Leu Asn Glu Glu Glu
    50                  55                  60

Ile Arg Ala Asn Val Ala Val Val Ser Gly Ala Pro Leu Gln Gly Gln
65                  70                  75                  80

Leu Val Ala Arg Pro Ser Ser Ile Asn Tyr Met Val Ala Pro Val Thr
                85                  90                  95

Gly Asn Asp Val Gly Ile Arg Arg Ala Glu Ile Lys Gln Gly Ile Arg
            100                 105                 110

Glu Val Ile Leu Cys Lys Asp Gln Asp Gly Lys Ile Gly Leu Arg Leu
        115                 120                 125

Lys Ser Ile Asp Asn Gly Ile Phe Val Gln Leu Val Gln Ala Asn Ser
    130                 135                 140

Pro Ala Ser Leu Val Gly Leu Arg Phe Gly Asp Gln Val Leu Gln Ile
145                 150                 155                 160
```

```
Asn Gly Glu Asn Cys Ala Gly Trp Ser Ser Asp Lys Ala His Lys Val
            165                 170                 175

Leu Lys Gln Ala Phe Gly Glu Lys Ile Thr Met Thr Ile Arg Asp Arg
        180                 185                 190

Pro Phe Glu Arg Thr Ile Thr Met His Lys Asp Ser Thr Gly His Val
        195                 200                 205

Gly Phe Ile Phe Lys Asn Gly Lys Ile Thr Ser Ile Val Lys Asp Ser
        210                 215                 220

Ser Ala Ala Arg Asn Gly Leu Leu Thr Glu His Asn Ile Cys Glu Ile
225                 230                 235                 240

Asn Gly Gln Asn Val Ile Gly Leu Lys Asp Ser Gln Ile Ala Asp Ile
            245                 250                 255

Leu Ser Thr Ser Gly Thr Val Val Thr Ile Thr Ile Met Pro Ala Phe
        260                 265                 270

Ile Phe Glu His Ile Ile Lys Arg Met Ala Pro Ser Ile Met Lys Ser
        275                 280                 285

Leu Met Asp His Thr Ile Pro Glu Val
        290                 295

<210> SEQ ID NO 16
<211> LENGTH: 292
<212> TYPE: PRT
<213> ORGANISM: Homo sapiens

<400> SEQUENCE: 16

Met Ser Ser Leu Tyr Pro Ser Leu Glu Asp Leu Lys Val Asp Gln Ala
1               5                   10                  15

Ile Gln Ala Gln Val Arg Ala Ser Pro Lys Met Pro Ala Leu Pro Val
            20                  25                  30

Gln Ala Thr Ala Ile Ser Pro Pro Val Leu Tyr Pro Asn Leu Ala
        35                  40                  45

Glu Leu Glu Asn Tyr Met Gly Leu Ser Leu Ser Ser Gln Glu Val Gln
50                  55                  60

Glu Ser Leu Leu Gln Ile Pro Glu Gly Asp Ser Thr Ala Val Ser Gly
65                  70                  75                  80

Pro Gly Pro Gly Gln Met Val Ala Pro Val Thr Gly Tyr Ser Leu Gly
            85                  90                  95

Val Arg Arg Ala Glu Ile Lys Pro Gly Val Arg Glu Ile His Leu Cys
        100                 105                 110

Lys Asp Glu Arg Gly Lys Thr Gly Leu Arg Leu Arg Lys Val Asp Gln
        115                 120                 125

Gly Leu Phe Val Gln Leu Val Gln Ala Asn Thr Pro Ala Ser Leu Val
    130                 135                 140

Gly Leu Arg Phe Gly Asp Gln Leu Leu Gln Ile Asp Gly Arg Asp Cys
145                 150                 155                 160

Ala Gly Trp Ser Ser His Lys Ala His Gln Val Val Lys Lys Ala Ser
            165                 170                 175

Gly Asp Lys Ile Val Val Val Arg Asp Arg Pro Phe Gln Arg Thr
        180                 185                 190

Val Thr Met His Lys Asp Ser Met Gly His Val Gly Phe Val Ile Lys
        195                 200                 205

Lys Gly Lys Ile Val Ser Leu Val Lys Gly Ser Ser Ala Ala Arg Asn
    210                 215                 220

Gly Leu Leu Thr Asn His Tyr Val Cys Glu Val Asp Gly Gln Asn Val
225                 230                 235                 240
```

Ile Gly Leu Lys Asp Lys Ile Met Glu Ile Leu Ala Thr Ala Gly
                245                 250                 255

Asn Val Val Thr Leu Thr Ile Ile Pro Ser Val Ile Tyr Glu His Met
            260                 265                 270

Val Lys Lys Leu Pro Pro Val Leu Leu His His Thr Met Asp His Ser
        275                 280                 285

Ile Pro Asp Ala
    290

<210> SEQ ID NO 17
<211> LENGTH: 410
<212> TYPE: PRT
<213> ORGANISM: Homo sapiens

<400> SEQUENCE: 17

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Leu Glu Leu Asn
            20                  25                  30

Leu Thr Asp Ser Glu Asn Ala Thr Cys Leu Tyr Ala Lys Trp Gln Met
        35                  40                  45

Asn Phe Thr Val Arg Tyr Glu Thr Thr Asn Lys Thr Tyr Lys Thr Val
50                  55                  60

Thr Ile Ser Asp His Gly Thr Val Thr Tyr Asn Gly Ser Ile Cys Gly
65                  70                  75                  80

Asp Asp Gln Asn Gly Pro Lys Ile Ala Val Gln Phe Gly Pro Gly Phe
                85                  90                  95

Ser Trp Ile Ala Asn Phe Thr Lys Ala Ala Ser Thr Tyr Ser Ile Asp
            100                 105                 110

Ser Val Ser Phe Ser Tyr Asn Thr Gly Asp Asn Thr Thr Phe Pro Asp
        115                 120                 125

Ala Glu Asp Lys Gly Ile Leu Thr Val Asp Glu Leu Leu Ala Ile Arg
    130                 135                 140

Ile Pro Leu Asn Asp Leu Phe Arg Cys Asn Ser Leu Ser Thr Leu Glu
145                 150                 155                 160

Lys Asn Asp Val Val Gln His Tyr Trp Asp Val Leu Val Gln Ala Phe
                165                 170                 175

Val Gln Asn Gly Thr Val Ser Thr Asn Glu Phe Leu Cys Asp Lys Asp
            180                 185                 190

Lys Thr Ser Thr Val Ala Pro Thr Ile His Thr Thr Val Pro Ser Pro
        195                 200                 205

Thr Thr Thr Pro Thr Pro Lys Glu Lys Pro Glu Ala Gly Thr Tyr Ser
    210                 215                 220

Val Asn Asn Gly Asn Asp Thr Cys Leu Leu Ala Thr Met Gly Leu Gln
225                 230                 235                 240

Leu Asn Ile Thr Gln Asp Lys Val Ala Ser Val Ile Asn Ile Asn Pro
                245                 250                 255

Asn Thr Thr His Ser Thr Gly Ser Cys Arg Ser His Thr Ala Leu Leu
            260                 265                 270

Arg Leu Asn Ser Ser Thr Ile Lys Tyr Leu Asp Phe Val Phe Ala Val
        275                 280                 285

Lys Asn Glu Asn Arg Phe Tyr Leu Lys Glu Val Asn Ile Ser Met Tyr
    290                 295                 300

Leu Val Asn Gly Ser Val Phe Ser Ile Ala Asn Asn Asn Leu Ser Tyr

```
                305                 310                 315                 320
Trp Asp Ala Pro Leu Gly Ser Ser Tyr Met Cys Asn Lys Glu Gln Thr
                325                 330                 335

Val Ser Val Ser Gly Ala Phe Gln Ile Asn Thr Phe Asp Leu Arg Val
                340                 345                 350

Gln Pro Phe Asn Val Thr Gln Gly Lys Tyr Ser Thr Ala Gln Asp Cys
                355                 360                 365

Ser Ala Asp Asp Asn Phe Leu Val Pro Ile Ala Val Gly Ala Ala
                370                 375                 380

Leu Ala Gly Val Leu Ile Leu Val Leu Leu Ala Tyr Phe Ile Gly Leu
385                 390                 395                 400

Lys His His His Ala Gly Tyr Glu Gln Phe
                405                 410

<210> SEQ ID NO 18
<211> LENGTH: 918
<212> TYPE: PRT
<213> ORGANISM: Homo sapiens

<400> SEQUENCE: 18

Met Leu Thr Leu Gln Thr Trp Leu Val Gln Ala Leu Phe Ile Phe Leu
1               5                   10                  15

Thr Thr Glu Ser Thr Gly Glu Leu Leu Asp Pro Cys Gly Tyr Ile Ser
                20                  25                  30

Pro Glu Ser Pro Val Val Gln Leu His Ser Asn Phe Thr Ala Val Cys
            35                  40                  45

Val Leu Lys Glu Lys Cys Met Asp Tyr Phe His Val Asn Ala Asn Tyr
50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Arg Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255

Tyr Asn Ile Gln Tyr Arg Thr Lys Asp Ala Ser Thr Trp Ser Gln Ile
            260                 265                 270
```

```
Pro Pro Glu Asp Thr Ala Ser Thr Arg Ser Ser Phe Thr Val Gln Asp
            275                 280                 285

Leu Lys Pro Phe Thr Glu Tyr Val Phe Arg Ile Arg Cys Met Lys Glu
    290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
    355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Val Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
    435                 440                 445

Ser Val Lys Lys Tyr Ile Leu Glu Trp Cys Val Leu Ser Asp Lys Ala
    450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
    515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
    595                 600                 605

Thr Thr Pro Lys Phe Ala Gln Gly Glu Ile Glu Ala Ile Val Val Pro
610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
    675                 680                 685

Thr Asp Val Ser Val Val Glu Ile Glu Ala Asn Asp Lys Lys Pro Phe
```

```
                690                 695                 700
Pro Glu Asp Leu Lys Ser Leu Asp Leu Phe Lys Lys Glu Lys Ile Asn
705                 710                 715                 720

Thr Glu Gly His Ser Ser Gly Ile Gly Gly Ser Ser Cys Met Ser Ser
                725                 730                 735

Ser Arg Pro Ser Ile Ser Ser Asp Glu Asn Glu Ser Ser Gln Asn
            740                 745                 750

Thr Ser Ser Thr Val Gln Tyr Ser Thr Val Val His Ser Gly Tyr Arg
            755                 760                 765

His Gln Val Pro Ser Val Gln Val Phe Ser Arg Ser Glu Ser Thr Gln
        770                 775                 780

Pro Leu Leu Asp Ser Glu Glu Arg Pro Glu Asp Leu Gln Leu Val Asp
785                 790                 795                 800

His Val Asp Gly Gly Asp Gly Ile Leu Pro Arg Gln Gln Tyr Phe Lys
                805                 810                 815

Gln Asn Cys Ser Gln His Glu Ser Ser Pro Asp Ile Ser His Phe Glu
            820                 825                 830

Arg Ser Lys Gln Val Ser Ser Val Asn Glu Glu Asp Phe Val Arg Leu
            835                 840                 845

Lys Gln Gln Ile Ser Asp His Ile Ser Gln Ser Cys Gly Ser Gly Gln
850                 855                 860

Met Lys Met Phe Gln Glu Val Ser Ala Ala Asp Ala Phe Gly Pro Gly
865                 870                 875                 880

Thr Glu Gly Gln Val Glu Arg Phe Glu Thr Val Gly Met Glu Ala Ala
                885                 890                 895

Thr Asp Glu Gly Met Pro Lys Ser Tyr Leu Pro Gln Thr Val Arg Gln
                900                 905                 910

Gly Gly Tyr Met Pro Gln
        915

<210> SEQ ID NO 19
<211> LENGTH: 455
<212> TYPE: PRT
<213> ORGANISM: Homo sapiens

<400> SEQUENCE: 19

Met Gly Leu Ser Thr Val Pro Asp Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140
```

```
Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
            165                 170                 175

Asn Glu Cys Val Ser Cys Ser Asn Cys Lys Lys Ser Leu Glu Cys Thr
        180                 185                 190

Lys Leu Cys Leu Pro Gln Ile Glu Asn Val Lys Gly Thr Glu Asp Ser
    195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
    275                 280                 285

Pro Ser Ser Thr Phe Thr Ser Ser Ser Thr Tyr Thr Pro Gly Asp Cys
    290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
    355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
    435                 440                 445

Pro Ala Pro Ser Leu Leu Arg
450                 455

<210> SEQ ID NO 20
<211> LENGTH: 201
<212> TYPE: PRT
<213> ORGANISM: Homo sapiens

<400> SEQUENCE: 20

Met Arg Arg Ala Trp Ile Leu Thr Leu Gly Leu Val Ala Cys Val
1               5                   10                  15

Ser Ala Glu Ser Arg Ala Glu Leu Thr Ser Asp Lys Asp Met Tyr Leu
            20                  25                  30

Asp Asn Ser Ser Ile Glu Glu Ala Ser Gly Val Tyr Pro Ile Asp Asp
        35                  40                  45

Asp Asp Tyr Ala Ser Ala Ser Gly Ser Gly Ala Asp Glu Asp Val Glu
    50                  55                  60
```

Ser Pro Glu Leu Thr Thr Ser Arg Pro Leu Pro Lys Ile Leu Leu Thr
65                  70                  75                  80

Ser Ala Ala Pro Lys Val Glu Thr Thr Thr Leu Asn Ile Gln Asn Lys
                85                  90                  95

Ile Pro Ala Gln Thr Lys Ser Pro Glu Glu Thr Asp Lys Glu Lys Val
            100                 105                 110

His Leu Ser Asp Ser Glu Arg Lys Met Asp Pro Ala Glu Glu Asp Thr
        115                 120                 125

Asn Val Tyr Thr Glu Lys His Ser Asp Ser Leu Phe Lys Arg Thr Glu
130                 135                 140

Val Leu Ala Ala Val Ile Ala Gly Gly Val Ile Gly Phe Leu Phe Ala
145                 150                 155                 160

Ile Phe Leu Ile Leu Leu Leu Val Tyr Arg Met Arg Lys Lys Asp Glu
                165                 170                 175

Gly Ser Tyr Asp Leu Gly Glu Arg Lys Pro Ser Ser Ala Ala Tyr Gln
            180                 185                 190

Lys Ala Pro Thr Lys Glu Phe Tyr Ala
            195                 200

<210> SEQ ID NO 21
<211> LENGTH: 442
<212> TYPE: PRT
<213> ORGANISM: Homo sapiens

<400> SEQUENCE: 21

Met Lys Pro Gly Pro Pro His Arg Ala Gly Ala Ala His Gly Ala Gly
1               5                   10                  15

Ala Gly Ala Gly Ala Ala Ala Gly Pro Gly Ala Arg Gly Leu Leu Leu
                20                  25                  30

Pro Pro Leu Leu Leu Leu Leu Leu Ala Gly Arg Ala Ala Gly Ala Gln
            35                  40                  45

Arg Trp Arg Ser Glu Asn Phe Glu Arg Pro Val Asp Leu Glu Gly Ser
50                  55                  60

Gly Asp Asp Asp Ser Phe Pro Asp Asp Glu Leu Asp Asp Leu Tyr Ser
65                  70                  75                  80

Gly Ser Gly Ser Gly Tyr Phe Glu Gln Glu Ser Gly Ile Glu Thr Ala
                85                  90                  95

Met Arg Phe Ser Pro Asp Val Ala Leu Ala Val Ser Thr Thr Pro Ala
            100                 105                 110

Val Leu Pro Thr Thr Asn Ile Gln Pro Val Gly Thr Pro Phe Glu Glu
        115                 120                 125

Leu Pro Ser Glu Arg Pro Thr Leu Glu Pro Ala Thr Ser Pro Leu Val
130                 135                 140

Val Thr Glu Val Pro Glu Glu Pro Ser Gln Arg Ala Thr Thr Val Ser
145                 150                 155                 160

Thr Thr Met Ala Thr Thr Ala Ala Thr Ser Thr Gly Asp Pro Thr Val
                165                 170                 175

Ala Thr Val Pro Ala Thr Val Ala Thr Ala Thr Pro Ser Thr Pro Ala
            180                 185                 190

Ala Pro Pro Phe Thr Ala Thr Thr Ala Val Ile Arg Thr Thr Gly Val
        195                 200                 205

Arg Arg Leu Leu Pro Leu Pro Leu Thr Thr Val Ala Thr Ala Arg Ala
210                 215                 220

Thr Thr Pro Glu Ala Pro Ser Pro Pro Thr Thr Ala Ala Val Leu Asp

```
                225                 230                 235                 240
        Thr Glu Ala Pro Thr Pro Arg Leu Val Ser Thr Ala Thr Ser Arg Pro
                        245                 250                 255

Arg Ala Leu Pro Arg Pro Ala Thr Thr Gln Glu Pro Asp Ile Pro Glu
                    260                 265                 270

Arg Ser Thr Leu Pro Leu Gly Thr Ala Pro Gly Pro Thr Glu Val
                275                 280                 285

Ala Gln Thr Pro Thr Pro Glu Thr Phe Leu Thr Thr Ile Arg Asp Glu
                290                 295                 300

Pro Glu Val Pro Val Ser Gly Gly Pro Ser Gly Asp Phe Glu Leu Pro
        305                 310                 315                 320

Glu Glu Glu Thr Thr Gln Pro Asp Thr Ala Asn Glu Val Val Ala Val
                        325                 330                 335

Gly Gly Ala Ala Ala Lys Ala Ser Ser Pro Pro Gly Thr Leu Pro Lys
                    340                 345                 350

Gly Ala Arg Pro Gly Pro Gly Leu Leu Asp Asn Ala Ile Asp Ser Gly
                355                 360                 365

Ser Ser Ala Ala Gln Leu Pro Gln Lys Ser Ile Leu Glu Arg Lys Glu
            370                 375                 380

Val Leu Val Ala Val Ile Val Gly Gly Val Val Gly Ala Leu Phe Ala
        385                 390                 395                 400

Ala Phe Leu Val Thr Leu Leu Ile Tyr Arg Met Lys Lys Lys Asp Glu
                        405                 410                 415

Gly Ser Tyr Thr Leu Glu Glu Pro Lys Gln Ala Ser Val Thr Tyr Gln
                    420                 425                 430

Lys Pro Asp Lys Gln Glu Glu Phe Tyr Ala
                435                 440

<210> SEQ ID NO 22
<211> LENGTH: 198
<212> TYPE: PRT
<213> ORGANISM: Homo sapiens

<400> SEQUENCE: 22

Met Ala Pro Ala Arg Leu Phe Ala Leu Leu Leu Phe Phe Val Gly Gly
        1               5                   10                  15

Val Ala Glu Ser Ile Arg Glu Thr Glu Val Ile Asp Pro Gln Asp Leu
                    20                  25                  30

Leu Glu Gly Arg Tyr Phe Ser Gly Ala Leu Pro Asp Asp Glu Asp Val
                35                  40                  45

Val Gly Pro Gly Gln Glu Ser Asp Asp Phe Glu Leu Ser Gly Ser Gly
            50                  55                  60

Asp Leu Asp Asp Leu Glu Asp Ser Met Ile Gly Pro Glu Val Val His
        65                  70                  75                  80

Pro Leu Val Pro Leu Asp Asn His Ile Pro Glu Arg Ala Gly Ser Gly
                        85                  90                  95

Ser Gln Val Pro Thr Glu Pro Lys Lys Leu Glu Glu Asn Glu Val Ile
                    100                 105                 110

Pro Lys Arg Ile Ser Pro Val Glu Glu Ser Glu Asp Val Ser Asn Lys
                115                 120                 125

Val Ser Met Ser Ser Thr Val Gln Gly Ser Asn Ile Phe Glu Arg Thr
            130                 135                 140

Glu Val Leu Ala Ala Leu Ile Val Gly Gly Ile Val Gly Ile Leu Phe
        145                 150                 155                 160
```

```
Ala Val Phe Leu Ile Leu Leu Leu Met Tyr Arg Met Lys Lys Asp
            165                 170                 175

Glu Gly Ser Tyr Asp Leu Gly Lys Lys Pro Ile Tyr Lys Ala Pro
            180                 185                 190

Thr Asn Glu Phe Tyr Ala
        195

<210> SEQ ID NO 23
<211> LENGTH: 59
<212> TYPE: PRT
<213> ORGANISM: Homo sapiens

<400> SEQUENCE: 23

Met Asp Gln Ala Arg Ser Ala Phe Ser Asn Leu Phe Gly Gly Glu Pro
1               5                   10                  15

Leu Ser Tyr Thr Arg Phe Ser Leu Ala Arg Gln Val Asp Gly Asp Asn
            20                  25                  30

Ser His Val Glu Met Lys Leu Ala Val Asp Glu Glu Asn Ala Asp
        35                  40                  45

Asn Asn Thr Lys Ala Asn Val Thr Lys Pro Lys
    50                  55

<210> SEQ ID NO 24
<211> LENGTH: 267
<212> TYPE: PRT
<213> ORGANISM: Homo sapiens

<400> SEQUENCE: 24

Met Gly Ser Ala Cys Ile Lys Val Thr Lys Tyr Phe Leu Phe Leu Phe
1               5                   10                  15

Asn Leu Ile Phe Phe Ile Leu Gly Ala Val Ile Leu Gly Phe Gly Val
            20                  25                  30

Trp Ile Leu Ala Asp Lys Ser Ser Phe Ile Ser Val Leu Gln Thr Ser
            35                  40                  45

Ser Ser Ser Leu Arg Met Gly Ala Tyr Val Phe Ile Gly Val Gly Ala
    50                  55                  60

Val Thr Met Leu Met Gly Phe Leu Gly Cys Ile Gly Ala Val Asn Glu
65                  70                  75                  80

Val Arg Cys Leu Leu Gly Leu Tyr Phe Ala Phe Leu Leu Leu Ile Leu
                85                  90                  95

Ile Ala Gln Val Thr Ala Gly Ala Leu Phe Tyr Phe Asn Met Gly Lys
            100                 105                 110

Leu Lys Gln Glu Met Gly Gly Ile Val Thr Glu Leu Ile Arg Asp Tyr
        115                 120                 125

Asn Ser Ser Arg Glu Asp Ser Leu Gln Asp Ala Trp Asp Tyr Val Gln
    130                 135                 140

Ala Gln Val Lys Cys Cys Gly Trp Val Ser Phe Tyr Asn Trp Thr Asp
145                 150                 155                 160

Asn Ala Glu Leu Met Asn Arg Pro Glu Val Thr Tyr Pro Cys Ser Cys
                165                 170                 175

Glu Val Lys Gly Glu Glu Asp Asn Ser Leu Ser Val Arg Lys Gly Phe
            180                 185                 190

Cys Glu Ala Pro Gly Asn Arg Thr Gln Ser Gly Asn His Pro Glu Asp
        195                 200                 205

Trp Pro Val Tyr Gln Glu Gly Cys Met Glu Lys Val Gln Ala Trp Leu
    210                 215                 220
```

-continued

Gln Glu Asn Leu Gly Ile Ile Leu Gly Val Gly Val Gly Val Ala Ile
225                 230                 235                 240

Ile Glu Leu Leu Gly Met Val Leu Ser Ile Cys Leu Cys Arg His Val
            245                 250                 255

His Ser Glu Asp Tyr Ser Lys Val Pro Lys Tyr
        260                 265

<210> SEQ ID NO 25
<211> LENGTH: 387
<212> TYPE: PRT
<213> ORGANISM: Homo sapiens

<400> SEQUENCE: 25

Met Pro Arg Pro Arg Leu Leu Ala Ala Leu Cys Gly Ala Leu Leu Cys
1               5                   10                  15

Ala Pro Ser Leu Leu Val Ala Leu Asp Ile Cys Ser Lys Asn Pro Cys
            20                  25                  30

His Asn Gly Gly Leu Cys Glu Glu Ile Ser Gln Glu Val Arg Gly Asp
        35                  40                  45

Val Phe Pro Ser Tyr Thr Cys Thr Cys Leu Lys Gly Tyr Ala Gly Asn
50                  55                  60

His Cys Glu Thr Lys Cys Val Glu Pro Leu Gly Met Glu Asn Gly Asn
65                  70                  75                  80

Ile Ala Asn Ser Gln Ile Ala Ala Ser Ser Val Arg Val Thr Phe Leu
                85                  90                  95

Gly Leu Gln His Trp Val Pro Glu Leu Ala Arg Leu Asn Arg Ala Gly
            100                 105                 110

Met Val Asn Ala Trp Thr Pro Ser Ser Asn Asp Asp Asn Pro Trp Ile
        115                 120                 125

Gln Val Asn Leu Leu Arg Arg Met Trp Val Thr Gly Val Val Thr Gln
130                 135                 140

Gly Ala Ser Arg Leu Ala Ser His Glu Tyr Leu Lys Ala Phe Lys Val
145                 150                 155                 160

Ala Tyr Ser Leu Asn Gly His Glu Phe Asp Phe Ile His Asp Val Asn
                165                 170                 175

Lys Lys His Lys Glu Phe Val Gly Asn Trp Asn Lys Asn Ala Val His
            180                 185                 190

Val Asn Leu Phe Glu Thr Pro Val Glu Ala Gln Tyr Val Arg Leu Tyr
        195                 200                 205

Pro Thr Ser Cys His Thr Ala Cys Thr Leu Arg Phe Glu Leu Leu Gly
210                 215                 220

Cys Glu Leu Asn Gly Cys Ala Asn Pro Leu Gly Leu Lys Asn Asn Ser
225                 230                 235                 240

Ile Pro Asp Lys Gln Ile Thr Ala Ser Ser Tyr Lys Thr Trp Gly
                245                 250                 255

Leu His Leu Phe Ser Trp Asn Pro Ser Tyr Ala Arg Leu Asp Lys Gln
            260                 265                 270

Gly Asn Phe Asn Ala Trp Val Ala Gly Ser Tyr Gly Asn Asp Gln Trp
        275                 280                 285

Leu Gln Val Asp Leu Gly Ser Ser Lys Glu Val Thr Gly Ile Ile Thr
290                 295                 300

Gln Gly Ala Arg Asn Phe Gly Ser Val Gln Phe Val Ala Ser Tyr Lys
305                 310                 315                 320

Val Ala Tyr Ser Asn Asp Ser Ala Asn Trp Thr Glu Tyr Gln Asp Pro
                325                 330                 335

Arg Thr Gly Ser Ser Lys Ile Phe Pro Gly Asn Trp Asp Asn His Ser
            340                 345                 350

His Lys Lys Asn Leu Phe Glu Thr Pro Ile Leu Ala Arg Tyr Val Arg
            355                 360                 365

Ile Leu Pro Val Ala Trp His Asn Arg Ile Ala Leu Arg Leu Glu Leu
370                 375                 380

Leu Gly Cys
385

<210> SEQ ID NO 26
<211> LENGTH: 556
<212> TYPE: PRT
<213> ORGANISM: Homo sapiens

<400> SEQUENCE: 26

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu Gln Arg Ala Leu Val Leu Arg

```
              305                 310                 315                 320
Arg Lys Arg Lys Arg Met Thr Asp Pro Thr Arg Arg Phe Phe Lys Val
                    325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480

Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
                500                 505                 510

Leu Arg Ser Ile Arg Gly Gln Pro Gly Pro Asn His Glu Glu Asp Ala
            515                 520                 525

Asp Ser Tyr Glu Asn Met Asp Asn Pro Asp Gly Pro Asp Pro Ala Trp
        530                 535                 540

Gly Gly Gly Gly Arg Met Gly Thr Trp Ser Thr Arg
545                 550                 555

<210> SEQ ID NO 27
<211> LENGTH: 595
<212> TYPE: PRT
<213> ORGANISM: Homo sapiens

<400> SEQUENCE: 27

Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
                20                  25                  30

Pro Ser His Tyr Tyr Asp Lys Ala Val Arg Arg Cys Cys Tyr Arg Cys
            35                  40                  45

Pro Met Gly Leu Phe Pro Thr Gln Gln Cys Pro Gln Arg Pro Thr Asp
        50                  55                  60

Cys Arg Lys Gln Cys Glu Pro Asp Tyr Tyr Leu Asp Glu Ala Asp Arg
65                  70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
            100                 105                 110

Phe Cys Ser Thr Ser Ala Val Asn Ser Cys Ala Arg Cys Phe His
        115                 120                 125
```

```
Ser Val Cys Pro Ala Gly Met Ile Val Lys Phe Pro Gly Thr Ala Gln
    130                 135                 140
Lys Asn Thr Val Cys Glu Pro Ala Ser Pro Gly Val Ser Pro Ala Cys
145                 150                 155                 160
Ala Ser Pro Glu Asn Cys Lys Glu Pro Ser Ser Gly Thr Ile Pro Gln
                165                 170                 175
Ala Lys Pro Thr Pro Val Ser Pro Ala Thr Ser Ser Ala Ser Thr Met
            180                 185                 190
Pro Val Arg Gly Gly Thr Arg Leu Ala Gln Glu Ala Ala Ser Lys Leu
        195                 200                 205
Thr Arg Ala Pro Asp Ser Pro Ser Ser Val Gly Arg Pro Ser Ser Asp
210                 215                 220
Pro Gly Leu Ser Pro Thr Gln Pro Cys Pro Glu Gly Ser Gly Asp Cys
225                 230                 235                 240
Arg Lys Gln Cys Glu Pro Asp Tyr Tyr Leu Asp Glu Ala Gly Arg Cys
                245                 250                 255
Thr Ala Cys Val Ser Cys Ser Arg Asp Asp Leu Val Glu Lys Thr Pro
            260                 265                 270
Cys Ala Trp Asn Ser Ser Arg Thr Cys Glu Cys Arg Pro Gly Met Ile
        275                 280                 285
Cys Ala Thr Ser Ala Thr Asn Ser Cys Ala Arg Cys Val Pro Tyr Pro
290                 295                 300
Ile Cys Ala Ala Glu Thr Val Thr Lys Pro Gln Asp Met Ala Glu Lys
305                 310                 315                 320
Asp Thr Thr Phe Glu Ala Pro Leu Gly Thr Gln Pro Asp Cys Asn
                325                 330                 335
Pro Thr Pro Glu Asn Gly Glu Ala Pro Ala Ser Thr Ser Pro Thr Gln
            340                 345                 350
Ser Leu Leu Val Asp Ser Gln Ala Ser Lys Thr Leu Pro Ile Pro Thr
        355                 360                 365
Ser Ala Pro Val Ala Leu Ser Ser Thr Gly Lys Pro Val Leu Asp Ala
370                 375                 380
Gly Pro Val Leu Phe Trp Val Ile Leu Val Leu Val Val Val Val Gly
385                 390                 395                 400
Ser Ser Ala Phe Leu Leu Cys His Arg Arg Ala Cys Arg Lys Arg Ile
                405                 410                 415
Arg Gln Lys Leu His Leu Cys Tyr Pro Val Gln Thr Ser Gln Pro Lys
            420                 425                 430
Leu Glu Leu Val Asp Ser Arg Pro Arg Arg Ser Ser Thr Gln Leu Arg
        435                 440                 445
Ser Gly Ala Ser Val Thr Glu Pro Val Ala Glu Glu Arg Gly Leu Met
450                 455                 460
Ser Gln Pro Leu Met Glu Thr Cys His Ser Val Gly Ala Ala Tyr Leu
465                 470                 475                 480
Glu Ser Leu Pro Leu Gln Asp Ala Ser Pro Ala Gly Gly Pro Ser Ser
                485                 490                 495
Pro Arg Asp Leu Pro Glu Pro Arg Val Ser Thr Glu His Thr Asn Asn
            500                 505                 510
Lys Ile Glu Lys Ile Tyr Ile Met Lys Ala Asp Thr Val Ile Val Gly
        515                 520                 525
Thr Val Lys Ala Glu Leu Pro Glu Gly Arg Gly Leu Ala Gly Pro Ala
530                 535                 540
Glu Pro Glu Leu Glu Glu Glu Leu Glu Ala Asp His Thr Pro His Tyr
```

```
545                 550                 555                 560
Pro Glu Gln Glu Thr Glu Pro Pro Leu Gly Ser Cys Ser Asp Val Met
                565                 570                 575

Leu Ser Val Glu Glu Glu Gly Lys Glu Asp Pro Leu Pro Thr Ala Ala
                580                 585                 590

Ser Gly Lys
        595

<210> SEQ ID NO 28
<211> LENGTH: 532
<212> TYPE: PRT
<213> ORGANISM: Homo Sapiens

<400> SEQUENCE: 28

Met Pro Leu Phe Leu Ile Leu Cys Leu Leu Gln Gly Ser Ser Phe Ala
1               5                   10                  15

Leu Pro Gln Lys Arg Pro His Pro Arg Trp Leu Trp Glu Gly Ser Leu
                20                  25                  30

Pro Ser Arg Thr His Leu Arg Ala Met Gly Thr Leu Arg Pro Ser Ser
            35                  40                  45

Pro Leu Cys Trp Arg Glu Glu Ser Ser Phe Ala Ala Pro Asn Ser Leu
50                  55                  60

Lys Gly Ser Arg Leu Val Ser Gly Glu Pro Gly Gly Ala Val Thr Ile
65                  70                  75                  80

Gln Cys His Tyr Ala Pro Ser Ser Val Asn Arg His Gln Arg Lys Tyr
                85                  90                  95

Trp Cys Arg Leu Gly Pro Pro Arg Trp Ile Cys Gln Thr Ile Val Ser
                100                 105                 110

Thr Asn Gln Tyr Thr His His Arg Tyr Arg Asp Arg Val Ala Leu Thr
            115                 120                 125

Asp Phe Pro Gln Arg Gly Leu Phe Val Val Arg Leu Ser Gln Leu Ser
130                 135                 140

Pro Asp Asp Ile Gly Cys Tyr Leu Cys Gly Ile Gly Ser Glu Asn Asn
145                 150                 155                 160

Met Leu Phe Leu Ser Met Asn Leu Thr Ile Ser Ala Gly Pro Ala Ser
                165                 170                 175

Thr Leu Pro Thr Ala Thr Pro Ala Ala Gly Glu Leu Thr Met Arg Ser
            180                 185                 190

Tyr Gly Thr Ala Ser Pro Val Ala Asn Arg Trp Thr Pro Gly Thr Thr
            195                 200                 205

Gln Thr Leu Gly Gln Gly Thr Ala Trp Asp Thr Val Ala Ser Thr Pro
210                 215                 220

Gly Thr Ser Lys Thr Thr Ala Ser Ala Glu Gly Arg Arg Thr Pro Gly
225                 230                 235                 240

Ala Thr Arg Pro Ala Ala Pro Gly Thr Gly Ser Trp Ala Glu Gly Ser
                245                 250                 255

Val Lys Ala Pro Ala Pro Ile Pro Glu Ser Pro Ser Lys Ser Arg
                260                 265                 270

Ser Met Ser Asn Thr Thr Glu Gly Val Trp Glu Gly Thr Arg Ser Ser
            275                 280                 285

Val Thr Asn Arg Ala Arg Ala Ser Lys Asp Arg Arg Glu Met Thr Thr
            290                 295                 300

Thr Lys Ala Asp Arg Pro Arg Glu Asp Ile Glu Gly Val Arg Ile Ala
305                 310                 315                 320
```

```
Leu Asp Ala Ala Lys Val Leu Gly Thr Ile Gly Pro Pro Ala Leu
            325                 330                 335

Val Ser Glu Thr Leu Ala Trp Glu Ile Leu Pro Gln Ala Thr Pro Val
        340                 345                 350

Ser Lys Gln Gln Ser Gln Gly Ser Ile Gly Glu Thr Thr Pro Ala Ala
            355                 360                 365

Gly Met Trp Thr Leu Gly Thr Pro Ala Ala Asp Val Trp Ile Leu Gly
370                 375                 380

Thr Pro Ala Ala Asp Val Trp Thr Ser Met Glu Ala Ala Ser Gly Glu
385                 390                 395                 400

Gly Ser Ala Ala Gly Asp Leu Asp Ala Ala Thr Gly Asp Arg Gly Pro
                405                 410                 415

Gln Ala Thr Leu Ser Gln Thr Pro Ala Val Gly Pro Trp Gly Pro Pro
            420                 425                 430

Gly Lys Glu Ser Ser Val Lys Arg Thr Phe Pro Glu Asp Glu Ser Ser
            435                 440                 445

Ser Arg Thr Leu Ala Pro Val Ser Thr Met Leu Ala Leu Phe Met Leu
        450                 455                 460

Met Ala Leu Val Leu Leu Gln Arg Lys Leu Trp Arg Arg Thr Ser
465                 470                 475                 480

Gln Glu Ala Glu Arg Val Thr Leu Ile Gln Met Thr His Phe Leu Glu
                485                 490                 495

Val Asn Pro Gln Ala Asp Gln Leu Pro His Val Glu Arg Lys Met Leu
            500                 505                 510

Gln Asp Asp Ser Leu Pro Ala Gly Ala Ser Leu Thr Ala Pro Glu Arg
            515                 520                 525

Asn Pro Gly Pro
        530

<210> SEQ ID NO 29
<211> LENGTH: 287
<212> TYPE: PRT
<213> ORGANISM: Homo Sapiens

<400> SEQUENCE: 29

Met Asp Pro Lys Gln Thr Thr Leu Leu Cys Leu Val Leu Cys Leu Gly
1               5                   10                  15

Gln Arg Ile Gln Ala Gln Glu Gly Asp Phe Pro Met Pro Phe Ile Ser
            20                  25                  30

Ala Lys Ser Ser Pro Val Ile Pro Leu Asp Gly Ser Val Lys Ile Gln
        35                  40                  45

Cys Gln Ala Ile Arg Glu Ala Tyr Leu Thr Gln Leu Met Ile Ile Lys
    50                  55                  60

Asn Ser Thr Tyr Arg Glu Ile Gly Arg Arg Leu Lys Phe Trp Asn Glu
65                  70                  75                  80

Thr Asp Pro Glu Phe Val Ile Asp His Met Asp Ala Asn Lys Ala Gly
                85                  90                  95

Arg Tyr Gln Cys Gln Tyr Arg Ile Gly His Tyr Arg Phe Arg Tyr Ser
            100                 105                 110

Asp Thr Leu Glu Leu Val Val Thr Gly Leu Tyr Gly Lys Pro Phe Leu
        115                 120                 125

Ser Ala Asp Arg Gly Leu Val Leu Met Pro Gly Glu Asn Ile Ser Leu
    130                 135                 140

Thr Cys Ser Ser Ala His Ile Pro Phe Asp Arg Phe Ser Leu Ala Lys
145                 150                 155                 160
```

```
Glu Gly Glu Leu Ser Leu Pro Gln His Gln Ser Gly Glu His Pro Ala
                165                 170                 175

Asn Phe Ser Leu Gly Pro Val Asp Leu Asn Val Ser Gly Ile Tyr Arg
            180                 185                 190

Cys Tyr Gly Trp Tyr Asn Arg Ser Pro Tyr Leu Trp Ser Phe Pro Ser
        195                 200                 205

Asn Ala Leu Glu Leu Val Val Thr Asp Ser Ile His Gln Asp Tyr Thr
    210                 215                 220

Thr Gln Asn Leu Ile Arg Met Ala Val Ala Gly Leu Val Leu Val Ala
225                 230                 235                 240

Leu Leu Ala Ile Leu Val Glu Asn Trp His Ser His Thr Ala Leu Asn
                245                 250                 255

Lys Glu Ala Ser Ala Asp Val Ala Glu Pro Ser Trp Ser Gln Gln Met
            260                 265                 270

Cys Gln Pro Gly Leu Thr Phe Ala Arg Thr Pro Ser Val Cys Lys
        275                 280                 285
```

<210> SEQ ID NO 30
<211> LENGTH: 86
<212> TYPE: PRT
<213> ORGANISM: Homo Sapiens

<400> SEQUENCE: 30

```
Met Ile Pro Ala Val Val Leu Leu Leu Leu Leu Val Glu Gln Ala
1               5                   10                  15

Ala Ala Leu Gly Glu Pro Gln Leu Cys Tyr Ile Leu Asp Ala Ile Leu
            20                  25                  30

Phe Leu Tyr Gly Ile Val Leu Thr Leu Leu Tyr Cys Arg Leu Lys Ile
        35                  40                  45

Gln Val Arg Lys Ala Ala Ile Thr Ser Tyr Glu Lys Ser Asp Gly Val
    50                  55                  60

Tyr Thr Gly Leu Ser Thr Arg Asn Gln Glu Thr Tyr Glu Thr Leu Lys
65                  70                  75                  80

His Glu Lys Pro Pro Gln
                85
```

<210> SEQ ID NO 31
<211> LENGTH: 374
<212> TYPE: PRT
<213> ORGANISM: Homo Sapiens

<400> SEQUENCE: 31

```
Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg
            100                 105                 110
```

Val Phe Thr Glu Gly Glu Pro Leu Ala Leu Arg Cys His Ala Trp Lys
            115                 120                 125

Asp Lys Leu Val Tyr Asn Val Leu Tyr Tyr Arg Asn Gly Lys Ala Phe
    130                 135                 140

Lys Phe Phe His Trp Asn Ser Asn Leu Thr Ile Leu Lys Thr Asn Ile
145                 150                 155                 160

Ser His Asn Gly Thr Tyr His Cys Ser Gly Met Gly Lys His Arg Tyr
                165                 170                 175

Thr Ser Ala Gly Ile Ser Val Thr Val Lys Glu Leu Phe Pro Ala Pro
            180                 185                 190

Val Leu Asn Ala Ser Val Thr Ser Pro Leu Leu Glu Gly Asn Leu Val
        195                 200                 205

Thr Leu Ser Cys Glu Thr Lys Leu Leu Leu Gln Arg Pro Gly Leu Gln
    210                 215                 220

Leu Tyr Phe Ser Phe Tyr Met Gly Ser Lys Thr Leu Arg Gly Arg Asn
225                 230                 235                 240

Thr Ser Ser Glu Tyr Gln Ile Leu Thr Ala Arg Arg Glu Asp Ser Gly
                245                 250                 255

Leu Tyr Trp Cys Glu Ala Ala Thr Glu Asp Gly Asn Val Leu Lys Arg
            260                 265                 270

Ser Pro Glu Leu Glu Leu Gln Val Leu Gly Leu Gln Leu Pro Thr Pro
        275                 280                 285

Val Trp Phe His Val Leu Phe Tyr Leu Ala Val Gly Ile Met Phe Leu
    290                 295                 300

Val Asn Thr Val Leu Trp Val Thr Ile Arg Lys Glu Leu Lys Arg Lys
305                 310                 315                 320

Lys Lys Trp Asp Leu Glu Ile Ser Leu Asp Ser Gly His Glu Lys Lys
                325                 330                 335

Val Ile Ser Ser Leu Gln Glu Asp Arg His Leu Glu Glu Glu Leu Lys
            340                 345                 350

Cys Gln Glu Gln Lys Glu Glu Gln Leu Gln Glu Gly Val His Arg Lys
        355                 360                 365

Glu Pro Gln Gly Ala Thr
    370

<210> SEQ ID NO 32
<211> LENGTH: 280
<212> TYPE: PRT
<213> ORGANISM: Homo Sapiens

<400> SEQUENCE: 32

Met Trp Phe Leu Thr Thr Leu Leu Leu Trp Val Pro Val Asp Gly Gln
1               5                   10                  15

Val Asp Thr Thr Lys Ala Val Ile Thr Leu Gln Pro Pro Trp Val Ser
            20                  25                  30

Val Phe Gln Glu Glu Thr Val Thr Leu His Cys Glu Val Leu His Leu
        35                  40                  45

Pro Gly Ser Ser Ser Thr Gln Trp Phe Leu Asn Gly Thr Ala Thr Gln
    50                  55                  60

Thr Ser Thr Pro Ser Tyr Arg Ile Thr Ser Ala Ser Val Asn Asp Ser
65                  70                  75                  80

Gly Glu Tyr Arg Cys Gln Arg Gly Leu Ser Gly Arg Ser Asp Pro Ile
                85                  90                  95

Gln Leu Glu Ile His Arg Gly Trp Leu Leu Leu Gln Val Ser Ser Arg

```
                100             105             110
Val Phe Met Glu Gly Glu Pro Leu Ala Leu Arg Cys His Ala Trp Lys
            115                 120             125

Asp Lys Leu Val Tyr Asn Val Leu Tyr Tyr Arg Asn Gly Lys Ala Phe
        130                 135             140

Lys Phe Phe His Trp Asn Ser Asn Leu Thr Ile Leu Lys Thr Asn Ile
145                 150             155                 160

Ser His Asn Gly Thr Tyr His Cys Ser Gly Met Gly Lys His Arg Tyr
                165             170             175

Thr Ser Ala Gly Ile Ser Gln Tyr Thr Val Lys Gly Leu Gln Leu Pro
            180             185             190

Thr Pro Val Trp Phe His Val Leu Phe Tyr Leu Ala Val Gly Ile Met
            195             200             205

Phe Leu Val Asn Thr Val Leu Trp Val Thr Ile Arg Lys Glu Leu Lys
        210             215             220

Arg Lys Lys Lys Trp Asn Leu Glu Ile Ser Leu Asp Ser Gly His Glu
225                 230             235                 240

Lys Lys Val Ile Ser Ser Leu Gln Glu Asp Arg His Leu Glu Glu Glu
            245             250             255

Leu Lys Cys Gln Glu Gln Lys Glu Glu Gln Leu Gln Glu Gly Val His
            260             265             270

Arg Lys Glu Pro Gln Gly Ala Thr
            275             280

<210> SEQ ID NO 33
<211> LENGTH: 416
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 33

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
    130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175
```

```
Asn Glu Cys Val Ser Cys Ser Asn Cys Lys Lys Ser Leu Glu Cys Thr
            180                 185                 190

Lys Leu Cys Leu Asn Gly Gly Gly Ser Gly Gly Gly Ser Gly
        195                 200                 205

Arg Asp Asn Lys Phe Asn Lys Glu Gln Gln Asn Ala Phe Tyr Glu Ile
        210                 215                 220

Leu His Leu Pro Asn Leu Asn Glu Glu Gln Arg Asn Ala Phe Ile Gln
225                 230                 235                 240

Ser Leu Lys Asp Asp Pro Ser Gln Ser Ala Asn Leu Leu Ala Glu Ala
                245                 250                 255

Lys Lys Leu Asn Asp Ala Gln Ala Pro Lys Pro Gln Gly Thr Glu Asp
            260                 265                 270

Ser Gly Thr Thr Val Leu Leu Pro Leu Val Ile Phe Phe Gly Leu Cys
        275                 280                 285

Leu Leu Ser Leu Leu Phe Ile Gly Leu Met Tyr Arg Tyr Gln Arg Trp
        290                 295                 300

Lys Gly Thr Asn Gly Gly Gly Ser Gly Arg Gly Tyr Ile Pro Glu
305                 310                 315                 320

Ala Pro Arg Asp Gly Gln Ala Tyr Val Arg Lys Asp Gly Glu Trp Val
                325                 330                 335

Phe Leu Ser Thr Phe Leu Ser Pro Ala Asn Gly Gly Gly Ser Gly
            340                 345                 350

Arg Ser Leu Tyr Pro Ser Leu Glu Asp Leu Lys Val Asp Lys Val Ile
        355                 360                 365

Gln Ala Gln Thr Ala Phe Ser Ala Asn Pro Ala Asn Pro Ala Ile Leu
        370                 375                 380

Ser Glu Ala Ser Ala Pro Ile Pro His Asp Gly Asn Leu Tyr Pro Arg
385                 390                 395                 400

Leu Tyr Pro Glu Leu Ser Gln Tyr Met Gly Leu Ser Leu Glu Gly Gly
                405                 410                 415

<210> SEQ ID NO 34
<211> LENGTH: 836
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 34

Met Ser Ala Pro Arg Ile Trp Leu Ala Gln Ala Leu Leu Phe Phe Leu
1               5                   10                  15

Thr Thr Glu Ser Ile Gly Gln Leu Leu Glu Pro Cys Gly Tyr Ile Tyr
                20                  25                  30

Pro Glu Phe Pro Val Val Gln Arg Gly Ser Asn Phe Thr Ala Ile Cys
            35                  40                  45

Val Leu Lys Glu Ala Cys Leu Gln His Tyr Tyr Val Asn Ala Ser Tyr
        50                  55                  60

Ile Val Trp Lys Thr Asn His Ala Ala Val Pro Arg Glu Gln Val Thr
65                  70                  75                  80

Val Ile Asn Arg Thr Thr Ser Ser Val Thr Phe Thr Asp Val Val Leu
                85                  90                  95

Pro Ser Val Gln Leu Thr Cys Asn Ile Leu Ser Phe Gly Gln Ile Glu
            100                 105                 110

Gln Asn Val Tyr Gly Val Thr Met Leu Ser Gly Phe Pro Pro Asp Lys
        115                 120                 125
```

```
Pro Thr Asn Leu Thr Cys Ile Val Asn Glu Gly Lys Asn Met Leu Cys
    130                 135                 140

Gln Trp Asp Pro Gly Arg Glu Thr Tyr Leu Glu Thr Asn Tyr Thr Leu
145                 150                 155                 160

Lys Ser Glu Trp Ala Thr Glu Lys Phe Pro Asp Cys Gln Ser Lys His
                165                 170                 175

Gly Thr Ser Cys Met Val Ser Tyr Met Pro Thr Tyr Tyr Val Asn Ile
                180                 185                 190

Glu Val Trp Val Glu Ala Glu Asn Ala Leu Gly Lys Val Ser Ser Glu
            195                 200                 205

Ser Ile Asn Phe Asp Pro Val Asp Lys Val Lys Pro Thr Pro Pro Tyr
210                 215                 220

Asn Leu Ser Val Thr Asn Ser Glu Leu Ser Ser Ile Leu Lys Leu
225                 230                 235                 240

Ser Trp Val Ser Ser Gly Leu Gly Gly Leu Leu Asp Leu Lys Ser Asp
                245                 250                 255

Ile Gln Tyr Arg Thr Lys Asp Ala Ser Thr Trp Ile Gln Val Pro Leu
                260                 265                 270

Glu Asp Thr Met Ser Pro Arg Thr Ser Phe Thr Val Gln Asp Leu Lys
            275                 280                 285

Pro Phe Thr Glu Tyr Val Phe Arg Ile Arg Ser Ile Lys Asp Ser Gly
290                 295                 300

Lys Gly Tyr Trp Ser Asp Trp Ser Glu Glu Ala Ser Gly Thr Thr Tyr
305                 310                 315                 320

Glu Asp Arg Pro Ser Arg Pro Pro Ser Phe Trp Tyr Lys Thr Asn Pro
                325                 330                 335

Ser His Gly Gln Glu Tyr Arg Ser Val Arg Leu Ile Trp Lys Ala Leu
            340                 345                 350

Pro Leu Ser Glu Ala Asn Gly Lys Ile Leu Asp Tyr Glu Val Ile Leu
    355                 360                 365

Thr Gln Ser Lys Ser Val Ser Gln Thr Tyr Thr Val Thr Gly Thr Glu
    370                 375                 380

Leu Thr Val Asn Leu Thr Asn Asp Arg Tyr Val Ala Ser Leu Ala Ala
385                 390                 395                 400

Arg Asn Lys Val Gly Lys Ser Ala Ala Ala Val Leu Thr Ile Pro Ser
                405                 410                 415

Pro His Val Thr Ala Gly Ser Gly Ser Gly Ser Gly Ser Arg
                420                 425                 430

Met Lys Gln Lys Lys Leu Val Gly Glu Arg Gly Ser Gly Ser Gly Ser
            435                 440                 445

Gly Ser Gly Ser Asp Asn Lys Phe Asn Lys Glu Gln Gln Asn Ala Phe
    450                 455                 460

Tyr Glu Ile Leu His Leu Pro Asn Leu Asn Glu Glu Gln Arg Asn Ala
465                 470                 475                 480

Phe Ile Gln Ser Leu Lys Asp Asp Pro Ser Gln Ser Ala Asn Leu Leu
                485                 490                 495

Ala Glu Ala Lys Lys Leu Asn Asp Ala Gln Ala Pro Lys Ala Ala Pro
            500                 505                 510

Ala Arg Gly Pro Thr Val Arg Thr Lys Lys Val Gly Lys Asn Glu Ala
            515                 520                 525

Val Leu Ala Trp Asp Gln Ile Pro Val Asp Asp Gln Asn Gly Phe Ile
530                 535                 540
```

```
Arg Asn Tyr Ser Ile Ser Tyr Arg Thr Ser Val Gly Lys Glu Met Val
545                 550                 555                 560

Val His Val Asp Ser Ser His Thr Glu Tyr Thr Leu Ser Ser Leu Ser
                565                 570                 575

Ser Asp Thr Leu Tyr Met Val Arg Met Ala Ala Tyr Thr Asp Glu Gly
            580                 585                 590

Gly Lys Asp Gly Pro Glu Phe Thr Phe Thr Thr Pro Lys Phe Ala Gln
        595                 600                 605

Gly Glu Ile Glu Ala Ile Val Val Pro Val Cys Leu Ala Phe Leu Leu
610                 615                 620

Thr Thr Leu Leu Gly Val Leu Phe Cys Phe Asn Lys Arg Asp Leu Ile
625                 630                 635                 640

Lys Lys His Ile Trp Pro Asn Val Pro Asp Pro Ser Lys Ser His Ile
                645                 650                 655

Ala Gln Trp Ser Pro His Thr Pro Pro Arg His Asn Phe Asn Ser Lys
            660                 665                 670

Asp Gln Gly Ser Gly Ser Gly Ser Gly Ser Arg Met Lys Gln
            675                 680                 685

Leu Glu Asp Lys Val Glu Glu Leu Leu Ser Lys Asn Tyr His Leu Glu
690                 695                 700

Asn Glu Val Ala Arg Leu Lys Lys Leu Val Gly Glu Arg Gly Ser Gly
705                 710                 715                 720

Ser Gly Ser Gly Ser Gly Ser Ser Leu Tyr Pro Ser Leu Glu Asp Leu
            725                 730                 735

Lys Val Asp Lys Val Ile Gln Ala Gln Thr Ala Tyr Ser Ala Asn Pro
        740                 745                 750

Ala Ser Gln Ala Phe Val Leu Val Asp Ala Ser Ala Ala Leu Pro Pro
    755                 760                 765

Asp Gly Asn Leu Tyr Pro Lys Leu Tyr Pro Glu Leu Ser Gln Tyr Met
770                 775                 780

Gly Leu Ser Leu Asn Glu Ala Glu Ile Cys Glu Ser Met Pro Met Val
785                 790                 795                 800

Ser Gly Ala Pro Ala Gln Gly Gln Leu Val Ala Arg Pro Ser Ser Val
            805                 810                 815

Asn Tyr Met Val Ala Pro Val Thr Gly Asn Asp Ala Gly Ile Arg Arg
        820                 825                 830

Ala Glu Ile Lys
        835

<210> SEQ ID NO 35
<211> LENGTH: 359
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 35

Ala Val Glu Gly Gly Met Lys Cys Val Lys Phe Leu Leu Tyr Val Leu
1               5                   10                  15

Leu Leu Ala Phe Cys Ala Cys Ala Val Gly Leu Ile Ala Val Gly Val
            20                  25                  30

Gly Ala Gln Leu Val Leu Ser Gln Thr Gly Thr Asp Asn Lys Phe Asn
        35                  40                  45

Lys Glu Gln Gln Asn Ala Phe Tyr Glu Ile Leu His Leu Pro Asn Leu
    50                  55                  60
```

```
Asn Glu Glu Gln Arg Asn Ala Phe Ile Gln Ser Leu Lys Asp Asp Pro
 65                  70                  75                  80

Ser Gln Ser Ala Asn Leu Leu Ala Glu Ala Lys Lys Leu Asn Asp Ala
             85                  90                  95

Gln Ala Pro Lys Gly Thr Ile Ile Gln Gly Ala Thr Pro Gly Ser Leu
            100                 105                 110

Leu Pro Val Val Ile Ile Ala Val Gly Val Phe Leu Phe Leu Val Ala
            115                 120                 125

Phe Val Gly Cys Cys Gly Ala Cys Lys Glu Asn Tyr Cys Leu Met Ile
130                 135                 140

Thr Phe Ala Ile Phe Leu Ser Leu Ile Met Leu Val Glu Val Ala Ala
145                 150                 155                 160

Ala Ile Ala Gly Tyr Val Phe Arg Asp Lys Val Met Ser Glu Phe Asn
                165                 170                 175

Asn Asn Phe Arg Gln Gln Met Glu Asn Tyr Pro Lys Asn Asn His Thr
            180                 185                 190

Ala Ser Ile Leu Asp Arg Met Gln Ala Asp Phe Lys Cys Cys Gly Ala
            195                 200                 205

Gly Ser Asp Asn Lys Phe Asn Lys Glu Gln Gln Asn Ala Phe Tyr Glu
210                 215                 220

Ile Leu His Leu Pro Asn Leu Asn Glu Glu Gln Arg Asn Ala Phe Ile
225                 230                 235                 240

Gln Ser Leu Lys Asp Asp Pro Ser Gln Ser Ala Asn Leu Leu Ala Glu
                245                 250                 255

Ala Lys Lys Leu Asn Asp Ala Gln Ala Pro Lys Gly Ser Ala Asn Tyr
            260                 265                 270

Thr Asp Trp Glu Lys Ile Pro Ser Met Ser Lys Asn Arg Val Pro Asp
275                 280                 285

Ser Cys Cys Ile Asn Val Thr Val Gly Cys Gly Ile Asn Phe Asn Glu
290                 295                 300

Lys Ala Ile His Lys Glu Gly Cys Val Glu Lys Ile Gly Gly Trp Leu
305                 310                 315                 320

Arg Lys Asn Val Leu Val Ala Ala Ala Leu Gly Ile Ala Phe
                325                 330                 335

Val Glu Val Leu Gly Ile Val Phe Ala Cys Cys Leu Val Lys Ser Ile
            340                 345                 350

Arg Ser Gly Tyr Glu Val Met
            355

<210> SEQ ID NO 36
<211> LENGTH: 532
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 36

Met Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Gly Ser Gly Ser Gly Gly
```

```
            50                  55                  60
Ser Gly Ser Gly Ser Val Cys Phe Arg Leu Phe Pro Val Pro Gly Ser
 65                  70                  75                  80

Gly Leu Val Leu Val Cys Leu Val Leu Gly Ala Val Arg Ser Tyr Ala
                     85                  90                  95

Lys Ser Ser Val Gly Arg Gln Gly Ser Gly Ser Gly Ser Gly Leu Glu
                    100                 105                 110

Leu Asn Leu Thr Asp Ser Glu Asn Ala Thr Cys Leu Tyr Ala Lys Trp
                115                 120                 125

Gln Met Asn Phe Thr Val Arg Tyr Glu Thr Asn Lys Thr Tyr Lys
            130                 135                 140

Thr Val Thr Ile Ser Asp His Gly Thr Val Thr Tyr Asn Gly Ser Ile
145                 150                 155                 160

Cys Gly Asp Asp Gln Asn Gly Pro Lys Ile Ala Val Gln Phe Gly Pro
                    165                 170                 175

Gly Phe Ser Trp Ile Ala Asn Phe Thr Lys Ala Ala Ser Thr Tyr Ser
                180                 185                 190

Ile Asp Ser Val Ser Phe Ser Tyr Asn Thr Gly Asp Asn Thr Thr Phe
                195                 200                 205

Pro Asp Ala Glu Asp Lys Gly Ile Leu Thr Val Asp Glu Leu Leu Ala
210                 215                 220

Ile Arg Ile Pro Leu Asn Asp Leu Phe Arg Cys Asn Ser Leu Ser Thr
225                 230                 235                 240

Leu Glu Lys Asn Asp Val Val Gln His Tyr Trp Asp Val Leu Val Gln
                245                 250                 255

Ala Phe Val Gln Asn Gly Thr Val Ser Thr Asn Glu Phe Leu Cys Asp
                260                 265                 270

Lys Asp Lys Thr Ser Thr Val Ala Pro Thr Ile His Thr Thr Val Pro
                275                 280                 285

Ser Pro Thr Thr Thr Pro Thr Pro Lys Glu Lys Pro Glu Ala Gly Thr
                290                 295                 300

Tyr Ser Val Asn Asn Gly Asn Asp Thr Cys Leu Leu Ala Thr Met Gly
305                 310                 315                 320

Leu Gln Leu Asn Ile Thr Gln Asp Lys Val Ala Ser Val Ile Asn Ile
                    325                 330                 335

Asn Pro Asn Thr Thr His Ser Thr Gly Ser Cys Arg Ser His Thr Ala
                340                 345                 350

Leu Leu Arg Leu Asn Ser Ser Thr Ile Lys Tyr Leu Asp Phe Val Phe
                355                 360                 365

Ala Val Lys Asn Glu Asn Arg Phe Tyr Leu Lys Glu Val Asn Ile Ser
370                 375                 380

Met Tyr Leu Val Asn Gly Ser Val Phe Ser Ile Ala Asn Asn Asn Leu
385                 390                 395                 400

Ser Tyr Trp Asp Ala Pro Leu Gly Ser Ser Tyr Met Cys Asn Lys Glu
                405                 410                 415

Gln Thr Val Ser Val Ser Gly Ala Phe Gln Ile Asn Thr Phe Asp Leu
                420                 425                 430

Arg Val Gln Pro Phe Asn Val Thr Gln Gly Lys Tyr Ser Thr Ala Gln
                435                 440                 445

Asp Cys Ser Ala Asp Asp Asn Phe Leu Val Pro Ile Ala Val Gly
                450                 455                 460

Ala Ala Leu Ala Gly Val Leu Ile Leu Val Leu Leu Ala Tyr Phe Ile
465                 470                 475                 480
```

-continued

Gly Leu Lys His His His Ala Gly Tyr Glu Gln Phe Gly Ser Gly Ser
              485                 490                 495

Gly Ser Gly Ser Gly Ser Gly Ser Thr Gly Gly Ser Arg Thr Gly Ser
          500                 505                 510

Gly Ser Gly Ser Gly Ser Gly Ser Gly Ser Pro Gly His His His His
          515                 520                 525

His His His His
          530

<210> SEQ ID NO 37
<211> LENGTH: 514
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 37

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Lys Ser Ser Val
            20                  25                  30

Gly Arg Gln Asp Asn Lys Phe Asn Lys Glu Gln Gln Asn Ala Phe Tyr
        35                  40                  45

Glu Ile Leu His Leu Pro Asn Leu Asn Glu Glu Gln Arg Asn Ala Phe
50                  55                  60

Ile Gln Ser Leu Lys Asp Asp Pro Ser Gln Ser Ala Asn Leu Leu Ala
65                  70                  75                  80

Glu Ala Lys Lys Leu Asn Asp Ala Gln Ala Pro Lys Gly Gly Gly Gly
                85                  90                  95

Ser Gly Gly Gly Gly Ser Leu Glu Leu Asn Leu Thr Asp Ser Glu Asn
            100                 105                 110

Ala Thr Cys Leu Tyr Ala Lys Trp Gln Met Asn Phe Thr Val Arg Tyr
        115                 120                 125

Glu Thr Thr Asn Lys Thr Tyr Lys Thr Val Thr Ile Ser Asp His Gly
130                 135                 140

Thr Val Thr Tyr Asn Gly Ser Ile Cys Gly Asp Asp Gln Asn Gly Pro
145                 150                 155                 160

Lys Ile Ala Val Gln Phe Gly Pro Gly Phe Ser Trp Ile Ala Asn Phe
                165                 170                 175

Thr Lys Ala Ala Ser Thr Tyr Ser Ile Asp Ser Val Ser Phe Ser Tyr
            180                 185                 190

Asn Thr Gly Asp Asn Thr Thr Phe Pro Asp Ala Glu Asp Lys Gly Ile
        195                 200                 205

Leu Thr Val Asp Glu Leu Leu Ala Ile Arg Ile Pro Leu Asn Asp Leu
210                 215                 220

Phe Arg Cys Asn Ser Leu Ser Thr Leu Glu Lys Asn Asp Val Val Gln
225                 230                 235                 240

His Tyr Trp Asp Val Leu Val Gln Ala Phe Val Gln Asn Gly Thr Val
                245                 250                 255

Ser Thr Asn Glu Phe Leu Cys Asp Lys Asp Lys Thr Ser Thr Val Ala
            260                 265                 270

Pro Thr Ile His Thr Thr Val Pro Ser Pro Thr Thr Thr Pro Thr Pro
        275                 280                 285

Lys Glu Lys Pro Glu Ala Gly Thr Tyr Ser Val Asn Asn Gly Asn Asp

-continued

```
            290                 295                 300
Thr Cys Leu Leu Ala Thr Met Gly Leu Gln Leu Asn Ile Thr Gln Asp
305                 310                 315                 320

Lys Val Ala Ser Val Ile Asn Ile Asn Pro Asn Thr Thr His Ser Thr
                325                 330                 335

Gly Ser Cys Arg Ser His Thr Ala Leu Leu Arg Leu Asn Ser Ser Thr
            340                 345                 350

Ile Lys Tyr Leu Asp Phe Val Phe Ala Val Lys Asn Glu Asn Arg Phe
        355                 360                 365

Tyr Leu Lys Glu Val Asn Ile Ser Met Tyr Leu Val Asn Gly Ser Val
    370                 375                 380

Phe Ser Ile Ala Asn Asn Asn Leu Ser Tyr Trp Asp Ala Pro Leu Gly
385                 390                 395                 400

Ser Ser Tyr Met Cys Asn Lys Glu Gln Thr Val Ser Val Ser Gly Ala
                405                 410                 415

Phe Gln Ile Asn Thr Phe Asp Leu Arg Val Gln Pro Phe Asn Val Thr
            420                 425                 430

Gln Gly Lys Tyr Ser Thr Ala Gln Asp Cys Ser Ala Asp Asp Asp Asn
        435                 440                 445

Phe Leu Val Pro Ile Ala Val Gly Ala Ala Leu Ala Gly Val Leu Ile
    450                 455                 460

Leu Val Leu Leu Ala Tyr Phe Ile Gly Leu Lys His His His Ala Gly
465                 470                 475                 480

Tyr Glu Gln Phe Gly Ser Gly Ser Gly Ser Gly Ser Gly Ser Gly Ser
                485                 490                 495

Thr Gly Gly Ser Arg Thr Gly Ser Gly Ser Gly Ser Gly Ser Gly Ser
            500                 505                 510

Gly Ser
```

<210> SEQ ID NO 38
<211> LENGTH: 826
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 38

```
Met Asp Gln Ala Arg Ser Ala Phe Ser Asn Leu Phe Gly Gly Glu Pro
1               5                   10                  15

Leu Ser Tyr Thr Arg Phe Ser Leu Ala Arg Gln Val Asp Gly Asp Asn
                20                  25                  30

Ser His Val Glu Met Lys Leu Ala Val Asp Glu Glu Asn Ala Asp
            35                  40                  45

Asn Asn Thr Lys Ala Asn Val Thr Lys Pro Lys Arg Cys Ser Gly Ser
        50                  55                  60

Ile Cys Tyr Gly Thr Ile Ala Val Ile Val Phe Phe Leu Ile Gly Phe
65                  70                  75                  80

Met Ile Gly Tyr Leu Gly Tyr Cys Lys Gly Val Glu Pro Lys Thr Glu
                85                  90                  95

Cys Glu Arg Leu Ala Gly Thr Glu Ser Pro Val Arg Glu Glu Pro Gly
            100                 105                 110

Glu Asp Phe Pro Ala Ala Arg Arg Leu Tyr Trp Asp Asp Leu Lys Arg
        115                 120                 125

Lys Leu Ser Glu Lys Leu Asp Ser Thr Asp Phe Thr Gly Thr Ile Lys
```

```
            130                 135                 140
Leu Leu Asn Glu Asn Ser Tyr Val Pro Arg Glu Ala Gly Ser Gln Lys
145                 150                 155                 160

Asp Glu Asn Leu Ala Leu Tyr Val Glu Asn Gln Phe Arg Glu Phe Lys
                165                 170                 175

Leu Ser Lys Val Trp Arg Asp Gln His Phe Val Lys Ile Gln Val Lys
                180                 185                 190

Asp Ser Ala Gln Asn Ser Val Ile Ile Val Asp Lys Asn Gly Arg Leu
                195                 200                 205

Val Tyr Leu Val Glu Asn Pro Gly Gly Tyr Val Ala Tyr Ser Lys Ala
        210                 215                 220

Ala Thr Val Thr Gly Lys Leu Val His Ala Asn Phe Gly Thr Lys Lys
225                 230                 235                 240

Asp Phe Glu Asp Leu Tyr Thr Pro Val Asn Gly Ser Ile Val Ile Val
                245                 250                 255

Arg Ala Gly Lys Ile Thr Phe Ala Glu Lys Val Ala Asn Ala Glu Ser
                260                 265                 270

Leu Asn Ala Ile Gly Val Leu Ile Tyr Met Asp Gln Thr Lys Phe Pro
        275                 280                 285

Ile Val Asn Ala Glu Leu Ser Phe Phe Gly His Ala His Leu Gly Thr
        290                 295                 300

Gly Asp Pro Tyr Thr Pro Gly Phe Pro Ser Phe Asn His Thr Gln Phe
305                 310                 315                 320

Pro Pro Ser Arg Ser Ser Gly Leu Pro Asn Ile Pro Val Gln Thr Ile
                325                 330                 335

Ser Arg Ala Ala Ala Glu Lys Leu Phe Gly Asn Met Glu Gly Asp Cys
                340                 345                 350

Pro Ser Asp Trp Lys Thr Asp Ser Thr Cys Arg Met Val Thr Ser Glu
                355                 360                 365

Ser Lys Asn Val Lys Leu Thr Val Ser Asn Val Leu Lys Glu Ile Lys
        370                 375                 380

Ile Leu Asn Ile Phe Gly Val Ile Lys Gly Phe Val Glu Pro Asp His
385                 390                 395                 400

Tyr Val Val Val Gly Ala Gln Arg Asp Ala Trp Gly Pro Gly Ala Ala
                405                 410                 415

Lys Ser Gly Val Gly Thr Ala Leu Leu Leu Lys Leu Ala Gln Met Phe
                420                 425                 430

Ser Asp Met Val Leu Lys Asp Gly Phe Gln Pro Ser Arg Ser Ile Ile
                435                 440                 445

Phe Ala Ser Trp Ser Ala Gly Asp Phe Gly Ser Val Gly Ala Thr Glu
        450                 455                 460

Trp Leu Glu Gly Tyr Leu Ser Ser Leu His Leu Lys Ala Phe Thr Tyr
465                 470                 475                 480

Ile Asn Leu Asp Lys Ala Val Leu Gly Thr Ser Asn Phe Lys Val Ser
                485                 490                 495

Ala Ser Pro Leu Leu Tyr Thr Leu Ile Glu Lys Thr Met Gln Asn Val
                500                 505                 510

Lys His Pro Val Thr Gly Gln Phe Leu Tyr Gln Asp Ser Asn Trp Ala
        515                 520                 525

Ser Lys Val Glu Lys Leu Thr Leu Asp Asn Ala Ala Phe Pro Phe Leu
        530                 535                 540

Ala Tyr Ser Gly Ile Pro Ala Val Ser Phe Cys Phe Cys Glu Asp Thr
545                 550                 555                 560
```

Asp Tyr Pro Tyr Leu Gly Thr Thr Met Asp Thr Tyr Lys Glu Leu Ile
            565                 570                 575

Glu Arg Ile Pro Glu Leu Asn Lys Val Ala Arg Ala Ala Ala Glu Val
            580                 585                 590

Ala Gly Gln Phe Val Ile Lys Leu Thr His Asp Val Glu Leu Asn Leu
            595                 600                 605

Asp Tyr Glu Arg Tyr Asn Ser Gln Leu Leu Ser Phe Val Arg Asp Leu
            610                 615                 620

Asn Gln Tyr Arg Ala Asp Ile Lys Glu Met Gly Leu Ser Leu Gln Trp
625                 630                 635                 640

Leu Tyr Ser Ala Arg Gly Asp Phe Phe Arg Ala Thr Ser Arg Leu Thr
            645                 650                 655

Thr Asp Phe Gly Asn Ala Glu Lys Thr Asp Arg Phe Val Met Lys Lys
            660                 665                 670

Leu Asn Asp Arg Val Met Arg Val Glu Tyr His Phe Leu Ser Pro Tyr
            675                 680                 685

Val Ser Pro Lys Glu Ser Pro Phe Arg His Val Phe Trp Gly Ser Gly
            690                 695                 700

Ser His Thr Leu Pro Ala Leu Leu Glu Asn Leu Lys Leu Arg Lys Gln
705                 710                 715                 720

Asn Asn Gly Ala Phe Asn Glu Thr Leu Phe Arg Asn Gln Leu Ala Leu
            725                 730                 735

Ala Thr Trp Thr Ile Gln Gly Ala Ala Asn Ala Leu Ser Gly Asp Val
            740                 745                 750

Trp Asp Ile Asp Asn Glu Phe Gly Gly Gly Ser Gly Gly Gly
            755                 760                 765

Ser Asp Asn Lys Phe Asn Lys Glu Gln Gln Asn Ala Phe Tyr Glu Ile
770                 775                 780

Leu His Leu Pro Asn Leu Asn Glu Glu Gln Arg Asn Ala Phe Ile Gln
785                 790                 795                 800

Ser Leu Lys Asp Asp Pro Ser Gln Ser Ala Asn Leu Leu Ala Glu Ala
            805                 810                 815

Lys Lys Leu Asn Asp Ala Gln Ala Pro Lys
            820                 825

<210> SEQ ID NO 39
<211> LENGTH: 726
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 39

Met Ala Glu Ser His Leu Ser Leu Leu Tyr His Leu Thr Ala Val Ser
1               5                   10                  15

Ser Pro Ala Pro Gly Thr Pro Ala Phe Trp Val Ser Gly Trp Leu Gly
            20                  25                  30

Pro Gln Gln Tyr Leu Ser Tyr Asn Ser Leu Arg Gly Glu Ala Glu Pro
            35                  40                  45

Cys Gly Ala Trp Val Trp Glu Asn Gln Val Ser Trp Tyr Trp Glu Lys
        50                  55                  60

Glu Thr Thr Asp Leu Arg Ile Lys Glu Lys Leu Phe Leu Glu Ala Phe
65                  70                  75                  80

Lys Ala Leu Gly Gly Lys Gly Pro Tyr Thr Leu Gln Gly Leu Leu Gly

```
            85                  90                  95
Cys Glu Leu Gly Pro Asp Asn Thr Ser Val Pro Thr Ala Lys Phe Ala
            100                 105                 110

Leu Asn Gly Glu Glu Phe Met Asn Phe Asp Leu Lys Gln Gly Thr Trp
            115                 120                 125

Gly Gly Asp Trp Pro Glu Ala Leu Ala Ile Ser Gln Arg Trp Gln Gln
            130                 135                 140

Gln Asp Lys Ala Ala Asn Lys Glu Leu Thr Phe Leu Leu Phe Ser Cys
145                 150                 155                 160

Pro His Arg Leu Arg Glu His Leu Glu Arg Gly Arg Gly Asn Leu Glu
            165                 170                 175

Trp Lys Glu Pro Pro Ser Met Arg Leu Lys Ala Arg Pro Ser Ser Pro
            180                 185                 190

Gly Phe Ser Val Leu Thr Cys Ser Ala Phe Ser Phe Tyr Pro Pro Glu
            195                 200                 205

Leu Gln Leu Arg Phe Leu Arg Asn Gly Leu Ala Ala Gly Thr Gly Gln
            210                 215                 220

Gly Asp Phe Gly Pro Asn Ser Asp Gly Ser Phe His Ala Ser Ser Ser
225                 230                 235                 240

Leu Thr Val Lys Ser Gly Asp Glu His His Tyr Cys Gly Ser Gly Ser
            245                 250                 255

Gly Gly Ser Gly Ser Gly Ser Val Cys Phe Arg Leu Phe Pro Val Pro
            260                 265                 270

Gly Ser Gly Leu Val Leu Val Cys Leu Val Leu Gly Ala Val Arg Ser
            275                 280                 285

Tyr Ala Lys Ser Ser Val Gly Arg Gln Gly Ser Gly Ser Gly Ser Gly
            290                 295                 300

Leu Glu Leu Asn Leu Thr Asp Ser Glu Asn Ala Thr Cys Leu Tyr Ala
305                 310                 315                 320

Lys Trp Gln Met Asn Phe Thr Val Arg Tyr Glu Thr Thr Asn Lys Thr
            325                 330                 335

Tyr Lys Thr Val Thr Ile Ser Asp His Gly Thr Val Thr Tyr Asn Gly
            340                 345                 350

Ser Ile Cys Gly Asp Asp Gln Asn Gly Pro Lys Ile Ala Val Gln Phe
            355                 360                 365

Gly Pro Gly Phe Ser Trp Ile Ala Asn Phe Thr Lys Ala Ala Ser Thr
            370                 375                 380

Tyr Ser Ile Asp Ser Val Ser Phe Ser Tyr Asn Thr Gly Asp Asn Thr
385                 390                 395                 400

Thr Phe Pro Asp Ala Glu Asp Lys Gly Ile Leu Thr Val Asp Glu Leu
            405                 410                 415

Leu Ala Ile Arg Ile Pro Leu Asn Asp Leu Phe Arg Cys Asn Ser Leu
            420                 425                 430

Ser Thr Leu Glu Lys Asn Asp Val Val Gln His Tyr Trp Asp Val Leu
            435                 440                 445

Val Gln Ala Phe Val Gln Asn Gly Thr Val Ser Thr Asn Glu Phe Leu
            450                 455                 460

Cys Asp Lys Asp Lys Thr Ser Val Ala Pro Thr Ile His Thr Thr
465                 470                 475                 480

Val Pro Ser Pro Thr Thr Thr Pro Thr Pro Lys Glu Lys Pro Glu Ala
            485                 490                 495

Gly Thr Tyr Ser Val Asn Asn Gly Asn Asp Thr Cys Leu Leu Ala Thr
            500                 505                 510
```

Met Gly Leu Gln Leu Asn Ile Thr Gln Asp Lys Val Ala Ser Val Ile
            515                 520                 525

Asn Ile Asn Pro Asn Thr Thr His Ser Thr Gly Ser Cys Arg Ser His
        530                 535                 540

Thr Ala Leu Leu Arg Leu Asn Ser Ser Thr Ile Lys Tyr Leu Asp Phe
545                 550                 555                 560

Val Phe Ala Val Lys Asn Glu Asn Arg Phe Tyr Leu Lys Glu Val Asn
                565                 570                 575

Ile Ser Met Tyr Leu Val Asn Gly Ser Val Phe Ser Ile Ala Asn Asn
                580                 585                 590

Asn Leu Ser Tyr Trp Asp Ala Pro Leu Gly Ser Ser Tyr Met Cys Asn
            595                 600                 605

Lys Glu Gln Thr Val Ser Val Ser Gly Ala Phe Gln Ile Asn Thr Phe
            610                 615                 620

Asp Leu Arg Val Gln Pro Phe Asn Val Thr Gln Gly Lys Tyr Ser Thr
625                 630                 635                 640

Ala Gln Asp Cys Ser Ala Asp Asp Asn Phe Leu Val Pro Ile Ala
                645                 650                 655

Val Gly Ala Ala Leu Ala Gly Val Leu Ile Leu Val Leu Leu Ala Tyr
            660                 665                 670

Phe Ile Gly Leu Lys His His His Ala Gly Tyr Glu Gln Phe Gly Ser
            675                 680                 685

Gly Ser Gly Ser Gly Ser Gly Ser Gly Ser Thr Gly Gly Ser Arg Thr
            690                 695                 700

Gly Ser Gly Ser Gly Ser Gly Ser Gly Ser Pro Gly His His
705                 710                 715                 720

His His His His His His
                725

<210> SEQ ID NO 40
<211> LENGTH: 710
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 40

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Lys Ser Ser Val
                20                  25                  30

Gly Arg Gln Ala Glu Ser His Leu Ser Leu Leu Tyr His Leu Thr Ala
            35                  40                  45

Val Ser Ser Pro Ala Pro Gly Thr Pro Ala Phe Trp Val Ser Gly Trp
50                  55                  60

Leu Gly Pro Gln Gln Tyr Leu Ser Tyr Asn Ser Leu Arg Gly Glu Ala
65                  70                  75                  80

Glu Pro Cys Gly Ala Trp Val Trp Glu Asn Gln Val Ser Trp Tyr Trp
                85                  90                  95

Glu Lys Glu Thr Thr Asp Leu Arg Ile Lys Glu Lys Leu Phe Leu Glu
                100                 105                 110

Ala Phe Lys Ala Leu Gly Gly Lys Gly Pro Tyr Thr Leu Gln Gly Leu
            115                 120                 125

Leu Gly Cys Glu Leu Gly Pro Asp Asn Thr Ser Val Pro Thr Ala Lys

```
              130                 135                 140
Phe Ala Leu Asn Gly Glu Glu Phe Met Asn Phe Asp Leu Lys Gln Gly
145                 150                 155                 160

Thr Trp Gly Gly Asp Trp Pro Glu Ala Leu Ala Ile Ser Gln Arg Trp
                165                 170                 175

Gln Gln Gln Asp Lys Ala Ala Asn Lys Glu Leu Thr Phe Leu Leu Phe
                180                 185                 190

Ser Cys Pro His Arg Leu Arg Glu His Leu Glu Arg Gly Arg Gly Asn
                195                 200                 205

Leu Glu Trp Lys Glu Pro Pro Ser Met Arg Leu Lys Ala Arg Pro Ser
210                 215                 220

Ser Pro Gly Phe Ser Val Leu Thr Cys Ser Ala Phe Ser Phe Tyr Pro
225                 230                 235                 240

Pro Glu Leu Gln Leu Arg Phe Leu Arg Asn Gly Leu Ala Ala Gly Thr
                245                 250                 255

Gly Gln Gly Asp Phe Gly Pro Asn Ser Asp Gly Ser Phe His Ala Ser
                260                 265                 270

Ser Ser Leu Thr Val Lys Ser Gly Asp Glu His His Tyr Cys Gly Gly
                275                 280                 285

Gly Gly Ser Gly Gly Gly Ser Leu Glu Leu Asn Leu Thr Asp Ser
                290                 295                 300

Glu Asn Ala Thr Cys Leu Tyr Ala Lys Trp Gln Met Asn Phe Thr Val
305                 310                 315                 320

Arg Tyr Glu Thr Thr Asn Lys Thr Tyr Lys Thr Val Thr Ile Ser Asp
                325                 330                 335

His Gly Thr Val Thr Tyr Asn Gly Ser Ile Cys Gly Asp Asp Gln Asn
                340                 345                 350

Gly Pro Lys Ile Ala Val Gln Phe Gly Pro Gly Phe Ser Trp Ile Ala
                355                 360                 365

Asn Phe Thr Lys Ala Ala Ser Thr Tyr Ser Ile Asp Ser Val Ser Phe
                370                 375                 380

Ser Tyr Asn Thr Gly Asp Asn Thr Thr Phe Pro Asp Ala Glu Asp Lys
385                 390                 395                 400

Gly Ile Leu Thr Val Asp Glu Leu Leu Ala Ile Arg Ile Pro Leu Asn
                405                 410                 415

Asp Leu Phe Arg Cys Asn Ser Leu Ser Thr Leu Glu Lys Asn Asp Val
                420                 425                 430

Val Gln His Tyr Trp Asp Val Leu Val Gln Ala Phe Val Gln Asn Gly
                435                 440                 445

Thr Val Ser Thr Asn Glu Phe Leu Cys Asp Lys Asp Lys Thr Ser Thr
450                 455                 460

Val Ala Pro Thr Ile His Thr Thr Val Pro Ser Pro Thr Thr Thr Pro
465                 470                 475                 480

Thr Pro Lys Glu Lys Pro Glu Ala Gly Thr Tyr Ser Val Asn Asn Gly
                485                 490                 495

Asn Asp Thr Cys Leu Leu Ala Thr Met Gly Leu Gln Leu Asn Ile Thr
                500                 505                 510

Gln Asp Lys Val Ala Ser Val Ile Asn Ile Asn Pro Asn Thr Thr His
                515                 520                 525

Ser Thr Gly Ser Cys Arg Ser His Thr Ala Leu Leu Arg Leu Asn Ser
                530                 535                 540

Ser Thr Ile Lys Tyr Leu Asp Phe Val Phe Ala Val Lys Asn Glu Asn
545                 550                 555                 560
```

-continued

```
Arg Phe Tyr Leu Lys Glu Val Asn Ile Ser Met Tyr Leu Val Asn Gly
                565                 570                 575

Ser Val Phe Ser Ile Ala Asn Asn Asn Leu Ser Tyr Trp Asp Ala Pro
            580                 585                 590

Leu Gly Ser Ser Tyr Met Cys Asn Lys Glu Gln Thr Val Ser Val Ser
        595                 600                 605

Gly Ala Phe Gln Ile Asn Thr Phe Asp Leu Arg Val Gln Pro Phe Asn
    610                 615                 620

Val Thr Gln Gly Lys Tyr Ser Thr Ala Gln Asp Cys Ser Ala Asp Asp
625                 630                 635                 640

Asp Asn Phe Leu Val Pro Ile Ala Val Gly Ala Ala Leu Ala Gly Val
                645                 650                 655

Leu Ile Leu Val Leu Leu Ala Tyr Phe Ile Gly Leu Lys His His His
                660                 665                 670

Ala Gly Tyr Glu Gln Phe Gly Ser Gly Ser Gly Ser Gly Ser Gly Ser
            675                 680                 685

Gly Ser Thr Gly Gly Ser Arg Thr Gly Ser Gly Ser Gly Ser Gly Ser
        690                 695                 700

Gly Ser Gly Ser Pro Gly
705                 710

<210> SEQ ID NO 41
<211> LENGTH: 1020
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 41

Met Asp Gln Ala Arg Ser Ala Phe Ser Asn Leu Phe Gly Gly Glu Pro
1               5                   10                  15

Leu Ser Tyr Thr Arg Phe Ser Leu Ala Arg Gln Val Asp Gly Asp Asn
            20                  25                  30

Ser His Val Glu Met Lys Leu Ala Val Asp Glu Glu Asn Ala Asp
        35                  40                  45

Asn Asn Thr Lys Ala Asn Val Thr Lys Pro Lys Arg Cys Ser Gly Ser
50                  55                  60

Ile Cys Tyr Gly Thr Ile Ala Val Ile Val Phe Phe Leu Ile Gly Phe
65                  70                  75                  80

Met Ile Gly Tyr Leu Gly Tyr Cys Lys Gly Val Glu Pro Lys Thr Glu
                85                  90                  95

Cys Glu Arg Leu Ala Gly Thr Glu Ser Pro Val Arg Glu Glu Pro Gly
            100                 105                 110

Glu Asp Phe Pro Ala Ala Arg Arg Leu Tyr Trp Asp Asp Leu Lys Arg
        115                 120                 125

Lys Leu Ser Glu Lys Leu Asp Ser Thr Asp Phe Thr Gly Thr Ile Lys
    130                 135                 140

Leu Leu Asn Glu Asn Ser Tyr Val Pro Arg Glu Ala Gly Ser Gln Lys
145                 150                 155                 160

Asp Glu Asn Leu Ala Leu Tyr Val Glu Asn Gln Phe Arg Glu Phe Lys
                165                 170                 175

Leu Ser Lys Val Trp Arg Asp Gln His Phe Val Lys Ile Gln Val Lys
            180                 185                 190

Asp Ser Ala Gln Asn Ser Val Ile Ile Val Asp Lys Asn Gly Arg Leu
```

-continued

```
            195                 200                 205
Val Tyr Leu Val Glu Pro Gly Gly Tyr Val Ala Tyr Ser Lys Ala
210                     215                 220

Ala Thr Val Thr Gly Lys Leu Val His Ala Asn Phe Gly Thr Lys Lys
225                     230                 235                 240

Asp Phe Glu Asp Leu Tyr Thr Pro Val Asn Gly Ser Ile Val Ile Val
                245                 250                 255

Arg Ala Gly Lys Ile Thr Phe Ala Glu Lys Val Ala Asn Ala Glu Ser
                260                 265                 270

Leu Asn Ala Ile Gly Val Leu Ile Tyr Met Asp Gln Thr Lys Phe Pro
            275                 280                 285

Ile Val Asn Ala Glu Leu Ser Phe Phe Gly His Ala His Leu Gly Thr
290                 295                 300

Gly Asp Pro Tyr Thr Pro Gly Phe Pro Ser Phe Asn His Thr Gln Phe
305                 310                 315                 320

Pro Pro Ser Arg Ser Ser Gly Leu Pro Asn Ile Pro Val Gln Thr Ile
                325                 330                 335

Ser Arg Ala Ala Ala Glu Lys Leu Phe Gly Asn Met Glu Gly Asp Cys
                340                 345                 350

Pro Ser Asp Trp Lys Thr Asp Ser Thr Cys Arg Met Val Thr Ser Glu
                355                 360                 365

Ser Lys Asn Val Lys Leu Thr Val Ser Asn Val Leu Lys Glu Ile Lys
370                 375                 380

Ile Leu Asn Ile Phe Gly Val Ile Lys Gly Phe Val Glu Pro Asp His
385                 390                 395                 400

Tyr Val Val Gly Ala Gln Arg Asp Ala Trp Gly Pro Gly Ala Ala
                405                 410                 415

Lys Ser Gly Val Gly Thr Ala Leu Leu Leu Lys Leu Ala Gln Met Phe
                420                 425                 430

Ser Asp Met Val Leu Lys Asp Gly Phe Gln Pro Ser Arg Ser Ile Ile
                435                 440                 445

Phe Ala Ser Trp Ser Ala Gly Asp Phe Gly Ser Val Gly Ala Thr Glu
450                 455                 460

Trp Leu Glu Gly Tyr Leu Ser Ser Leu His Leu Lys Ala Phe Thr Tyr
465                 470                 475                 480

Ile Asn Leu Asp Lys Ala Val Leu Gly Thr Ser Asn Phe Lys Val Ser
                485                 490                 495

Ala Ser Pro Leu Leu Tyr Thr Leu Ile Glu Lys Thr Met Gln Asn Val
                500                 505                 510

Lys His Pro Val Thr Gly Gln Phe Leu Tyr Gln Asp Ser Asn Trp Ala
            515                 520                 525

Ser Lys Val Glu Lys Leu Thr Leu Asp Asn Ala Ala Phe Pro Phe Leu
            530                 535                 540

Ala Tyr Ser Gly Ile Pro Ala Val Ser Phe Cys Phe Cys Glu Asp Thr
545                 550                 555                 560

Asp Tyr Pro Tyr Leu Gly Thr Thr Met Asp Thr Tyr Lys Glu Leu Ile
                565                 570                 575

Glu Arg Ile Pro Glu Leu Asn Lys Val Ala Arg Ala Ala Ala Glu Val
                580                 585                 590

Ala Gly Gln Phe Val Ile Lys Leu Thr His Asp Val Glu Leu Asn Leu
            595                 600                 605

Asp Tyr Glu Arg Tyr Asn Ser Gln Leu Leu Ser Phe Val Arg Asp Leu
610                 615                 620
```

```
Asn Gln Tyr Arg Ala Asp Ile Lys Glu Met Gly Leu Ser Leu Gln Trp
625                 630                 635                 640

Leu Tyr Ser Ala Arg Gly Asp Phe Phe Arg Ala Thr Ser Arg Leu Thr
            645                 650                 655

Thr Asp Phe Gly Asn Ala Glu Lys Thr Asp Arg Phe Val Met Lys Lys
        660                 665                 670

Leu Asn Asp Arg Val Met Arg Val Glu Tyr His Phe Leu Ser Pro Tyr
    675                 680                 685

Val Ser Pro Lys Glu Ser Pro Phe Arg His Val Phe Trp Gly Ser Gly
690                 695                 700

Ser His Thr Leu Pro Ala Leu Leu Glu Asn Leu Lys Leu Arg Lys Gln
705                 710                 715                 720

Asn Asn Gly Ala Phe Asn Glu Thr Leu Phe Arg Asn Gln Leu Ala Leu
            725                 730                 735

Ala Thr Trp Thr Ile Gln Gly Ala Ala Asn Ala Leu Ser Gly Asp Val
        740                 745                 750

Trp Asp Ile Asp Asn Glu Phe Gly Gly Gly Ser Gly Gly Gly Gly
    755                 760                 765

Ser Ala Glu Ser His Leu Ser Leu Leu Tyr His Leu Thr Ala Val Ser
770                 775                 780

Ser Pro Ala Pro Gly Thr Pro Ala Phe Trp Val Ser Gly Trp Leu Gly
785                 790                 795                 800

Pro Gln Gln Tyr Leu Ser Tyr Asn Ser Leu Arg Gly Glu Ala Glu Pro
            805                 810                 815

Cys Gly Ala Trp Val Trp Glu Asn Gln Val Ser Trp Tyr Trp Glu Lys
        820                 825                 830

Glu Thr Thr Asp Leu Arg Ile Lys Glu Lys Leu Phe Leu Glu Ala Phe
    835                 840                 845

Lys Ala Leu Gly Gly Lys Gly Pro Tyr Thr Leu Gln Gly Leu Leu Gly
850                 855                 860

Cys Glu Leu Gly Pro Asp Asn Thr Ser Val Pro Thr Ala Lys Phe Ala
865                 870                 875                 880

Leu Asn Gly Glu Glu Phe Met Asn Phe Asp Leu Lys Gln Gly Thr Trp
            885                 890                 895

Gly Gly Asp Trp Pro Glu Ala Leu Ala Ile Ser Gln Arg Trp Gln Gln
        900                 905                 910

Gln Asp Lys Ala Ala Asn Lys Glu Leu Thr Phe Leu Leu Phe Ser Cys
    915                 920                 925

Pro His Arg Leu Arg Glu His Leu Glu Arg Gly Arg Gly Asn Leu Glu
930                 935                 940

Trp Lys Glu Pro Pro Ser Met Arg Leu Lys Ala Arg Pro Ser Ser Pro
945                 950                 955                 960

Gly Phe Ser Val Leu Thr Cys Ser Ala Phe Ser Phe Tyr Pro Pro Glu
            965                 970                 975

Leu Gln Leu Arg Phe Leu Arg Asn Gly Leu Ala Ala Gly Thr Gly Gln
        980                 985                 990

Gly Asp Phe Gly Pro Asn Ser Asp  Gly Ser Phe His Ala  Ser Ser Ser
    995                 1000                1005

Leu Thr  Val Lys Ser Gly Asp  Glu His His Tyr Cys
    1010                1015                1020

<210> SEQ ID NO 42
<211> LENGTH: 610
```

<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 42

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Asn Gly Gly Gly Ser Gly Gly Gly Ser Gly
        195                 200                 205

Arg Ala Glu Ser His Leu Ser Leu Leu Tyr His Leu Thr Ala Val Ser
210                 215                 220

Ser Pro Ala Pro Gly Thr Pro Ala Phe Trp Val Ser Gly Trp Leu Gly
225                 230                 235                 240

Pro Gln Gln Tyr Leu Ser Tyr Asn Ser Leu Arg Gly Glu Ala Glu Pro
                245                 250                 255

Cys Gly Ala Trp Val Trp Glu Asn Gln Val Ser Trp Tyr Trp Glu Lys
            260                 265                 270

Glu Thr Thr Asp Leu Arg Ile Lys Glu Lys Leu Phe Leu Glu Ala Phe
        275                 280                 285

Lys Ala Leu Gly Gly Lys Gly Pro Tyr Thr Leu Gln Gly Leu Leu Gly
290                 295                 300

Cys Glu Leu Gly Pro Asp Asn Thr Ser Val Pro Thr Ala Lys Phe Ala
305                 310                 315                 320

Leu Asn Gly Glu Glu Phe Met Asn Phe Asp Leu Lys Gln Gly Thr Trp
                325                 330                 335

Gly Gly Asp Trp Pro Glu Ala Leu Ala Ile Ser Gln Arg Trp Gln Gln
            340                 345                 350

Gln Asp Lys Ala Ala Asn Lys Glu Leu Thr Phe Leu Leu Phe Ser Cys
        355                 360                 365

Pro His Arg Leu Arg Glu His Leu Glu Arg Gly Arg Gly Asn Leu Glu
370                 375                 380

```
Trp Lys Glu Pro Pro Ser Met Arg Leu Lys Ala Arg Pro Ser Ser Pro
385                 390                 395                 400

Gly Phe Ser Val Leu Thr Cys Ser Ala Phe Ser Phe Tyr Pro Pro Glu
            405                 410                 415

Leu Gln Leu Arg Phe Leu Arg Asn Gly Leu Ala Ala Gly Thr Gly Gln
        420                 425                 430

Gly Asp Phe Gly Pro Asn Ser Asp Gly Ser Phe His Ala Ser Ser Ser
    435                 440                 445

Leu Thr Val Lys Ser Gly Asp Glu His His Tyr Cys Pro Gln Gly Thr
450                 455                 460

Glu Asp Ser Gly Thr Thr Val Leu Leu Pro Leu Val Ile Phe Phe Gly
465                 470                 475                 480

Leu Cys Leu Leu Ser Leu Leu Phe Ile Gly Leu Met Tyr Arg Tyr Gln
                485                 490                 495

Arg Trp Lys Gly Thr Asn Gly Gly Gly Ser Gly Arg Gly Tyr Ile
                500                 505                 510

Pro Glu Ala Pro Arg Asp Gly Gln Ala Tyr Val Arg Lys Asp Gly Glu
            515                 520                 525

Trp Val Phe Leu Ser Thr Phe Leu Ser Pro Ala Asn Gly Gly Gly Gly
        530                 535                 540

Ser Gly Arg Ser Leu Tyr Pro Ser Leu Glu Asp Leu Lys Val Asp Lys
545                 550                 555                 560

Val Ile Gln Ala Gln Thr Ala Phe Ser Ala Asn Pro Ala Asn Pro Ala
                565                 570                 575

Ile Leu Ser Glu Ala Ser Ala Pro Ile Pro His Asp Gly Asn Leu Tyr
                580                 585                 590

Pro Arg Leu Tyr Pro Glu Leu Ser Gln Tyr Met Gly Leu Ser Leu Glu
        595                 600                 605

Gly Gly
    610
```

<210> SEQ ID NO 43
<211> LENGTH: 1030
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 43

```
Met Ser Ala Pro Arg Ile Trp Leu Ala Gln Ala Leu Leu Phe Phe Leu
1               5                   10                  15

Thr Thr Glu Ser Ile Gly Gln Leu Leu Glu Pro Cys Gly Tyr Ile Tyr
            20                  25                  30

Pro Glu Phe Pro Val Val Gln Arg Gly Ser Asn Phe Thr Ala Ile Cys
        35                  40                  45

Val Leu Lys Glu Ala Cys Leu Gln His Tyr Tyr Val Asn Ala Ser Tyr
    50                  55                  60

Ile Val Trp Lys Thr Asn His Ala Ala Val Pro Arg Glu Gln Val Thr
65                  70                  75                  80

Val Ile Asn Arg Thr Thr Ser Ser Val Thr Phe Thr Asp Val Val Leu
                85                  90                  95

Pro Ser Val Gln Leu Thr Cys Asn Ile Leu Ser Phe Gly Gln Ile Glu
            100                 105                 110

Gln Asn Val Tyr Gly Val Thr Met Leu Ser Gly Phe Pro Pro Asp Lys
```

```
            115                 120                 125
Pro Thr Asn Leu Thr Cys Ile Val Asn Glu Gly Lys Asn Met Leu Cys
130                 135                 140

Gln Trp Asp Pro Gly Arg Glu Thr Tyr Leu Glu Thr Asn Tyr Thr Leu
145                 150                 155                 160

Lys Ser Glu Trp Ala Thr Glu Lys Phe Pro Asp Cys Gln Ser Lys His
                165                 170                 175

Gly Thr Ser Cys Met Val Ser Tyr Met Pro Thr Tyr Tyr Val Asn Ile
            180                 185                 190

Glu Val Trp Val Glu Ala Glu Asn Ala Leu Gly Lys Val Ser Ser Glu
        195                 200                 205

Ser Ile Asn Phe Asp Pro Val Asp Lys Val Lys Pro Thr Pro Pro Tyr
    210                 215                 220

Asn Leu Ser Val Thr Asn Ser Glu Glu Leu Ser Ser Ile Leu Lys Leu
225                 230                 235                 240

Ser Trp Val Ser Ser Gly Leu Gly Gly Leu Leu Asp Leu Lys Ser Asp
                245                 250                 255

Ile Gln Tyr Arg Thr Lys Asp Ala Ser Thr Trp Ile Gln Val Pro Leu
            260                 265                 270

Glu Asp Thr Met Ser Pro Arg Thr Ser Phe Thr Val Gln Asp Leu Lys
        275                 280                 285

Pro Phe Thr Glu Tyr Val Phe Arg Ile Arg Ser Ile Lys Asp Ser Gly
    290                 295                 300

Lys Gly Tyr Trp Ser Asp Trp Ser Glu Ala Ser Gly Thr Thr Tyr
305                 310                 315                 320

Glu Asp Arg Pro Ser Arg Pro Pro Ser Phe Trp Tyr Lys Thr Asn Pro
                325                 330                 335

Ser His Gly Gln Glu Tyr Arg Ser Val Arg Leu Ile Trp Lys Ala Leu
            340                 345                 350

Pro Leu Ser Glu Ala Asn Gly Lys Ile Leu Asp Tyr Glu Val Ile Leu
        355                 360                 365

Thr Gln Ser Lys Ser Val Ser Gln Thr Tyr Thr Val Thr Gly Thr Glu
    370                 375                 380

Leu Thr Val Asn Leu Thr Asn Asp Arg Tyr Val Ala Ser Leu Ala Ala
385                 390                 395                 400

Arg Asn Lys Val Gly Lys Ser Ala Ala Val Leu Thr Ile Pro Ser
                405                 410                 415

Pro His Val Thr Ala Gly Ser Gly Ser Gly Ser Gly Ser Arg
            420                 425                 430

Met Lys Gln Lys Lys Leu Val Gly Glu Arg Gly Ser Gly Ser Gly Ser
        435                 440                 445

Gly Ser Gly Ser Ala Glu Ser His Leu Ser Leu Tyr His Leu Thr
    450                 455                 460

Ala Val Ser Ser Pro Ala Pro Gly Thr Pro Ala Phe Trp Val Ser Gly
465                 470                 475                 480

Trp Leu Gly Pro Gln Gln Tyr Leu Ser Tyr Asn Ser Leu Arg Gly Glu
                485                 490                 495

Ala Glu Pro Cys Gly Ala Trp Val Trp Glu Asn Gln Val Ser Trp Tyr
            500                 505                 510

Trp Glu Lys Glu Thr Thr Asp Leu Arg Ile Lys Glu Lys Leu Phe Leu
        515                 520                 525

Glu Ala Phe Lys Ala Leu Gly Gly Lys Gly Pro Tyr Thr Leu Gln Gly
    530                 535                 540
```

```
Leu Leu Gly Cys Glu Leu Gly Pro Asp Asn Thr Ser Val Pro Thr Ala
545                 550                 555                 560

Lys Phe Ala Leu Asn Gly Glu Glu Phe Met Asn Phe Asp Leu Lys Gln
                565                 570                 575

Gly Thr Trp Gly Gly Asp Trp Pro Glu Ala Leu Ala Ile Ser Gln Arg
            580                 585                 590

Trp Gln Gln Asp Lys Ala Ala Asn Lys Glu Leu Thr Phe Leu Leu
        595                 600                 605

Phe Ser Cys Pro His Arg Leu Arg Glu His Leu Glu Arg Gly Arg Gly
    610                 615                 620

Asn Leu Glu Trp Lys Glu Pro Pro Ser Met Arg Leu Lys Ala Arg Pro
625                 630                 635                 640

Ser Ser Pro Gly Phe Ser Val Leu Thr Cys Ser Ala Phe Ser Phe Tyr
                645                 650                 655

Pro Pro Glu Leu Gln Leu Arg Phe Leu Arg Asn Gly Leu Ala Ala Gly
            660                 665                 670

Thr Gly Gln Gly Asp Phe Gly Pro Asn Ser Asp Gly Ser Phe His Ala
        675                 680                 685

Ser Ser Ser Leu Thr Val Lys Ser Gly Asp Glu His His Tyr Cys Ala
690                 695                 700

Ala Pro Ala Arg Gly Pro Thr Val Arg Thr Lys Lys Val Gly Lys Asn
705                 710                 715                 720

Glu Ala Val Leu Ala Trp Asp Gln Ile Pro Val Asp Gln Asn Gly
                725                 730                 735

Phe Ile Arg Asn Tyr Ser Ile Ser Tyr Arg Thr Ser Val Gly Lys Glu
            740                 745                 750

Met Val Val His Val Asp Ser Ser His Thr Glu Tyr Thr Leu Ser Ser
        755                 760                 765

Leu Ser Ser Asp Thr Leu Tyr Met Val Arg Met Ala Ala Tyr Thr Asp
770                 775                 780

Glu Gly Gly Lys Asp Gly Pro Glu Phe Thr Phe Thr Thr Pro Lys Phe
785                 790                 795                 800

Ala Gln Gly Glu Ile Glu Ala Ile Val Val Pro Val Cys Leu Ala Phe
                805                 810                 815

Leu Leu Thr Thr Leu Leu Gly Val Leu Phe Cys Phe Asn Lys Arg Asp
            820                 825                 830

Leu Ile Lys Lys His Ile Trp Pro Asn Val Pro Asp Pro Ser Lys Ser
        835                 840                 845

His Ile Ala Gln Trp Ser Pro His Thr Pro Pro Arg His Asn Phe Asn
850                 855                 860

Ser Lys Asp Gln Gly Ser Gly Ser Gly Ser Gly Ser Arg Met
865                 870                 875                 880

Lys Gln Leu Glu Asp Lys Val Glu Glu Leu Leu Ser Lys Asn Tyr His
                885                 890                 895

Leu Glu Asn Glu Val Ala Arg Leu Lys Lys Leu Val Gly Glu Arg Gly
            900                 905                 910

Ser Gly Ser Gly Ser Gly Ser Gly Ser Ser Leu Tyr Pro Ser Leu Glu
        915                 920                 925

Asp Leu Lys Val Asp Lys Val Ile Gln Ala Gln Thr Ala Tyr Ser Ala
930                 935                 940

Asn Pro Ala Ser Gln Ala Phe Val Leu Val Asp Ala Ser Ala Ala Leu
945                 950                 955                 960
```

-continued

```
Pro Pro Asp Gly Asn Leu Tyr Pro Lys Leu Tyr Pro Glu Leu Ser Gln
            965                 970                 975

Tyr Met Gly Leu Ser Leu Asn Glu Ala Glu Ile Cys Gly Ser Met Pro
        980                 985                 990

Met Val Ser Gly Ala Pro Ala Gln Gly Gln Leu Val Ala Arg Pro Ser
        995                 1000                1005

Ser Val Asn Tyr Met Val Ala Pro Val Thr Gly Asn Asp Ala Gly
        1010                1015                1020

Ile Arg Arg Ala Glu Ile Lys
        1025                1030

<210> SEQ ID NO 44
<211> LENGTH: 747
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 44

Ala Val Glu Gly Gly Met Lys Cys Val Lys Phe Leu Leu Tyr Val Leu
1               5                   10                  15

Leu Leu Ala Phe Cys Ala Cys Ala Val Gly Leu Ile Ala Val Gly Val
            20                  25                  30

Gly Ala Gln Leu Val Leu Ser Gln Thr Gly Thr Ala Glu Ser His Leu
        35                  40                  45

Ser Leu Leu Tyr His Leu Thr Ala Val Ser Ser Pro Ala Pro Gly Thr
    50                  55                  60

Pro Ala Phe Trp Val Ser Gly Trp Leu Gly Pro Gln Gln Tyr Leu Ser
65                  70                  75                  80

Tyr Asn Ser Leu Arg Gly Glu Ala Glu Pro Cys Gly Ala Trp Val Trp
                85                  90                  95

Glu Asn Gln Val Ser Trp Tyr Trp Glu Lys Glu Thr Thr Asp Leu Arg
            100                 105                 110

Ile Lys Glu Lys Leu Phe Leu Glu Ala Phe Lys Ala Leu Gly Gly Lys
        115                 120                 125

Gly Pro Tyr Thr Leu Gln Gly Leu Leu Gly Cys Glu Leu Gly Pro Asp
    130                 135                 140

Asn Thr Ser Val Pro Thr Ala Lys Phe Ala Leu Asn Gly Glu Glu Phe
145                 150                 155                 160

Met Asn Phe Asp Leu Lys Gln Gly Thr Trp Gly Gly Asp Trp Pro Glu
                165                 170                 175

Ala Leu Ala Ile Ser Gln Arg Trp Gln Gln Gln Asp Lys Ala Ala Asn
            180                 185                 190

Lys Glu Leu Thr Phe Leu Leu Phe Ser Cys Pro His Arg Leu Arg Glu
        195                 200                 205

His Leu Glu Arg Gly Arg Gly Asn Leu Glu Trp Lys Glu Pro Pro Ser
    210                 215                 220

Met Arg Leu Lys Ala Arg Pro Ser Ser Pro Gly Phe Ser Val Leu Thr
225                 230                 235                 240

Cys Ser Ala Phe Ser Phe Tyr Pro Pro Glu Leu Gln Leu Arg Phe Leu
                245                 250                 255

Arg Asn Gly Leu Ala Ala Gly Thr Gly Gln Gly Asp Phe Gly Pro Asn
            260                 265                 270

Ser Asp Gly Ser Phe His Ala Ser Ser Ser Leu Thr Val Lys Ser Gly
        275                 280                 285
```

```
Asp Glu His His Tyr Cys Gly Thr Ile Ile Gln Gly Ala Thr Pro Gly
    290             295                 300

Ser Leu Leu Pro Val Val Ile Ile Ala Val Gly Val Phe Leu Phe Leu
305             310                 315                     320

Val Ala Phe Val Gly Cys Cys Gly Ala Cys Lys Glu Asn Tyr Cys Leu
                325             330                     335

Met Ile Thr Phe Ala Ile Phe Leu Ser Leu Ile Met Leu Val Glu Val
            340             345                 350

Ala Ala Ala Ile Ala Gly Tyr Val Phe Arg Asp Lys Val Met Ser Glu
        355             360             365

Phe Asn Asn Asn Phe Arg Gln Gln Met Glu Asn Tyr Pro Lys Asn Asn
    370             375                 380

His Thr Ala Ser Ile Leu Asp Arg Met Gln Ala Asp Phe Lys Cys Cys
385             390             395                     400

Gly Ala Gly Ser Ala Glu Ser His Leu Ser Leu Leu Tyr His Leu Thr
                405             410                 415

Ala Val Ser Ser Pro Ala Pro Gly Thr Pro Ala Phe Trp Val Ser Gly
            420             425

Trp Leu Gly Pro Gln Gln Tyr Leu Ser Tyr Asn Ser Leu Arg Gly Glu
        435             440                 445

Ala Glu Pro Cys Gly Ala Trp Val Trp Glu Asn Gln Val Ser Trp Tyr
    450             455                 460

Trp Glu Lys Glu Thr Thr Asp Leu Arg Ile Lys Glu Lys Leu Phe Leu
465             470                 475                     480

Glu Ala Phe Lys Ala Leu Gly Gly Lys Gly Pro Tyr Thr Leu Gln Gly
                485             490                     495

Leu Leu Gly Cys Glu Leu Gly Pro Asp Asn Thr Ser Val Pro Thr Ala
            500             505                 510

Lys Phe Ala Leu Asn Gly Glu Glu Phe Met Asn Phe Asp Leu Lys Gln
        515             520                 525

Gly Thr Trp Gly Gly Asp Trp Pro Glu Ala Leu Ala Ile Ser Gln Arg
    530             535                 540

Trp Gln Gln Gln Asp Lys Ala Ala Asn Lys Glu Leu Thr Phe Leu Leu
545             550                 555                     560

Phe Ser Cys Pro His Arg Leu Arg Glu His Leu Glu Arg Gly Arg Gly
                565             570                     575

Asn Leu Glu Trp Lys Glu Pro Pro Ser Met Arg Leu Lys Ala Arg Pro
            580             585                 590

Ser Ser Pro Gly Phe Ser Val Leu Thr Cys Ser Ala Phe Ser Phe Tyr
        595             600                 605

Pro Pro Glu Leu Gln Leu Arg Phe Leu Arg Asn Gly Leu Ala Ala Gly
    610             615                 620

Thr Gly Gln Gly Asp Phe Gly Pro Asn Ser Asp Gly Ser Phe His Ala
625             630                 635                     640

Ser Ser Ser Leu Thr Val Lys Ser Gly Asp Glu His His Tyr Cys Gly
                645             650                     655

Ser Ala Asn Tyr Thr Asp Trp Glu Lys Ile Pro Ser Met Ser Lys Asn
            660             665                 670

Arg Val Pro Asp Ser Cys Cys Ile Asn Val Thr Val Gly Cys Gly Ile
        675             680                 685

Asn Phe Asn Glu Lys Ala Ile His Lys Glu Gly Cys Val Glu Lys Ile
    690             695                 700
```

```
Gly Gly Trp Leu Arg Lys Asn Val Leu Val Ala Ala Ala Ala Leu
705                 710                 715                 720

Gly Ile Ala Phe Val Glu Val Leu Gly Ile Val Phe Ala Cys Cys Leu
                725                 730                 735

Val Lys Ser Ile Arg Ser Gly Tyr Glu Val Met
            740                 745

<210> SEQ ID NO 45
<211> LENGTH: 610
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 45

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
                20                  25                  30

His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Asn Gly Gly Gly Ser Gly Gly Gly Ser Gly
        195                 200                 205

Arg Gln Val Asp Thr Thr Lys Ala Val Ile Thr Leu Gln Pro Pro Trp
210                 215                 220

Val Ser Val Phe Gln Glu Thr Val Thr Leu His Cys Glu Val Leu
225                 230                 235                 240

His Leu Pro Gly Ser Ser Ser Thr Gln Trp Phe Leu Asn Gly Thr Ala
            245                 250                 255

Thr Gln Thr Ser Thr Pro Ser Tyr Arg Ile Thr Ser Ala Ser Val Asn
                260                 265                 270

Asp Ser Gly Glu Tyr Arg Cys Gln Arg Gly Leu Ser Gly Arg Ser Asp
            275                 280                 285

Pro Ile Gln Leu Glu Ile His Arg Gly Trp Leu Leu Leu Gln Val Ser
        290                 295                 300

Ser Arg Val Phe Thr Glu Gly Glu Pro Leu Ala Leu Arg Cys His Ala
305                 310                 315                 320
```

```
Trp Lys Asp Lys Leu Val Tyr Asn Val Leu Tyr Tyr Arg Asn Gly Lys
            325                 330                 335

Ala Phe Lys Phe Phe His Trp Asn Ser Asn Leu Thr Ile Leu Lys Thr
            340                 345                 350

Asn Ile Ser His Asn Gly Thr Tyr His Cys Ser Gly Met Gly Lys His
            355                 360                 365

Arg Tyr Thr Ser Ala Gly Ile Ser Val Thr Val Lys Glu Leu Phe Pro
            370                 375                 380

Ala Pro Val Leu Asn Ala Ser Val Thr Ser Pro Leu Leu Glu Gly Asn
385                 390                 395                 400

Leu Val Thr Leu Ser Cys Glu Thr Lys Leu Leu Leu Gln Arg Pro Gly
            405                 410                 415

Leu Gln Leu Tyr Phe Ser Phe Tyr Met Gly Ser Lys Thr Leu Arg Gly
            420                 425                 430

Arg Asn Thr Ser Ser Glu Tyr Gln Ile Leu Thr Ala Arg Arg Glu Asp
            435                 440                 445

Ser Gly Leu Tyr Trp Cys Glu Ala Ala Thr Glu Asp Pro Gln Gly Thr
            450                 455                 460

Glu Asp Ser Gly Thr Thr Val Leu Leu Pro Leu Val Ile Phe Phe Gly
465                 470                 475                 480

Leu Cys Leu Leu Ser Leu Leu Phe Ile Gly Leu Met Tyr Arg Tyr Gln
            485                 490                 495

Arg Trp Lys Gly Thr Asn Gly Gly Gly Ser Gly Arg Gly Tyr Ile
            500                 505                 510

Pro Glu Ala Pro Arg Asp Gly Gln Ala Tyr Val Arg Lys Asp Gly Glu
            515                 520                 525

Trp Val Phe Leu Ser Thr Phe Leu Ser Pro Ala Asn Gly Gly Gly Gly
            530                 535                 540

Ser Gly Arg Ser Leu Tyr Pro Ser Leu Glu Asp Leu Lys Val Asp Lys
545                 550                 555                 560

Val Ile Gln Ala Gln Thr Ala Phe Ser Ala Asn Pro Ala Asn Pro Ala
            565                 570                 575

Ile Leu Ser Glu Ala Ser Ala Pro Ile Pro His Asp Gly Asn Leu Tyr
            580                 585                 590

Pro Arg Leu Tyr Pro Glu Leu Ser Gln Tyr Met Gly Leu Ser Leu Glu
            595                 600                 605

Gly Gly
    610

<210> SEQ ID NO 46
<211> LENGTH: 1030
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 46

Met Ser Ala Pro Arg Ile Trp Leu Ala Gln Ala Leu Leu Phe Phe Leu
1               5                   10                  15

Thr Thr Glu Ser Ile Gly Gln Leu Leu Glu Pro Cys Gly Tyr Ile Tyr
            20                  25                  30

Pro Glu Phe Pro Val Val Gln Arg Gly Ser Asn Phe Thr Ala Ile Cys
            35                  40                  45

Val Leu Lys Glu Ala Cys Leu Gln His Tyr Tyr Val Asn Ala Ser Tyr
```

```
            50                  55                  60
Ile Val Trp Lys Thr Asn His Ala Ala Val Pro Arg Glu Gln Val Thr
 65                  70                  75                  80

Val Ile Asn Arg Thr Thr Ser Ser Val Thr Phe Thr Asp Val Val Leu
                     85                  90                  95

Pro Ser Val Gln Leu Thr Cys Asn Ile Leu Ser Phe Gly Gln Ile Glu
                100                 105                 110

Gln Asn Val Tyr Gly Val Thr Met Leu Ser Gly Phe Pro Pro Asp Lys
            115                 120                 125

Pro Thr Asn Leu Thr Cys Ile Val Asn Glu Gly Lys Asn Met Leu Cys
130                 135                 140

Gln Trp Asp Pro Gly Arg Glu Thr Tyr Leu Glu Thr Asn Tyr Thr Leu
145                 150                 155                 160

Lys Ser Glu Trp Ala Thr Glu Lys Phe Pro Asp Cys Gln Ser Lys His
                165                 170                 175

Gly Thr Ser Cys Met Val Ser Tyr Met Pro Thr Tyr Tyr Val Asn Ile
            180                 185                 190

Glu Val Trp Val Glu Ala Glu Asn Ala Leu Gly Lys Val Ser Ser Glu
            195                 200                 205

Ser Ile Asn Phe Asp Pro Val Asp Lys Val Lys Pro Thr Pro Pro Tyr
210                 215                 220

Asn Leu Ser Val Thr Asn Ser Glu Glu Leu Ser Ser Ile Leu Lys Leu
225                 230                 235                 240

Ser Trp Val Ser Ser Gly Leu Gly Gly Leu Leu Asp Leu Lys Ser Asp
                245                 250                 255

Ile Gln Tyr Arg Thr Lys Asp Ala Ser Thr Trp Ile Gln Val Pro Leu
            260                 265                 270

Glu Asp Thr Met Ser Pro Arg Thr Ser Phe Thr Val Gln Asp Leu Lys
            275                 280                 285

Pro Phe Thr Glu Tyr Val Phe Arg Ile Arg Ser Ile Lys Asp Ser Gly
290                 295                 300

Lys Gly Tyr Trp Ser Asp Trp Ser Glu Glu Ala Ser Gly Thr Thr Tyr
305                 310                 315                 320

Glu Asp Arg Pro Ser Arg Pro Pro Ser Phe Trp Tyr Lys Thr Asn Pro
                325                 330                 335

Ser His Gly Gln Glu Tyr Arg Ser Val Arg Leu Ile Trp Lys Ala Leu
            340                 345                 350

Pro Leu Ser Glu Ala Asn Gly Lys Ile Leu Asp Tyr Glu Val Ile Leu
            355                 360                 365

Thr Gln Ser Lys Ser Val Ser Gln Thr Tyr Thr Val Thr Gly Thr Glu
370                 375                 380

Leu Thr Val Asn Leu Thr Asn Asp Arg Tyr Val Ala Ser Leu Ala Ala
385                 390                 395                 400

Arg Asn Lys Val Gly Lys Ser Ala Ala Val Leu Thr Ile Pro Ser
                405                 410                 415

Pro His Val Thr Ala Gly Ser Gly Ser Gly Ser Gly Ser Gly Ser Arg
                420                 425                 430

Met Lys Gln Lys Lys Leu Val Gly Glu Arg Gly Ser Gly Ser Gly Ser
            435                 440                 445

Gly Ser Gly Ser Gln Val Asp Thr Lys Ala Val Ile Thr Leu Gln
            450                 455                 460

Pro Pro Trp Val Ser Val Phe Gln Glu Glu Thr Val Thr Leu His Cys
465                 470                 475                 480
```

-continued

```
Glu Val Leu His Leu Pro Gly Ser Ser Thr Gln Trp Phe Leu Asn
            485                 490                 495
Gly Thr Ala Thr Gln Thr Ser Thr Pro Ser Tyr Arg Ile Thr Ser Ala
            500                 505                 510
Ser Val Asn Asp Ser Gly Glu Tyr Arg Cys Gln Arg Gly Leu Ser Gly
            515                 520                 525
Arg Ser Asp Pro Ile Gln Leu Glu Ile His Arg Gly Trp Leu Leu Leu
            530                 535                 540
Gln Val Ser Ser Arg Val Phe Thr Glu Gly Glu Pro Leu Ala Leu Arg
545                 550                 555                 560
Cys His Ala Trp Lys Asp Lys Leu Val Tyr Asn Val Leu Tyr Tyr Arg
                565                 570                 575
Asn Gly Lys Ala Phe Lys Phe Phe His Trp Asn Ser Asn Leu Thr Ile
                580                 585                 590
Leu Lys Thr Asn Ile Ser His Asn Gly Thr Tyr His Cys Ser Gly Met
                595                 600                 605
Gly Lys His Arg Tyr Thr Ser Ala Gly Ile Ser Val Thr Val Lys Glu
            610                 615                 620
Leu Phe Pro Ala Pro Val Leu Asn Ala Ser Val Thr Ser Pro Leu Leu
625                 630                 635                 640
Glu Gly Asn Leu Val Thr Leu Ser Cys Glu Thr Lys Leu Leu Leu Gln
                645                 650                 655
Arg Pro Gly Leu Gln Leu Tyr Phe Ser Phe Tyr Met Gly Ser Lys Thr
                660                 665                 670
Leu Arg Gly Arg Asn Thr Ser Ser Glu Tyr Gln Ile Leu Thr Ala Arg
            675                 680                 685
Arg Glu Asp Ser Gly Leu Tyr Trp Cys Glu Ala Ala Thr Glu Asp Ala
            690                 695                 700
Ala Pro Ala Arg Gly Pro Thr Val Arg Thr Lys Lys Val Gly Lys Asn
705                 710                 715                 720
Glu Ala Val Leu Ala Trp Asp Gln Ile Pro Val Asp Gln Asn Gly
                725                 730                 735
Phe Ile Arg Asn Tyr Ser Ile Ser Tyr Arg Thr Ser Val Gly Lys Glu
                740                 745                 750
Met Val Val His Val Asp Ser Ser His Thr Glu Tyr Thr Leu Ser Ser
                755                 760                 765
Leu Ser Ser Asp Thr Leu Tyr Met Val Arg Met Ala Ala Tyr Thr Asp
            770                 775                 780
Glu Gly Gly Lys Asp Gly Pro Glu Phe Thr Phe Thr Thr Pro Lys Phe
785                 790                 795                 800
Ala Gln Gly Glu Ile Glu Ala Ile Val Val Pro Val Cys Leu Ala Phe
                805                 810                 815
Leu Leu Thr Thr Leu Leu Gly Val Leu Phe Cys Phe Asn Lys Arg Asp
                820                 825                 830
Leu Ile Lys Lys His Ile Trp Pro Asn Val Pro Asp Pro Ser Lys Ser
            835                 840                 845
His Ile Ala Gln Trp Ser Pro His Thr Pro Pro Arg His Asn Phe Asn
            850                 855                 860
Ser Lys Asp Gln Gly Ser Gly Ser Gly Ser Gly Ser Gly Ser Arg Met
865                 870                 875                 880
Lys Gln Leu Glu Asp Lys Val Glu Glu Leu Leu Ser Lys Asn Tyr His
                885                 890                 895
```

```
Leu Glu Asn Glu Val Ala Arg Leu Lys Lys Leu Val Gly Glu Arg Gly
            900                 905                 910

Ser Gly Ser Gly Ser Gly Ser Gly Ser Ser Leu Tyr Pro Ser Leu Glu
        915                 920                 925

Asp Leu Lys Val Asp Lys Val Ile Gln Ala Gln Thr Ala Tyr Ser Ala
        930                 935                 940

Asn Pro Ala Ser Gln Ala Phe Val Leu Val Asp Ala Ser Ala Ala Leu
945                 950                 955                 960

Pro Pro Asp Gly Asn Leu Tyr Pro Lys Leu Tyr Pro Glu Leu Ser Gln
                965                 970                 975

Tyr Met Gly Leu Ser Leu Asn Glu Ala Glu Ile Cys Glu Ser Met Pro
        980                 985                 990

Met Val Ser Gly Ala Pro Ala Gln Gly Gln Leu Val Ala Arg Pro Ser
        995                1000                1005

Ser Val Asn Tyr Met Val Ala Pro Val Thr Gly Asn Asp Ala Gly
       1010                1015                1020

Ile Arg Arg Ala Glu Ile Lys
       1025                1030

<210> SEQ ID NO 47
<211> LENGTH: 747
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 47

Ala Val Glu Gly Gly Met Lys Cys Val Lys Phe Leu Leu Tyr Val Leu
1               5                  10                  15

Leu Leu Ala Phe Cys Ala Cys Ala Val Gly Leu Ile Ala Val Gly Val
                20                  25                  30

Gly Ala Gln Leu Val Leu Ser Gln Thr Gly Thr Gln Val Asp Thr Thr
            35                  40                  45

Lys Ala Val Ile Thr Leu Gln Pro Pro Trp Val Ser Val Phe Gln Glu
        50                  55                  60

Glu Thr Val Thr Leu His Cys Glu Val Leu His Leu Pro Gly Ser Ser
65                  70                  75                  80

Ser Thr Gln Trp Phe Leu Asn Gly Thr Ala Thr Gln Thr Ser Thr Pro
                85                  90                  95

Ser Tyr Arg Ile Thr Ser Ala Ser Val Asn Asp Ser Gly Glu Tyr Arg
            100                 105                 110

Cys Gln Arg Gly Leu Ser Gly Arg Ser Asp Pro Ile Gln Leu Glu Ile
        115                 120                 125

His Arg Gly Trp Leu Leu Leu Gln Val Ser Ser Arg Val Phe Thr Glu
    130                 135                 140

Gly Glu Pro Leu Ala Leu Arg Cys His Ala Trp Lys Asp Lys Leu Val
145                 150                 155                 160

Tyr Asn Val Leu Tyr Tyr Arg Asn Gly Lys Ala Phe Lys Phe Phe His
                165                 170                 175

Trp Asn Ser Asn Leu Thr Ile Leu Lys Thr Asn Ile Ser His Asn Gly
            180                 185                 190

Thr Tyr His Cys Ser Gly Met Gly Lys His Arg Tyr Thr Ser Ala Gly
        195                 200                 205

Ile Ser Val Thr Val Lys Glu Leu Phe Pro Ala Pro Val Leu Asn Ala
    210                 215                 220
```

```
Ser Val Thr Ser Pro Leu Leu Glu Gly Asn Leu Val Thr Leu Ser Cys
225                 230                 235                 240

Glu Thr Lys Leu Leu Leu Gln Arg Pro Gly Leu Gln Leu Tyr Phe Ser
            245                 250                 255

Phe Tyr Met Gly Ser Lys Thr Leu Arg Gly Arg Asn Thr Ser Ser Glu
        260                 265                 270

Tyr Gln Ile Leu Thr Ala Arg Arg Glu Asp Ser Gly Leu Tyr Trp Cys
        275                 280                 285

Glu Ala Ala Thr Glu Asp Gly Thr Ile Ile Gln Gly Ala Thr Pro Gly
290                 295                 300

Ser Leu Leu Pro Val Val Ile Ala Val Gly Val Phe Leu Phe Leu
305                 310                 315                 320

Val Ala Phe Val Gly Cys Cys Gly Ala Cys Lys Glu Asn Tyr Cys Leu
            325                 330                 335

Met Ile Thr Phe Ala Ile Phe Leu Ser Leu Ile Met Leu Val Glu Val
            340                 345                 350

Ala Ala Ala Ile Ala Gly Tyr Val Phe Arg Asp Lys Val Met Ser Glu
            355                 360                 365

Phe Asn Asn Phe Arg Gln Gln Met Glu Asn Tyr Pro Lys Asn Asn
370                 375                 380

His Thr Ala Ser Ile Leu Asp Arg Met Gln Ala Asp Phe Lys Cys Cys
385                 390                 395                 400

Gly Ala Gly Ser Gln Val Asp Thr Thr Lys Ala Val Ile Thr Leu Gln
                405                 410                 415

Pro Pro Trp Val Ser Val Phe Gln Glu Thr Val Thr Leu His Cys
                420                 425                 430

Glu Val Leu His Leu Pro Gly Ser Ser Ser Thr Gln Trp Phe Leu Asn
            435                 440                 445

Gly Thr Ala Thr Gln Thr Ser Thr Pro Ser Tyr Arg Ile Thr Ser Ala
450                 455                 460

Ser Val Asn Asp Ser Gly Glu Tyr Arg Cys Gln Arg Gly Leu Ser Gly
465                 470                 475                 480

Arg Ser Asp Pro Ile Gln Leu Glu Ile His Arg Gly Trp Leu Leu Leu
                485                 490                 495

Gln Val Ser Ser Arg Val Phe Thr Glu Gly Glu Pro Leu Ala Leu Arg
            500                 505                 510

Cys His Ala Trp Lys Asp Lys Leu Val Tyr Asn Val Leu Tyr Tyr Arg
            515                 520                 525

Asn Gly Lys Ala Phe Lys Phe Phe His Trp Asn Ser Asn Leu Thr Ile
            530                 535                 540

Leu Lys Thr Asn Ile Ser His Asn Gly Thr Tyr His Cys Ser Gly Met
545                 550                 555                 560

Gly Lys His Arg Tyr Thr Ser Ala Gly Ile Ser Val Thr Val Lys Glu
            565                 570                 575

Leu Phe Pro Ala Pro Val Leu Asn Ala Ser Val Thr Ser Pro Leu Leu
                580                 585                 590

Glu Gly Asn Leu Val Thr Leu Ser Cys Glu Thr Lys Leu Leu Leu Gln
            595                 600                 605

Arg Pro Gly Leu Gln Leu Tyr Phe Ser Phe Tyr Met Gly Ser Lys Thr
            610                 615                 620

Leu Arg Gly Arg Asn Thr Ser Ser Glu Tyr Gln Ile Leu Thr Ala Arg
625                 630                 635                 640
```

```
Arg Glu Asp Ser Gly Leu Tyr Trp Cys Glu Ala Ala Thr Glu Asp Gly
                645                 650                 655

Ser Ala Asn Tyr Thr Asp Trp Glu Lys Ile Pro Ser Met Ser Lys Asn
            660                 665                 670

Arg Val Pro Asp Ser Cys Cys Ile Asn Val Thr Val Gly Cys Gly Ile
        675                 680                 685

Asn Phe Asn Glu Lys Ala Ile His Lys Glu Gly Cys Val Glu Lys Ile
    690                 695                 700

Gly Gly Trp Leu Arg Lys Asn Val Leu Val Ala Ala Ala Ala Ala Leu
705                 710                 715                 720

Gly Ile Ala Phe Val Glu Val Leu Gly Ile Val Phe Ala Cys Cys Leu
                725                 730                 735

Val Lys Ser Ile Arg Ser Gly Tyr Glu Val Met
                740                 745

<210> SEQ ID NO 48
<211> LENGTH: 726
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 48

Met Gln Val Asp Thr Thr Lys Ala Val Ile Thr Leu Gln Pro Pro Trp
1               5                   10                  15

Val Ser Val Phe Gln Glu Glu Thr Val Thr Leu His Cys Glu Val Leu
                20                  25                  30

His Leu Pro Gly Ser Ser Ser Thr Gln Trp Phe Leu Asn Gly Thr Ala
            35                  40                  45

Thr Gln Thr Ser Thr Pro Ser Tyr Arg Ile Thr Ser Ala Ser Val Asn
        50                  55                  60

Asp Ser Gly Glu Tyr Arg Cys Gln Arg Gly Leu Ser Gly Arg Ser Asp
65                  70                  75                  80

Pro Ile Gln Leu Glu Ile His Arg Gly Trp Leu Leu Leu Gln Val Ser
                85                  90                  95

Ser Arg Val Phe Thr Glu Gly Glu Pro Leu Ala Leu Arg Cys His Ala
                100                 105                 110

Trp Lys Asp Lys Leu Val Tyr Asn Val Leu Tyr Tyr Arg Asn Gly Lys
            115                 120                 125

Ala Phe Lys Phe Phe His Trp Asn Ser Asn Leu Thr Ile Leu Lys Thr
        130                 135                 140

Asn Ile Ser His Asn Gly Thr Tyr His Cys Ser Gly Met Gly Lys His
145                 150                 155                 160

Arg Tyr Thr Ser Ala Gly Ile Ser Val Thr Val Lys Glu Leu Phe Pro
                165                 170                 175

Ala Pro Val Leu Asn Ala Ser Val Thr Ser Pro Leu Leu Glu Gly Asn
            180                 185                 190

Leu Val Thr Leu Ser Cys Glu Thr Lys Leu Leu Leu Gln Arg Pro Gly
        195                 200                 205

Leu Gln Leu Tyr Phe Ser Phe Tyr Met Gly Ser Lys Thr Leu Arg Gly
    210                 215                 220

Arg Asn Thr Ser Ser Glu Tyr Gln Ile Leu Thr Ala Arg Arg Glu Asp
225                 230                 235                 240

Ser Gly Leu Tyr Trp Cys Glu Ala Ala Thr Glu Asp Gly Ser Gly Ser
                245                 250                 255
```

-continued

```
Gly Gly Ser Gly Ser Gly Ser Val Cys Phe Arg Leu Phe Pro Val Pro
            260                 265                 270
Gly Ser Gly Leu Val Leu Val Cys Leu Val Leu Gly Ala Val Arg Ser
            275                 280                 285
Tyr Ala Lys Ser Ser Val Gly Arg Gln Gly Ser Gly Ser Gly Ser Gly
            290                 295                 300
Leu Glu Leu Asn Leu Thr Asp Ser Glu Asn Ala Thr Cys Leu Tyr Ala
305                 310                 315                 320
Lys Trp Gln Met Asn Phe Thr Val Arg Tyr Glu Thr Asn Lys Thr
                    325                 330                 335
Tyr Lys Thr Val Thr Ile Ser Asp His Gly Thr Val Thr Tyr Asn Gly
            340                 345                 350
Ser Ile Cys Gly Asp Asp Gln Asn Gly Pro Lys Ile Ala Val Gln Phe
            355                 360                 365
Gly Pro Gly Phe Ser Trp Ile Ala Asn Phe Thr Lys Ala Ala Ser Thr
            370                 375                 380
Tyr Ser Ile Asp Ser Val Ser Phe Ser Tyr Asn Thr Gly Asp Asn Thr
385                 390                 395                 400
Thr Phe Pro Asp Ala Glu Asp Lys Gly Ile Leu Thr Val Asp Glu Leu
                    405                 410                 415
Leu Ala Ile Arg Ile Pro Leu Asn Asp Leu Phe Arg Cys Asn Ser Leu
                    420                 425                 430
Ser Thr Leu Glu Lys Asn Asp Val Val Gln His Tyr Trp Asp Val Leu
            435                 440                 445
Val Gln Ala Phe Val Gln Asn Gly Thr Val Ser Thr Asn Glu Phe Leu
            450                 455                 460
Cys Asp Lys Asp Lys Thr Ser Thr Val Ala Pro Thr Ile His Thr Thr
465                 470                 475                 480
Val Pro Ser Pro Thr Thr Thr Pro Thr Pro Lys Glu Lys Pro Glu Ala
                    485                 490                 495
Gly Thr Tyr Ser Val Asn Asn Gly Asn Asp Thr Cys Leu Leu Ala Thr
            500                 505                 510
Met Gly Leu Gln Leu Asn Ile Thr Gln Asp Lys Val Ala Ser Val Ile
            515                 520                 525
Asn Ile Asn Pro Asn Thr Thr His Ser Thr Gly Ser Cys Arg Ser His
            530                 535                 540
Thr Ala Leu Leu Arg Leu Asn Ser Ser Thr Ile Lys Tyr Leu Asp Phe
545                 550                 555                 560
Val Phe Ala Val Lys Asn Glu Asn Arg Phe Tyr Leu Lys Glu Val Asn
                    565                 570                 575
Ile Ser Met Tyr Leu Val Asn Gly Ser Val Phe Ser Ile Ala Asn Asn
            580                 585                 590
Asn Leu Ser Tyr Trp Asp Ala Pro Leu Gly Ser Ser Tyr Met Cys Asn
            595                 600                 605
Lys Glu Gln Thr Val Ser Val Ser Gly Ala Phe Gln Ile Asn Thr Phe
            610                 615                 620
Asp Leu Arg Val Gln Pro Phe Asn Val Thr Gln Gly Lys Tyr Ser Thr
625                 630                 635                 640
Ala Gln Asp Cys Ser Ala Asp Asp Asn Phe Leu Val Pro Ile Ala
                    645                 650                 655
Val Gly Ala Ala Leu Ala Gly Val Leu Ile Leu Val Leu Leu Ala Tyr
            660                 665                 670
```

```
Phe Ile Gly Leu Lys His His His Ala Gly Tyr Glu Gln Phe Gly Ser
            675                 680                 685

Gly Ser Gly Ser Gly Ser Gly Ser Thr Gly Gly Ser Arg Thr
    690                 695                 700

Gly Ser Gly Ser Gly Ser Gly Ser Gly Ser Pro Gly His His
705                 710                 715                 720

His His His His His His
            725

<210> SEQ ID NO 49
<211> LENGTH: 710
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 49

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Lys Ser Ser Val
            20                  25                  30

Gly Arg Gln Gln Val Asp Thr Thr Lys Ala Val Ile Thr Leu Gln Pro
        35                  40                  45

Pro Trp Val Ser Val Phe Gln Glu Glu Thr Val Thr Leu His Cys Glu
    50                  55                  60

Val Leu His Leu Pro Gly Ser Ser Ser Thr Gln Trp Phe Leu Asn Gly
65                  70                  75                  80

Thr Ala Thr Gln Thr Ser Thr Pro Ser Tyr Arg Ile Thr Ser Ala Ser
                85                  90                  95

Val Asn Asp Ser Gly Glu Tyr Arg Cys Gln Arg Gly Leu Ser Gly Arg
            100                 105                 110

Ser Asp Pro Ile Gln Leu Glu Ile His Arg Gly Trp Leu Leu Leu Gln
        115                 120                 125

Val Ser Ser Arg Val Phe Thr Glu Gly Glu Pro Leu Ala Leu Arg Cys
    130                 135                 140

His Ala Trp Lys Asp Lys Leu Val Tyr Asn Val Leu Tyr Tyr Arg Asn
145                 150                 155                 160

Gly Lys Ala Phe Lys Phe Phe His Trp Asn Ser Asn Leu Thr Ile Leu
                165                 170                 175

Lys Thr Asn Ile Ser His Asn Gly Thr Tyr His Cys Ser Gly Met Gly
            180                 185                 190

Lys His Arg Tyr Thr Ser Ala Gly Ile Ser Val Thr Val Lys Glu Leu
        195                 200                 205

Phe Pro Ala Pro Val Leu Asn Ala Ser Val Thr Ser Pro Leu Leu Glu
    210                 215                 220

Gly Asn Leu Val Thr Leu Ser Cys Glu Thr Lys Leu Leu Leu Gln Arg
225                 230                 235                 240

Pro Gly Leu Gln Leu Tyr Phe Ser Phe Tyr Met Gly Ser Lys Thr Leu
                245                 250                 255

Arg Gly Arg Asn Thr Ser Ser Glu Tyr Gln Ile Leu Thr Ala Arg Arg
            260                 265                 270

Glu Asp Ser Gly Leu Tyr Trp Cys Glu Ala Ala Thr Glu Asp Gly Gly
        275                 280                 285

Gly Gly Ser Gly Gly Gly Gly Ser Leu Glu Leu Asn Leu Thr Asp Ser
    290                 295                 300
```

```
Glu Asn Ala Thr Cys Leu Tyr Ala Lys Trp Gln Met Asn Phe Thr Val
305                 310                 315                 320

Arg Tyr Glu Thr Thr Asn Lys Thr Tyr Lys Thr Val Thr Ile Ser Asp
                325                 330                 335

His Gly Thr Val Thr Tyr Asn Gly Ser Ile Cys Gly Asp Asp Gln Asn
            340                 345                 350

Gly Pro Lys Ile Ala Val Gln Phe Gly Pro Gly Phe Ser Trp Ile Ala
            355                 360                 365

Asn Phe Thr Lys Ala Ala Ser Thr Tyr Ser Ile Asp Ser Val Ser Phe
        370                 375                 380

Ser Tyr Asn Thr Gly Asp Asn Thr Thr Phe Pro Asp Ala Glu Asp Lys
385                 390                 395                 400

Gly Ile Leu Thr Val Asp Glu Leu Leu Ala Ile Arg Ile Pro Leu Asn
                405                 410                 415

Asp Leu Phe Arg Cys Asn Ser Leu Ser Thr Leu Glu Lys Asn Asp Val
            420                 425                 430

Val Gln His Tyr Trp Asp Val Leu Val Gln Ala Phe Val Gln Asn Gly
        435                 440                 445

Thr Val Ser Thr Asn Glu Phe Leu Cys Asp Lys Asp Lys Thr Ser Thr
    450                 455                 460

Val Ala Pro Thr Ile His Thr Thr Val Pro Ser Pro Thr Thr Thr Pro
465                 470                 475                 480

Thr Pro Lys Glu Lys Pro Glu Ala Gly Thr Tyr Ser Val Asn Asn Gly
                485                 490                 495

Asn Asp Thr Cys Leu Leu Ala Thr Met Gly Leu Gln Leu Asn Ile Thr
            500                 505                 510

Gln Asp Lys Val Ala Ser Val Ile Asn Ile Asn Pro Asn Thr Thr His
        515                 520                 525

Ser Thr Gly Ser Cys Arg Ser His Thr Ala Leu Leu Arg Leu Asn Ser
    530                 535                 540

Ser Thr Ile Lys Tyr Leu Asp Phe Val Phe Ala Val Lys Asn Glu Asn
545                 550                 555                 560

Arg Phe Tyr Leu Lys Glu Val Asn Ile Ser Met Tyr Leu Val Asn Gly
                565                 570                 575

Ser Val Phe Ser Ile Ala Asn Asn Asn Leu Ser Tyr Trp Asp Ala Pro
            580                 585                 590

Leu Gly Ser Ser Tyr Met Cys Asn Lys Glu Gln Thr Val Ser Val Ser
        595                 600                 605

Gly Ala Phe Gln Ile Asn Thr Phe Asp Leu Arg Val Gln Pro Phe Asn
    610                 615                 620

Val Thr Gln Gly Lys Tyr Ser Thr Ala Gln Asp Cys Ser Ala Asp Asp
625                 630                 635                 640

Asp Asn Phe Leu Val Pro Ile Ala Val Gly Ala Ala Leu Ala Gly Val
                645                 650                 655

Leu Ile Leu Val Leu Leu Ala Tyr Phe Ile Gly Leu Lys His His His
            660                 665                 670

Ala Gly Tyr Glu Gln Phe Gly Ser Gly Ser Gly Ser Gly Ser Gly Ser
        675                 680                 685

Gly Ser Thr Gly Gly Ser Arg Thr Gly Ser Gly Ser Gly Ser Gly Ser
    690                 695                 700

Gly Ser Gly Ser Pro Gly
705                 710
```

```
<210> SEQ ID NO 50
<211> LENGTH: 1020
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 50

Met Asp Gln Ala Arg Ser Ala Phe Ser Asn Leu Phe Gly Gly Glu Pro
1               5                   10                  15

Leu Ser Tyr Thr Arg Phe Ser Leu Ala Arg Gln Val Asp Gly Asp Asn
            20                  25                  30

Ser His Val Glu Met Lys Leu Ala Val Asp Glu Glu Asn Ala Asp
        35                  40                  45

Asn Asn Thr Lys Ala Asn Val Thr Lys Pro Lys Arg Cys Ser Gly Ser
50                  55                  60

Ile Cys Tyr Gly Thr Ile Ala Val Ile Val Phe Phe Leu Ile Gly Phe
65                  70                  75                  80

Met Ile Gly Tyr Leu Gly Tyr Cys Lys Gly Val Glu Pro Lys Thr Glu
            85                  90                  95

Cys Glu Arg Leu Ala Gly Thr Glu Ser Pro Val Arg Glu Glu Pro Gly
            100                 105                 110

Glu Asp Phe Pro Ala Ala Arg Arg Leu Tyr Trp Asp Asp Leu Lys Arg
            115                 120                 125

Lys Leu Ser Glu Lys Leu Asp Ser Thr Asp Phe Thr Gly Thr Ile Lys
        130                 135                 140

Leu Leu Asn Glu Asn Ser Tyr Val Pro Arg Glu Ala Gly Ser Gln Lys
145                 150                 155                 160

Asp Glu Asn Leu Ala Leu Tyr Val Glu Asn Gln Phe Arg Glu Phe Lys
                165                 170                 175

Leu Ser Lys Val Trp Arg Asp Gln His Phe Val Lys Ile Gln Val Lys
            180                 185                 190

Asp Ser Ala Gln Asn Ser Val Ile Ile Val Asp Lys Asn Gly Arg Leu
            195                 200                 205

Val Tyr Leu Val Glu Asn Pro Gly Gly Tyr Val Ala Tyr Ser Lys Ala
            210                 215                 220

Ala Thr Val Thr Gly Lys Leu Val His Ala Asn Phe Gly Thr Lys Lys
225                 230                 235                 240

Asp Phe Glu Asp Leu Tyr Thr Pro Val Asn Gly Ser Ile Val Ile Val
                245                 250                 255

Arg Ala Gly Lys Ile Thr Phe Ala Glu Lys Val Ala Asn Ala Glu Ser
            260                 265                 270

Leu Asn Ala Ile Gly Val Leu Ile Tyr Met Asp Gln Thr Lys Phe Pro
            275                 280                 285

Ile Val Asn Ala Glu Leu Ser Phe Phe Gly His Ala His Leu Gly Thr
            290                 295                 300

Gly Asp Pro Tyr Thr Pro Gly Phe Pro Ser Phe Asn His Thr Gln Phe
305                 310                 315                 320

Pro Pro Ser Arg Ser Ser Gly Leu Pro Asn Ile Pro Val Gln Thr Ile
                325                 330                 335

Ser Arg Ala Ala Ala Glu Lys Leu Phe Gly Asn Met Glu Gly Asp Cys
            340                 345                 350

Pro Ser Asp Trp Lys Thr Asp Ser Thr Cys Arg Met Val Thr Ser Glu
            355                 360                 365
```

```
Ser Lys Asn Val Lys Leu Thr Val Ser Asn Val Leu Lys Glu Ile Lys
    370                 375                 380

Ile Leu Asn Ile Phe Gly Val Ile Lys Gly Phe Val Glu Pro Asp His
385                 390                 395                 400

Tyr Val Val Gly Ala Gln Arg Asp Ala Trp Gly Pro Gly Ala Ala
                405                 410                 415

Lys Ser Gly Val Gly Thr Ala Leu Leu Lys Leu Ala Gln Met Phe
                420                 425                 430

Ser Asp Met Val Leu Lys Asp Gly Phe Gln Pro Ser Arg Ser Ile Ile
            435                 440                 445

Phe Ala Ser Trp Ser Ala Gly Asp Phe Gly Ser Val Gly Ala Thr Glu
450                 455                 460

Trp Leu Glu Gly Tyr Leu Ser Ser Leu His Leu Lys Ala Phe Thr Tyr
465                 470                 475                 480

Ile Asn Leu Asp Lys Ala Val Leu Gly Thr Ser Asn Phe Lys Val Ser
                485                 490                 495

Ala Ser Pro Leu Leu Tyr Thr Leu Ile Glu Lys Thr Met Gln Asn Val
            500                 505                 510

Lys His Pro Val Thr Gly Gln Phe Leu Tyr Gln Asp Ser Asn Trp Ala
        515                 520                 525

Ser Lys Val Glu Lys Leu Thr Leu Asp Asn Ala Ala Phe Pro Phe Leu
530                 535                 540

Ala Tyr Ser Gly Ile Pro Ala Val Ser Phe Cys Phe Cys Glu Asp Thr
545                 550                 555                 560

Asp Tyr Pro Tyr Leu Gly Thr Thr Met Asp Thr Tyr Lys Glu Leu Ile
                565                 570                 575

Glu Arg Ile Pro Glu Leu Asn Lys Val Ala Arg Ala Ala Ala Glu Val
            580                 585                 590

Ala Gly Gln Phe Val Ile Lys Leu Thr His Asp Val Glu Leu Asn Leu
        595                 600                 605

Asp Tyr Glu Arg Tyr Asn Ser Gln Leu Leu Ser Phe Val Arg Asp Leu
    610                 615                 620

Asn Gln Tyr Arg Ala Asp Ile Lys Glu Met Gly Leu Ser Leu Gln Trp
625                 630                 635                 640

Leu Tyr Ser Ala Arg Gly Asp Phe Phe Arg Ala Thr Ser Arg Leu Thr
                645                 650                 655

Thr Asp Phe Gly Asn Ala Glu Lys Thr Asp Arg Phe Val Met Lys Lys
                660                 665                 670

Leu Asn Asp Arg Val Met Arg Val Glu Tyr His Phe Leu Ser Pro Tyr
        675                 680                 685

Val Ser Pro Lys Glu Ser Pro Phe Arg His Val Phe Trp Gly Ser Gly
690                 695                 700

Ser His Thr Leu Pro Ala Leu Leu Glu Asn Leu Lys Leu Arg Lys Gln
705                 710                 715                 720

Asn Asn Gly Ala Phe Asn Glu Thr Leu Phe Arg Asn Gln Leu Ala Leu
                725                 730                 735

Ala Thr Trp Thr Ile Gln Gly Ala Ala Asn Ala Leu Ser Gly Asp Val
                740                 745                 750

Trp Asp Ile Asp Asn Glu Phe Gly Gly Gly Ser Gly Gly Gly
        755                 760                 765

Ser Gln Val Asp Thr Thr Lys Ala Val Ile Thr Leu Gln Pro Pro Trp
770                 775                 780
```

```
Val Ser Val Phe Gln Glu Glu Thr Val Thr Leu His Cys Glu Val Leu
785                 790                 795                 800

His Leu Pro Gly Ser Ser Thr Gln Trp Phe Leu Asn Gly Thr Ala
                805                 810                 815

Thr Gln Thr Ser Thr Pro Ser Tyr Arg Ile Thr Ser Ala Ser Val Asn
            820                 825                 830

Asp Ser Gly Glu Tyr Arg Cys Gln Arg Gly Leu Ser Gly Arg Ser Asp
        835                 840                 845

Pro Ile Gln Leu Glu Ile His Arg Gly Trp Leu Leu Leu Gln Val Ser
    850                 855                 860

Ser Arg Val Phe Thr Glu Gly Glu Pro Leu Ala Leu Arg Cys His Ala
865                 870                 875                 880

Trp Lys Asp Lys Leu Val Tyr Asn Val Leu Tyr Tyr Arg Asn Gly Lys
                885                 890                 895

Ala Phe Lys Phe Phe His Trp Asn Ser Asn Leu Thr Ile Leu Lys Thr
            900                 905                 910

Asn Ile Ser His Asn Gly Thr Tyr His Cys Ser Gly Met Gly Lys His
        915                 920                 925

Arg Tyr Thr Ser Ala Gly Ile Ser Val Thr Val Lys Glu Leu Phe Pro
    930                 935                 940

Ala Pro Val Leu Asn Ala Ser Val Thr Ser Pro Leu Leu Glu Gly Asn
945                 950                 955                 960

Leu Val Thr Leu Ser Cys Glu Thr Lys Leu Leu Leu Gln Arg Pro Gly
                965                 970                 975

Leu Gln Leu Tyr Phe Ser Phe Tyr Met Gly Ser Lys Thr Leu Arg Gly
            980                 985                 990

Arg Asn Thr Ser Ser Glu Tyr Gln Ile Leu Thr Ala Arg Arg Glu Asp
        995                 1000                1005

Ser Gly Leu Tyr Trp Cys Glu Ala Ala Thr Glu Asp
    1010                1015                1020

<210> SEQ ID NO 51
<211> LENGTH: 565
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 51

Met Gly Leu Ser Thr Val Pro Asp Leu Leu Leu Pro Leu Val Leu Leu
1               5                   10                  15

Glu Leu Leu Val Gly Ile Tyr Pro Ser Gly Val Ile Gly Leu Val Pro
            20                  25                  30

His Leu Gly Asp Arg Glu Lys Arg Asp Ser Val Cys Pro Gln Gly Lys
        35                  40                  45

Tyr Ile His Pro Gln Asn Asn Ser Ile Cys Cys Thr Lys Cys His Lys
    50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125
```

```
Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
                180                 185                 190

Lys Leu Cys Leu Asn Gly Gly Gly Ser Gly Gly Gly Gly Ser Gly
            195                 200                 205

Arg Gln Glu Gly Asp Phe Pro Met Pro Phe Ile Ser Ala Lys Ser Ser
210                 215                 220

Pro Val Ile Pro Leu Asp Gly Ser Val Lys Ile Gln Cys Gln Ala Ile
225                 230                 235                 240

Arg Glu Ala Tyr Leu Thr Gln Leu Met Ile Ile Lys Asn Ser Thr Tyr
                245                 250                 255

Arg Glu Ile Gly Arg Arg Leu Lys Phe Trp Asn Glu Thr Asp Pro Glu
                260                 265                 270

Phe Val Ile Asp His Met Asp Ala Asn Lys Ala Gly Arg Tyr Gln Cys
                275                 280                 285

Gln Tyr Arg Ile Gly His Tyr Arg Phe Arg Tyr Ser Asp Thr Leu Glu
290                 295                 300

Leu Val Val Thr Gly Leu Tyr Gly Lys Pro Phe Leu Ser Ala Asp Arg
305                 310                 315                 320

Gly Leu Val Leu Met Pro Gly Glu Asn Ile Ser Leu Thr Cys Ser Ser
                325                 330                 335

Ala His Ile Pro Phe Asp Arg Phe Ser Leu Ala Lys Glu Gly Glu Leu
                340                 345                 350

Ser Leu Pro Gln His Gln Ser Gly Glu His Pro Ala Asn Phe Ser Leu
                355                 360                 365

Gly Pro Val Asp Leu Asn Val Ser Gly Ile Tyr Arg Cys Tyr Gly Trp
370                 375                 380

Tyr Asn Arg Ser Pro Tyr Leu Trp Ser Phe Pro Ser Asn Ala Leu Glu
385                 390                 395                 400

Leu Val Val Thr Asp Ser Ile His Gln Asp Tyr Thr Thr Gln Asn Pro
                405                 410                 415

Gln Gly Thr Glu Asp Ser Gly Thr Thr Val Leu Leu Pro Leu Val Ile
                420                 425                 430

Phe Phe Gly Leu Cys Leu Leu Ser Leu Leu Phe Ile Gly Leu Met Tyr
                435                 440                 445

Arg Tyr Gln Arg Trp Lys Gly Thr Asn Gly Gly Gly Ser Gly Arg
450                 455                 460

Gly Tyr Ile Pro Glu Ala Pro Arg Asp Gly Gln Ala Tyr Val Arg Lys
465                 470                 475                 480

Asp Gly Glu Trp Val Phe Leu Ser Thr Phe Leu Ser Pro Ala Asn Gly
                485                 490                 495

Gly Gly Gly Ser Gly Arg Ser Leu Tyr Pro Ser Leu Glu Asp Leu Lys
            500                 505                 510

Val Asp Lys Val Ile Gln Ala Gln Thr Ala Phe Ser Ala Asn Pro Ala
                515                 520                 525

Asn Pro Ala Ile Leu Ser Glu Ala Ser Ala Pro Ile Pro His Asp Gly
530                 535                 540
```

```
Asn Leu Tyr Pro Arg Leu Tyr Pro Glu Leu Ser Gln Tyr Met Gly Leu
545                 550                 555                 560

Ser Leu Glu Gly Gly
            565

<210> SEQ ID NO 52
<211> LENGTH: 985
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 52

Met Ser Ala Pro Arg Ile Trp Leu Ala Gln Ala Leu Leu Phe Phe Leu
1               5                   10                  15

Thr Thr Glu Ser Ile Gly Gln Leu Leu Glu Pro Cys Gly Tyr Ile Tyr
            20                  25                  30

Pro Glu Phe Pro Val Val Gln Arg Gly Ser Asn Phe Thr Ala Ile Cys
        35                  40                  45

Val Leu Lys Glu Ala Cys Leu Gln His Tyr Tyr Val Asn Ala Ser Tyr
    50                  55                  60

Ile Val Trp Lys Thr Asn His Ala Ala Val Pro Arg Glu Gln Val Thr
65                  70                  75                  80

Val Ile Asn Arg Thr Thr Ser Ser Val Thr Phe Thr Asp Val Val Leu
                85                  90                  95

Pro Ser Val Gln Leu Thr Cys Asn Ile Leu Ser Phe Gly Gln Ile Glu
            100                 105                 110

Gln Asn Val Tyr Gly Val Thr Met Leu Ser Gly Phe Pro Pro Asp Lys
        115                 120                 125

Pro Thr Asn Leu Thr Cys Ile Val Asn Glu Gly Lys Asn Met Leu Cys
    130                 135                 140

Gln Trp Asp Pro Gly Arg Glu Thr Tyr Leu Glu Thr Asn Tyr Thr Leu
145                 150                 155                 160

Lys Ser Glu Trp Ala Thr Glu Lys Phe Pro Asp Cys Gln Ser Lys His
                165                 170                 175

Gly Thr Ser Cys Met Val Ser Tyr Met Pro Thr Tyr Tyr Val Asn Ile
            180                 185                 190

Glu Val Trp Val Glu Ala Glu Asn Ala Leu Gly Lys Val Ser Ser Glu
        195                 200                 205

Ser Ile Asn Phe Asp Pro Val Asp Lys Val Lys Pro Thr Pro Pro Tyr
    210                 215                 220

Asn Leu Ser Val Thr Asn Ser Glu Glu Leu Ser Ser Ile Leu Lys Leu
225                 230                 235                 240

Ser Trp Val Ser Ser Gly Leu Gly Gly Leu Leu Asp Leu Lys Ser Asp
                245                 250                 255

Ile Gln Tyr Arg Thr Lys Asp Ala Ser Thr Trp Ile Gln Val Pro Leu
            260                 265                 270

Glu Asp Thr Met Ser Pro Arg Thr Ser Phe Thr Val Gln Asp Leu Lys
        275                 280                 285

Pro Phe Thr Glu Tyr Val Phe Arg Ile Arg Ser Ile Lys Asp Ser Gly
    290                 295                 300

Lys Gly Tyr Trp Ser Asp Trp Ser Glu Ala Ser Gly Thr Thr Tyr
305                 310                 315                 320

Glu Asp Arg Pro Ser Arg Pro Ser Phe Trp Tyr Lys Thr Asn Pro
            325                 330                 335
```

```
Ser His Gly Gln Glu Tyr Arg Ser Val Arg Leu Ile Trp Lys Ala Leu
        340                 345                 350

Pro Leu Ser Glu Ala Asn Gly Lys Ile Leu Asp Tyr Glu Val Ile Leu
        355                 360                 365

Thr Gln Ser Lys Ser Val Ser Gln Thr Tyr Thr Val Thr Gly Thr Glu
    370                 375                 380

Leu Thr Val Asn Leu Thr Asn Asp Arg Tyr Val Ala Ser Leu Ala Ala
385                 390                 395                 400

Arg Asn Lys Val Gly Lys Ser Ala Ala Val Leu Thr Ile Pro Ser
                405                 410                 415

Pro His Val Thr Ala Gly Ser Gly Ser Gly Ser Gly Ser Arg
            420                 425                 430

Met Lys Gln Lys Lys Leu Val Gly Glu Arg Gly Ser Gly Ser Gly Ser
        435                 440                 445

Gly Ser Gly Ser Gln Glu Gly Asp Phe Pro Met Pro Phe Ile Ser Ala
    450                 455                 460

Lys Ser Ser Pro Val Ile Pro Leu Asp Gly Ser Val Lys Ile Gln Cys
465                 470                 475                 480

Gln Ala Ile Arg Glu Ala Tyr Leu Thr Gln Leu Met Ile Ile Lys Asn
                485                 490                 495

Ser Thr Tyr Arg Glu Ile Gly Arg Arg Leu Lys Phe Trp Asn Glu Thr
            500                 505                 510

Asp Pro Glu Phe Val Ile Asp His Met Asp Ala Asn Lys Ala Gly Arg
        515                 520                 525

Tyr Gln Cys Gln Tyr Arg Ile Gly His Tyr Arg Phe Arg Tyr Ser Asp
    530                 535                 540

Thr Leu Glu Leu Val Val Thr Gly Leu Tyr Gly Lys Pro Phe Leu Ser
545                 550                 555                 560

Ala Asp Arg Gly Leu Val Leu Met Pro Gly Glu Asn Ile Ser Leu Thr
                565                 570                 575

Cys Ser Ser Ala His Ile Pro Phe Asp Arg Phe Ser Leu Ala Lys Glu
            580                 585                 590

Gly Glu Leu Ser Leu Pro Gln His Gln Ser Gly Glu His Pro Ala Asn
        595                 600                 605

Phe Ser Leu Gly Pro Val Asp Leu Asn Val Ser Gly Ile Tyr Arg Cys
    610                 615                 620

Tyr Gly Trp Tyr Asn Arg Ser Pro Tyr Leu Trp Ser Phe Pro Ser Asn
625                 630                 635                 640

Ala Leu Glu Leu Val Val Thr Asp Ser Ile His Gln Asp Tyr Thr Thr
                645                 650                 655

Gln Asn Ala Ala Pro Ala Arg Gly Pro Thr Val Arg Thr Lys Lys Val
            660                 665                 670

Gly Lys Asn Glu Ala Val Leu Ala Trp Asp Gln Ile Pro Val Asp Asp
        675                 680                 685

Gln Asn Gly Phe Ile Arg Asn Tyr Ser Ile Ser Tyr Arg Thr Ser Val
    690                 695                 700

Gly Lys Glu Met Val Val His Val Asp Ser Ser His Thr Glu Tyr Thr
705                 710                 715                 720

Leu Ser Ser Leu Ser Ser Asp Thr Leu Tyr Met Val Arg Met Ala Ala
                725                 730                 735

Tyr Thr Asp Glu Gly Gly Lys Asp Gly Pro Glu Phe Thr Phe Thr Thr
            740                 745                 750
```

```
Pro Lys Phe Ala Gln Gly Glu Ile Glu Ala Ile Val Pro Val Cys
        755                 760                 765
Leu Ala Phe Leu Leu Thr Thr Leu Leu Gly Val Leu Phe Cys Phe Asn
    770                 775                 780
Lys Arg Asp Leu Ile Lys Lys His Ile Trp Pro Asn Val Pro Asp Pro
785                 790                 795                 800
Ser Lys Ser His Ile Ala Gln Trp Ser Pro His Thr Pro Pro Arg His
            805                 810                 815
Asn Phe Asn Ser Lys Asp Gln Gly Ser Gly Ser Gly Ser Gly Ser Gly
            820                 825                 830
Ser Arg Met Lys Gln Leu Glu Asp Lys Val Glu Glu Leu Leu Ser Lys
        835                 840                 845
Asn Tyr His Leu Glu Asn Glu Val Ala Arg Leu Lys Lys Leu Val Gly
    850                 855                 860
Glu Arg Gly Ser Gly Ser Gly Ser Gly Ser Ser Leu Tyr Pro
865                 870                 875                 880
Ser Leu Glu Asp Leu Lys Val Asp Lys Val Ile Gln Ala Gln Thr Ala
            885                 890                 895
Tyr Ser Ala Asn Pro Ala Ser Gln Ala Phe Val Leu Val Asp Ala Ser
        900                 905                 910
Ala Ala Leu Pro Pro Asp Gly Asn Leu Tyr Pro Lys Leu Tyr Pro Glu
    915                 920                 925
Leu Ser Gln Tyr Met Gly Leu Ser Leu Asn Glu Ala Glu Ile Cys Glu
    930                 935                 940
Ser Met Pro Met Val Ser Gly Ala Pro Ala Gln Gly Gln Leu Val Ala
945                 950                 955                 960
Arg Pro Ser Ser Val Asn Tyr Met Val Ala Pro Val Thr Gly Asn Asp
            965                 970                 975
Ala Gly Ile Arg Arg Ala Glu Ile Lys
            980                 985

<210> SEQ ID NO 53
<211> LENGTH: 657
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 53

Ala Val Glu Gly Gly Met Lys Cys Val Lys Phe Leu Leu Tyr Val Leu
1               5                   10                  15
Leu Leu Ala Phe Cys Ala Cys Ala Val Gly Leu Ile Ala Val Gly Val
            20                  25                  30
Gly Ala Gln Leu Val Leu Ser Gln Thr Gly Thr Gln Gly Asp Phe
        35                  40                  45
Pro Met Pro Phe Ile Ser Ala Lys Ser Ser Pro Val Ile Pro Leu Asp
    50                  55                  60
Gly Ser Val Lys Ile Gln Cys Gln Ala Ile Arg Glu Ala Tyr Leu Thr
65                  70                  75                  80
Gln Leu Met Ile Ile Lys Asn Ser Thr Tyr Arg Glu Ile Gly Arg Arg
            85                  90                  95
Leu Lys Phe Trp Asn Glu Thr Asp Pro Glu Phe Val Ile Asp His Met
        100                 105                 110
Asp Ala Asn Lys Ala Gly Arg Tyr Gln Cys Gln Tyr Arg Ile Gly His
    115                 120                 125
```

```
Tyr Arg Phe Arg Tyr Ser Asp Thr Leu Glu Leu Val Val Thr Gly Leu
        130                 135                 140

Tyr Gly Lys Pro Phe Leu Ser Ala Asp Arg Gly Leu Val Leu Met Pro
145                 150                 155                 160

Gly Glu Asn Ile Ser Leu Thr Cys Ser Ser Ala His Ile Pro Phe Asp
                165                 170                 175

Arg Phe Ser Leu Ala Lys Glu Gly Glu Leu Ser Leu Pro Gln His Gln
                180                 185                 190

Ser Gly Glu His Pro Ala Asn Phe Ser Leu Gly Pro Val Asp Leu Asn
                195                 200                 205

Val Ser Gly Ile Tyr Arg Cys Tyr Gly Trp Tyr Asn Arg Ser Pro Tyr
210                 215                 220

Leu Trp Ser Phe Pro Ser Asn Ala Leu Glu Leu Val Val Thr Asp Ser
225                 230                 235                 240

Ile His Gln Asp Tyr Thr Thr Gln Asn Gly Thr Ile Ile Gln Gly Ala
                245                 250                 255

Thr Pro Gly Ser Leu Leu Pro Val Val Ile Ala Val Gly Val Phe
                260                 265                 270

Leu Phe Leu Val Ala Phe Val Gly Cys Cys Gly Ala Cys Lys Glu Asn
        275                 280                 285

Tyr Cys Leu Met Ile Thr Phe Ala Ile Phe Leu Ser Leu Ile Met Leu
        290                 295                 300

Val Glu Val Ala Ala Ala Ile Ala Gly Tyr Val Phe Arg Asp Lys Val
305                 310                 315                 320

Met Ser Glu Phe Asn Asn Asn Phe Arg Gln Gln Met Glu Asn Tyr Pro
                325                 330                 335

Lys Asn Asn His Thr Ala Ser Ile Leu Asp Arg Met Gln Ala Asp Phe
                340                 345                 350

Lys Cys Cys Gly Ala Gly Ser Gln Glu Gly Asp Phe Pro Met Pro Phe
                355                 360                 365

Ile Ser Ala Lys Ser Ser Pro Val Ile Pro Leu Asp Gly Ser Val Lys
370                 375                 380

Ile Gln Cys Gln Ala Ile Arg Glu Ala Tyr Leu Thr Gln Leu Met Ile
385                 390                 395                 400

Ile Lys Asn Ser Thr Tyr Arg Glu Ile Gly Arg Arg Leu Lys Phe Trp
                405                 410                 415

Asn Glu Thr Asp Pro Glu Phe Val Ile Asp His Met Asp Ala Asn Lys
                420                 425                 430

Ala Gly Arg Tyr Gln Cys Gln Tyr Arg Ile Gly His Tyr Arg Phe Arg
                435                 440                 445

Tyr Ser Asp Thr Leu Glu Leu Val Val Thr Gly Leu Tyr Gly Lys Pro
450                 455                 460

Phe Leu Ser Ala Asp Arg Gly Leu Val Leu Met Pro Gly Glu Asn Ile
465                 470                 475                 480

Ser Leu Thr Cys Ser Ser Ala His Ile Pro Phe Asp Arg Phe Ser Leu
                485                 490                 495

Ala Lys Glu Gly Glu Leu Ser Leu Pro Gln His Gln Ser Gly Glu His
                500                 505                 510

Pro Ala Asn Phe Ser Leu Gly Pro Val Asp Leu Asn Val Ser Gly Ile
                515                 520                 525

Tyr Arg Cys Tyr Gly Trp Tyr Asn Arg Ser Pro Tyr Leu Trp Ser Phe
530                 535                 540
```

```
Pro Ser Asn Ala Leu Glu Leu Val Val Thr Asp Ser Ile His Gln Asp
545                 550                 555                 560

Tyr Thr Thr Gln Asn Gly Ser Ala Asn Tyr Thr Asp Trp Glu Lys Ile
                565                 570                 575

Pro Ser Met Ser Lys Asn Arg Val Pro Asp Ser Cys Cys Ile Asn Val
            580                 585                 590

Thr Val Gly Cys Gly Ile Asn Phe Asn Glu Lys Ala Ile His Lys Glu
        595                 600                 605

Gly Cys Val Glu Lys Ile Gly Gly Trp Leu Arg Lys Asn Val Leu Val
    610                 615                 620

Val Ala Ala Ala Leu Gly Ile Ala Phe Val Glu Val Leu Gly Ile
625                 630                 635                 640

Val Phe Ala Cys Cys Leu Val Lys Ser Ile Arg Ser Gly Tyr Glu Val
                645                 650                 655

Met

<210> SEQ ID NO 54
<211> LENGTH: 681
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 54

Met Gln Glu Gly Asp Phe Pro Met Pro Phe Ile Ser Ala Lys Ser Ser
1               5                   10                  15

Pro Val Ile Pro Leu Asp Gly Ser Val Lys Ile Gln Cys Gln Ala Ile
            20                  25                  30

Arg Glu Ala Tyr Leu Thr Gln Leu Met Ile Ile Lys Asn Ser Thr Tyr
        35                  40                  45

Arg Glu Ile Gly Arg Arg Leu Lys Phe Trp Asn Glu Thr Asp Pro Glu
    50                  55                  60

Phe Val Ile Asp His Met Asp Ala Asn Lys Ala Gly Arg Tyr Gln Cys
65                  70                  75                  80

Gln Tyr Arg Ile Gly His Tyr Arg Phe Arg Tyr Ser Asp Thr Leu Glu
                85                  90                  95

Leu Val Val Thr Gly Leu Tyr Gly Lys Pro Phe Leu Ser Ala Asp Arg
            100                 105                 110

Gly Leu Val Leu Met Pro Gly Glu Asn Ile Ser Leu Thr Cys Ser Ser
        115                 120                 125

Ala His Ile Pro Phe Asp Arg Phe Ser Leu Ala Lys Glu Gly Glu Leu
    130                 135                 140

Ser Leu Pro Gln His Gln Ser Gly Glu His Pro Ala Asn Phe Ser Leu
145                 150                 155                 160

Gly Pro Val Asp Leu Asn Val Ser Gly Ile Tyr Arg Cys Tyr Gly Trp
                165                 170                 175

Tyr Asn Arg Ser Pro Tyr Leu Trp Ser Phe Pro Ser Asn Ala Leu Glu
            180                 185                 190

Leu Val Val Thr Asp Ser Ile His Gln Asp Tyr Thr Thr Gln Asn Gly
        195                 200                 205

Ser Gly Ser Gly Gly Ser Gly Ser Gly Val Cys Phe Arg Leu Phe
    210                 215                 220

Pro Val Pro Gly Ser Gly Leu Val Leu Val Cys Leu Val Leu Gly Ala
225                 230                 235                 240
```

-continued

```
Val Arg Ser Tyr Ala Lys Ser Ser Val Gly Arg Gln Gly Ser Gly Ser
            245                 250                 255

Gly Ser Gly Leu Glu Leu Asn Leu Thr Asp Ser Glu Asn Ala Thr Cys
        260                 265                 270

Leu Tyr Ala Lys Trp Gln Met Asn Phe Thr Val Arg Tyr Glu Thr Thr
    275                 280                 285

Asn Lys Thr Tyr Lys Thr Val Thr Ile Ser Asp His Gly Thr Val Thr
290                 295                 300

Tyr Asn Gly Ser Ile Cys Gly Asp Asp Gln Asn Gly Pro Lys Ile Ala
305                 310                 315                 320

Val Gln Phe Gly Pro Gly Phe Ser Trp Ile Ala Asn Phe Thr Lys Ala
                325                 330                 335

Ala Ser Thr Tyr Ser Ile Asp Ser Val Ser Phe Ser Tyr Asn Thr Gly
            340                 345                 350

Asp Asn Thr Thr Phe Pro Asp Ala Glu Asp Lys Gly Ile Leu Thr Val
        355                 360                 365

Asp Glu Leu Leu Ala Ile Arg Ile Pro Leu Asn Asp Leu Phe Arg Cys
    370                 375                 380

Asn Ser Leu Ser Thr Leu Glu Lys Asn Asp Val Val Gln His Tyr Trp
385                 390                 395                 400

Asp Val Leu Val Gln Ala Phe Val Gln Asn Gly Thr Val Ser Thr Asn
                405                 410                 415

Glu Phe Leu Cys Asp Lys Asp Lys Thr Ser Thr Val Ala Pro Thr Ile
            420                 425                 430

His Thr Thr Val Pro Ser Pro Thr Thr Pro Thr Pro Lys Glu Lys
        435                 440                 445

Pro Glu Ala Gly Thr Tyr Ser Val Asn Asn Gly Asn Asp Thr Cys Leu
    450                 455                 460

Leu Ala Thr Met Gly Leu Gln Leu Asn Ile Thr Gln Asp Lys Val Ala
465                 470                 475                 480

Ser Val Ile Asn Ile Asn Pro Asn Thr Thr His Ser Thr Gly Ser Cys
                485                 490                 495

Arg Ser His Thr Ala Leu Leu Arg Leu Asn Ser Ser Thr Ile Lys Tyr
            500                 505                 510

Leu Asp Phe Val Phe Ala Val Lys Asn Glu Asn Arg Phe Tyr Leu Lys
        515                 520                 525

Glu Val Asn Ile Ser Met Tyr Leu Val Asn Gly Ser Val Phe Ser Ile
    530                 535                 540

Ala Asn Asn Asn Leu Ser Tyr Trp Asp Ala Pro Leu Gly Ser Ser Tyr
545                 550                 555                 560

Met Cys Asn Lys Glu Gln Thr Val Ser Val Ser Gly Ala Phe Gln Ile
                565                 570                 575

Asn Thr Phe Asp Leu Arg Val Gln Pro Phe Asn Val Thr Gln Gly Lys
            580                 585                 590

Tyr Ser Thr Ala Gln Asp Cys Ser Ala Asp Asp Asn Phe Leu Val
        595                 600                 605

Pro Ile Ala Val Gly Ala Ala Leu Ala Gly Val Leu Ile Leu Val Leu
    610                 615                 620

Leu Ala Tyr Phe Ile Gly Leu Lys His His Ala Gly Tyr Glu Gln
625                 630                 635                 640

Phe Gly Ser Gly Ser Gly Ser Gly Ser Gly Ser Thr Gly Gly
                645                 650                 655

Ser Arg Thr Gly Ser Gly Ser Gly Ser Gly Ser Gly Ser Pro
```

-continued

```
                    660                 665                 670
Gly His His His His His His His
        675                 680

<210> SEQ ID NO 55
<211> LENGTH: 665
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 55

Met Val Cys Phe Arg Leu Phe Pro Val Pro Gly Ser Gly Leu Val Leu
1               5                   10                  15

Val Cys Leu Val Leu Gly Ala Val Arg Ser Tyr Ala Lys Ser Ser Val
            20                  25                  30

Gly Arg Gln Gln Glu Gly Asp Phe Pro Met Pro Phe Ile Ser Ala Lys
        35                  40                  45

Ser Ser Pro Val Ile Pro Leu Asp Gly Ser Val Lys Ile Gln Cys Gln
    50                  55                  60

Ala Ile Arg Glu Ala Tyr Leu Thr Gln Leu Met Ile Ile Lys Asn Ser
65                  70                  75                  80

Thr Tyr Arg Glu Ile Gly Arg Arg Leu Lys Phe Trp Asn Glu Thr Asp
                85                  90                  95

Pro Glu Phe Val Ile Asp His Met Asp Ala Asn Lys Ala Gly Arg Tyr
            100                 105                 110

Gln Cys Gln Tyr Arg Ile Gly His Tyr Arg Phe Arg Tyr Ser Asp Thr
        115                 120                 125

Leu Glu Leu Val Val Thr Gly Leu Tyr Gly Lys Pro Phe Leu Ser Ala
    130                 135                 140

Asp Arg Gly Leu Val Leu Met Pro Gly Glu Asn Ile Ser Leu Thr Cys
145                 150                 155                 160

Ser Ser Ala His Ile Pro Phe Asp Arg Phe Ser Leu Ala Lys Glu Gly
                165                 170                 175

Glu Leu Ser Leu Pro Gln His Gln Ser Gly Glu His Pro Ala Asn Phe
            180                 185                 190

Ser Leu Gly Pro Val Asp Leu Asn Val Ser Gly Ile Tyr Arg Cys Tyr
        195                 200                 205

Gly Trp Tyr Asn Arg Ser Pro Tyr Leu Trp Ser Phe Pro Ser Asn Ala
    210                 215                 220

Leu Glu Leu Val Val Thr Asp Ser Ile His Gln Asp Tyr Thr Thr Gln
225                 230                 235                 240

Asn Gly Gly Gly Gly Ser Gly Gly Gly Ser Leu Glu Leu Asn Leu
                245                 250                 255

Thr Asp Ser Glu Asn Ala Thr Cys Leu Tyr Ala Lys Trp Gln Met Asn
            260                 265                 270

Phe Thr Val Arg Tyr Glu Thr Thr Asn Lys Thr Tyr Lys Thr Val Thr
        275                 280                 285

Ile Ser Asp His Gly Thr Val Thr Tyr Asn Gly Ser Ile Cys Gly Asp
    290                 295                 300

Asp Gln Asn Gly Pro Lys Ile Ala Val Gln Phe Gly Pro Gly Phe Ser
305                 310                 315                 320

Trp Ile Ala Asn Phe Thr Lys Ala Ala Ser Thr Tyr Ser Ile Asp Ser
                325                 330                 335
```

Val Ser Phe Ser Tyr Asn Thr Gly Asp Asn Thr Thr Phe Pro Asp Ala
                340                 345                 350

Glu Asp Lys Gly Ile Leu Thr Val Asp Glu Leu Leu Ala Ile Arg Ile
            355                 360                 365

Pro Leu Asn Asp Leu Phe Arg Cys Asn Ser Leu Ser Thr Leu Glu Lys
370                 375                 380

Asn Asp Val Val Gln His Tyr Trp Asp Val Leu Val Gln Ala Phe Val
385                 390                 395                 400

Gln Asn Gly Thr Val Ser Thr Asn Glu Phe Leu Cys Asp Lys Asp Lys
                405                 410                 415

Thr Ser Thr Val Ala Pro Thr Ile His Thr Thr Val Pro Ser Pro Thr
            420                 425                 430

Thr Thr Pro Thr Pro Lys Glu Lys Pro Glu Ala Gly Thr Tyr Ser Val
        435                 440                 445

Asn Asn Gly Asn Asp Thr Cys Leu Leu Ala Thr Met Gly Leu Gln Leu
450                 455                 460

Asn Ile Thr Gln Asp Lys Val Ala Ser Val Ile Asn Ile Asn Pro Asn
465                 470                 475                 480

Thr Thr His Ser Thr Gly Ser Cys Arg Ser His Thr Ala Leu Leu Arg
            485                 490                 495

Leu Asn Ser Ser Thr Ile Lys Tyr Leu Asp Phe Val Phe Ala Val Lys
        500                 505                 510

Asn Glu Asn Arg Phe Tyr Leu Lys Glu Val Asn Ile Ser Met Tyr Leu
            515                 520                 525

Val Asn Gly Ser Val Phe Ser Ile Ala Asn Asn Leu Ser Tyr Trp
530                 535                 540

Asp Ala Pro Leu Gly Ser Ser Tyr Met Cys Asn Lys Glu Gln Thr Val
545                 550                 555                 560

Ser Val Ser Gly Ala Phe Gln Ile Asn Thr Phe Asp Leu Arg Val Gln
                565                 570                 575

Pro Phe Asn Val Thr Gln Gly Lys Tyr Ser Thr Ala Gln Asp Cys Ser
            580                 585                 590

Ala Asp Asp Asn Phe Leu Val Pro Ile Ala Val Gly Ala Ala Leu
        595                 600                 605

Ala Gly Val Leu Ile Leu Val Leu Leu Ala Tyr Phe Ile Gly Leu Lys
        610                 615                 620

His His His Ala Gly Tyr Glu Gln Phe Gly Ser Gly Ser Gly Ser Gly
625                 630                 635                 640

Ser Gly Ser Gly Ser Thr Gly Gly Ser Arg Thr Gly Ser Gly Ser Gly
                645                 650                 655

Ser Gly Ser Gly Ser Gly Ser Pro Gly
            660                 665

<210> SEQ ID NO 56
<211> LENGTH: 975
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 56

Met Asp Gln Ala Arg Ser Ala Phe Ser Asn Leu Phe Gly Gly Glu Pro
1               5                   10                  15

Leu Ser Tyr Thr Arg Phe Ser Leu Ala Arg Gln Val Asp Gly Asp Asn
            20                  25                  30

-continued

```
Ser His Val Glu Met Lys Leu Ala Val Asp Glu Glu Asn Ala Asp
         35                  40                  45

Asn Asn Thr Lys Ala Asn Val Thr Lys Pro Lys Arg Cys Ser Gly Ser
 50                  55                  60

Ile Cys Tyr Gly Thr Ile Ala Val Ile Val Phe Phe Leu Ile Gly Phe
 65                  70                  75                  80

Met Ile Gly Tyr Leu Gly Tyr Cys Lys Gly Val Glu Pro Lys Thr Glu
                 85                  90                  95

Cys Glu Arg Leu Ala Gly Thr Glu Ser Pro Val Arg Glu Glu Pro Gly
             100                 105                 110

Glu Asp Phe Pro Ala Ala Arg Arg Leu Tyr Trp Asp Asp Leu Lys Arg
             115                 120                 125

Lys Leu Ser Glu Lys Leu Asp Ser Thr Asp Phe Thr Gly Thr Ile Lys
 130                 135                 140

Leu Leu Asn Glu Asn Ser Tyr Val Pro Arg Glu Ala Gly Ser Gln Lys
145                 150                 155                 160

Asp Glu Asn Leu Ala Leu Tyr Val Glu Asn Gln Phe Arg Glu Phe Lys
                 165                 170                 175

Leu Ser Lys Val Trp Arg Asp Gln His Phe Val Lys Ile Gln Val Lys
             180                 185                 190

Asp Ser Ala Gln Asn Ser Val Ile Ile Val Asp Lys Asn Gly Arg Leu
             195                 200                 205

Val Tyr Leu Val Glu Asn Pro Gly Gly Tyr Val Ala Tyr Ser Lys Ala
 210                 215                 220

Ala Thr Val Thr Gly Lys Leu Val His Ala Asn Phe Gly Thr Lys Lys
225                 230                 235                 240

Asp Phe Glu Asp Leu Tyr Thr Pro Val Asn Gly Ser Ile Val Ile Val
                 245                 250                 255

Arg Ala Gly Lys Ile Thr Phe Ala Glu Lys Val Ala Asn Ala Glu Ser
             260                 265                 270

Leu Asn Ala Ile Gly Val Leu Ile Tyr Met Asp Gln Thr Lys Phe Pro
             275                 280                 285

Ile Val Asn Ala Glu Leu Ser Phe Phe Gly His Ala His Leu Gly Thr
 290                 295                 300

Gly Asp Pro Tyr Thr Pro Gly Phe Pro Ser Phe Asn His Thr Gln Phe
305                 310                 315                 320

Pro Pro Ser Arg Ser Ser Gly Leu Pro Asn Ile Pro Val Gln Thr Ile
                 325                 330                 335

Ser Arg Ala Ala Ala Glu Lys Leu Phe Gly Asn Met Glu Gly Asp Cys
             340                 345                 350

Pro Ser Asp Trp Lys Thr Asp Ser Thr Cys Arg Met Val Thr Ser Glu
             355                 360                 365

Ser Lys Asn Val Lys Leu Thr Val Ser Asn Val Leu Lys Glu Ile Lys
 370                 375                 380

Ile Leu Asn Ile Phe Gly Val Ile Lys Gly Phe Val Glu Pro Asp His
385                 390                 395                 400

Tyr Val Val Val Gly Ala Gln Arg Asp Ala Trp Gly Pro Gly Ala Ala
                 405                 410                 415

Lys Ser Gly Val Gly Thr Ala Leu Leu Leu Lys Leu Ala Gln Met Phe
             420                 425                 430

Ser Asp Met Val Leu Lys Asp Gly Phe Gln Pro Ser Arg Ser Ile Ile
             435                 440                 445
```

```
Phe Ala Ser Trp Ser Ala Gly Asp Phe Gly Ser Val Gly Ala Thr Glu
450                 455                 460
Trp Leu Glu Gly Tyr Leu Ser Ser Leu His Leu Lys Ala Phe Thr Tyr
465                 470                 475                 480
Ile Asn Leu Asp Lys Ala Val Leu Gly Thr Ser Asn Phe Lys Val Ser
                485                 490                 495
Ala Ser Pro Leu Leu Tyr Thr Leu Ile Glu Lys Thr Met Gln Asn Val
            500                 505                 510
Lys His Pro Val Thr Gly Gln Phe Leu Tyr Gln Asp Ser Asn Trp Ala
            515                 520                 525
Ser Lys Val Glu Lys Leu Thr Leu Asp Asn Ala Ala Phe Pro Phe Leu
530                 535                 540
Ala Tyr Ser Gly Ile Pro Ala Val Ser Phe Cys Phe Cys Glu Asp Thr
545                 550                 555                 560
Asp Tyr Pro Tyr Leu Gly Thr Thr Met Asp Thr Tyr Lys Glu Leu Ile
                565                 570                 575
Glu Arg Ile Pro Glu Leu Asn Lys Val Ala Arg Ala Ala Ala Glu Val
            580                 585                 590
Ala Gly Gln Phe Val Ile Lys Leu Thr His Asp Val Glu Leu Asn Leu
            595                 600                 605
Asp Tyr Glu Arg Tyr Asn Ser Gln Leu Leu Ser Phe Val Arg Asp Leu
610                 615                 620
Asn Gln Tyr Arg Ala Asp Ile Lys Glu Met Gly Leu Ser Leu Gln Trp
625                 630                 635                 640
Leu Tyr Ser Ala Arg Gly Asp Phe Phe Arg Ala Thr Ser Arg Leu Thr
                645                 650                 655
Thr Asp Phe Gly Asn Ala Glu Lys Thr Asp Arg Phe Val Met Lys Lys
            660                 665                 670
Leu Asn Asp Arg Val Met Arg Val Glu Tyr His Phe Leu Ser Pro Tyr
            675                 680                 685
Val Ser Pro Lys Glu Ser Pro Phe Arg His Val Phe Trp Gly Ser Gly
690                 695                 700
Ser His Thr Leu Pro Ala Leu Leu Glu Asn Leu Lys Leu Arg Lys Gln
705                 710                 715                 720
Asn Asn Gly Ala Phe Asn Glu Thr Leu Phe Arg Asn Gln Leu Ala Leu
                725                 730                 735
Ala Thr Trp Thr Ile Gln Gly Ala Ala Asn Ala Leu Ser Gly Asp Val
            740                 745                 750
Trp Asp Ile Asp Asn Glu Phe Gly Gly Gly Ser Gly Gly Gly Gly
            755                 760                 765
Ser Gln Glu Gly Asp Phe Pro Met Pro Phe Ile Ser Ala Lys Ser Ser
770                 775                 780
Pro Val Ile Pro Leu Asp Gly Ser Val Lys Ile Gln Cys Gln Ala Ile
785                 790                 795                 800
Arg Glu Ala Tyr Leu Thr Gln Leu Met Ile Ile Lys Asn Ser Thr Tyr
                805                 810                 815
Arg Glu Ile Gly Arg Arg Leu Lys Phe Trp Asn Glu Thr Asp Pro Glu
            820                 825                 830
Phe Val Ile Asp His Met Asp Ala Asn Lys Ala Gly Tyr Gln Cys
            835                 840                 845
Gln Tyr Arg Ile Gly His Tyr Arg Phe Arg Tyr Ser Asp Thr Leu Glu
850                 855                 860
Leu Val Val Thr Gly Leu Tyr Gly Lys Pro Phe Leu Ser Ala Asp Arg
```

```
            865                 870                 875                 880
Gly Leu Val Leu Met Pro Gly Glu Asn Ile Ser Leu Thr Cys Ser Ser
                        885                 890                 895

Ala His Ile Pro Phe Asp Arg Phe Ser Leu Ala Lys Glu Gly Glu Leu
                        900                 905                 910

Ser Leu Pro Gln His Gln Ser Gly Glu His Pro Ala Asn Phe Ser Leu
                        915                 920                 925

Gly Pro Val Asp Leu Asn Val Ser Gly Ile Tyr Arg Cys Tyr Gly Trp
                        930                 935                 940

Tyr Asn Arg Ser Pro Tyr Leu Trp Ser Phe Pro Ser Asn Ala Leu Glu
945                     950                 955                 960

Leu Val Val Thr Asp Ser Ile His Gln Asp Tyr Thr Thr Gln Asn
                        965                 970                 975

<210> SEQ ID NO 57
<211> LENGTH: 376
<212> TYPE: PRT
<213> ORGANISM: Streptococcus pyogenes

<400> SEQUENCE: 57

Met Thr Arg Gln Gln Thr Lys Lys Asn Tyr Ser Leu Arg Lys Leu Lys
1               5                   10                  15

Thr Gly Thr Ala Ser Val Ala Val Ala Leu Thr Val Leu Gly Ala Gly
                20                  25                  30

Phe Ala Asn Gln Thr Thr Val Lys Ala Glu Gly Ala Lys Ile Asp Trp
            35                  40                  45

Gln Glu Glu Tyr Lys Lys Leu Asp Glu Asp Asn Ala Lys Leu Val Glu
        50                  55                  60

Val Val Glu Thr Thr Ser Leu Glu Asn Glu Lys Leu Lys Ser Glu Asn
65                  70                  75                  80

Glu Glu Asn Lys Lys Asn Leu Asp Lys Leu Ser Lys Glu Asn Gln Gly
                85                  90                  95

Lys Leu Glu Lys Leu Glu Leu Asp Tyr Leu Lys Lys Leu Asp His Glu
                100                 105                 110

His Lys Glu His Gln Lys Glu Gln Glu Gln Glu Glu Arg Gln Lys
            115                 120                 125

Asn Gln Glu Gln Leu Glu Arg Lys Tyr Gln Arg Glu Val Glu Lys Arg
        130                 135                 140

Tyr Gln Glu Gln Leu Gln Lys Gln Gln Leu Glu Thr Glu Lys Gln
145                 150                 155                 160

Ile Ser Glu Ala Ser Arg Lys Ser Leu Ser Arg Asp Leu Glu Ala Ser
                165                 170                 175

Arg Ala Ala Lys Lys Asp Leu Glu Ala Glu His Gln Lys Leu Glu Ala
                180                 185                 190

Glu His Gln Lys Leu Lys Glu Asp Lys Gln Ile Ser Asp Ala Ser Arg
            195                 200                 205

Gln Gly Leu Ser Arg Asp Leu Glu Ala Ser Arg Ala Ala Lys Lys Glu
        210                 215                 220

Leu Glu Ala Asn His Gln Lys Leu Glu Ala Glu His Gln Lys Leu Lys
225                 230                 235                 240

Glu Asp Lys Gln Ile Ser Asp Ala Ser Arg Gln Gly Leu Ser Arg Asp
                245                 250                 255

Leu Glu Ala Ser Arg Ala Ala Lys Lys Glu Leu Glu Ala Asn His Gln
                260                 265                 270
```

```
Lys Leu Glu Ala Glu Ala Lys Ala Leu Lys Glu Gln Leu Ala Lys Gln
        275                 280                 285

Ala Glu Glu Leu Ala Lys Leu Arg Ala Gly Lys Ala Ser Asp Ser Gln
        290                 295                 300

Thr Pro Asp Thr Lys Pro Gly Asn Lys Ala Val Pro Gly Lys Gly Gln
305                 310                 315                 320

Ala Pro Gln Ala Gly Thr Lys Pro Asn Gln Asn Lys Ala Pro Met Lys
                325                 330                 335

Glu Thr Lys Arg Gln Leu Pro Ser Thr Gly Glu Thr Ala Asn Pro Phe
                340                 345                 350

Phe Thr Ala Ala Ala Leu Thr Val Met Ala Thr Ala Gly Val Ala Ala
        355                 360                 365

Val Val Lys Arg Lys Glu Glu Asn
        370                 375

<210> SEQ ID NO 58
<211> LENGTH: 450
<212> TYPE: PRT
<213> ORGANISM: Staphylococcus aureus

<400> SEQUENCE: 58

Met Lys Lys Lys Asn Ile Tyr Ser Ile Arg Lys Leu Gly Val Gly Ile
1               5                   10                  15

Ala Ser Val Thr Leu Gly Thr Leu Leu Ile Ser Gly Gly Val Thr Pro
                20                  25                  30

Ala Ala Asn Ala Ala Gln His Asp Glu Ala Gln Gln Asn Ala Phe Tyr
            35                  40                  45

Gln Val Leu Asn Met Pro Asn Leu Asn Ala Asp Gln Arg Asn Gly Phe
        50                  55                  60

Ile Gln Ser Leu Lys Asp Asp Pro Ser Gln Ser Ala Asn Val Leu Gly
65                  70                  75                  80

Glu Ala Gln Lys Leu Asn Asp Ser Gln Ala Pro Lys Ala Asp Ala Gln
                85                  90                  95

Gln Asn Asn Phe Asn Lys Asp Gln Gln Ser Ala Phe Tyr Glu Ile Leu
            100                 105                 110

Asn Met Pro Asn Leu Asn Glu Ala Gln Arg Asn Gly Phe Ile Gln Ser
        115                 120                 125

Leu Lys Asp Asp Pro Ser Gln Ser Thr Asn Val Leu Gly Glu Ala Lys
    130                 135                 140

Lys Leu Asn Glu Ser Gln Ala Pro Lys Ala Asp Asn Asn Phe Asn Lys
145                 150                 155                 160

Glu Gln Gln Asn Ala Phe Tyr Glu Ile Leu Asn Met Pro Asn Leu Asn
                165                 170                 175

Glu Glu Gln Arg Asn Gly Phe Ile Gln Ser Leu Lys Asp Asp Pro Ser
            180                 185                 190

Gln Ser Ala Asn Leu Leu Ser Glu Ala Lys Lys Leu Asn Glu Ser Gln
        195                 200                 205

Ala Pro Lys Ala Asp Asn Lys Phe Asn Lys Glu Gln Gln Asn Ala Phe
    210                 215                 220

Tyr Glu Ile Leu His Leu Pro Asn Leu Asn Glu Glu Gln Arg Asn Gly
225                 230                 235                 240

Phe Ile Gln Ser Leu Lys Asp Asp Pro Ser Val Ser Lys Glu Ile Leu
                245                 250                 255

Ala Glu Ala Lys Lys Leu Asn Asp Ala Gln Ala Pro Lys Glu Glu Asp
            260                 265                 270
```

```
Asn Lys Lys Pro Gly Lys Glu Asp Gly Asn Lys Pro Gly Lys Glu Asp
        275                 280                 285

Gly Asn Lys Pro Gly Lys Glu Asp Asn Lys Pro Gly Lys Glu Asp
        290                 295                 300

Gly Asn Lys Pro Gly Lys Glu Asp Asn Lys Pro Gly Lys Glu Asp
305                 310                 315                 320

Gly Asn Lys Pro Gly Lys Glu Asp Asn Lys Pro Gly Lys Glu Asp
            325                 330                 335

Gly Asn Lys Pro Gly Lys Glu Asp Gly Asn Lys Pro Gly Lys Glu Asp
            340                 345                 350

Gly Asn Gly Val His Val Val Lys Pro Gly Asp Thr Val Asn Asp Ile
            355                 360                 365

Ala Lys Ala Asn Gly Thr Thr Ala Asp Lys Ile Ala Ala Asp Asn Lys
        370                 375                 380

Leu Ala Asp Lys Asn Met Ile Lys Pro Gly Gln Glu Leu Val Val Asp
385                 390                 395                 400

Lys Lys Gln Pro Ala Asn His Ala Asp Ala Asn Lys Ala Gln Ala Leu
            405                 410                 415

Pro Glu Thr Gly Glu Glu Asn Pro Phe Ile Gly Thr Thr Val Phe Gly
            420                 425                 430

Gly Leu Ser Leu Ala Leu Gly Ala Ala Leu Leu Ala Gly Arg Arg Arg
            435                 440                 445

Glu Leu
    450

<210> SEQ ID NO 59
<211> LENGTH: 593
<212> TYPE: PRT
<213> ORGANISM: Streptococcus sp

<400> SEQUENCE: 59

Met Glu Lys Glu Lys Lys Val Lys Tyr Phe Leu Arg Lys Ser Ala Phe
1               5                   10                  15

Gly Leu Ala Ser Val Ser Ala Ala Phe Leu Val Gly Ser Thr Val Phe
            20                  25                  30

Ala Val Asp Ser Pro Ile Glu Asp Thr Pro Ile Ile Arg Asn Gly Gly
        35                  40                  45

Glu Leu Thr Asn Leu Leu Gly Asn Ser Glu Thr Thr Leu Ala Leu Arg
    50                  55                  60

Asn Glu Glu Ser Ala Thr Ala Asp Leu Thr Ala Ala Val Ala Asp
65                  70                  75                  80

Thr Val Ala Ala Ala Ala Glu Asn Ala Gly Ala Ala Ala Trp Glu
                85                  90                  95

Ala Ala Ala Ala Asp Ala Leu Ala Lys Ala Lys Ala Asp Ala Leu
            100                 105                 110

Lys Glu Phe Asn Lys Tyr Gly Val Ser Asp Tyr Tyr Lys Asn Leu Ile
            115                 120                 125

Asn Asn Ala Lys Thr Val Glu Gly Val Lys Asp Leu Gln Ala Gln Val
        130                 135                 140

Val Glu Ser Ala Lys Lys Ala Arg Ile Ser Glu Ala Thr Asp Gly Leu
145                 150                 155                 160

Ser Asp Phe Leu Lys Ser Gln Thr Pro Ala Glu Asp Thr Val Lys Ser
                165                 170                 175

Ile Glu Leu Ala Glu Ala Lys Val Leu Ala Asn Arg Glu Leu Asp Lys
```

```
                180                 185                 190
Tyr Gly Val Ser Asp Tyr His Lys Asn Leu Ile Asn Asn Ala Lys Thr
            195                 200                 205
Val Glu Gly Val Lys Asp Leu Gln Ala Gln Val Val Glu Ser Ala Lys
            210                 215                 220
Lys Ala Arg Ile Ser Glu Ala Thr Asp Gly Leu Ser Asp Phe Leu Lys
225                 230                 235                 240
Ser Gln Thr Pro Ala Glu Asp Thr Val Lys Ser Ile Glu Leu Ala Glu
            245                 250                 255
Ala Lys Val Leu Ala Asn Arg Glu Leu Asp Lys Tyr Gly Val Ser Asp
            260                 265                 270
Tyr Tyr Lys Asn Leu Ile Asn Asn Ala Lys Thr Val Glu Gly Val Lys
            275                 280                 285
Ala Leu Ile Asp Glu Ile Leu Ala Ala Leu Pro Lys Thr Asp Thr Tyr
            290                 295                 300
Lys Leu Ile Leu Asn Gly Lys Thr Leu Lys Gly Glu Thr Thr Thr Glu
305                 310                 315                 320
Ala Val Asp Ala Ala Thr Ala Glu Lys Val Phe Lys Gln Tyr Ala Asn
            325                 330                 335
Asp Asn Gly Val Asp Gly Glu Trp Thr Tyr Asp Asp Ala Thr Lys Thr
            340                 345                 350
Phe Thr Val Thr Glu Lys Pro Glu Val Ile Asp Ala Ser Glu Leu Thr
            355                 360                 365
Pro Ala Val Thr Thr Tyr Lys Leu Val Ile Asn Gly Lys Thr Leu Lys
            370                 375                 380
Gly Glu Thr Thr Thr Glu Ala Val Asp Ala Ala Thr Ala Glu Lys Val
385                 390                 395                 400
Phe Lys Gln Tyr Ala Asn Asp Asn Gly Val Asp Gly Glu Trp Thr Tyr
            405                 410                 415
Asp Asp Ala Thr Lys Thr Phe Thr Val Thr Glu Lys Pro Glu Val Ile
            420                 425                 430
Asp Ala Ser Glu Leu Thr Pro Ala Val Thr Thr Tyr Lys Leu Val Ile
            435                 440                 445
Asn Gly Lys Thr Leu Lys Gly Glu Thr Thr Thr Lys Ala Val Asp Ala
            450                 455                 460
Glu Thr Ala Glu Lys Ala Phe Lys Gln Tyr Ala Asn Asp Asn Gly Val
465                 470                 475                 480
Asp Gly Val Trp Thr Tyr Asp Asp Ala Thr Lys Thr Phe Thr Val Thr
            485                 490                 495
Glu Met Val Thr Glu Val Pro Gly Asp Ala Pro Thr Glu Pro Glu Lys
            500                 505                 510
Pro Glu Ala Ser Ile Pro Leu Val Pro Leu Thr Pro Ala Thr Pro Ile
            515                 520                 525
Ala Lys Asp Asp Ala Lys Lys Asp Asp Thr Lys Lys Glu Asp Ala Lys
            530                 535                 540
Lys Pro Glu Ala Lys Lys Glu Asp Ala Lys Lys Ala Glu Thr Leu Pro
545                 550                 555                 560
Thr Thr Gly Glu Gly Ser Asn Pro Phe Phe Thr Ala Ala Ala Leu Ala
            565                 570                 575
Val Met Ala Gly Ala Gly Ala Leu Ala Val Ala Ser Lys Arg Lys Glu
            580                 585                 590
Asp
```

```
<210> SEQ ID NO 60
<211> LENGTH: 10
<212> TYPE: PRT
<213> ORGANISM: Artificial sequence
<220> FEATURE: BINDING
<223> OTHER INFORMATION: Fc binding peptide known as SpA mimic 1

<400> SEQUENCE: 60

Thr Trp Lys Thr Ser Arg Ile Ser Ile Phe
1               5                   10

<210> SEQ ID NO 61
<211> LENGTH: 13
<212> TYPE: PRT
<213> ORGANISM: Artificial sequence
<220> FEATURE: BINDING
<223> OTHER INFORMATION: Fc binding peptide known as SpA mimic 2

<400> SEQUENCE: 61

Asp Cys Ala Trp His Leu Gly Glu Leu Val Trp Cys Thr
1               5                   10

<210> SEQ ID NO 62
<211> LENGTH: 10
<212> TYPE: PRT
<213> ORGANISM: Artificial sequence
<220> FEATURE: BINDING
<223> OTHER INFORMATION: Fc binding peptide known as SpA mimic 3

<400> SEQUENCE: 62

Phe Gly Arg Leu Val Ser Ser Ile Arg Tyr
1               5                   10

<210> SEQ ID NO 63
<211> LENGTH: 12
<212> TYPE: PRT
<213> ORGANISM: Artificial sequence
<220> FEATURE: BINDING
<223> OTHER INFORMATION: Fc binding peptide known as SpA mimic 4

<400> SEQUENCE: 63

Glu Pro Ile His Arg Ser Thr Leu Thr Ala Leu Leu
1               5                   10

<210> SEQ ID NO 64
<211> LENGTH: 6
<212> TYPE: PRT
<213> ORGANISM: Artificial sequence
<220> FEATURE: BINDING
<223> OTHER INFORMATION: Fc binding peptide known as SpA mimic 5

<400> SEQUENCE: 64

His Trp Arg Gly Trp Val
1               5

<210> SEQ ID NO 65
<211> LENGTH: 6
<212> TYPE: PRT
<213> ORGANISM: Artificial sequence
<220> FEATURE: BINDING
<223> OTHER INFORMATION: Fc binding peptide known as SpA mimic 6

<400> SEQUENCE: 65

His Tyr Phe Lys Phe Asp
1               5
```

```
<210> SEQ ID NO 66
<211> LENGTH: 6
<212> TYPE: PRT
<213> ORGANISM: Artificial sequence
<220> FEATURE: BINDING
<223> OTHER INFORMATION: Fc binding peptide known as SpA mimic 7

<400> SEQUENCE: 66

His Phe Arg Arg His Leu
1               5

<210> SEQ ID NO 67
<211> LENGTH: 8
<212> TYPE: PRT
<213> ORGANISM: Artificial sequence
<220> FEATURE: BINDING
<223> OTHER INFORMATION: Fc binding peptide known as Fcgamma mimic 1

<400> SEQUENCE: 67

Asn Lys Phe Arg Gly Lys Tyr Lys
1               5

<210> SEQ ID NO 68
<211> LENGTH: 8
<212> TYPE: PRT
<213> ORGANISM: Artificial sequence
<220> FEATURE: BINDING
<223> OTHER INFORMATION: Fc binding peptide known as Fcgamma mimic 2

<400> SEQUENCE: 68

Asn Ala Arg Lys Phe Tyr Lys Gly
1               5

<210> SEQ ID NO 69
<211> LENGTH: 8
<212> TYPE: PRT
<213> ORGANISM: Artificial sequence
<220> FEATURE: BINDING
<223> OTHER INFORMATION: Fc binding peptide known as SpA mimic 8

<400> SEQUENCE: 69

Phe Tyr Trp His Cys Leu Asp Glu
1               5

<210> SEQ ID NO 70
<211> LENGTH: 8
<212> TYPE: PRT
<213> ORGANISM: Artificial sequence
<220> FEATURE: BINDING
<223> OTHER INFORMATION: Fc binding peptide known as SpA mimic 9

<400> SEQUENCE: 70

Phe Tyr Cys His Trp Ala Leu Glu
1               5

<210> SEQ ID NO 71
<211> LENGTH: 8
<212> TYPE: PRT
<213> ORGANISM: Artificial sequence
<220> FEATURE: BINDING
<223> OTHER INFORMATION: Fc binding peptide known as SpA mimic 10

<400> SEQUENCE: 71

Phe Tyr Cys His Thr Ile Asp Glu
1               5

<210> SEQ ID NO 72
```

<211> LENGTH: 429
<212> TYPE: PRT
<213> ORGANISM: Artificial sequence
<220> FEATURE: BINDING
<223> OTHER INFORMATION: Fc binding polypeptide known as protein A/G

<400> SEQUENCE: 72

```
Asn Ala Ala Gln His Asp Glu Ala Gln Gln Asn Ala Phe Tyr Gln Val
1               5                   10                  15

Leu Asn Met Pro Asn Leu Asn Ala Asp Gln Arg Asn Gly Phe Ile Gln
            20                  25                  30

Ser Leu Lys Asp Asp Pro Ser Gln Ser Ala Asn Val Leu Gly Glu Ala
        35                  40                  45

Gln Lys Leu Asn Asp Ser Gln Ala Pro Lys Ala Asp Ala Gln Gln Asn
    50                  55                  60

Asn Phe Asn Lys Asp Gln Gln Ser Ala Phe Tyr Glu Ile Leu Asn Met
65                  70                  75                  80

Pro Asn Leu Asn Glu Ala Gln Arg Asn Gly Phe Ile Gln Ser Leu Lys
                85                  90                  95

Asp Asp Pro Ser Gln Ser Thr Asn Val Leu Gly Glu Ala Lys Lys Leu
            100                 105                 110

Asn Glu Ser Gln Ala Pro Lys Ala Asp Asn Asn Phe Asn Lys Glu Gln
        115                 120                 125

Gln Asn Ala Phe Tyr Glu Ile Leu Asn Met Pro Asn Leu Asn Glu Glu
    130                 135                 140

Gln Arg Asn Gly Phe Ile Gln Ser Leu Lys Asp Asp Pro Ser Gln Ser
145                 150                 155                 160

Ala Asn Leu Leu Ser Glu Ala Lys Lys Leu Asn Glu Ser Gln Ala Pro
                165                 170                 175

Lys Ala Asp Asn Lys Phe Asn Lys Glu Gln Gln Asn Ala Phe Tyr Glu
            180                 185                 190

Ile Leu His Leu Pro Asn Leu Asn Glu Glu Gln Arg Asn Gly Phe Ile
        195                 200                 205

Gln Ser Leu Lys Asp Asp Pro Ser Gln Ser Ala Asn Leu Leu Ala Glu
    210                 215                 220

Ala Lys Lys Leu Asn Asp Ala Gln Ala Pro Lys Ala Asp Asn Lys Phe
225                 230                 235                 240

Asn Lys Glu Gln Gln Asn Ala Phe Tyr Glu Ile Leu His Leu Pro Asn
                245                 250                 255

Leu Thr Glu Glu Gln Arg Asn Gly Phe Ile Gln Ser Leu Lys Asp Asp
            260                 265                 270

Pro Ser Val Ser Lys Glu Ile Leu Ala Glu Ala Lys Lys Leu Asn Asp
        275                 280                 285

Ala Gln Ala Pro Lys Glu Glu Asp Ser Leu Glu Gly Ser Gly Ser Gly
    290                 295                 300

Thr Tyr Lys Leu Ile Leu Asn Gly Lys Thr Leu Lys Gly Glu Thr Thr
305                 310                 315                 320

Thr Glu Ala Val Asp Ala Ala Thr Ala Glu Lys Val Phe Lys Gln Tyr
                325                 330                 335

Ala Asn Asp Asn Gly Val Asp Gly Glu Trp Thr Tyr Asp Asp Ala Thr
            340                 345                 350

Lys Thr Phe Thr Val Thr Glu Lys Pro Glu Val Ile Asp Ala Ser Glu
        355                 360                 365

Leu Thr Pro Ala Val Thr Thr Tyr Lys Leu Val Ile Asn Gly Lys Thr
    370                 375                 380
```

```
Leu Lys Gly Glu Thr Thr Thr Lys Ala Val Asp Ala Glu Thr Ala Glu
385                 390                 395                 400

Lys Ala Phe Lys Gln Tyr Ala Asn Asp Asn Gly Val Asp Gly Val Trp
            405                 410                 415

Thr Tyr Asp Asp Ala Thr Lys Thr Phe Thr Val Thr Glu
            420                 425
```

<210> SEQ ID NO 73
<211> LENGTH: 57
<212> TYPE: PRT
<213> ORGANISM: Artificial sequence
<220> FEATURE: BINDING
<223> OTHER INFORMATION: Fc binding polypeptide known as Z domain

<400> SEQUENCE: 73

```
Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Ala Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys
    50                  55
```

<210> SEQ ID NO 74
<211> LENGTH: 114
<212> TYPE: PRT
<213> ORGANISM: Artificial sequence
<220> FEATURE: BINDING
<223> OTHER INFORMATION: Fc binding polypeptide known as ZZ domain

<400> SEQUENCE: 74

```
Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Ala Phe Ile Gln Ser
            20                  25                  30

Leu Lys Asp Asp Pro Ser Gln Ser Ala Asn Leu Leu Ala Glu Ala Lys
        35                  40                  45

Lys Leu Asn Asp Ala Gln Ala Pro Lys Asp Asn Lys Phe Asn Lys Glu
    50                  55                  60

Gln Gln Asn Ala Phe Tyr Glu Ile Leu His Leu Pro Asn Leu Asn Glu
65                  70                  75                  80

Glu Gln Arg Asn Ala Phe Ile Gln Ser Leu Lys Asp Asp Pro Ser Gln
                85                  90                  95

Ser Ala Asn Leu Leu Ala Glu Ala Lys Lys Leu Asn Asp Ala Gln Ala
            100                 105                 110

Pro Lys
```

<210> SEQ ID NO 75
<211> LENGTH: 665
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 75

```
Met Gly Val Glu Gly Cys Thr Lys Cys Ile Lys Tyr Leu Leu Phe Val
1               5                   10                  15
```

Phe Asn Phe Val Phe Trp Leu Ala Gly Gly Val Ile Leu Gly Val Ala
                20                  25                  30

Leu Trp Leu Arg His Asp Pro Gln Thr Thr Asn Leu Leu Tyr Leu Glu
        35                  40                  45

Leu Gly Asp Lys Pro Ala Pro Asn Thr Phe Tyr Val Gly Ile Tyr Ile
    50                  55                  60

Leu Ile Ala Val Gly Ala Val Met Met Phe Val Gly Phe Leu Gly Cys
65                  70                  75                  80

Tyr Gly Ala Ile Gln Glu Ser Gln Cys Leu Leu Gly Thr Phe Phe Thr
                85                  90                  95

Cys Leu Val Ile Leu Phe Ala Cys Glu Val Ala Ala Gly Ile Trp Gly
                100                 105                 110

Phe Val Asn Lys Asp Gln Ile Ala Lys Asp Val Lys Gln Phe Tyr Asp
            115                 120                 125

Gln Ala Leu Gln Gln Ala Val Val Asp Asp Asp Ala Asn Asn Ala Lys
            130                 135                 140

Ala Val Val Lys Thr Phe His Glu Thr Leu Asp Cys Cys Gly Ser Ser
145                 150                 155                 160

Thr Leu Thr Ala Leu Thr Thr Ser Asn Ala Ala Gln His Asp Glu Ala
                165                 170                 175

Gln Gln Asn Ala Phe Tyr Gln Val Leu Asn Met Pro Asn Leu Asn Ala
            180                 185                 190

Asp Gln Arg Asn Gly Phe Ile Gln Ser Leu Lys Asp Asp Pro Ser Gln
            195                 200                 205

Ser Ala Asn Val Leu Gly Glu Ala Gln Lys Leu Asn Asp Ser Gln Ala
    210                 215                 220

Pro Lys Ala Asp Ala Gln Gln Asn Asn Phe Asn Lys Asp Gln Gln Ser
225                 230                 235                 240

Ala Phe Tyr Glu Ile Leu Asn Met Pro Asn Leu Asn Glu Ala Gln Arg
                245                 250                 255

Asn Gly Phe Ile Gln Ser Leu Lys Asp Asp Pro Ser Gln Ser Thr Asn
            260                 265                 270

Val Leu Gly Glu Ala Lys Lys Leu Asn Glu Ser Gln Ala Pro Lys Ala
    275                 280                 285

Asp Asn Asn Phe Asn Lys Glu Gln Gln Asn Ala Phe Tyr Glu Ile Leu
290                 295                 300

Asn Met Pro Asn Leu Asn Glu Glu Gln Arg Asn Gly Phe Ile Gln Ser
305                 310                 315                 320

Leu Lys Asp Asp Pro Ser Gln Ser Ala Asn Leu Leu Ser Glu Ala Lys
            325                 330                 335

Lys Leu Asn Glu Ser Gln Ala Pro Lys Ala Asp Asn Lys Phe Asn Lys
        340                 345                 350

Glu Gln Gln Asn Ala Phe Tyr Glu Ile Leu His Leu Pro Asn Leu Asn
        355                 360                 365

Glu Glu Gln Arg Asn Gly Phe Ile Gln Ser Leu Lys Asp Asp Pro Ser
    370                 375                 380

Gln Ser Ala Asn Leu Leu Ala Glu Ala Lys Lys Leu Asn Asp Ala Gln
385                 390                 395                 400

Ala Pro Lys Ala Asp Asn Lys Phe Asn Lys Glu Gln Gln Asn Ala Phe
                405                 410                 415

Tyr Glu Ile Leu His Leu Pro Asn Leu Thr Glu Glu Gln Arg Asn Gly
            420                 425                 430

Phe Ile Gln Ser Leu Lys Asp Asp Pro Ser Val Ser Lys Glu Ile Leu

```
                435                 440                 445
Ala Glu Ala Lys Lys Leu Asn Asp Ala Gln Ala Pro Lys Glu Glu Asp
        450                 455                 460

Ser Leu Glu Gly Ser Gly Ser Gly Thr Tyr Lys Leu Ile Leu Asn Gly
465                 470                 475                 480

Lys Thr Leu Lys Gly Glu Thr Thr Thr Glu Ala Val Asp Ala Ala Thr
                485                 490                 495

Ala Glu Lys Val Phe Lys Gln Tyr Ala Asn Asp Asn Gly Val Asp Gly
                500                 505                 510

Glu Trp Thr Tyr Asp Asp Ala Thr Lys Thr Phe Thr Val Thr Glu Lys
                515                 520                 525

Pro Glu Val Ile Asp Ala Ser Glu Leu Thr Pro Ala Val Thr Thr Tyr
        530                 535                 540

Lys Leu Val Ile Asn Gly Lys Thr Leu Lys Gly Glu Thr Thr Thr Lys
545                 550                 555                 560

Ala Val Asp Ala Glu Thr Ala Glu Lys Ala Phe Lys Gln Tyr Ala Asn
                565                 570                 575

Asp Asn Gly Val Asp Gly Val Trp Thr Tyr Asp Asp Ala Thr Lys Thr
            580                 585                 590

Phe Thr Val Thr Glu Val Leu Lys Asn Asn Leu Cys Pro Ser Gly Ser
            595                 600                 605

Asn Ile Ile Ser Asn Leu Phe Lys Glu Asp Cys His Gln Lys Ile Asp
        610                 615                 620

Asp Leu Phe Ser Gly Lys Leu Tyr Leu Ile Gly Ile Ala Ala Ile Val
625                 630                 635                 640

Val Ala Val Ile Met Ile Phe Glu Met Ile Leu Ser Met Val Leu Cys
                645                 650                 655

Cys Gly Ile Arg Asn Ser Ser Val Tyr
                660                 665

<210> SEQ ID NO 76
<211> LENGTH: 342
<212> TYPE: PRT
<213> ORGANISM: Artificial sequence
<220> FEATURE:
<223> OTHER INFORMATION: Artificial sequence comprising at least one
      exosomal polypeptide and at least one Fc binding polypeptide

<400> SEQUENCE: 76

Met Pro Val Lys Gly Gly Thr Lys Cys Ile Lys Tyr Leu Leu Phe Gly
1               5                   10                  15

Phe Asn Phe Ile Phe Trp Leu Ala Gly Ile Ala Val Leu Ala Ile Gly
                20                  25                  30

Leu Trp Leu Arg Phe Asp Ser Gln Thr Lys Ser Ile Phe Glu Gln Glu
            35                  40                  45

Thr Asn Asn Asn Asn Ser Ser Phe Tyr Thr Gly Val Tyr Ile Leu Ile
        50                  55                  60

Gly Ala Gly Ala Leu Met Met Leu Val Gly Phe Leu Gly Cys Cys Gly
65                  70                  75                  80

Ala Val Gln Glu Ser Gln Cys Met Leu Gly Leu Phe Phe Gly Phe Leu
                85                  90                  95

Leu Val Ile Phe Ala Ile Glu Ile Ala Ala Ala Ile Trp Gly Tyr Ser
                100                 105                 110

His Lys Asp Glu Val Ile Lys Glu Val Gln Glu Phe Tyr Lys Asp Thr
            115                 120                 125
```

```
Tyr Asn Lys Leu Lys Thr Lys Asp Glu Pro Gln Arg Glu Thr Leu Lys
130                 135                 140

Ala Ile His Tyr Ala Leu Asn Cys Cys Gly Leu Ala Gly Gly Val Glu
145                 150                 155                 160

Gln Phe Ile Ser Asp Asp Asn Lys Phe Asn Lys Glu Gln Gln Asn Ala
                165                 170                 175

Phe Tyr Glu Ile Leu His Leu Pro Asn Leu Asn Glu Glu Gln Arg Asn
                180                 185                 190

Ala Phe Ile Gln Ser Leu Lys Asp Asp Pro Ser Gln Ser Ala Asn Leu
                195                 200                 205

Leu Ala Glu Ala Lys Lys Leu Asn Asp Ala Gln Ala Pro Lys Asp Asn
210                 215                 220

Lys Phe Asn Lys Glu Gln Gln Asn Ala Phe Tyr Glu Ile Leu His Leu
225                 230                 235                 240

Pro Asn Leu Asn Glu Glu Gln Arg Asn Ala Phe Ile Gln Ser Leu Lys
                245                 250                 255

Asp Asp Pro Ser Gln Ser Ala Asn Leu Leu Ala Glu Ala Lys Lys Leu
                260                 265                 270

Asn Asp Ala Gln Ala Pro Lys Ile Cys Pro Lys Lys Asp Val Leu Glu
                275                 280                 285

Thr Phe Thr Val Lys Ser Cys Pro Asp Ala Ile Lys Glu Val Phe Asp
290                 295                 300

Asn Lys Phe His Ile Ile Gly Ala Val Gly Ile Gly Ile Ala Val Val
305                 310                 315                 320

Met Ile Phe Gly Met Ile Phe Ser Met Ile Leu Cys Cys Ala Ile Arg
                325                 330                 335

Arg Asn Arg Glu Met Val
                340

<210> SEQ ID NO 77
<211> LENGTH: 296
<212> TYPE: PRT
<213> ORGANISM: Staphylococcus aureus

<400> SEQUENCE: 77

Asn Ala Ala Gln His Asp Glu Ala Gln Gln Asn Ala Phe Tyr Gln Val
1               5                   10                  15

Leu Asn Met Pro Asn Leu Asn Ala Asp Gln Arg Asn Gly Phe Ile Gln
                20                  25                  30

Ser Leu Lys Asp Asp Pro Ser Gln Ser Ala Asn Val Leu Gly Glu Ala
                35                  40                  45

Gln Lys Leu Asn Asp Ser Gln Ala Pro Lys Ala Asp Ala Gln Gln Asn
50                  55                  60

Asn Phe Asn Lys Asp Gln Ser Ala Phe Tyr Glu Ile Leu Asn Met
65                  70                  75                  80

Pro Asn Leu Asn Glu Ala Gln Arg Asn Gly Phe Ile Gln Ser Leu Lys
                85                  90                  95

Asp Asp Pro Ser Gln Ser Thr Asn Val Leu Gly Glu Ala Lys Lys Leu
                100                 105                 110

Asn Glu Ser Gln Ala Pro Lys Ala Asp Asn Phe Asn Lys Glu Gln
                115                 120                 125

Gln Asn Ala Phe Tyr Glu Ile Leu Asn Met Pro Asn Leu Asn Glu Glu
                130                 135                 140

Gln Arg Asn Gly Phe Ile Gln Ser Leu Lys Asp Asp Pro Ser Gln Ser
145                 150                 155                 160
```

```
Ala Asn Leu Leu Ser Glu Ala Lys Lys Leu Asn Glu Ser Gln Ala Pro
                165                 170                 175

Lys Ala Asp Asn Lys Phe Asn Lys Glu Gln Gln Asn Ala Phe Tyr Glu
            180                 185                 190

Ile Leu His Leu Pro Asn Leu Asn Glu Glu Gln Arg Asn Gly Phe Ile
        195                 200                 205

Gln Ser Leu Lys Asp Asp Pro Ser Gln Ser Ala Asn Leu Leu Ala Glu
    210                 215                 220

Ala Lys Lys Leu Asn Asp Ala Gln Ala Pro Lys Ala Asp Asn Lys Phe
225                 230                 235                 240

Asn Lys Glu Gln Gln Asn Ala Phe Tyr Glu Ile Leu His Leu Pro Asn
                245                 250                 255

Leu Thr Glu Glu Gln Arg Asn Gly Phe Ile Gln Ser Leu Lys Asp Asp
            260                 265                 270

Pro Ser Val Ser Lys Glu Ile Leu Ala Glu Ala Lys Lys Leu Asn Asp
        275                 280                 285

Ala Gln Ala Pro Lys Glu Glu Asp
    290                 295

<210> SEQ ID NO 78
<211> LENGTH: 125
<212> TYPE: PRT
<213> ORGANISM: Streptococcus dysgalactiae

<400> SEQUENCE: 78

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu Lys Pro Glu Val Ile Asp Ala Ser Glu
    50                  55                  60

Leu Thr Pro Ala Val Thr Thr Tyr Lys Leu Val Ile Asn Gly Lys Thr
65                  70                  75                  80

Leu Lys Gly Glu Thr Thr Thr Lys Ala Val Asp Ala Glu Thr Ala Glu
                85                  90                  95

Lys Ala Phe Lys Gln Tyr Ala Asn Asp Asn Gly Val Asp Gly Val Trp
            100                 105                 110

Thr Tyr Asp Asp Ala Thr Lys Thr Phe Thr Val Thr Glu
        115                 120                 125

<210> SEQ ID NO 79
<211> LENGTH: 404
<212> TYPE: PRT
<213> ORGANISM: Mus musculus

<400> SEQUENCE: 79

Met Ile Leu Thr Ser Phe Gly Asp Asp Met Trp Leu Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60
```

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
            115                 120                 125

Pro Leu Ala Leu Arg Cys His Gly Trp Lys Asn Lys Leu Val Tyr Asn
130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175

Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
            195                 200                 205

Ser Pro Phe Pro Glu Gly Ser Leu Val Thr Leu Asn Cys Glu Thr Asn
210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu Leu Gln
            275                 280                 285

Val Leu Gly Pro Gln Ser Ser Ala Pro Val Trp Phe His Ile Leu Phe
290                 295                 300

Tyr Leu Ser Val Gly Ile Met Phe Ser Leu Asn Thr Val Leu Tyr Val
305                 310                 315                 320

Lys Ile His Arg Leu Gln Arg Glu Lys Lys Tyr Asn Leu Glu Val Pro
                325                 330                 335

Leu Val Ser Glu Gln Gly Lys Lys Ala Asn Ser Phe Gln Gln Val Arg
            340                 345                 350

Ser Asp Gly Val Tyr Glu Glu Val Thr Ala Thr Ala Ser Gln Thr Thr
            355                 360                 365

Pro Lys Glu Ala Pro Asp Gly Pro Arg Ser Ser Val Gly Asp Cys Gly
370                 375                 380

Pro Glu Gln Pro Glu Pro Leu Pro Pro Ser Asp Ser Thr Gly Ala Gln
385                 390                 395                 400

Thr Ser Gln Ser

<210> SEQ ID NO 80
<211> LENGTH: 330
<212> TYPE: PRT
<213> ORGANISM: Mus musculus

<400> SEQUENCE: 80

Met Glu Ser Asn Trp Thr Val His Val Phe Ser Arg Thr Leu Cys His
1               5                   10                  15

Met Leu Leu Trp Thr Ala Val Leu Asn Leu Ala Ala Gly Thr His Asp
            20                  25                  30

Leu Pro Lys Ala Val Val Lys Leu Glu Pro Pro Trp Ile Gln Val Leu
                35                  40                  45

Lys Glu Asp Thr Val Thr Leu Thr Cys Glu Gly Thr His Asn Pro Gly
 50                  55                  60

Asn Ser Ser Thr Gln Trp Phe His Asn Gly Arg Ser Ile Arg Ser Gln
 65                  70                  75                  80

Val Gln Ala Ser Tyr Thr Phe Lys Ala Thr Val Asn Asp Ser Gly Glu
                 85                  90                  95

Tyr Arg Cys Gln Met Glu Gln Thr Arg Leu Ser Asp Pro Val Asp Leu
                100                 105                 110

Gly Val Ile Ser Asp Trp Leu Leu Leu Gln Thr Pro Gln Leu Val Phe
                115                 120                 125

Leu Glu Gly Glu Thr Ile Thr Leu Arg Cys His Ser Trp Arg Asn Lys
130                 135                 140

Leu Leu Asn Arg Ile Ser Phe Phe His Asn Glu Lys Ser Val Arg Tyr
145                 150                 155                 160

His His Tyr Ser Ser Asn Phe Ser Ile Pro Lys Ala Asn His Ser His
                165                 170                 175

Ser Gly Asp Tyr Tyr Cys Lys Gly Ser Leu Gly Arg Thr Leu His Gln
                180                 185                 190

Ser Lys Pro Val Thr Ile Thr Val Gln Gly Pro Lys Ser Ser Arg Ser
                195                 200                 205

Leu Pro Val Leu Thr Ile Val Ala Ala Val Thr Gly Ile Ala Val Ala
                210                 215                 220

Ala Ile Val Ile Ile Leu Val Ser Leu Val Tyr Leu Lys Lys Lys Gln
225                 230                 235                 240

Val Pro Ala Leu Pro Gly Asn Pro Asp His Arg Glu Met Gly Glu Thr
                245                 250                 255

Leu Pro Glu Glu Val Gly Glu Tyr Arg Gln Pro Ser Gly Gly Ser Val
                260                 265                 270

Pro Val Ser Pro Gly Pro Pro Ser Gly Leu Glu Pro Thr Ser Ser Ser
                275                 280                 285

Pro Tyr Asn Pro Pro Asp Leu Glu Glu Ala Ala Lys Thr Glu Ala Glu
                290                 295                 300

Asn Thr Ile Thr Tyr Ser Leu Leu Lys His Pro Glu Ala Leu Asp Glu
305                 310                 315                 320

Glu Thr Glu His Asp Tyr Gln Asn His Ile
                325                 330

<210> SEQ ID NO 81
<211> LENGTH: 261
<212> TYPE: PRT
<213> ORGANISM: Mus musculus

<400> SEQUENCE: 81

Met Phe Gln Asn Ala His Ser Gly Ser Gln Trp Leu Leu Pro Pro Leu
 1               5                  10                  15

Thr Ile Leu Leu Leu Phe Ala Phe Ala Asp Arg Gln Ser Ala Ala Leu
                20                  25                  30

Pro Lys Ala Val Val Lys Leu Asp Pro Pro Trp Ile Gln Val Leu Lys
                35                  40                  45

Glu Asp Met Val Thr Leu Met Cys Glu Gly Thr His Asn Pro Gly Asn
 50                  55                  60

Ser Ser Thr Gln Trp Phe His Asn Gly Arg Ser Ile Arg Ser Gln Val

```
                65                  70                  75                  80
        Gln Ala Ser Tyr Thr Phe Lys Ala Thr Val Asn Asp Ser Gly Glu Tyr
                        85                  90                  95
        Arg Cys Gln Met Glu Gln Thr Arg Leu Ser Asp Pro Val Asp Leu Gly
                        100                 105                 110
        Val Ile Ser Asp Trp Leu Leu Leu Gln Thr Pro Gln Arg Val Phe Leu
                        115                 120                 125
        Glu Gly Glu Thr Ile Thr Leu Arg Cys His Ser Trp Arg Asn Lys Leu
                        130                 135                 140
        Leu Asn Arg Ile Ser Phe Phe His Asn Glu Lys Ser Val Arg Tyr His
        145                 150                 155                 160
        His Tyr Lys Ser Asn Phe Ser Ile Pro Lys Ala Asn His Ser His Ser
                        165                 170                 175
        Gly Asp Tyr Tyr Cys Lys Gly Ser Leu Gly Ser Thr Gln His Gln Ser
                        180                 185                 190
        Lys Pro Val Thr Ile Thr Val Gln Asp Pro Ala Thr Thr Ser Ser Ile
                        195                 200                 205
        Ser Leu Val Trp Tyr His Thr Ala Phe Ser Leu Val Met Cys Leu Leu
                        210                 215                 220
        Phe Ala Val Asp Thr Gly Leu Tyr Phe Tyr Val Arg Arg Asn Leu Gln
        225                 230                 235                 240
        Thr Pro Arg Glu Tyr Trp Arg Lys Ser Leu Ser Ile Arg Lys His Gln
                        245                 250                 255
        Ala Pro Gln Asp Lys
                        260

<210> SEQ ID NO 82
<211> LENGTH: 249
<212> TYPE: PRT
<213> ORGANISM: Mus musculus

<400> SEQUENCE: 82

Met Trp Gln Leu Leu Leu Pro Thr Ala Leu Leu Thr Ala Phe Ser
        1               5                   10                  15
        Gly Ile Gln Ala Gly Leu Gln Lys Ala Val Val Asn Leu Asp Pro Lys
                        20                  25                  30
        Trp Val Arg Val Leu Glu Glu Asp Ser Val Thr Leu Arg Cys Gln Gly
                        35                  40                  45
        Thr Phe Ser Pro Glu Asp Asn Ser Ile Lys Trp Phe His Asn Glu Ser
                        50                  55                  60
        Leu Ile Pro His Gln Asp Ala Asn Tyr Val Ile Gln Ser Ala Arg Val
        65                  70                  75                  80
        Lys Asp Ser Gly Met Tyr Arg Cys Gln Thr Ala Leu Ser Thr Ile Ser
                        85                  90                  95
        Asp Pro Val Gln Leu Glu Val His Met Gly Trp Leu Leu Leu Gln Thr
                        100                 105                 110
        Thr Lys Trp Leu Phe Gln Glu Gly Asp Pro Ile His Leu Arg Cys His
                        115                 120                 125
        Ser Trp Gln Asn Arg Pro Val Arg Lys Val Thr Tyr Leu Gln Asn Gly
                        130                 135                 140
        Lys Gly Lys Lys Tyr Phe His Glu Asn Ser Glu Leu Leu Ile Pro Lys
        145                 150                 155                 160
        Ala Thr His Asn Asp Ser Gly Ser Tyr Phe Cys Arg Gly Leu Ile Gly
                        165                 170                 175
```

His Asn Asn Lys Ser Ser Ala Ser Phe Arg Ile Ser Leu Gly Asp Pro
                180                 185                 190

Gly Ser Pro Ser Met Phe Pro Pro Trp His Gln Ile Thr Phe Cys Leu
            195                 200                 205

Leu Ile Gly Leu Leu Phe Ala Ile Asp Thr Val Leu Tyr Phe Ser Val
        210                 215                 220

Arg Arg Gly Leu Gln Ser Pro Val Ala Asp Tyr Glu Glu Pro Lys Ile
225                 230                 235                 240

Gln Trp Ser Lys Glu Pro Gln Asp Lys
                245

<210> SEQ ID NO 83
<211> LENGTH: 365
<212> TYPE: PRT
<213> ORGANISM: Mus musculus

<400> SEQUENCE: 83

Met Gly Met Pro Leu Pro Trp Ala Leu Ser Leu Leu Val Leu Leu
1               5                   10                  15

Pro Gln Thr Trp Gly Ser Glu Thr Arg Pro Pro Leu Met Tyr His Leu
            20                  25                  30

Thr Ala Val Ser Asn Pro Ser Thr Gly Leu Pro Ser Phe Trp Ala Thr
        35                  40                  45

Gly Trp Leu Gly Pro Gln Gln Tyr Leu Thr Tyr Asn Ser Leu Arg Gln
    50                  55                  60

Glu Ala Asp Pro Cys Gly Ala Trp Met Trp Glu Asn Gln Val Ser Trp
65                  70                  75                  80

Tyr Trp Glu Lys Glu Thr Thr Asp Leu Lys Ser Lys Glu Gln Leu Phe
                85                  90                  95

Leu Glu Ala Leu Lys Thr Leu Glu Lys Ile Leu Asn Gly Thr Tyr Thr
            100                 105                 110

Leu Gln Gly Leu Leu Gly Cys Glu Leu Ala Ser Asp Asn Ser Ser Val
        115                 120                 125

Pro Thr Ala Val Phe Ala Leu Asn Gly Glu Glu Phe Met Lys Phe Asn
130                 135                 140

Pro Arg Ile Gly Asn Trp Thr Gly Glu Trp Pro Glu Thr Glu Ile Val
145                 150                 155                 160

Ala Asn Leu Trp Met Lys Gln Pro Asp Ala Ala Arg Lys Glu Ser Glu
                165                 170                 175

Phe Leu Leu Asn Ser Cys Pro Glu Arg Leu Leu Gly His Leu Glu Arg
            180                 185                 190

Gly Arg Arg Asn Leu Glu Trp Lys Glu Pro Pro Ser Met Arg Leu Lys
        195                 200                 205

Ala Arg Pro Gly Asn Ser Gly Ser Ser Val Leu Thr Cys Ala Ala Phe
210                 215                 220

Ser Phe Tyr Pro Pro Glu Leu Lys Phe Arg Phe Leu Arg Asn Gly Leu
225                 230                 235                 240

Ala Ser Gly Ser Gly Asn Cys Ser Thr Gly Pro Asn Gly Asp Gly Ser
                245                 250                 255

Phe His Ala Trp Ser Leu Leu Glu Val Lys Arg Gly Asp Glu His His
            260                 265                 270

Tyr Gln Cys Gln Val Glu His Glu Gly Leu Ala Gln Pro Leu Thr Val
        275                 280                 285

Asp Leu Asp Ser Ser Ala Arg Ser Ser Val Pro Val Val Gly Ile Val
290                 295                 300

-continued

```
Leu Gly Leu Leu Leu Val Val Ala Ile Ala Gly Gly Val Leu Leu
305                 310             315                 320

Trp Gly Arg Met Arg Ser Gly Leu Pro Ala Pro Trp Leu Ser Leu Ser
            325                 330                 335

Gly Asp Asp Ser Gly Asp Leu Leu Pro Gly Gly Asn Leu Pro Pro Glu
            340                 345                 350

Ala Glu Pro Gln Gly Ala Asn Ala Phe Pro Ala Thr Ser
        355             360             365
```

EXTRACELLULAR VESICLE COMPRISING A FUSION PROTEIN HAVING FC BINDING CAPACITY

RELATED APPLICATIONS

This application is a U.S. National Phase Application, filed under 35 U.S.C. § 371, of International PCT Application No. PCT/EP2017/068476, filed Jul. 21, 2017, which claims the priority benefit of GB 1612643.5, filed Jul. 21, 2016, the contents of each of which are herein incorporated by reference in their entirety.

INCORPORATION-BY-REFERENCE OF SEQUENCE LISTING

The contents of the file named "EVOX-006_N01 US SeqListing_ST25", which was created on Jan. 16, 2019, and is 313 KB in size are hereby incorporated by reference in their entirety.

TECHNICAL FIELD

The present invention pertains to extracellular vesicle (EV) therapeutics, wherein the EVs are coated with proteins comprising Fc domains (such as antibodies) for i.a. targeting and therapeutic applications.

BACKGROUND ART

Protein biologics are routinely used in the treatment and/or prevention of a wide range of diseases, including cancer, genetic disorders and autoimmune diseases. Antibodies and chimeric receptors, among which many of today's blockbuster drugs can be found, are typically administered in naked form, i.e. without any delivery vehicles. Extracellular vesicles (EVs) are nano-sized vesicles that are released by EV-producing cells into the extracellular environment. EVs and in particular exosomes have been shown to be able to transport protein biologics, such as antibodies and decoy receptors, into target cells, enabling an entirely novel form of advanced biological therapeutics harnessing the properties of EVs in combination with the specificity of recombinant proteins.

The use of EVs to deliver protein therapeutics provides a number of advantages over conventional direct administration of biologics. For example, when biotherapeutics are delivered using EVs they are protected from degradation and are more stable; EVs constitute a multivalent drug delivery modality which may lead to enhanced efficacy; EVs may improve the pharmacokinetics and the pharmacodynamics of a protein biologic; EVs can be targeted to tissues and cells of interest; EVs may have inherent therapeutic effects reflecting their cellular origin; and, EVs also enable penetration of the blood-brain-barrier and improved CNS delivery.

Despite all their advantages, loading of large and complex protein biologics into EVs for subsequent delivery to a target cell has not proved entirely straightforward. WO2013/084000 and WO2014/168548 both describe successful loading of protein-based biologics (such as antibodies and decoy receptors) into and onto EVs. WO2013/084000 discloses both so called endogenous and exogenous loading of for instance antibodies into EVs such as exosomes. Exogenous loading refers to loading of EVs via introduction of a protein cargo molecule directly into EVs after their isolation from an EV-producing cell in culture. Exogenous introduction of a protein may be carried out, as in WO2013/084000, using for instance electroporation or transfection of the polypeptide of interest post isolation from the parental cell. Endogenous loading on the other hand involves, as taught for instance by WO2014/168548, transfecting an EV-producing cell with a polynucleotide construct which encodes the therapeutic protein of interest. WO2015/058148 teaches an example of endogenous loading of proteins of interest, namely genetic engineering of NK cells with construct encoding for Fc receptors such as CD64, CD32 and CD16. However, genetic modification of e.g. NK cells to express Fc receptors is not a particularly effective way of loading proteins of interest, as it will only result in a low number of Fc receptors per EV. Thus, the approach taught by WO2015/058148 does not at all address the challenges associated with efficient loading of EVs with multiple large and complex protein biologics, especially in a controllable, predictable, scalable, and cost-efficient manner.

SUMMARY OF THE INVENTION

It is hence an object of the present invention to overcome the above-identified problems associated with the loading of EVs with protein biologics, and especially loading of antibodies and other proteins comprising Fc domains, for subsequent therapeutic application. Furthermore, the present invention aims to satisfy other existing needs within the art, for instance to enable high-affinity and high-density coating of EVs with a substantial plurality of therapeutic, targeting, or anti-clearance antibodies and other proteins comprising Fc domains (either naturally or as a result of protein engineering), to considerably enhance the therapeutic potential of EVs for therapeutic protein delivery.

The present invention achieves these and other objectives by utilizing fusion constructs comprising exosomal proteins fused to Fc binding polypeptides (herein often referred to as Fc binders) of human and/or non-human origin. The use of exosomal proteins as modalities for loading of EVs enables displaying a large number of Fc binders on the surface of EVs, which is important in order to be able to densely coat the EVs with proteins comprising Fc domains (herein often referred to as Fc containing proteins), which are bound to the EV via interaction between the Fc binders and the proteins comprising Fc domains (such Fc containing proteins may in advantageous embodiments be antibodies). Fc domains of human and/or mammalian origin that may be fused onto proteins natively lacking Fc domains may be selected from the following non-limiting list of alternatives: human IGHM (as a non-limiting example the accession number P01871), human IGHA1 (as a non-limiting example the accession number P01876), human IGHA2 (as a non-limiting example the accession number P01877), human IGKC (as a non-limiting example the accession number P01834), human IGHG1 (as a non-limiting example the accession number P01857), human IGHG2 (as a non-limiting example the accession number P01859), human IGHG3 (as a non-limiting example the accession number P01860), human IGHG4 (as a non-limiting example the accession number P01861), human IGHD (as a non-limiting example the accession number P01880), human IGHE (as a non-limiting example the accession number P01854), and any domains, derivatives, or combinations thereof. The use of non-human Fc binding polypeptides such as Protein A/G and the so called Z domain and the dimeric ZZ domain may result in higher binding affinity between the Fc binder and its interaction partner(s), i.e. the Fc domains of an Fc containing protein. Furthermore, non-human Fc binders are often smaller in size than human Fc binding proteins. On the other hand, Fc binding proteins and polypeptide domains of human and/or mammal origin, such as human FCGRI (CD64) (as a non-limiting example the SEQ ID NO 31), FCGR2A (CD32A) (as a non-limiting example the accession number P12318), FCGR2B (CD32B) (as a non-limiting example the accession number P31994), FCGR2C (CD32C) (as a non-limiting example the accession number P31995), FCGR3A (CD16A) (as a non-limiting example the accession number P0837), FCGR3B (CD16B) (as a non-limiting example the accession number O75015), FCAMR (as a non-limiting example the SEQ ID NO 28), FCERA (as a non-limiting example the SEQ ID NO 30), FCAR (as a non-limiting example the SEQ ID NO 29), or mouse FCGRI (as a non-limiting example the SEQ ID NO 79), FCGRIIB (as a non-limiting example the SEQ ID NO 80), FCGRIII (as a non-limiting example the SEQ ID NO 81), FCGRIV (as a non-limiting example the SEQ ID NO 82), FCGRn (as a non-limiting example the SEQ ID NO 83), may offer advantages as they are mammal proteins and as such may be less immunostimulatory. Regardless, it is key to engineer the EVs so as to ensure that they comprise fusion constructs of the Fc binding polypeptides as opposed to merely overexpressed proteins that bind to Fc domains, in order to ensure adequate numbers of Fc binding polypeptides being displayed on EVs and to enable controllable production.

Furthermore, the Fc binder polypeptides of the present invention may be engineered to be smaller than natively expressed Fc binding proteins, which makes it easier to direct them to EV surfaces with the aid of fusion constructs with EV proteins. Moreover, one significant difference between non-human Fc binders (which may be e.g. bacterial in origin) and human Fc binders is the fact that such non-human Fc binders can in certain instances simultaneously bind more than one Fc domain, which may lead to increased surface coating of the EVs with the protein of interest comprising an Fc domain. For instance, Protein A/G, which is a fusion protein between Protein A derived from *Staphylococcus* aureus and from *Streptococcus dysgalactiae*, has seven binding regions for the Fc domain of IgG antibodies. This multivalency can lead to multiple proteins comprising Fc domains, such as antibodies, being bound to each Fc binder (in this case Protein A/G), enabling denser coating of the EVs with Fc domain-containing proteins, such as antibodies. The denser coating of the EVs with the Fc binders importantly may also enable e.g. a higher avidity between e.g. antibodies and their corresponding antigens, meaning that the binding to the target of interest will be enhanced, which may be beneficial from a targeting and/or therapeutic standpoint.

In one aspect, the present invention relates to EVs comprising fusion proteins, wherein the fusion proteins comprise at least one polypeptide-based Fc binder fused to an exosomal polypeptide. As a result of the fusion with the EV protein, the Fc binders are efficiently displayed in high numbers on the surface of EVs, enabling dense coating of EVs with Fc domain-containing proteins such as antibodies. Coating of EVs with antibodies and other proteins comprising Fc domains (naturally or as a result of molecular biology engineering) is advantageous for several reasons: (1) antibodies or other proteins targeting a specific cell types, tissue, and/or organs represent a highly useful approach to re-directing distribution and optimizing delivery of EV-based therapeutics, (2) therapeutic antibodies or other Fc domain-containing proteins that interact with a target antigen of interest can be efficiently delivered to tissues of interest using EVs (for instance to the CNS or to the brain), (3) multiplexed antibodies or other Fc domain-containing proteins on the surface of EVs may be significantly better at binding targets, such as target antigens, (4) EVs are an advantageous modality for delivery of antibody-drug conjugates (ADCs) or receptor-drug conjugates, as multiplexing of ADCs may significantly enhance their therapeutic efficacy and their presence on EVs means they can also enter target cells, (5) EVs comprising Fc binders facilitate cellular internalization of Fc domain-containing proteins, such as antibodies, ADCs or essentially any protein comprising an Fc domain, either naturally or as a result of engineering, and (6) coating of EVs with antibodies or Fc domain-containing proteins may reduce opsonization and/or immune-mediated clearance of EVs, which may in turn be important for their therapeutic activity.

In another aspect, the present invention relates to complexes between fusion proteins as per the present invention and Fc domain-containing proteins (such as antibodies and virtually any biopharmaceutical to which an Fc domain can be fused, e.g. an intracellularly active enzyme such as NPC1 or the nuclease Cas9). As above-mentioned the fusion protein comprises an Fc-binding polypeptide fused to an exosomal polypeptide, and the Fc binder binds to the Fc domain of the Fc domain-containing protein in the complex, which Fc domain-containing protein may be any protein of interest, for instance an antibody or any other protein comprising an Fc domain, either naturally or as a result of engineering of the protein in question. As a result of the EV trafficking capabilities of EV proteins, such non-covalent complexes between fusion proteins and Fc domain-containing proteins are typically present, e.g. anchored in the membrane of EV, resulting in an EV coated with a plurality of Fc domain-containing proteins which are capable of exerting their biological effects. The complexes may additionally or alternatively reside inside an EV.

In a further aspect, the present invention pertains to pharmaceutical compositions comprising EVs and/or non-covalent complexes, such as nanoparticle complexes (i.e. EVs decorated inside, outside, and/or in the EV membrane with a plurality of at least one type of Fc containing proteins) as per the present invention, and a pharmaceutically acceptable carrier. In further aspects, the present invention thus also relates to EVs, EV-protein complexes, and/or pharmaceutical compositions comprising such EVs and EV-protein complexes for use in medicine, preferably in the treatment of diseases which would benefit from antibody- or Fc domain-containing protein-based treatment, ADC-based treatment, and/or antibody-mediated targeting.

In further aspects, the present invention pertains to methods for producing EVs capable of binding to proteins comprising an Fc domain. Such methods may comprise the steps of: (i) introducing into an EV source cell a polynucleotide construct encoding a fusion protein comprising at least one Fc binder polypeptide and at least one exosomal polypeptide, and (ii) harvesting EVs which are secreted from the EV source cell, said EVs comprising the fusion protein of interest.

Additionally, the present invention relates to methods for coating EVs with at least one protein comprising an Fc domain, comprising the steps of (i) providing an EV comprising a fusion protein comprising at least one Fc binder and at least one exosomal polypeptide, and (ii) allowing the Fc binder of the fusion protein to bind the Fc domain of at least one protein comprising an Fc domain.

Finally, the present invention also relates to fusion proteins comprising at least one Fc binder and at least one exosomal polypeptide, and polynucleotide constructs encoding for such fusion proteins, as well as vectors, EVs and cells comprising such constructs.

DETAILED DESCRIPTION OF THE INVENTION

Figure 1:
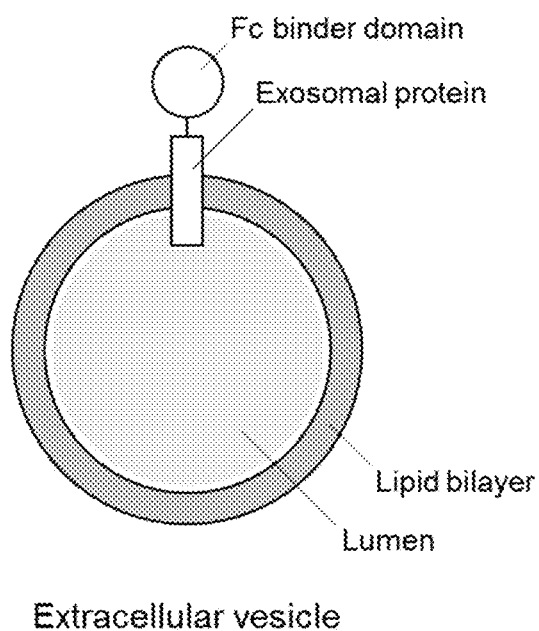
FIG. 1. Schematic illustration of an EV comprising a fusion protein comprising an exosomal protein fused to an Fc binding polypeptide (i.e. the Fc binder domain). The Fc binder is capable of binding e.g. an antibody and/or any other protein comprising an Fc domain, thereby turning the EV into a multivalent delivery vehicle for protein therapeutics.

The present invention relates to various aspects and embodiments pertaining to EVs comprising fusion proteins comprising at least one Fc binder fused to an exosomal polypeptide, to enable dense coating of EVs with antibodies and other Fc domain-containing proteins that can be sequestered by the Fc binder and used for therapeutic application in the treatment of various diseases and disorders.

For convenience and clarity, certain terms employed herein are collected and described below. Unless otherwise defined, all technical and scientific terms used herein have the same meaning as commonly understood by one of ordinary skill in the art to which this invention belongs.

Where features, aspects, embodiments, or alternatives of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the Fc binding polypeptides described herein in connection with the EVs comprising fusion proteins comprising such Fc binding polypeptides are to be understood to be disclosed, relevant, and compatible with all other aspects, teachings and embodiments herein, for instance aspects and/or embodiments relating to the methods for producing or coating the EVs, or relating to the polynucleotide and polypeptide constructs described herein. Furthermore, certain embodiments described in connection with certain aspects, for instance the administration routes of the EVs comprising the fusion protein comprising the Fc binding polypeptide and the exosome polypeptide, as described in relation to aspects pertaining to treating certain medical indications, may naturally also be relevant in connection with other aspects and/or embodiment such as those pertaining to the pharmaceutical compositions and/or the Fc binding polypeptide-Fc containing protein complexes of the present invention. Furthermore, all polypeptides and proteins identified herein can be freely combined in fusion proteins using conventional strategies for fusing polypeptides. As a non-limiting example, all Fc binding polypeptides described herein may be freely combined in any combination with one or more exosomal polypeptides. Also, Fc binding polypeptides may be combined with each other to generate constructs comprising more than one Fc binding polypeptide. Moreover, any and all features (for instance any and all members of a Markush group) can be freely combined with any and all other features (for instance any and all members of any other Markush group), e.g. any Fc binding protein may be combined with any Fc containing protein such as any antibody, or any exosomal polypeptide may be combined with any Fc binding polypeptide. Furthermore, when teachings herein refer to EVs (and/or the EV-anchored fusion protein-Fc containing protein complexes) in singular and/or to EVs as discrete natural nanoparticle-like vesicles it should be understood that all such teachings are equally relevant for and applicable to a plurality of EVs and populations of EVs and the EVs coated with Fc containing proteins. As a general remark, the Fc binding polypeptides, the Fc containing proteins such as the antibodies, the EV-producing cell sources, the exosomal proteins, and all other aspects, embodiments, and alternatives in accordance with the present invention may be freely combined in any and all possible combinations without deviating from the scope and the gist of the invention. Furthermore, any polypeptide or polynucleotide or any polypeptide or polynucleotide sequences (amino acid sequences or nucleotide sequences, respectively) of the present invention may deviate considerably from the original polypeptides, polynucleotides and sequences as long as any given molecule retains the ability to carry out the desired technical effect associated therewith. As long as their biological properties are maintained the polypeptide and/or polynucleotide sequences according to the present application may deviate with as much as 50% (calculated using for instance BLAST or ClustalW) as compared to the native sequence, although a sequence identity that is as high as possible is preferable (for instance 60%, 70%, 80%, or e.g. 90% or higher). The combination (fusion) of e.g. at least one Fc binding polypeptide and at least one exosomal protein implies that certain segments of the respective polypeptides may be replaced and/or modified and/or that the sequences may be interrupted by insertion of other amino acid stretches, meaning that the deviation from the native sequence may be considerable as long as the key properties (e.g. Fc binding properties, trafficking to the surface of exosomes, therapeutic activity, etc.) are conserved. Similar reasoning thus naturally applies to the polynucleotide sequences encoding for such polypeptides. All accession numbers and SEQ ID NOs mentioned herein in connection with peptides, polypeptides and proteins shall only be seen as examples and for information only, and all peptides, polypeptides and proteins shall be given their ordinary meaning as the skilled person would understand them. Thus, as above-mentioned, the skilled person will also understand that the present invention encompasses not merely the specific SEQ ID NOs and/or accession numbers referred to herein but also variants and derivatives thereof. All accession numbers referred to herein are UniProtKB accession numbers as per the 22 Jun. 2017 version of the database, and all proteins, polypeptides, peptides, nucleotides and polynucleotides mentioned herein are to be construed according to their conventional meaning as understood by a skilled person.

The terms "extracellular vesicle" or "EV" or "exosome" are used interchangeably herein and shall be understood to relate to any type of vesicle that is obtainable from a cell in any form, for instance a microvesicle (e.g. any vesicle shed from the plasma membrane of a cell), an exosome (e.g. any vesicle derived from the endo-lysosomal pathway), an apoptotic body (e.g. obtainable from apoptotic cells), a microparticle (which may be derived from e.g. platelets), an ectosome (derivable from e.g. neutrophils and monocytes in serum), prostatosome (e.g. obtainable from prostate cancer cells), or a cardiosome (e.g. derivable from cardiac cells), etc. The sizes of EVs may vary considerably but an EV typically has a nano-sized hydrodynamic radius, i.e. a radius below 1000 nm. Clearly, EVs may be derived from any cell type, both in vivo, ex vivo, and in vitro. Furthermore, the said terms shall also be understood to relate to extracellular vesicle mimics, cell membrane-based vesicles obtained through for instance membrane extrusion, sonication, or other techniques, etc. It will be clear to the skilled artisan that when describing medical and scientific uses and applications of the EVs, the present invention normally relates to a plurality of EVs, i.e. a population of EVs which may comprise thousands, millions, billions or even trillions of EVs. As can be seen from the experimental section below, EVs may be present in concentrations such as $10^5$, $10^8$, $10^{10}$, $10^{11}$, $10^{12}$, $10^{13}$, $10^{14}$, $10^{15}$, $10^{18}$, $10^{25}$, $10^{30}$ EVs (often termed "particles") per unit of volume (for instance per ml), or any other number larger, smaller or anywhere in between. In the same vein, the term "population", which may e.g. relate to an EV comprising a certain fusion protein between an exosomal polypeptide and an Fc binding polypeptide which in turn may be bound to an Fc containing protein of interest, shall be understood to encompass a plurality of entities constituting such a population. In other words, individual EVs when present in a plurality constitute an EV population. Thus, naturally, the present invention pertains both to individual EVs and populations comprising EVs, as will be clear to the skilled person. The dosages of EVs when applied in vivo may naturally vary considerably depending on the disease to be treated, the administration route, the Fc containing protein of interest, any targeting moieties present on the EVs, the pharmaceutical formulation, etc. Furthermore, the EVs of the present invention may also comprise additional therapeutic agents, in addition to the Fc containing proteins which may be bound to the EV surfaces. In some embodiments, the additional therapeutic agent may be at least one therapeutic small molecule drug. In some embodiments, the therapeutic small molecule drug may be selected from the group consisting of DNA damaging agents, agents that inhibit DNA synthesis, microtubule and tubulin binding agents, anti-metabolites, inducers of oxidative damage, anti-angiogenics, endocrine therapies, anti-estrogens, immuno-modulators such as Toll-like receptor agonists or antagonists, histone deacetylase inhibitors, inhibitors of signal transduction such as inhibitors of kinases, inhibitors of heat shock proteins, retinoids, inhibitors of growth factor receptors, anti-mitotic compounds, anti-inflammatories, cell cycle regulators, transcription factor inhibitors, and apoptosis inducers, and any combination thereof. In further embodiments, the additional therapeutic agent may be a therapeutic nucleic acid-based agent. Such nucleic acid-based therapeutic agents may be selected from the group comprising single-stranded RNA or DNA, double-stranded RNA or DNA, oligonucleotides such as siRNA, splice-switching RNA, CRISPR guide strands, short hairpin RNA (shRNA), miRNA, antisense oligonucleotides, polynucleotides such as mRNA, plasmids, or any other RNA or DNA vector. Of particular interest are nucleic acid-based agents which are chemically synthesized and/or which comprise chemically modified nucleotides such as 2'-O-Me, 2'-O-Allyl, 2'-O-MOE, 2'-F, 2'-CE, 2'-EA 2'-FANA, LNA, CLNA, ENA, PNA, phosphorothioates, tricyclo-DNA, etc. In yet further embodiments, the EVs as per the present invention may comprise additional therapeutic agents which may be protein and/or peptides. Such proteins and/or peptides may be present inside of the EVs, inserted into the EV membrane or in association with the EV membrane, or may be protruding from the EV into the extravesicular environment. Such therapeutic protein and/or peptide agents may be selected from a group of non-limiting examples including: antibodies, intrabodies, single chain variable fragments (scFv), affibodies, bi- and multispecific antibodies or binders, affibodies, darpins, receptors, ligands, enzymes for e.g. enzyme replacement therapy or gene editing, tumor suppressors, viral or bacterial inhibitors, cell component proteins, DNA and/or RNA binding proteins, DNA repair inhibitors, nucleases, proteinases, integrases, transcription factors, growth factors, apoptosis inhibitors and inducers, toxins (for instance pseudomonas exotoxins), structural proteins, neurotrophic factors such as NT3/4, brain-derived neurotrophic factor (BDNF) and nerve growth factor (NGF) and its individual subunits such as the 2.5 S beta subunit, ion channels, membrane transporters, proteostasis factors, proteins involved in cellular signaling, translation- and transcription related proteins, nucleotide binding proteins, protein binding proteins, lipid binding proteins, glycosaminoglycans (GAGs) and GAG-binding proteins, metabolic proteins, cellular stress regulating proteins, inflammation and immune system regulating proteins, mitochondrial proteins, and heat shock proteins, etc. In a preferred embodiment, the therapeutic agent may be a CRISPR-associated (Cas) polypeptide (such as Cas9 (as a non-limiting example the accession number Q99ZW2)) with intact nuclease activity which is associated with (i.e. carries with it) an RNA strand that enables the Cas polypeptide to carry out its nuclease activity in a target cell once delivered by the EV. Alternatively, in another preferred embodiment, the Cas polypeptide may be catalytically inactive, to enable targeted genetic engineering. Yet another alternative may be any other type of CRISPR effector such as the single RNA-guided endonuclease Cpf1 (from species such as Acidaminococcus or Lachnospiraceae) (as non-limiting examples the accession numbers U2UMQ6 and A0Q7Q2). Additional preferred embodiments include therapeutic proteins selected from the group comprising enzymes for lysosomal storage disorders, for instance glucocerebrosidases such as imiglucerase, alpha-galactosidase, alpha-L-iduronidase, iduronate-2-sulfatase and idursulfase, arylsulfatase, galsulfase, acid-alpha glucosidase, sphingomyelinase, galactocerebrosidase, galactosylceramidase, glucosylceramidase (as a non-limiting example the accession number P04062) ceramidase, alpha-N-acetylgalactosaminidase, beta-galactosidase, lysosomal acid lipase, acid sphingomyelinase, NPC1 (as a non-limiting example the accession number O15118), NPC2 (as a non-limiting example the accession number P61916), heparan sulfamidase, N-acetyl-glucosaminidase, heparan-α-glucosaminide-N-acetyltransferase, N-acetylglucosamine 6-sulfatase, galactose-6-sulfate sulfatase, galactose-6-sulfate sulfatase, hyaluronidase, alpha-N-acetyl neuraminidase, GlcNAc phosphotransferase, mucolipin1, palmitoyl-protein thioesterase, tripeptidyl peptidase I, palm itoyl-protein thioesterase 1, tripeptidyl peptidase 1, battenin, linclin, alpha-D-mannosidase, beta-mannosidase, aspartylglucosaminidase, alpha-L-fucosidase, cystinosin, cathepsin K, sialin, LAMP2, and hexoaminidase. In other preferred embodiments, the therapeutic protein may be e.g. an intracellular protein that modifies inflammatory responses, for instance epigenetic proteins such as methylases and bromodomains, or an intracellular protein that modifies muscle function, e.g. transcription factors such as MyoD (as a non-limiting example the accession number P15172) or Myf5, proteins regulating muscle contractility e.g. myosin, actin, calcium/binding proteins such as troponin, or structural proteins such as dystrophin (as a non-limiting example the accession number P11532), mini dystrophin (as a non-limiting example the accession number P15172), utrophin, titin, nebulin, dystrophin-associated proteins such as dystrobrevin, syntrophin, syncoilin, desmin, sarcoglycan, dystroglycan, sarcospan, agrin, and/or fukutin. Importantly, all of the above-mentioned therapeutic proteins may be engineered to contain an Fc domain, in order to enable binding to the Fc binding polypeptide present on the EVs. Another non-limiting example is the fusion of an Fc domain onto the enzyme NPC1 for subsequent delivery into a target cell. Yet another non-limiting example which may be utilized to improve intracellular bioactivity of EV-delivered Fc containing proteins (for instance Fc-Cas9 or antibodies) is to fuse an Fc domain to an endosomal escape peptide or protein, such as HA2, cell-penetrating peptides (CPPs) such as the TAT peptide, transportan, peneratin, poly-lysine, or gp41, cholera toxin, Shiga toxin, saporin, diphtheria toxin peptides, etc. Displaying such endosomal escape domains on the surface of an EV may enhance both internalization into target cells and subsequent endosomal escape. An advantageous non-limiting example of how an Fc domain can be fused onto a protein of interest is the fusion of an Fc domain onto Cas9, Cpf1, non-cleaving Cas variants, or any other type of gene editing protein or ribonucleoprotein (RNP) for EV-mediated delivery into a target cell. In a preferred embodiment, an Fc domain is fused either N-terminally or C-terminally to Cas9, which has been pre-loaded in vitro with the single guide RNA (sgRNA) strand (Cas pre-loaded with RNA forms a so called ribonucleoprotein (RNP) complex). The resulting Fc domain-containing RNP complex thus formed is then allowed to be bound by the Fc binding polypeptides of a suitable EV to attached them to the EV surface, followed by delivery into target cells. Creation of the RNP complex can be achieved in different ways and with different RNA components, such as conventional single guide RNA, a synthetic guide RNA comprising both the crRNA and the tracrRNA optionally combined with a hairpin loop, crRNA, tracrRNA, and various combinations thereof. Repair templates for homology-directed recombination or non-homologous end-joining or any other repair or replacement mechanism may also be included in a pre-formed RNP which can then be attached to EVs using the Fc domain-Fc binding polypeptide linkage.

The terms "antibody" and "mAb" and "Ab" as described herein is to be understood to include both antibodies in their entirety (i.e. whole antibodies) and any derivatives thereof with antigen-binding properties. Conventionally, an antibody refers to a glycoprotein comprising at least two heavy (H) chains and two light (L) chains inter-connected by disulfide bonds, or an antigen binding-portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR). Importantly, for the purposes of the present invention an antibody of interest preferably has an Fc domain or a derivative thereof to which the Fc binding polypeptides of the present invention can bind, in order to enable coating of the EV surface. Antibodies of use in the invention may be monoclonal antibodies (mAbs) or polyclonal antibodies, preferably mAbs. Antibodies of particular utility in the invention may be chimeric antibodies, CDR-grafted antibodies, nanobodies, human or humanised antibodies or any derivative thereof as long as it can be bound by the Fc binding polypeptide, which are typically comprised in the fusion proteins as per the present invention. The production of antibodies is outside of the scope of the present invention but typically both monoclonal and polyclonal antibodies are raised experimental non-human mammals such as goat, rabbit, llama, camelids, rat or mouse, but suitable antibodies may also be the result of other production methodologies, e.g. the standard somatic cell hybridization technique of Kohler and Milstein. Hybridoma production in e.g. the mouse is a very well-established procedure and can be achieved using techniques well known in the art. An antibody of use in the invention may be a human antibody, humanized antibody, and/or any type of chimeric antibody. The term "human antibody", as used herein, is intended to include antibodies having variable regions in which both the framework and CDR regions are derived from human germline immunoglobulin sequences. The human antibodies of use in the invention may include amino acid residues not encoded by human germline immunoglobulin sequences (e.g., mutations introduced by random or site-specific mutagenesis in vitro or by somatic mutation in vivo). The term "antibody derivatives" refers to any modified form of an antibody, e.g. an antibody having an amino acid sequence that is modified in any way, or a conjugate of the antibody and another agent or antibody, bispecific antibodies, multispecific antibodies, antibody domains, etc. The term "humanized antibody" refers to antibodies in which CDR sequences derived from another mammalian species, such as a mouse, camelid, llama, etc., have been grafted onto human framework sequences. Additional framework region modifications may be made within the human framework sequences. Antibodies in accordance with the present invention may include all isotypes and subtypes such as IgG (for instance IgG1, IgG2, IgG3, IgG4, IgG2a, IgG2d, and IgG2c), IgA, IgM, IgM, IgD, etc., and monomers, dimers, and oligomers thereof. Further, antibodies as per the present invention may have several functions when displayed on EVs: (1) antibodies may target specific cell types, tissues, and/or organs in order to re-direct distribution and optimize delivery of EV-based therapeutics, (2) therapeutic antibodies that interact with a target antigen of interest can be efficiently delivered to tissues of interest using EVs (for instance to the CNS or to the brain), (3) multiplexed antibodies on the surface of EVs may be significantly better at binding target antigens, (4) antibody-drug conjugates (ADCs) may be multiplexed on EVs to significantly enhance their therapeutic efficacy, (5) antibodies bound by Fc binding polypeptide may have higher affinity for the target, (6) antibodies coated onto EVs as per the present invention may be delivered intracellularly, and (7) coating of EVs with antibodies may reduce opsonization and/or immune-mediated clearance of EVs, which may in turn be important for therapeutic activity.

The terms "Fc containing protein" and "protein comprising an Fc domain" and "Fc domain-containing protein" and "Fc domain containing protein" and "Fc domain protein" and similar terms are used interchangeably herein and shall be understood to relate to any protein, polypeptide, or peptide (i.e. any molecule comprising a sequence of amino acids) which comprises at least one Fc domain, either naturally or as a result of engineering of the protein in question to introduce an Fc domain. Fc stands for "fragment crystallizable", which is the name of the tail regions of antibodies. Fc domains can however also be created and used on other proteins, not only antibodies. Non-limiting examples of such Fc domain-containing proteins include antibodies and antibody derivatives, Fc-modified decoy receptors and/or signal transducers such as interleukin decoy receptors for IL1, IL2, IL3, IL4, IL5, IL6 (such as the signal transducer gp130 (as a non-limiting example the accession number P40189)), IL7, IL8, IL9, IL10, IL11, IL12, IL13, IL14, IL15, IL17 (such as IL17R, with as a non-limiting example the accession number Q96F46), IL23 (such as IL23R, with as a non-limiting example the accession number Q5VWK5), etc., Fc domain-containing bi- and multi-specific binders, any type of Fc domain-containing receptors or ligands, Fc domain-modified enzymes for e.g. enzyme replacement therapy or gene editing, nucleases such as Cas and Cas9 onto which an Fc domain has been grafted, tumor suppressors fused to Fc domains, etc. Suitable Fc domains that may be fused with a protein of interest natively lacking an Fc domain include the following non-limiting examples: human IGHM (as a non-limiting example the accession number P01871), human IGHA1 (as a non-limiting example the accession number P01876), human IGHA2 (as a non-limiting example the accession number P01877), human IGKC (as a non-limiting example the accession number P01834), human IGHG1 (as a non-limiting example the accession number P01857), human IGHG2 (as a non-limiting example the accession number P01859), human IGHG3 (as a non-limiting example the accession number P01860), human IGHG4 (as a non-limiting example the accession number P01861), human IGHD (as a non-limiting example the accession number P01880), human IGHE (as a non-limiting example the accession number P01854), and any domains, derivatives, or combinations thereof. In essence, any protein of interest may be modified to incorporate an Fc domain. Non-limiting examples of proteins onto which an Fc domain can be introduced include for instance tumor suppressors, viral or bacterial inhibitors, cell component proteins, DNA and/or RNA binding proteins, DNA repair inhibitors, nucleases, proteinases, integrases, transcription factors, growth factors, apoptosis inhibitors and inducers, toxins (for instance pseudomonas exotoxins), structural proteins, neurotrophic factors such as NT3/4, brain-derived neurotrophic factor (BDNF) and nerve growth factor (NGF) and its individual subunits such as the 2.5 S beta subunit, ion channels, membrane transporters, proteostasis factors, proteins involved in cellular signaling, translation- and transcription related proteins, nucleotide binding proteins, protein binding proteins, lipid binding proteins, glycosaminoglycans (GAGs) and GAG-binding proteins, metabolic proteins, cellular stress regulating proteins, inflammation and immune system regulating proteins, mitochondrial proteins, and heat shock proteins, etc. The above list of proteins of interest is not exhaustive and other proteins may also be relevant, as long as the protein either comprises an Fc domain or as long as it is possible to engineer the protein in question to comprise an Fc domain. One non-limiting example of such engineering of a protein to introduce an Fc domain includes adding an Fc domain to a decoy receptor, e.g. adding an Fc domain onto the Cas or Cas9 enzymes for bioactive delivery into target cells to enable gene editing. Another non-limiting example of such engineering of a protein to introduce an Fc domain includes adding an Fc domain onto an enzyme for enzyme replacement therapy (for instance Fc domain-glucocerebrosidase or Fc domain-α-galactosidase or Fc domain-NPC1). A well-known example of a commercially available Fc domain-modified protein is etanercept, which is a biopharmaceutical for the treatment of various autoimmune disease, comprising the Fc domain of IgG fused onto TNF receptor 2. Thus, as is clear from the above, Fc domain-containing proteins as per the present invention may be essentially any protein of interest that contains an Fc domain, either naturally or as a result of introduction thereof.

The Fc containing proteins are often described herein as being "attached to" an EV and/or to an Fc binding polypeptide. Alternatively, EVs are sometimes referred to as being "coated by" Fc containing proteins, or as having "bound to their surface" or "attached to their surface" the Fc containing proteins. These terms shall be understood in the context of the conventional interaction between an Fc binding polypeptide and an Fc domain, that is that the two polypeptides are interacting with each other in a way that results in a chemical bond (typically a non-covalent bond) forming between the Fc binder and the Fc domain. Thus, this normally means that the EV which comprises the Fc binding polypeptide therefore has attached to it, by virtue of the chemical bond, the Fc domain of the Fc containing protein. As will be understood by the skilled person, an EV may consequently have a plurality of such Fc containing proteins bound (attached) to it, resulting in a form of coating when the binding is taking place on the EV surface.

The terms "Fc binding polypeptide" and "Fc binding protein" and "Fc binder" and "Fc-binding protein" and "binder" are used interchangeably herein and shall be understood to relate to any protein, polypeptide, or peptide (i.e. any molecule comprising a sequence of amino acids) which can bind an Fc domain of any protein of interest. Typically, the Fc binding polypeptides of the present invention are derived from various sources that are either human or non-human (e.g. mammal sources, bacteria, etc.), they have high affinity for Fc domains of various antibody isotypes, subtypes, and species (for instance IgG (as non-limiting examples in the case of IgG, IgG1, IgG2, IgG3, IgG4, IgG2a, IgG2d, and/or IgG2c), IgA, IgM, IgM, IgD, etc.), and they can be fused to EV proteins. Non-limiting examples of Fc binding polypeptides in accordance with the present invention include, in addition to other Fc binding polypeptides mentioned through the present application, Protein A (as a non-limiting example the SEQ ID NO 77), Protein G (as a non-limiting example the SEQ ID NO 78), Protein A/G (as a non-limiting example the SEQ ID NO 72), Z domain (as a non-limiting example the SEQ ID NO 73), ZZ domain (two operably linked copies of as a non-limiting example the SEQ ID NO 73, i.e. as a non-limiting example the SEQ ID NO 74), human FCGRI (as a non-limiting example the SEQ ID NO 31), human FCGRIIA (as a non-limiting example the SEQ ID NO 33), human FCGRIIB (as a non-limiting example the accession number 31994), human FCGRIIC (as a non-limiting example the accession number 31995), human FCGRIIIA (as a non-limiting example the accession number P08637), human FCGR3B (as a non-limiting example the accession number O75015), human FCAMR (as a non-limiting example the SEQ ID NO 28), human FCERA, human FCAR, mouse FCGRI (as a non-limiting example the SEQ ID NO 79), mouse FCGRIIB (as a non-limiting example the SEQ ID NO 80), mouse FCGRIII (as a non-limiting example the SEQ ID NO 81), mouse FCGRIV (as a non-limiting example the SEQ ID NO 82), mouse FCGRn (as a non-limiting example the SEQ ID NO 83), and various combinations, derivatives, or alternatives thereof.

The terms "EV protein" and "EV polypeptide" and "exosomal polypeptide" and "exosomal protein" are used interchangeably herein and shall be understood to relate to any polypeptide that can be utilized to transport a polypeptide construct (which typically comprises, in addition to the EV protein, an Fc binding polypeptide) to a suitable vesicular structure, i.e. to a suitable EV. More specifically, these terms shall be understood as comprising any polypeptide that enables transporting, trafficking or shuttling of a fusion protein construct to a vesicular structure, such as an EV. Examples of such exosomal polypeptides are for instance CD9 (as a non-limiting example the SEQ ID NO 1), CD53 (as a non-limiting example the SEQ ID NO 2), CD63 (as a non-limiting example the SEQ ID NO 3), CD81 (as a non-limiting example the SEQ ID NO 4), CD54 (as a non-limiting example the SEQ ID NO 5), CD50 (as a non-limiting example the SEQ ID NO 6), FLOT1 (as a non-limiting example the SEQ ID NO 7), FLOT2 (as a non-limiting example the SEQ ID NO 8), CD49d (as a non-limiting example the SEQ ID NO 9), CD71 (also known as the transferrin receptor) (as a non-limiting example the SEQ ID NO 10) and its endosomal sorting domain, i.e. the transferrin receptor endosomal sorting domain (as a non-limiting example the SEQ ID NO 23), CD133 (as a non-limiting example the SEQ ID NO 11), CD138 (syndecan-1) (as a non-limiting example the SEQ ID NO 12), CD235a (as a non-limiting example the SEQ ID NO 13), ALIX (as a non-limiting example the SEQ ID NO 14), Syntenin-1 (as a non-limiting example the SEQ ID NO 15), Syntenin-2 (as a non-limiting example the SEQ ID NO 16), Lamp2b (as a non-limiting example the SEQ ID NO 17), syndecan-2 (as a non-limiting example the SEQ ID NO 20), syndecan-3 (as a non-limiting example the SEQ ID NO 21), syndecan-4 (as a non-limiting example the SEQ ID NO 22), TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fc receptors, interleukin receptors, immunoglobulins, MHC-I or MHC-II components, CD2, CD3 epsilon, CD3 zeta, CD13, CD18, CD19 (as a non-limiting example the SEQ ID NO 26), CD30 (as a non-limiting example the SEQ ID NO 27), TSG101, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, VTI1B, other exosomal polypeptides, and any combinations thereof, but numerous other polypeptides capable of transporting a polypeptide construct to an EV are comprised within the scope of the present invention. Typically, in many embodiments of the present invention, at least one exosomal polypeptide is fused to at least one Fc binding polypeptide, in order to form a fusion protein present in an EV. Such fusion proteins may also comprise various other components to optimize their function(s), including linkers, transmembrane domains, cytosolic domains, multimerization domains, etc.

The terms "source cell" or "EV source cell" or "parental cell" or "cell source" or "EV-producing cell" or any other similar terminology shall be understood to relate to any type of cell that is capable of producing EVs under suitable conditions, for instance in suspension culture or in adherent culture or any in other type of culturing system. Source cells as per the present invention may also include cells producing exosomes in vivo. The source cells per the present invention may be select from a wide range of cells and cell lines, for instance mesenchymal stem or stromal cells or fibroblasts (obtainable from e.g. bone marrow, adipose tissue, Wharton's jelly, perinatal tissue, tooth buds, umbilical cord blood, skin tissue, etc.), amnion cells and more specifically amnion epithelial cells optionally expressing various early markers, myeloid suppressor cells, M2 polarized macrophages, adipocytes, endothelial cells, fibroblasts, etc. Cell lines of particular interest include human umbilical cord endothelial cells (HUVECs), human embryonic kidney (HEK) cells, endothelial cell lines such as microvascular or lymphatic endothelial cells, chondrocytes, MSCs of different origin, airway or alveolar epithelial cells, fibroblasts, endothelial cells, etc. Also, immune cells such as B cells, T cells, NK cells, macrophages, monocytes, dendritic cells (DCs) are also within the scope of the present invention, and essentially any type of cell which is capable of producing EVs is also encompassed herein. Generally, EVs may be derived from essentially any cell source, be it a primary cell source or an immortalized cell line. The EV source cells may be any embryonic, fetal, and adult somatic stem cell types, including induced pluripotent stem cells (iPSCs) and other stem cells derived by any method. When treating neurological diseases, one may contemplate to utilize as source cells e.g. primary neurons, astrocytes, oligodendrocytes, microglia, and neural progenitor cells. The source cell may be either allogeneic, autologous, or even xenogeneic in nature to the patient to be treated, i.e. the cells may be from the patient himself or from an unrelated, matched or unmatched donor. In certain contexts, allogeneic cells may be preferable from a medical standpoint, as they could provide immuno-modulatory effects that may not be obtainable from autologous cells of a patient suffering from a certain indication. For instance, in the context of treating systemic, peripheral and/or neurological inflammation, allogeneic MSCs may be preferable as EVs obtainable from such cells may enable immuno-modulation via e.g. macrophage and/or neutrophil phenotypic switching (from pro-inflammatory M1 or N1 phenotypes to anti-inflammatory M2 or N2 phenotypes, respectively).

In a first aspect, the present invention relates to EVs comprising fusion proteins, wherein the fusion proteins comprise at least one Fc binding polypeptide fused to an exosomal polypeptide. As a result of the fusion with the EV protein, the Fc binding polypeptide are efficiently transported to and displayed in high numbers on the surface of EVs, which enables subsequent coating of EVs with a various types of Fc containing proteins, typically therapeutic proteins endowed with an Fc domain, targeting antibodies, therapeutic antibodies, antibody-drug conjugates, and/or antibodies that are passively bound in vivo or purposely selected to reduce opsonization and recognition by immune cells (to prolong the circulation time of the EVs).

Thus, in an embodiment, an EV according to the first aspect has bound to it a plurality of Fc containing proteins through interaction between the Fc binding polypeptide and the Fc domains of the plurality of Fc containing proteins, wherein the plurality of Fc containing proteins may be the same or different. The EVs may be coated with a plurality of proteins comprising an Fc domain through the non-covalent interaction between the Fc binder and the at least one protein comprising an Fc domain. Said plurality may be at least 10, at least 20 or at least 30 proteins comprising an Fc domain.

In one embodiment of the invention, the Fc binders are of non-human origin, they may be obtained e.g. from bacteria, viruses, or non-human mammals. In another embodiment, the Fc binders are of human or mammal origin. In preferred embodiments, the at least one Fc binding polypeptide may be selected from the group comprising Protein A (as a non-limiting example the SEQ ID NO 77), Protein G (as a non-limiting example the SEQ ID NO 78), Protein A/G (as a non-limiting example the SEQ ID NO 72), Z domain (as a non-limiting example the SEQ ID NO 73), ZZ domain (as a non-limiting example the SEQ ID NO 74), Protein L (as a non-limiting example the pdb id no 1 HEZ), Protein LG, human FCGRI (as a non-limiting example the SEQ ID NO 31), human FCGR2A (as a non-limiting example the accession number P12318), human FCGR2B (as a non-limiting example the accession number P31994), human FCGR2C (as a non-limiting example the accession number P31994), human FCGR3A (as a non-limiting example the accession number P08637), human FCGR3B (as a non-limiting example the accession number O75015), human FCGRB (as a non-limiting example the accession number Q92637) (as a non-limiting example the SEQ ID NO 32), human FCAMR (as a non-limiting example the SEQ ID NO 28), human FCERA (as a non-limiting example the SEQ ID NO 30), human FCAR (as a non-limiting example the SEQ ID NO 29), mouse FCGRI (as a non-limiting example the SEQ ID NO 79), mouse FCGRIIB (as a non-limiting example the SEQ ID NO 80), mouse FCGRIII (as a non-limiting example the SEQ ID NO 81), mouse FCGRIV (as a non-limiting example the SEQ ID NO 82), mouse FCGRn (as a non-limiting example the SEQ ID NO 83), and any combination of any of the above Fc binding polypeptides. Other suitable Fc binding polypeptides, which have been obtained from e.g. phage display screening and via bioinformatics, include the Fc binding peptides SPH (as a non-limiting example the SEQ ID NO 57), SPA (as a non-limiting example the SEQ ID NO 58), SPG2 (as a non-limiting example the SEQ ID NO 59), SpA mimic 1 (as a non-limiting example the SEQ ID NO 60), SpA mimic 2 (as a non-limiting example the SEQ ID NO 61), SpA mimic 3 (as a non-limiting example the SEQ ID NO 62), SpA mimic 4 (as a non-limiting example the SEQ ID NO 63), SpA mimic 5 (as a non-limiting example the SEQ ID NO 64), SpA mimic 6 (as a non-limiting example the SEQ ID NO 65), SpA mimic 7 (as a non-limiting example the SEQ ID NO 66), SpA mimic 8 (as a non-limiting example the SEQ ID NO 69), SpA mimic 9 (as a non-limiting example the SEQ ID NO 70), SpA mimic 10 (as a non-limiting example the SEQ ID NO 71), Fcγ mimic 1 (as a non-limiting example the SEQ ID NO 67), and Fcγ mimic 2 (as a non-limiting example the SEQ ID NO 68), and any combination or derivative thereof. The selection of the most suitable Fc binding polypeptide for a particular construct depends heavily on the desired binding characteristics, the affinity, the orientation of the Fc binding polypeptide when fused to an exosomal polypeptide, and various other factors.

Protein A/G is a recombinant genetically engineered protein comprised of 7 Fc-binding domains EDABC-C1C3, with the Protein A part being obtained from *Staphylococcus aureus* segments E, D, A, B and C, and the Protein G part from *Streptococcus* segments C1 and C3. Advantageously, Protein A/G (as a non-limiting example the SEQ ID NO 72) has a broader binding capacity than either Protein A (as a non-limiting example the SEQ ID NO 77) or Protein G (as a non-limiting example the SEQ ID NO 78) alone and it has a broad binding affinity for antibodies from various species. Protein A/G binds to various human, mouse and rat IgG subclasses such as the human IgG1, IgG2, IgG3, IgG4; mouse IgG2a, IgG2b, IgG3 and rat IgG2a, IgG2c. In addition, Protein A/G binds to total IgG from cow, goat, sheep, horse, rabbit, guinea pig, pig, dog and cat. Protein A/G has been engineered to remove the cell wall-binding region, the cell membrane-binding region and albumin-binding region to enable strong binding to the Fc domain of a protein of interest. Thus, in advantageous embodiments as per the present invention, the Fc binder comprises more than one Fc binding region, as is the case with Protein A, Protein G, and Protein A/G. In an alternative embodiment, the Fc binder may be multiplied in order to enable binding to more than one copy of an antibody of interest. For instance, the short Z domain Fc binder may be included in the fusion protein in more than one copy, through an operational linkage allowing for binding to more than one Fc domain. This way it is possible to multiplex antibodies and other Fc domain-containing proteins not only between separate fusion proteins but also within one single fusion protein, which thus may bind more than one antibody. For instance, when Fc binding polypeptides are introduced into EV proteins belonging to the tetraspanin family (such as CD63) it may be advantageous to insert one Fc binder on one loop and another Fc binder (which can be the same or different) on another loop of the protein. The Fc binder can be placed on inward-facing and/or outward-facing loops, depending on whether the Fc containing protein is meant to be loaded into the lumen of the EV or onto the surface of the EV. Some non-limiting examples of fusion proteins as per the present invention can be described schematically as follows (the below notation is not to be construed as illustrating any C and/or N terminal direction, it is merely meant for illustrative purposes):

Exosomal polypeptide-Fc binding polypeptide-Fc binding polypeptide

Exosomal polypeptide domain-Fc binding polypeptide-Exosomal polypeptide domain-Fc binding polypeptide Exosomal polypeptide domain-Fc binding polypeptide A-Exosomal polypeptide domain-Fc binding polypeptide B In some embodiments, the fusion proteins comprising the exosomal polypeptide and the Fc binding polypeptide may also contain additional polypeptides, polypeptide domains or sequences. Such additional polypeptide domains may exert various functions, for instance such domains may (i) contribute to enhancing the EV surface display of the fusion protein, (ii) lead to clustering of the fusion proteins thereby increasing the avidity of the Fc binding polypeptides, (iii) function as linkers to optimize the interaction between the exosomal polypeptides and the Fc binding polypeptide, and/or (iv) improve anchoring in the EV membrane, as well as various other functions. Two such additional polypeptides that may advantageously be included in part or as a whole in the fusion proteins of the preset invention are gp130 (as a non-limiting example the SEQ ID NO 18) and the tumor necrosis factor receptor 1 (TNFR1) (as a non-limiting example the SEQ ID NO 19). In particular, the transmembrane domains of these additional polypeptides may be highly useful to optimize the insertion into the EV membrane and the display of the Fc binding polypeptide. Overall, various transmembrane domains may be highly advantageous as additional domains in the fusion proteins. For instance, when using the exosomal protein syntenin it is highly advantageous to insert an additional polypeptide domain, such the transmembrane domain of TNFR or the transmembrane domain of gp130, between syntenin and the Fc binding polypeptide of the fusion protein. Further additional domains may include multimerization domains such as fold-on domains, leucine zipper domains and/or trimerization domains, in order to increase surface display and/or avidity. A non-limiting schematic example of this is shown below:

Syntenin-cytosolicTNRF-Foldon trimerization domain-transmembraneTNFR domain-Z domain-extracellularTNFR domain Syndecan-leuzine zipper domain-gp130cytosolic domain-gp130 transmembrane domaine-Fc binding polypeptide-gp130 extracellular domain In a further embodiment, the exosomal polypeptide may be selected from the group comprising CD9, CD53, CD63, CD81, CD54, CD50, FLOT1, FLOT2, CD49d, CD71, CD133, CD138, CD235a, ALIX, Syntenin-1, Syntenin-2, Lamp2b, TSPAN8, syndecan-1, syndecan-2, syndecan-3, syndecan-4, TSPAN14, CD37, CD82 (as a non-limiting example the SEQ ID NO 24), CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fc receptors, interleukin receptors, immunoglobulins, MHC-I or MHC-II components, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8 (as a non-limiting example the SEQ ID NO 25), SLIT2, STX3, TCRA, TCRB, TCRD, TCRG, VTI1A, VTI1B, other exosomal polypeptides, and any combinations thereof.

Particularly advantageous fusion proteins as per the present invention may comprise the human exosomal proteins CD63, CD81, CD9, CD71 (transferrin receptor), Lamp2, and syntenin, fused to at least one copy of the following Fc binding polypeptides: Z domain, Protein A, Protein G, Protein A/G, FCGRI, human FCGR2A, human FCGR2B, human FCGR2C, human FCGR3A, human FCGR3B, human FCGR3C, human FCAMR, human FCAR, and human FCERA. Specifically, fusion of two Z domains to the EV protein CD63 (as a non-limiting example the SEQ ID NO 3) results in a highly potent Fc binder which is displayed in high quantities on the surface of EVs, as a consequence of the small size of the Z domain and the high EV surface expression of CD63. Display of the Fc binder on the outer surface of EVs is naturally preferable in order to enable exogenous binding of Fc domain-containing proteins of interest. In the case of CD63-ZZ domain fusion proteins, Z domains may be inserted into the first and second loop of CD63, to enable display on the outer EV surface after anchoring of CD63 into the EV membrane. Furthermore, as above-mentioned, suitable additional polypeptides and polypeptide domains and linkers may also be included in the fusion proteins, which normally comprises an exosomal polypeptide and an Fc binding polypeptide. Such additional polypeptides include domains from various cytokine receptors such as TNFR1 and TNFR2, the IL6 signal transducer gp130, and various other cytokines and cytokine-related polypeptides. In certain instances, cytokines and cytokine-related polypeptides (such as various cytokine receptors) may alone be able to transport Fc binding polypeptides to EVs. Linkers of particular utility are multiples and/or combinations of small and flexible amino acids such as glycine (G) and serine (S), typically denoted GS, for instance 2XGS or 4XGS. His tags for simplifying purification and assaying may also be added, both C terminally and N terminally, and so may various fluorescent proteins such as GFP. The following are particularly advantageous non-limiting examples of fusion proteins comprising at least one exosomal polypeptide and at least one Fc binding polypeptide, often connected via linkers and optionally including an additional polypeptide(s) or polypeptide domains:

CD81-Protein A/G CD81 Second loop (as a non-limiting example the SEQ ID NO 75)

CD9-ZZ domain CD9 Second loop (as a non-limiting example the SEQ ID NO 76)

FCAR extracellular domain-2XGGGgSlinker-Lamp2b (as a non-limiting example the SEQ ID NO 55)

FCAR extracellular domain-4XGSlinker-Lamp2b (as a non-limiting example the SEQ ID NO 54)

FCGR1A Extracellular domain-2XGGGgSlinker-Lamp2b (as a non-limiting example the SEQ ID NO 49)

FCGR1A Extracellular domain-4XGSlinker-Lamp2b (as a non-limiting example the SEQ ID NO 48)

FcRN Extracellular domain-4XGSlinker-Lamp2b (as a non-limiting example the SEQ ID NO 39)

FcRN-2XGGGgSlinker-Lamp2b (as a non-limiting example the SEQ ID NO 40).

Gp130 Extracellular domain-2XGGGGS linker-FCAR extracellular domain-Gp130 transmembrane domain-Leucine Zipper-N terminal syntenin (as a non-limiting example the SEQ ID NO 52)

Gp130 Extracellular domain-2XGGGGS linker-FCGR1A Extracellular domain-Gp130 transmembrane domain-Leucine Zipper-N terminal syntenin (as a non-limiting example the SEQ ID NO 46)

Gp130 Extracellular domain-2XGGGGS linker-FcRN Extracellular domain-Gp130 transmembrane domain-Leucine Zipper-N terminal syntenin (as a non-limiting example the SEQ ID NO 43)

Gp130 Extracellular domain-2XGGGGS linker-Z domain-Gp130 transmembrane domain-Leucine Zipper-N terminal syntenin (as a non-limiting example the SEQ ID NO 34)

Transferrin receptor-2XGGGGSlinker-FCAR extracellular domain (as a non-limiting example the SEQ ID NO 56)

Transferrin receptor-2XGGGGSlinker-FCGR1A Extracellular domain (as a non-limiting example the SEQ ID NO 50)

Transferrin receptor-2XGGGGSlinker-FcRN Extracellular domain (as a non-limiting example the SEQ ID NO 41)

Transferrin receptor-2XGGGGSlinker-Z domain (as a non-limiting example the SEQ ID NO 38)

CD63-FCAR extracellular domain CD63 First loop and CD63 Second loop (as a non-limiting example the SEQ ID NO 53)

CD63-FCGR1A Extracellular domain CD63 First loop and CD63 Second loop (as a non-limiting example the SEQ ID NO 47)

CD63-FcRN Extracellular domain CD63 First loop and CD63 Second loop (as a non-limiting example the SEQ ID NO 44)

CD63-Z domain CD63 First loop and CD63 Second loop (as a non-limiting example the SEQ ID NO 35)

TNFR Extracellular domain-2XGGGGS linker-FCAR extracellular domain-TNFR transmembrane domain-foldon-N terminal syntenin (as a non-limiting example the SEQ ID NO 51)

TNFR Extracellular domain-2XGGGGS linker-FCGR1A Extracellular domain-TNFR transmembrane domain-foldon-N terminal syntenin (as a non-limiting example the SEQ ID NO 45)

TNFR Extracellular domain-2XGGGGS linker-FcRN Extracellular domain-TNFR transmembrane domain-foldon-N terminal syntenin (as a non-limiting example the SEQ ID NO 42)

TNFR Extracellular domain-2XGGGGS linker-Z domain-TNFR transmembrane domain-foldon-N terminal syntenin (as a non-limiting example the SEQ ID NO 33)

Z domain-2XGGGgSlinker-Lamp2b (as a non-limiting example the SEQ ID NO 37)

Z domain-4XGSlinker-Lamp2b (as a non-limiting example the SEQ ID NO 36)

Transferrin receptor-Protein AG (as a non-limiting example the SEQ ID NO 10 operably fused to as a non-limiting example the SEQ ID NO 72)

The above-mentioned fusion proteins are merely examples of the many engineering possibilities the present invention allows for and as such they are merely non-limiting embodiments of the present invention. All components of the fusion proteins as per the present invention may be freely combined, e.g. the fusion proteins may contain one or several exosomal polypeptides which may be placed C terminally, N terminally, or both, or anywhere in the fusion protein. Further, the fusion proteins may also contain one or several Fc binding polypeptides, which may be placed C terminally, N terminally, or both, or on one or more of any loops of e.g. transmembrane parts, or anywhere in the fusion protein. For clarity, more than one type of exosomal polypeptide and more than one type of Fc binding polypeptide may be comprised in a single construct. Furthermore, additional stretches of amino acids such as linkers (often comprising the amino acids glycine and serine) and His tags may be included to simplify purification, assaying and visualization. Also, other peptides and polypeptide domains may also be included anywhere in the fusion protein sequence. For instance, various domains and regions from various cytokine receptors may advantageously be included, for instance various domains of TNFR1, TNFR2, IL17R, IL23R, gp130, IL6R, etc.

In a further embodiment, the Fc binding polypeptides may as above-mentioned bind to any protein comprising an Fc domain, not only antibodies but also other proteins comprising Fc domains, both naturally occurring and engineered Fc domain-containing proteins, such as the ones mentioned in several instances above. Advantageously, the present invention results in EVs coated with a plurality of proteins comprising an Fc domain, through interaction between the Fc binding polypeptide and at least one Fc containing protein. The interaction between the Fc binder and the Fc containing protein is normally based on non-covalent bonds between the Fc binding polypeptide and the Fc domain of the Fc containing protein. Naturally, one single EV may be coated with more than one type of Fc domain-containing protein. In one non-limiting example, the Fc binding EVs are coated with one antibody targeting a suitable target along the PD1 axis, whereas another antibody is targeting a suitable target along the CTLA4 axis. In another non-limiting example, the Fc binding EVs are coated with an antibody targeting a tumor cell surface receptor and Cas9 fused to an Fc domain. One single EV may also, as is typically the case, comprise a substantial plurality of one single type of Fc domain-containing protein, such as one type of monoclonal antibody. Various combinations of targeting antibodies, therapeutic antibodies, Fc containing non-antibody therapeutic proteins of interest, antibody-drug conjugates (ADCs), and antibodies for reducing opsonization and/or immune cell-mediated clearance constitute preferred embodiments of the present invention. In advantageous embodiments, the EVs according to the present invention are coated with a plurality of proteins comprising an Fc domain. For instance, when using a highly expressed EV protein such as CD63 or CD81 or syntenin one can achieve very dense coating of the surface of EVs. Thus, the present invention may be coated with at least 10 proteins comprising an Fc domain, preferably at least 20 proteins comprising an Fc domain, even more preferably at least 30 proteins comprising an Fc domain. Such proteins may be copies of the same protein (e.g. 50 etanercept molecules coating one EV, by way of example) or more than one protein (e.g. 30 etanercept molecules and 30 gp130-Fc domain fusion proteins coating one EV, by way of example). By selecting an optimal combination of EV protein and Fc binder it may be possibly to increase the display further, in certain cases it may be possible to coat an EV with more than 50 proteins comprising an Fc domain, or even more than approximately 75 proteins comprising an Fc domain.

In a further aspect, the present invention also relates to cells comprising a fusion protein between a display polypeptide and an Fc binding polypeptide. The display polypeptide may typically be a transmembrane protein. Various exosomal polypeptides can be used for this purpose, and so can regular cellular transmembrane proteins such as T cell receptor transmembrane domains, interleukin receptors, transferrin receptor, stannin, sarcolipin, phospholamban, and various other membrane proteins such as channels and symporters/importers, which can transport the Fc binding polypeptide to the cell membrane for display on the outside or on the inside of the cell membrane, depending on whether the Fc containing protein of interest is going to be present inside the cell or displayed on the surface of the cell. In a preferred embodiment, the Fc containing protein is an antibody and the cell is a cell intended for cellular therapy, such as a chimeric antigen receptor (CAR) T cell. Using this approach, a cell could be targeted to a particular tissue of interest, in the case of a CAR-T cell the tissue of interest is likely to be tumor tissue. In the case of an immune-modulatory cell such as an MSC, the tissue of interest is likely to be a site of inflammation and/or injury. All antibodies and other Fc containing proteins herein are equally suitable for being displayed on a cell for the same reasons as for the EVs.

In another aspect, the present invention relates to a complex formed between a fusion protein comprising (i) an exosomal polypeptide and (ii) an Fc binding polypeptide, and a protein comprising an Fc domain. EVs per the present invention thus typically comprise a plurality of such complexes, and typically the higher number of such complexes displayed on an EV without issues relating to for instance to steric hindrance the more potent the EV becomes from a therapeutic and/or targeting standpoint. Such fusion protein-Fc containing protein complexes are typically present in the lipid membrane of an EV, by virtue of the presence of the exosomal protein which mediates transport and anchoring into exosomal membranes. However, the complexes may also be present in other lipid membranes, for instance cell membranes or membranes of cell organelles. The EVs as per the present invention also form a type of nanoparticle complex with the Fc containing proteins. Typically, as above-mentioned, each EV comprising the Fc binding polypeptide binds to a plurality of Fc containing proteins, which results in EVs that are coated (decorated) and/or contains a plurality of the Fc containing protein of interest. An example of this is that Fc-binding EVs that are allowed to bind to antibodies through incubation with such antibodies become decorated on their surface with a plurality of antibodies, e.g. at least 10 antibodies per EV, or more frequently at least 20 or 30 antibodies per EV. Thus, this EV-antibody complex constitutes a type of nanoparticle complex with significant utility for targeting, therapy, and intracellular delivery.

Importantly, the present invention also provides for a method of loading Fc containing proteins into EVs in an endogenous fashion. Such endogenous loading methods comprise co-expression in an EV-producing cell of (i) a fusion protein comprising an exosomal polypeptide and an Fc binding polypeptide, and (ii) a protein of interest comprising an Fc domain. The exosomal polypeptide fused to the Fc binding domain enables active sorting of the fusion protein into EVs in the EV-producing cell, and the presence of the Fc binding protein enables the fusion protein to drag along (transport) the Fc containing protein into an EV. As above-mentioned, various exosomal proteins can be used to sort fusion proteins into EVs and especially in the case of endogenous loading the choice of protein is highly important. Soluble EV proteins such as Alix and syntenin may be suitable for the loading of Fc containing proteins that are meant to be soluble in the target environment, such as Cas9 which preferably is soluble inside a target cell. However, endogenous loading of Fc containing proteins can also be achieved with transmembrane and/or membrane-associated EV proteins such as CD9, CD81, CD63, etc. When utilizing membrane-bound exosomal proteins for endogenous loading the Fc binding polypeptide is instead placed on a loop on the luminal side of the EV membrane as opposed to on the extravesicular side, enabling luminal as opposed to extravesicular loading. The EVs as per the present invention thus normally comprise a plurality of such fusion protein-Fc domain-containing protein complexes ("a plurality" shall be understood to relate to multiple copies of the same Fc domain-containing protein or several different Fc domain containing proteins), either anchored in or associated with the EV membrane on the inside or on the outside, or in essentially soluble form luminally in the EV.

In a further aspect, the present invention relates to methods for producing EVs capable of binding to proteins comprising an Fc domain, such as antibodies and proteins engineered to comprise Fc domains. Such methods typically comprise the steps of (i) introducing into an EV source cell a polynucleotide construct which encodes a fusion protein comprising at least one Fc binding polypeptide and at least one exosomal polypeptide, and (ii) collecting EVs that have been secreted by the EV-producing source cells, wherein the EVs comprise the fusion protein which has been expressed from the polynucleotide construct. In a subsequent step, the EVs comprising the fusion protein may be purified using a suitable purification technique, followed by being exposed to an Fc domain-containing protein, such as an antibody, to enable binding of the Fc containing protein through interaction between the Fc binding polypeptide and the Fc domain of the protein of interest. As above-mentioned, in an alternative embodiment, step (i) may also include expressing the Fc containing protein of interest from a polynucleotide construct in the same EV source cell, thereby achieving endogenous loading of the EV. The fusion protein (between the exosomal polypeptide and the Fc binding polypeptide) and the Fc containing protein may be expressed from the same or from different polynucleotide construct, depending on the construct design.

In yet another aspect, the present invention relates to a method for attaching at least one protein comprising an Fc domain, such as an antibody, to an EV. In an embodiment, the method is for coating an EV with said at least one protein comprising an Fc domain. Such methods comprise the steps of (i) providing an EV comprising a fusion protein comprising at least one Fc binding protein fused to at least one exosomal polypeptide, and (ii) allowing the Fc binding protein of the fusion protein to bind the Fc domain of at least one protein comprising an Fc domain. The EV source cells used for production of EVs comprising the fusion proteins as per the present invention may be either stably or transiently transfected with the polynucleotide construct needed to generate the EVs carrying the fusion protein-Fc containing protein complex. Stable transfection is advantageous as it enables creation of master cell banks (MCBs) and working cell banks (WCBs). However, transient transfection is also advantageous in certain instances, for example when assessing different constructs or e.g. when rapidly creating an autologous therapy comprising EVs obtained from a patient's own EV-producing cells.

In a further aspect, the present invention relates to methods for delivery of a protein of interest into the intracellular environment of target cells, either in vitro, ex vivo or in vivo. Such methods comprise the steps of (i) providing EVs comprising at least one Fc binding polypeptide, (ii) putting the EV comprising the Fc binding polypeptide in contact with an Fc containing protein, in order to enable binding between the Fc binding polypeptide comprised in the EV and the Fc domain of the Fc containing protein, and (iii) putting the complex formed between the EV and the Fc containing protein(s) (i.e. an EV having at least one Fc containing protein attached to it through the interaction between the Fc binding polypeptide and the Fc domain) in contact with the target cell(s). In a preferred embodiment, the Fc binding polypeptide is comprised in a fusion protein together with at least an exosomal polypeptide, but optionally other polypeptides and domains as well. Due to the unique ability of EVs to internalize into target cells, the Fc containing protein will also be internalized. This is highly advantageous and opens up the intracellular space for delivery of virtually any protein-based therapeutics. As above-mentioned, the EV-mediated internalization of Fc containing proteins take place both in vivo and in vitro, and these methods may thus have significant impact for therapy development but also for research and diagnostic purposes.

In a further aspect, the present invention pertains to the use of EVs as delivery vehicles for antibodies and other Fc domain containing proteins of interest. Furthermore, the present invention also provides for the use of EVs attached to Fc containing proteins as delivery vehicles for other therapeutic agents of interest. As a non-limiting example, EVs having attached to their surface a targeting antibody may also contain additional therapeutic agents which may be present either inside the EV and/or in the EV membrane. For instance, an antibody-coated EV may be used to deliver an RNA therapeutics cargo (such as an mRNA, an siRNA, an oligonucleotide, etc.) to a target cell, tissue and/or organ. In another non-limiting example, EVs having attached to their surface an Fc containing targeting protein (such as a scFv which have been engineered to contain an Fc domain) and comprising inside the EV or in/on the EV membrane a therapeutic protein such as Cas9 for gene editing, optionally together with a CRISPR RNA guide strand.

In further aspects, the methods of the present invention may also comprise exposing the EV source cells to serum starvation, hypoxia, bafilomycin, or cytokines such as TNF-alpha and/or IFN-gamma, in order to influence the yield or properties of the resulting EVs. The EV production scale and timeline will be heavily dependent on the EV-producing cell or cell line and may thus be adapted accordingly by a person skilled in the art. The methods as per the present invention may further comprise an EV purification step, which may be carried out prior to co-incubating the EVs comprising the fusion protein with the Fc domain-containing protein (such as an antibody) to be attached to (e.g. coated on) the EVs. EVs may be purified through a procedure selected from a group of techniques comprising liquid chromatography (LC), high-performance liquid chromatography (HPLC), bead-eluate chromatography, spin filtration, tangential flow filtration (TFF), hollow fiber filtration, centrifugation, immunoprecipitation, flow field fractionation, dialysis, microfluidic-based separation, etc., or any combination thereof. In an advantageous embodiment, the purification of the EVs is carried out using a sequential combination of filtration (preferably ultrafiltration (UF), tangential flow filtration or hollow fiber filtration) and size exclusion liquid chromatography (LC) or bead-eluate chromatography. This combination of purification steps results in optimized purification, which in turn leads to superior therapeutic activity. Further, as compared to ultracentrifugation (UC), which is routinely employed for purifying exosomes, sequential filtration-chromatography is considerably faster and possible to scale to higher manufacturing volumes, which is a significant drawback of the current UC methodology that dominates the prior art. Another advantageous purification methodology is tangential flow filtration (TFF), which offers scalability and purity, and which may be combined with any other type of purification technique.

In yet another aspect, the present invention pertains to pharmaceutical compositions comprising EVs, normally in the form of populations of EVs, as per the present invention. Typically, the pharmaceutical compositions as per the present invention comprise one type of therapeutic EV (i.e. a population of EVs comprising a certain type of fusion protein and being coated by one or more types of Fc containing proteins, such as antibodies; Cas9-Fc fusion proteins and Fc-RNP fusion complexes; lysosomal storage disorder enzymes fused to Fc domains, etc.) formulated with at least one pharmaceutically acceptable excipient. However, more than one type of EV population may naturally be comprised in a single pharmaceutical composition, for instance in cases where a combinatorial antibody treatment is desirable. Naturally however, as above-mentioned, a single EV or a single population of EVs may comprise more than one Fc-containing protein (e.g. an antibody) bound to the EV surface. The at least one pharmaceutically acceptable excipient may be selected from the group comprising any pharmaceutically acceptable material, composition or vehicle, for instance a solid or liquid filler, a diluent, an excipient, a carrier, a solvent or an encapsulating material, which may be involved in e.g. suspending, maintaining the activity of or carrying or transporting the EV population from one organ, or portion of the body, to another organ, or portion of the body (e.g. from the blood to any tissue and/or organ and/or body part of interest).

The present invention also relates to cosmetic applications of EVs. Thus, the present invention may pertain to skin care products such as creams, lotions, gels, emulsions, ointments, pastes, powders, liniments, sunscreens, shampoos, etc., comprising a suitable EV, in order to improve and/or alleviate symptoms and problems such as dry skin, wrinkles, folds, ridges, and/or skin creases. In one embodiment, EVs (carrying a fusion protein bound to e.g. an antibody of interest) are obtained from a suitable EV-producing cell source with regenerative properties (for instance an MSC) are comprised in a cosmetic cream, lotion, or gel for use in the cosmetic or therapeutic alleviation of wrinkles, lines, folds, ridges and/or skin creases.

In yet another aspect, the present invention relates to EVs as per the present invention for use in medicine. Naturally, when an EV comprising a fusion protein bound to an Fc domain of a protein of interest (such as an antibody) is used in medicine, it is in fact normally a population of EVs that is being used. The dose of EVs administered to a patient will depend on the number of e.g. antibodies of interest that has been coated on the EV surface, the disease or the symptoms to be treated or alleviated, the administration route, the pharmacological action of the therapeutic protein itself, the inherent properties of the EVs, the presence of any targeting antibodies or other targeting entities, as well as various other parameters of relevance known to a skilled person.

The EVs of the present invention carrying the Fc containing proteins may be used for several different therapeutic and pharmaceutical aspects. In one embodiment, the EVs are covered with antibodies or other Fc containing proteins that target a specific cell type, tissue, and/or organ. This is a highly powerful way of targeting EVs, which may comprise other pharmaceutical agents in addition to the Fc containing protein, to tissues of interest, and could represent a step chance in targeted drug delivery. In another embodiment, therapeutic antibodies or other Fc domain-containing proteins that interact with a target antigen of interest can be efficiently delivered to tissues of interest that are typically hard to reach, using EVs with ability to cross biological barriers. This approach may for instance enable delivery of monoclonal antibodies into the central nervous system or into the brain. In yet another embodiment, coating of EVs with Fc containing proteins is a way of multiplexing the Fc containing protein of interest, in order to enhance or influence its target avidity or the conformation of its binding to a target of interest. In yet another embodiment, the EVs as per the present invention enable improved delivery and efficacy of antibody-drug conjugates (ADCs) or receptor-drug conjugates, as multiplexing of ADCs may significantly enhance their therapeutic efficacy and their presence on EVs means they can also enter target cells. In a further embodiment, the ability of EVs to enter target cells means that the EVs of the present invention opens up the entire intracellular space and make it druggable by essentially any protein comprising an Fc domain and/or any protein onto which an Fc domain can be fused (such as an enzyme for enzyme replacement therapy, nuclease such as Cas9, or a tumor suppressor such as any one of p53, pVHL, APC, CD95, ST5, YPEL3, ST7, and ST14).

The EVs and the EV populations thereof as per the present invention may thus be used for prophylactic and/or therapeutic purposes, e.g. for use in the prophylaxis and/or treatment and/or alleviation of various diseases and disorders. A non-limiting sample of diseases wherein the EVs as per the present invention may be applied comprises Crohn's disease, ulcerative colitis, ankylosing spondylitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barré syndrome, acute myocardial infarction, ARDS, sepsis, meningitis, encephalitis, liver failure, non-alcoholic steatohepatitis (NASH), non-alcoholic fatty liver disease (NAFLD), kidney failure, heart failure or any acute or chronic organ failure and the associated underlying etiology, graft-vs-host disease, Duchenne muscular dystrophy and other muscular dystrophies, lysosomal storage diseases such as Gaucher disease, Fabry's disease, MPS I, II (Hunter syndrome), and III, Niemann-Pick disease, Pompe disease, etc., neurodegenerative diseases including Alzheimer's disease, Parkinson's disease, Huntington's disease and other trinucleotide repeat-related diseases, dementia, ALS, cancer-induced cachexia, anorexia, diabetes mellitus type 2, and various cancers. Virtually all types of cancer are relevant disease targets for the present invention, for instance, Acute lymphoblastic leukemia (ALL), Acute myeloid leukemia, Adrenocortical carcinoma, AIDS-related cancers, AIDS-related lymphoma, Anal cancer, Appendix cancer, Astrocytoma, cerebellar or cerebral, Basal-cell carcinoma, Bile duct cancer, Bladder cancer, Bone tumor, Brainstem glioma, Brain cancer, Brain tumor (cerebellar astrocytoma, cerebral astrocytoma/malignant glioma, ependymoma, medulloblastoma, supratentorial primitive neuroectodermal tumors, visual pathway and hypothalamic glioma), Breast cancer, Bronchial adenomas/carcinoids, Burkitt's lymphoma, Carcinoid tumor (childhood, gastrointestinal), Carcinoma of unknown primary, Central nervous system lymphoma, Cerebellar astrocytoma/Malignant glioma, Cervical cancer, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Extracranial germ cell tumor, Extragonadal Germ cell tumor, Extrahepatic bile duct cancer, Eye Cancer (Intraocular melanoma, Retinoblastoma), Gallbladder cancer, Gastric (Stomach) cancer, Gastrointestinal Carcinoid Tumor, Gastrointestinal stromal tumor (GIST), Germ cell tumor (extracranial, extragonadal, or ovarian), Gestational trophoblastic tumor, Glioma (glioma of the brain stem, Cerebral Astrocytoma, Visual Pathway and Hypothalamic glioma), Gastric carcinoid, Hairy cell leukemia, Head and neck cancer, Heart cancer, Hepatocellular (liver) cancer, Hodgkin lymphoma, Hypopharyngeal cancer, Intraocular Melanoma, Islet Cell Carcinoma (Endocrine Pancreas), Kaposi sarcoma, Kidney cancer (renal cell cancer), Laryngeal Cancer, Leukemias ((acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia)), Lip and Oral, Cavity Cancer, Liposarcoma, Liver Cancer (Primary), Lung Cancer (Non-Small Cell, Small Cell), Lymphomas, AIDS-related lymphoma, Burkitt lymphoma, cutaneous T-Cell lymphoma, Hodgkin lymphoma, Non-Hodgkin, Medulloblastoma, Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic/Myeloproliferative Diseases, Myelogenous Leukemia, Chronic Myeloid Leukemia (Acute, Chronic), Myeloma, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic islet cell cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Pleuropulmonary blastoma, Prostate cancer, Rectal cancer, Renal cell carcinoma (kidney cancer), Retinoblastoma, Rhabdomyosarcoma, Salivary gland cancer, Sarcoma (Ewing family of tumors sarcoma, Kaposi sarcoma, soft tissue sarcoma, uterine sarcoma), Sézary syndrome, Skin cancer (nonmelanoma, melanoma), Small intestine cancer, Squamous cell, Squamous neck cancer, Stomach cancer, Supratentorial primitive neuroectodermal tumor, Testicular cancer, Throat cancer, Thymoma and Thymic carcinoma, Thyroid cancer, Transitional cell cancer of the renal pelvis and ureter, Urethral cancer, Uterine cancer, Uterine sarcoma, Vaginal cancer, Vulvar cancer, Waldenström macroglobulinemia, and/or Wilm's tumor.

The EVs as per the present invention may be administered to a human or animal subject via various different administration routes, for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intrailleal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated and/or the characteristics of the antibody or the EV population as such.

Suitable targeting antibodies in accordance with the present invention may target antigens deriving from e.g. tumors, solid organs, bodily structures, cell or tissue types. Non-limiting examples of the origin of antigens that may be targeted by targeting antibodies include liver, lung, kidney, heart, pancreas, adrenal glands, thyroid glands, parathyroid glands, brain including all brain regions (for instance thalamus, hypothalamus, striatum, etc.), the blood-brain-barrier, the CNS, the PNS, bone marrow, the skin, the vascular system, the lymphatic system including the spleen, joints, eyes, muscle tissues, sites of inflammation, sites of injury, and cell types such as adipocytes, muscle cells (myoblasts and myotubes), satellite cells, cardiac cells, endothelial cells, fibroblasts, hepatocytes, renal cells, pericytes, neurons, glia cells, astrocytes, oligodendrocytes, macrophages, DC-cells, B-cells, T-cells, NK-cells, chrondrocytes, osteoblast, osteocytes, epithelial cells, erythrocytes, earlier progenitors such as multipotential hematopoietic stem cells/hemocytoblasts, myeloid progenitors, lymphoid progenitors, etc. Non-limiting examples of antigens relevant for targeting cancer includes adenocarcinoma antigen, alpha-fetoprotein, BAFF, C242 antigen, CA-125, carbonic anhydrase 9 (CA-IX), disialoganglioside (GD2), 4-IBB, 5T4, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DR5, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgGI, LI-CAM, IL-13, IL-6, insulin-like growth factor I receptor, integrin α5β1, integrin αvβ3, legumain, MORAb-009, MS4A1, MUC1, mucin CanAg, C-MET, CCR4, CD 152, CD 10, CD 19, CD20, CD200, N-glycolylneuraminic acid, NPC-IC, PDGF-Ra, PDL192, phosphatidylserine, tumor antigen CTAA16.88, VEGF-A, VEGFR-1, VEGFR2, vimentin, RANKL, RON, ROR1, SCH 900105, SDC1, SLAMF7, TAG-72, tenascin C, TGF beta 2, TGF-β, TRAIL-R1, TRAIL-R2, folic acid receptor, transferrin receptors and any combination thereof.

Antibodies or other Fc domain-containing proteins coating EVs in order to prevent or reduce opsonization and/or immune cell-mediated EV clearance in accordance with the present invention may be essentially any Fc-containing protein, such as an antibody, that is present naturally in serum or in any other body fluid. Such antibodies may thus be of any type, e.g. IgG, IgA, IgM, IgE and/or IgD, but any other protein comprising an Fc domain and having the capacity to prevent opsonization of EVs in vivo may also be used to coat the EV. Thus, coating of EVs to avoid or reduce clearance by immune may be carried out actively or passively, wherein the active coating may involve decorating the EV in question with a suitable protein comprising an Fc domain prior to application in vivo. Suitable Fc containing proteins for this purpose include Factor H and/or Factor I fused to an Fc domain. Factor H and Factor I are negative regulators of the complement system (by inhibiting C3 conversion to C3b), thereby resulting in reduced EV clearance when fused to an Fc domain and attached to the EV surface through the binding between the Fc binding polypeptide and the Fc domain of the fusion proteins. Passive coating on the other hand may entail allowing the EV in question to sequester proteins in vivo with its available non-bound Fc binders.

In a further embodiment, suitable non-limiting examples of therapeutic and/or targeting antibodies in accordance with the present invention may be any one or more of Abagovomab, Abciximab, Actoxumab, Adalimumab, Adecatumumab, Adotrastuzumab emtansine, Aducanumab, Afelimomab, Afutuzumab, Alacizumab Alemtuzumab, Alirocumab, Altumomab pentetate, Amatuximab, Anatumomab mafenatox, Anifrolumab, Anrukinzumab, Apolizumab, Arcitumomab, Aselizumab, Atezolizumab, Atinumab, Atlizumab, Atorolimuma, Avelumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, cBR96-doxorubicin immunoconjugate, Cedelizumab, Certolizumab pegol, Cetuximab, Citatuzumab bogatox, Cixutumumab, Clazakizumab, Clenoliximab, Clivatuzumab tetraxetan, Conatumumab, Concizumab, Crenezumab, CR6261, Dacetuzumab, Daclizumab, Dalotuzumab, Daratumumab, Demcizumab, Denosumab, Detumomab, Dinutuximab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etanercept, Etaracizumab, Etrolizumab, Evolocumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, IMAB362, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Mavrilimumab, Matuzumab, Mepolizumab, Metelimumab, Milatuzumab, Minretumomab, Mitumomab, Mogamulizumab, Morolimumab Motavizumab, Moxetumomab pasudotox, Muromonab-CD3, Nacolomab tafenatox, Nam ilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Ontuxizumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Risankizumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, Ticilimumab, Tildrakizumab, Tigatuzumab, Tocilizumab, Toralizumab, Tositumomab, Bexxar, Tovetumab, Tralokinumab, Trastuzumab, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, Zolimomab aritox, or any combination thereof. Importantly, the present invention provides for the delivery of any antibody, regardless of whether its target is intracellular and/or extracellular. The ability of the EVs of the present invention to efficiently internalize antibodies represent a step-change in monoclonal antibody development and may enable targeting antigens and targets across the entire intracellular compartment of target cells. Importantly, antibodies and Fc containing proteins as per the present invention may advantageously be labelled for detection and imaging purposes, for instance using fluorophores, MRI agents, PET agents, radioactive agents, enzymes, nanoparticles, metals, organic and inorganic compounds, etc.

It shall be understood that the above described exemplifying aspects, embodiments, alternatives, and variants can be modified without departing from the scope of the invention. The invention will now be further exemplified with the enclosed examples, which naturally also can be modified considerably without departing from the scope and the gist of the invention.

EXPERIMENTAL PART

Materials and Methods

Construct design and cloning: Various fusion proteins comprising at least one exosomal polypeptide and at least one Fc binding polypeptide have been constructed, cloned into vectors and produced in several different EV-producing cell sources. ORFs were typically generated by synthesis and cloned into the mammalian expression vector pSF-CAG-Amp. Briefly, synthesized DNA and vector plasmid were digested with enzymes NotI and SalI as per manufacturers instruction (NEB). Restricted, purified DNA fragments were ligated together using T4 ligase as per manufacturers instruction (NEB). Successful ligation events were selected for by bacterial transformation on ampicillin-supplemented plates. Plasmid for transfection was generated by 'maxi-prep', as per manufacturers instruction.

In cases where Fc containing proteins were endogenously produced in the same EV-producing cell source that expresses the fusion protein, ORF sequences were purchased (Origene Technologies, Inc.) and amplified and cloned into the MSC A site of pIRES bicistronic expression vector (Clonetech, Laboratories Inc.) such that upon translation the exosomal polypeptide was fused to the Fc binding polypeptide in one construct, whereas the Fc containing protein of interest was translated separately (from a separate construct or from the same construct) and transported into the EV to be formed in the EV-producing cell source. Most of the cloning was performed using the NEBuilder HiFi DNA Assembly Cloning Kit (NEB, Inc.) and confirmed using Sanger sequencing (Source BioScience). The pIRES vector enables bicistronic expression of both transgenes simultaneously, ensuring EV-producing cells would express both the fusion protein and the Fc containing protein of interest simultaneously. Plasmids were transformed into the NEB 5-alpha Competent *E. coli* cells (NEB, Inc.) and grown overnight in a shaking incubator according to manufacturer's recommendations. Plasmids were isolated and purified using the 'maxi-prep plasmid DNA purification kit' (Qiagen), as per manufacturer's instruction.

Cell Culture and Transfection

Depending on the experimental design and assays, in certain cases, non-viral transient transfection and exosome production was carried out in conventional 2D cell culture, whereas in other cases virus-mediated transduction was employed to create stable cell lines, which were typically cultured in bioreactors of different type. For conciseness, only a few examples are mentioned herein.

HEK293T cells were typically seeded into 15 cm dishes ($9 \times 10^6$ cells per dish) and left overnight in serum-containing DMEM as recommended by ATCC. The following day the cells were transiently transfected with lipoplexed DNA added directly onto cells. Briefly, DNA and polyethyleneimine (PEI) were separately incubated in OptiMEM for 5 minutes before combining together for 20 minutes at room temperature. Lipoplexed DNA and cells were co-incubated for 6 hours following which conditioned culture media was changed to OptiMEM for 48 hours. Other cells and cell lines that were evaluated in dishes, flasks and other cell culture vessels included bone marrow-derived mesenchymal stromal cells (BM-MSCs) and Wharton's jelly-derived MSCs (WJ-MSCs), amnion cells, fibroblasts, various endothelial and epithelial cells, as well as various immune cells and cell lines.

In the case of viral transduction and creation of stable cell lines for various combinations of fusion proteins and Fc containing proteins of interest, cell sources such as BM-MSCs, WJ-MSC, fibroblasts, amnion cells, fibroblasts, various endothelial and epithelial cells, were virus-transduced, typically using lentivirus (LV). Typically, 24 hours before infection, 100.000 cells (e.g. fibroblasts, MSCs, etc.) or 200.000 cells (e.g. HEK293T) are plated in a 6-well plate. 2 uL of LV and optionally Polybrene (or hexadimethrine bromide, final concentration on the well of 8 ug/mL) are added, and 24 hours post transduction the cell medium of transduced cells is changed to fresh complete media. At 72 hours post transduction, puromycin selection (4-6 µg/ml) is performed, normally for 7 days followed by analysis of stable expression of the fusion protein construct comprising the exosomal polypeptide and the Fc binding polypeptide.

Stable cells were cultured in either 2D culture or in bioreactors, typically hollow-fiber bioreactors or stir-rank bioreactors, and conditioned media was subsequently harvested for exosome preparation. Various preparation and purification steps were carried out. The standard workflow comprises the steps of pre-clearing of the supernatant, filtration-based concentration, chromatography-based removal of protein contaminants, and optional formulation of the resultant exosome composition in a suitable buffer for in vitro and/or in vivo assays.

Assays and Analytics

Western blot is a highly convenient analytical method to evaluate the enrichment of fusion proteins in EVs. Briefly, SDS-PAGE was performed according to manufacturer's instruction (Invitrogen, Novex PAGE 4-12% gels), whereby $1\times10^{10}$ exosomes and 20 ug cell lysate were loaded per well. Proteins from the SDS-PAGE gel were transferred to PVDF membrane according to manufacturer's instruction (Immobilon, Invitrogen). Membranes were blocked in Odyssey blocking buffer (Licor) and probed with antibodies against the Fc binding polypeptide and/or the exosomal protein according to supplier's instruction (Primary antibodies—Abcam, Secondary antibodies—Licor). Molecular probes visualized at 680 and 800 nm wavelengths.

For EV size determination, nanoparticle tracking analysis (NTA) was performed with a NanoSight instrument equipped with analytical software. For all recordings, we used a camera level of 13 or 15 and automatic function for all post-acquisition settings. Electron microscopy and fluorescence microscopy were frequently used to understand intracellular location and release and to quantitate and analyze EVs.

EVs were isolated and purified using a variety of methods, typically a combination of filtration such as TFF and LC, in particular bead-elute LC. Typically, EV-containing media was collected and subjected to a low speed spin at 300 g for 5 minutes, followed by 2000 g spin for 10 minutes to remove larger particles and cell debris. The supernatant was then filtered with a 0.22 µm syringe filter and subjected to different purification steps. Large volumes were diafiltrated and concentrated to roughly 20 ml using the Vivaflow 50R tangential flow (TFF) device (Sartorius) with 100 kDa cutoff filters or the KR2i TFF system (Spectrum Labs) with 100 or 300 kDa cutoff hollow fibre filters. The preconcentrated medium was subsequently loaded onto the bead-eluate columns (HiScreen or HiTrap Capto Core 700 column, GE Healthcare Life Sciences), connected to an AKTAprime plus or AKTA Pure 25 chromatography system (GE Healthcare Life Sciences). Flow rate settings for column equilibration, sample loading and column cleaning in place procedure were chosen according to the manufacturer's instructions. The sample was collected according to the UV absorbance chromatogram and concentrated using an Amicon Ultra-15 10 kDa molecular weight cut-off spin-filter (Millipore) to a final volume of 100 µl and stored at −80° C. for further downstream analysis. To assess the protein and RNA elution profiles, media was concentrated and diafiltrated with KR2i TFF system using 100 kDa and 300 kDa hollow fibre filters and a sample analysed on a Tricorn 10/300 Sepharose 4 Fast Flow (S4FF) column (GE Healthcare Life Sciences).

EXAMPLES

Example 1: Binding of IgG to EVs Comprising Fc Binding Polypeptides (Fc-Binding EVs)

EVs were isolated from the conditioned medium from engineered HEK293T cells (control versus Fc-binding construct that stably express Gp130 Extracellular domain-2XGGGGS linker-Z domain-Gp130 transmembrane domain-Leucine Zipper-N terminal syntenin-His tag) using tangential flow filtration with 300 kd hollow fiber columns, followed by ultrafiltration using 10 kd spin filters for concentration. The binding capacity for IgG by the Fc-binding EVs were then assessed using electron microscopy and flow cytometry.

Figure 2:
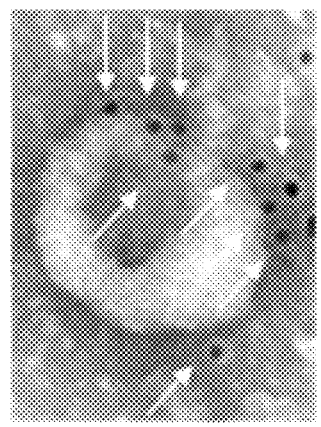
FIG. 2. Electron microscopy pictures of EVs comprising Fc binding polypeptides (A) are decorated with nanogold labeled antibodies (i.e. Fc containing proteins), whereas control EVs (B), which lack Fc binding polypeptides, do not have any antibodies bound to their surfaces.
Figure 2:
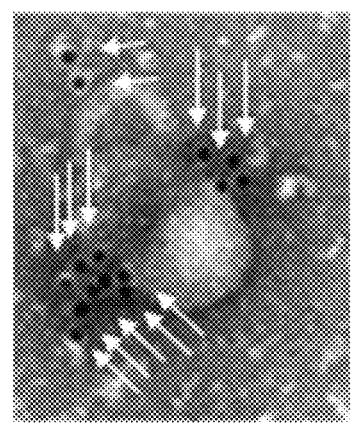
Figure 2:
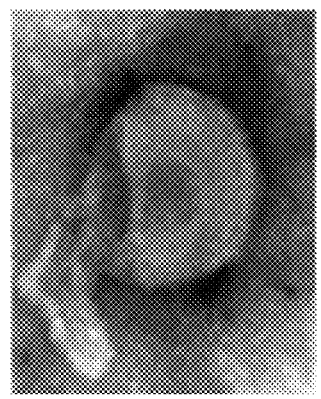
Figure 2:
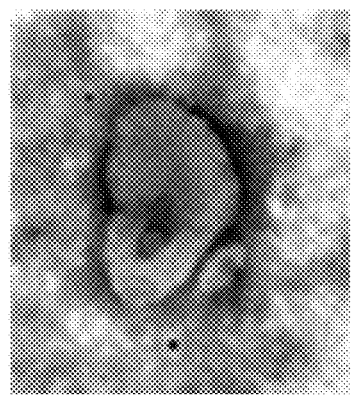

For electron microscopy, $1\times10^9$ EVs were incubated with Rabbit anti-goat 10 nm antibody conjugated with gold Nanoparticles for 2 h at 37° C. As shown in FIG. 2, Fc-binding EVs (A) are decorated with nanogold labeled antibodies (i.e. Fc containing proteins), whereas control EVs (B) do not have any antibodies bound.

Figure 3:
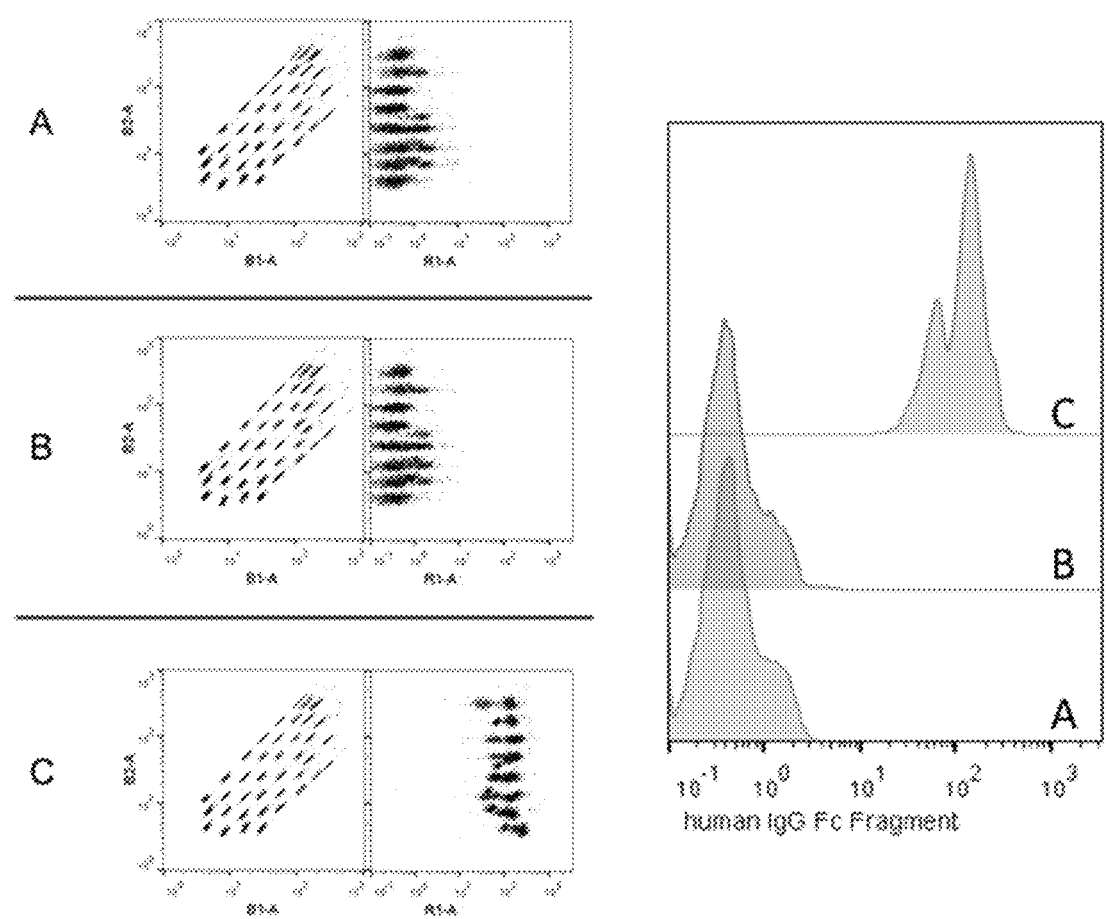
FIG. 3. Flow cytometry data showing that the EVs comprising Fc binding polypeptides bind Fc containing proteins of interest (human IgG). The binding is very efficient to all bead populations included in the kit, including the unspecific/Isotype/negative control bead populations FIG. 4. Anti-HER2 antibody increases uptake of antibody-decorated EVs as compared to isotype control-decorated and wild type EVs only in HER2 high-expressing cell line MDA-MB-361, but not in HER2 low-expressing cell line MDA-MB-231.

For flow cytometry, $1\times10^8$ EVs were incubated overnight on an orbital shaker at 450 rpm for 16 hours in 120 µl PBS with 15 µl antibody-coated capture beads from the MACSPIex Exosome Kit, human (Miltenyi Biotec, Order no 130-108-813). After washing, 3 µg of AlexaFluor647-conjugated human IgG Fc fragments (Jackson Laboratories, Catalogue 009-600-008) were added to controls without EVs (A), control EVs (B), or Fc-binding EVs (Syntheningp130-zDomain-gp130) (C). After 1 hour incubation at room temperature, unbound Fc fragments were washed away and samples were analyzed via flow cytometry. In FIG. 3 respective left dotplots show hard-dyed capture bead populations using B1-A (Excitation: 488 nm, Emission Filter: 500-550 nm; Area) versus B2-A (Excitation: 488 nm, Emission Filter: 565-605 nm, Area) parameters. Respective right plots show R1-A (Excitation: 635 nm, Emission Filter: 655-730 nm, Area) versus B2-A parameters, demonstrating binding of AlexaFluor647 labeled Fc-Fragments to EVs which have bound to the capture beads only in (C). FIG. 3 shows that the Fc-binding EVs bind both to AlexaFluor647-labelled Fc fragments (human IgG) and very efficiently also to the Fc domains of all 39 different antibodies which are coated on all capture bead populations by the manufacturer included in the kit, including the two negative control bead populations.

Example 2: FCGR1A Lamp2B EVs for Delivery of anti-HER2 Antibody

Figure 4:
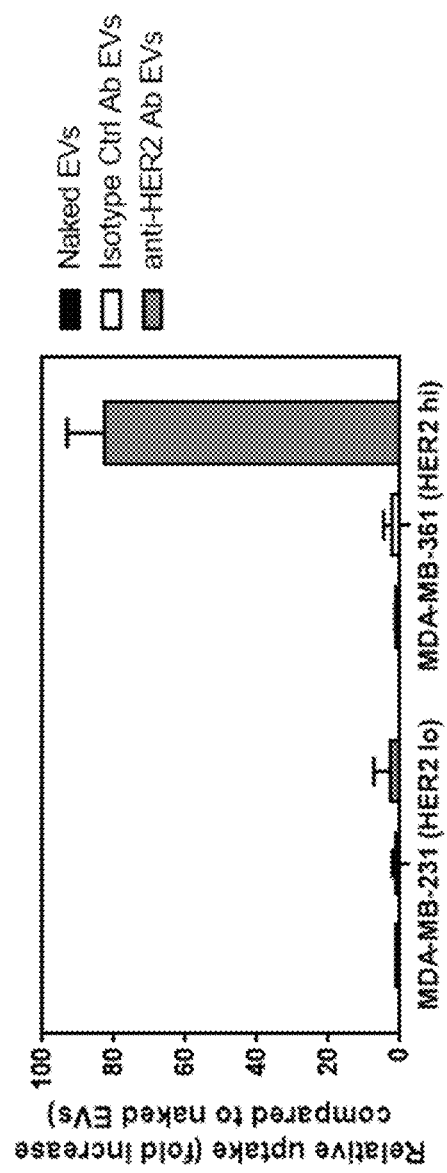

EVs were isolated from HEK293T cells (either stably expressing FCGR1A Extracellular domain-4XGSlinker-Lamp2b or their wild type controls) using ultrafiltration and size exclusion chromatography. EVs were labelled with PKH26 red fluorescent dye, and decorated with anti-HER2 antibody or its isotype control by co-incubating EVs and antibody for 1 h at 37° C. Unbound antibody was removed by size exclusion chromatography. Uptake of antibody decorated EVs was characterized in HER2 low-expressing cell line MDA-MB-231 and in HER2 high-expressing cell line MDA-MB-361 using flow cytometry. FIG. 4 shows that anti-HER2 antibody increases uptake of decorated EVs as compared to isotype control decorated and wild type EVs only in HER2 high-expressing cell line MDA-MB-361, but not in HER2 low-expressing cell line MDA-MB-231. Similar results were obtained with EVs expressing CD63-ZZ fusion proteins.

Figure 5:
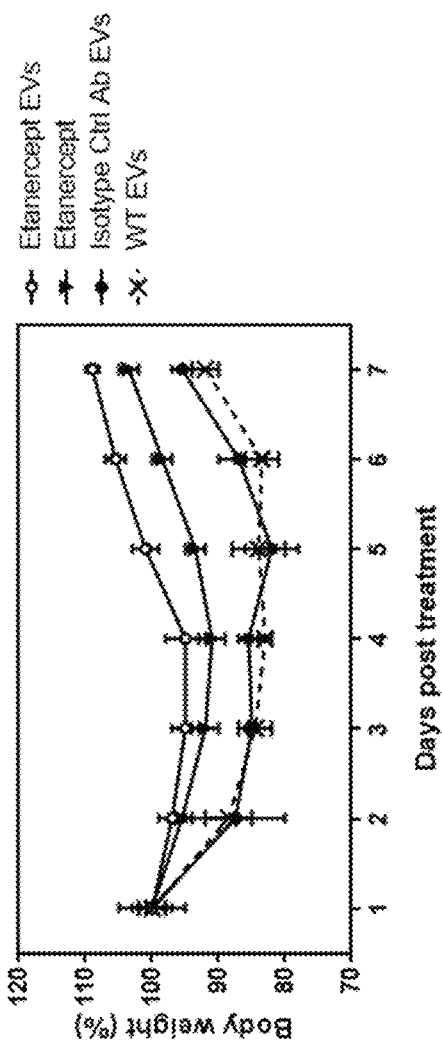
FIG. 5. Etanercept-coated EVs protects mice from loss of body weight, as opposed to WT or control decorated-EVs, and displayed higher activity than naked etanercept, possible due to higher affinity between etanercept and TNFalpha when etanercept is multiplexed and/or when the Fc binding polypeptide binds to its Fc domain.

Example 3: Etanercept Delivery by EVs Comprising CD81-Protein A/G Fusion Proteins EVs were isolated from HEK293T cells (either stably expressing CD81-ProteinA/G CD81 Second loop fusion protein or their wild type control) using ultrafiltration and size exclusion chromatography. EVs were decorated with etanercept or a control antibody by co-incubating EVs and etanercept for 1 h at 37° C. Unbound etanercept was removed by size exclusion chromatography. To study anti-inflammatory effect of the etanercept-decorated EVs, the well-studied TNBS-induced colitis mouse model was used. This model simulates the gut inflammation, cytokine storm and weight decrease associated with IBD patients. 24 mice were divided into four treatment groups, with 6 mice per group. The mice were pre-sensitized by applying 150 µl of a olive oil-acetate solution with 2% TNBS, on the skin, 1 week prior to colitis induction. Colitis was then induced by giving a rectal infusion of 100 µl solution containing 1.5% TNBS in 40% ethanol. Immediately post colitis induction, 10E10 EVs/g EVs in 200 µl were administrated intravenously in the tail vein. FIG. 5 shows that etanercept-coated EVs protected mice from loss of body weight, as opposed to WT or control decorated-EVs, and displayed higher activity than naked etanercept, possible due to higher affinity between etanercept and TNFalpha when etanercept is multiplexed and/or when the Fc binding polypeptide binds to its Fc domain.

Example 4: Intracellular Uptake and Delivery of Antibodies Via Fc-Binding EVs

Figure 6:
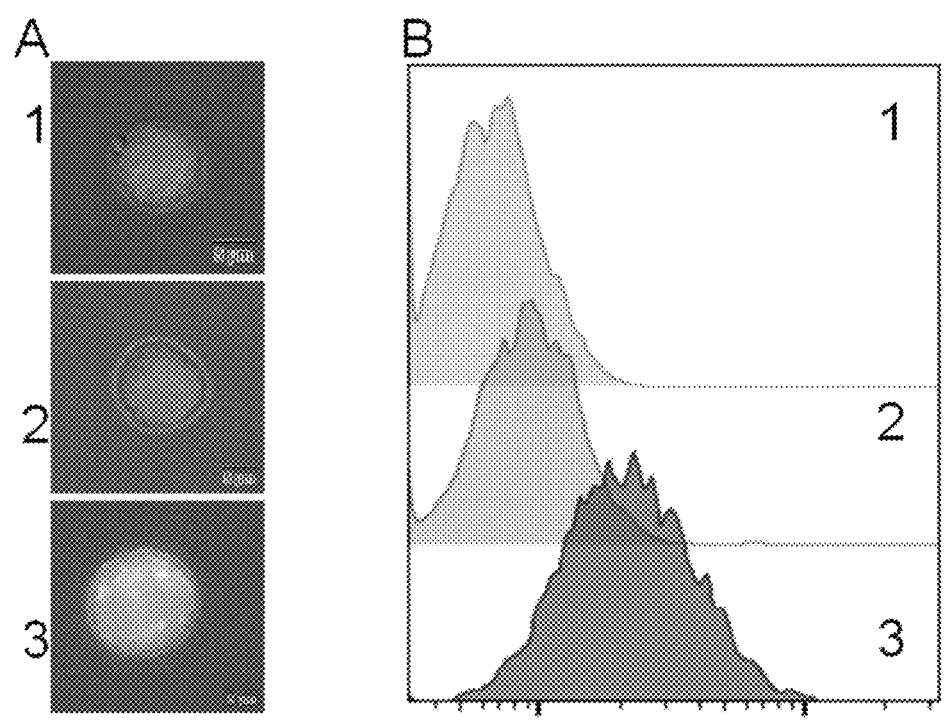
FIG. 6. Signals of fluorescently labelled antibodies are clearly present in cells treated with Fc-binding EVs having attached to their surfaces antibodies comprising Fc domains, while fluorescence signals are absent in untreated (1) or control EV treated (2) cells, measured by fluorescence microscopy (A) and flow cytometry (B). This demonstrates that Fc containing proteins such as antibodies can be delivered intracellularly by Fc binding EVs, and that binding to EVs dramatically increases uptake of antibodies into cells.

EVs were isolated from the conditioned medium of Wharton's jelly-derived MSCs (either stably expressing TNFR Extracellular domain-2XGGGGS linker-Z domain-TNFR transmembrane domain-foldon-N terminal syntenin fusion proteins or control) using ultrafiltration and size exclusion chromatography. In order to investigate whether Fc-binding EVs can be employed for intracellular delivery of Abs, $4 \times 10^{\wedge}11$ EVs were incubated in 400 µl for 16 hours (overnight) with total 3 µg AlexaFluor488-labelled anti-Lamin B2 IgGs [abcam ab200426, Rabbit monoclonal EPR9701 (B)]. For the uptake experiment, Huh7 cells were plated in 48 well plates at 30,000 cells per well and incubated for 16 hours before $0.675 \times 10^{\wedge}11$ antibody-labelled EVs were added. Cells were incubated for 2 hours at 37° C. and 5% $CO_2$ in a humidified atmosphere before they were trypsinized and analyzed by fluorescence microscopy (A) and flow cytometry (B) as shown in FIG. 6; A) show green fluorescence signals merged with phase contrast images. Histograms in B) show the green fluorescence intensity on a logarithmic scale on the x-axis and the normalized frequency on the y-axis. 1: HuH7 cells not treated with any antibody or EVs. 2: HuH7 cells treated with control EVs which were incubated with anti-Lamin B2 antibodies. 3: HuH7 cells treated with Fc-binding EVs which were incubated with anti-Lamin B2 antibodies. FIG. 6 shows that signals of fluorescent antibodies are clearly present in cells treated with Fc-binding EVs plus antibody, while fluorescence signals are absent in untreated (1) or control EV treated (2). This demonstrates that antibodies can be delivered intracellularly via Fc-binding EVs, and that binding to EVs dramatically increases uptake of antibodies into cells.

Figure 7:
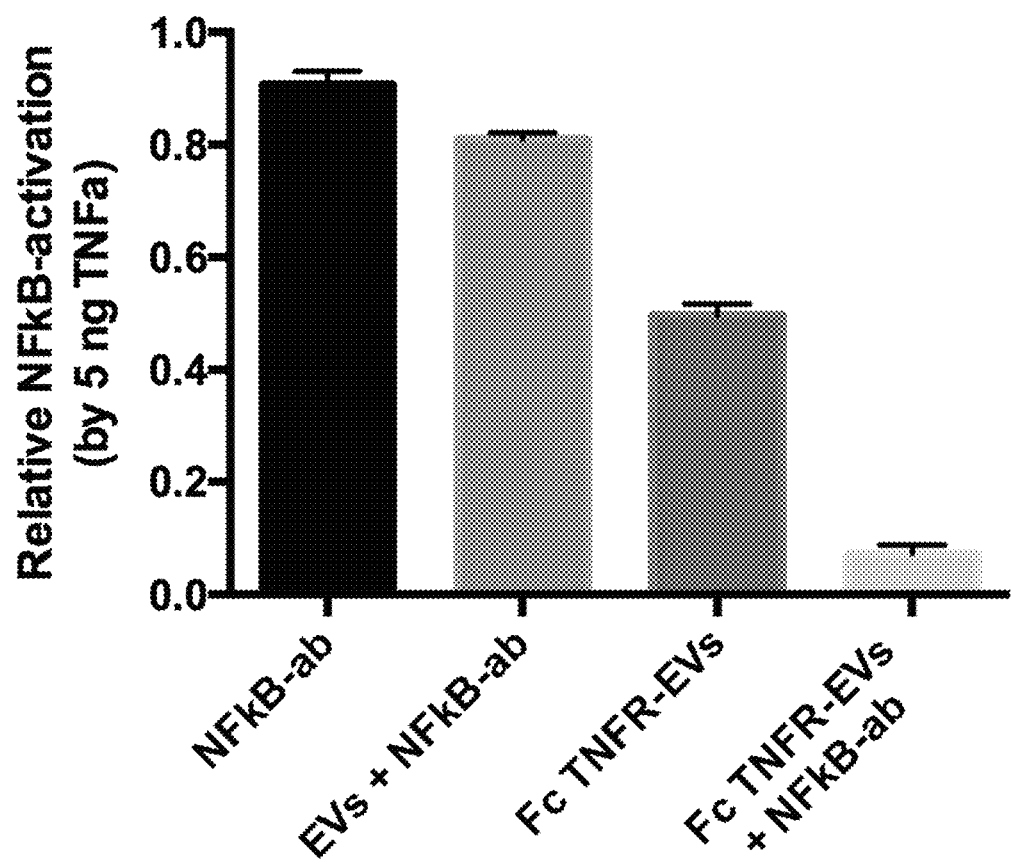
FIG. 7. Successful inhibition of NFkB-mediated intracellular signals when an anti-NFkB antibody is delivered into cells by Fc-binding EVs (i.e. EVs comprising at least one Fc binding polypeptide fused to at least one exosomal polypeptide).

To demonstrate functional intracellular delivery, anti-NFkB antibodies (anti-NFkB-Ab) were incubated with respective EVs for 1 h at 37° C. A reporter cell line, HEK cells stably expressing NFkB-luciferase, were treated with 5 ng/ml hTNF-alpha and the EV-Ab-mix. After 6 hours of treatment the luciferase activity was measured. FIG. 7 shows successful inhibition when the anti-NFkB-ab is delivered by Fc-binding EVs.

Figure 8:
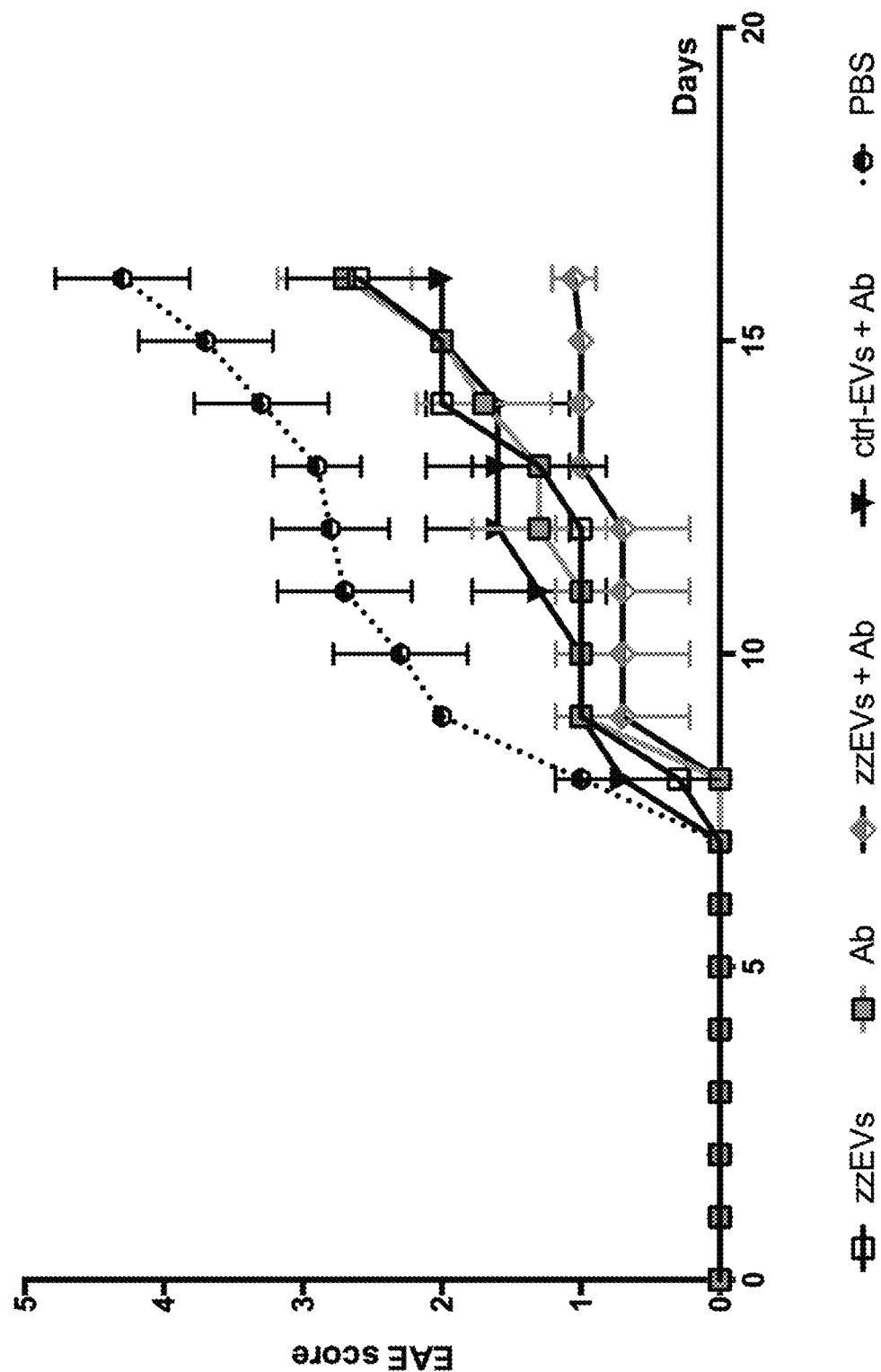
FIG. 8. Control EVs, as well as single treatment with an anti-integrin-4a antibody display moderate protective effect from EAE development in mice, whereas zz domain EVs coated with the same anti-integrin-4a antibody almost completely abrogates EAE development in vivo.

Example 5: EAE Treatment Using Fc-Binding EVs Decorated with Anti-Integrin-4-Alpha-Ab C57BL/6 mice were induced with experimental autoimmune encephalitis (EAE) by s.c. injection of 100 ul of $MOG_{35-55}$-CFA emulsion and i.p. injection of 400 ng pertussis toxin on the same day and two days following immunization. EVs were isolated as described in example 1, from conditioned media of bone marrow-derived MSCs (either stably expressing CD9-ZZ (a fusion construct comprising as a non-limiting example the SEQ ID NO 1 operably linked to as a non-limiting example the SEQ ID NO 74) domain fusion proteins or their wild type controls). Anti-integrin-4-alpha antibodies (Ab) were incubated with respective EVs (zzEVs or ctrl-EVs). The EAE mice were injected with anti-integrin-4a-Ab with or without EVs at day 7. FIG. 8 shows that ctrl-EVs, as well as anti-integrin-4a-Ab display moderate protective effect from EAE development per se, whereas zzEVs incubated with anti-integrin-4a-Ab displayed almost complete inhibition of EAE development.

Figure 9:
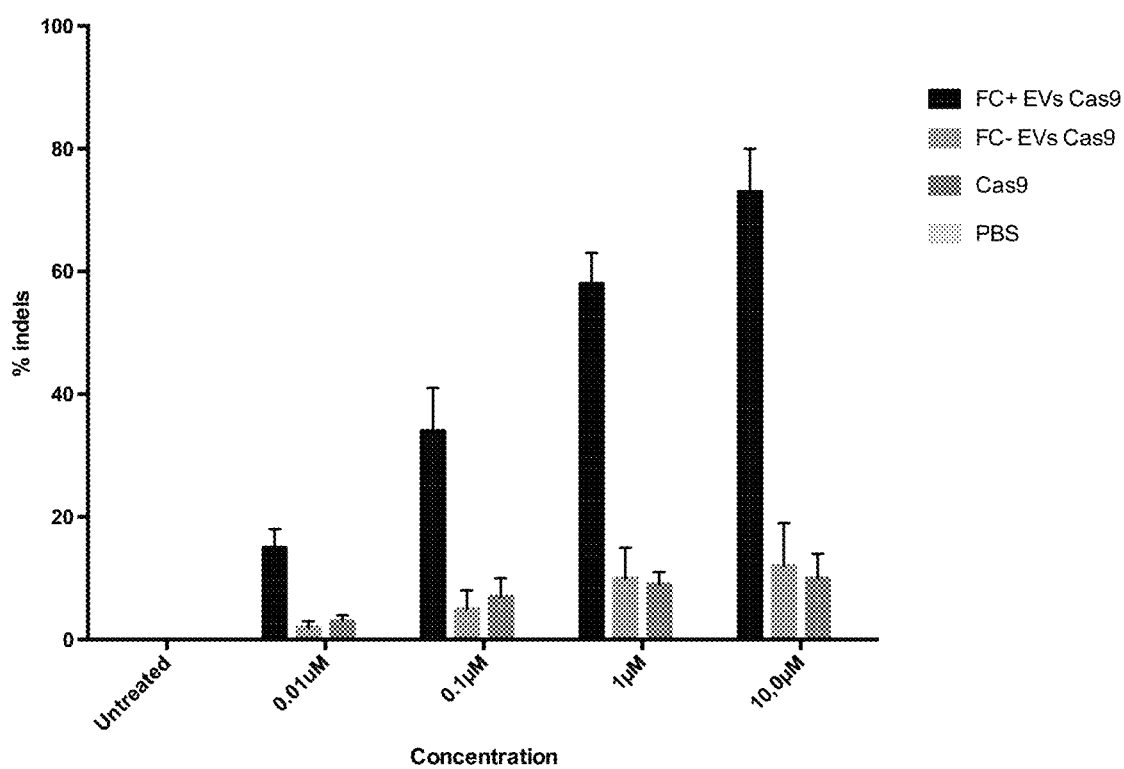
FIG. 9. Intracellular delivery of CRISPR-Cas9 guide RNA complexes for targeted genome editing, graph showing targeted genomic cleavage after delivery of Fc Cas9 guide RNA complexes through Fc binding domain-Lamp2b engineered EVs.

Example 6: Targeted Genomic Deletion by Delivering Fc-Cas9 Endonuclease Using Fc-Binding EVs EVs were purified as stated in example 1 from cell culture medium obtained from adipocytes (stably transfected FCGR1A Extracellular domain-4XGSlinker-Lamp2b fusion protein or Lamp2b GFP as a control). Varying amounts of EVs was used (100 µg, 500 µg, 2.5 mg, 5 mg and 10 mg), whilst the amount of Fc (IGHG1) tagged-Cas9 Guide RNA complexes (so called RNP complexes) targeting HPRT remained at 100 µg. The final weight ratios of Cas9 complex to EVs were 1:1, 1:5, 1:25, 1:50 and 1:100 respectively and incubated at 22° C. for 60 minutes. Maximum loading of Cas9 on EVs was obtained with 1:5 weight ratio of Cas9 complexes to EVs, free Cas9 complexes were removed by ultrafiltration. Then Cas9 loaded Fc+ Adipocytes-EVs were used to treat Huh7 cells with different concentration. After 24 hours cells were harvested and GeneArt Genomic Cleavage detection kit (Thermo scientific) was used as per manufacture protocol for preparing samples genomic cleavage assay and run on a 2% agarose gel. Indels were then quantified using Image J software. FIG. 9 shows dose-dependent gene editing in target cells. Various other pairs of Fc binding polypeptides and Fc domains fused to Cas9 were also evaluated in the same setup. Human FCAMR (IgA and IgM binding), human FCGR3A (IgG binding), and human FCGRB (IgG binding) fused to CD83 and combined with Cas9 fused to several different human Fc domains (e.g. IGHM, IGHA1, IGHG1, etc.) were also evaluated in the same setup. Overall, all construct showed gene editing activity but with lower potency than the FCGR1A Extracellular domain-4XGSlinker-Lamp2b fusion protein (data not shown).

Example 7: EV Decoration with Soluble Lysosomal Proteins Using the Human-Fc/pH-Sensing Protein G Complex The C2 domain of Protein G fused to various exosomal proteins such as CD63, Lamp2, and the transferrin receptor were evaluated for their expression and EV display levels. To facilitate the tethering of a lysosomal protein to the surface of EVs, a human Fc domain (deriving from IgG) (hFc) was fused to either the N or C terminus of the enzyme GBA. In the case of the N-fusion construct, the hFc domain was inserted following the signal peptide native to GBA. Co-expression of both constructs led to a significant enrichment of GBA with EVs, more so than over expression of wild-type GBA. In addition to the wt C2 domain of Protein G, a pH-sensing C2 domain was also displayed on the EV surface in a manner previously described. While the pH sensing C2 domain has the capacity to effectively bind the human Fc region, the affinity for complex formation drops over a thousand-fold at pH 4. Following cellular uptake of GBA-decorated by pH-sensing C2 domain EVs, they are trafficked to the lysosomal compartment. Within the low pH of the compartment, the tethered GBA and pH-sensing c2 domain dissociate, facilitating the presence of free untethered GBA within the lumen of the lysosome.

Figure 10:
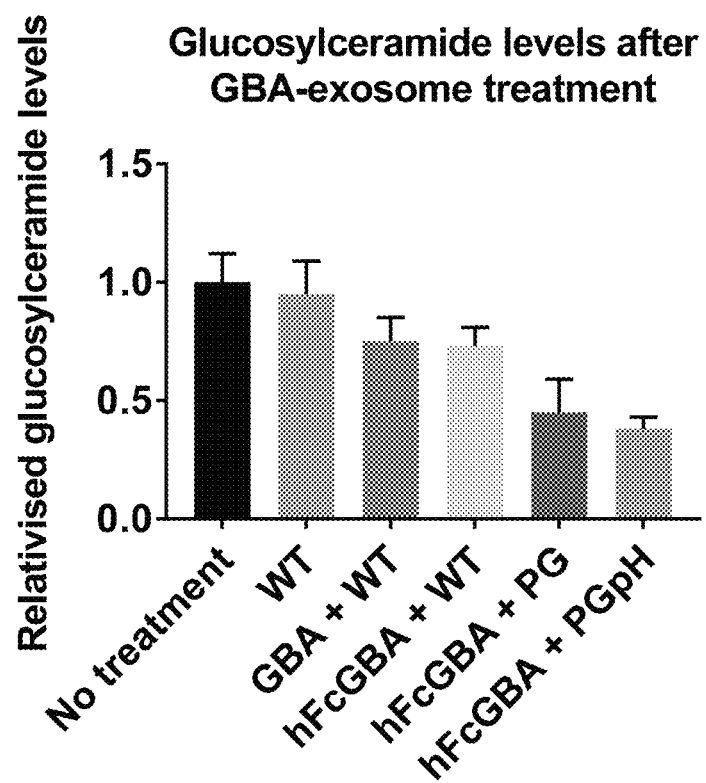
FIG. 10. Intracellular delivery of the lysosomal storage disorder enzyme GBA fused to an Fc domain, and bound to HEK-derived EVs comprising an Fc binding polypeptide.

Conditioned media isolated from Hek293T cells producing wild type exosomes, C2 domain of Protein G decorated exosomes or pH-sensing C2 domain of Protein G decorated exosomes was combined with conditioned media from Hek293T cells expressing wild type GBA or human Fc-GBA fusion for 1 hour at 37° C. In addition, a co-incubation was performed in which the conditioned media was acidified to pH 4. EVs were then isolated by ultrafiltration and bead elution chromatography. To assess the levels of exosome-tethered GBA, purified vesicles were analyzed by western blot and probed for the presence of GBA. To assess the GBA activity of the GBA-carrying exosomes, patient-derived GBA deficient fibroblasts were co-incubated with GBA-enriched exosomes and analyzed for glucosylceramide levels 48 hours later. FIG. 10 shows the outcome of this experiment: WT—wildtype Hek293t exosomes; GBA—wildtype GBA; hFc-GBA—human Fc fragment-GBA fusion; PG—exosomes decorated with the C2 domain of Protein G; PGpH—exosomes decorated with the C2 domain of pH sensing Protein G. n=3. In an analogous experiment, Protein L and Protein LG were also evaluated as Fc binding polypeptides in the same setup, resulting in similar outcomes (data not shown).

Example 8: EVs Coated with siRNA-Loaded Ago2 Fused to a Human Fc Domain

Figure 11:
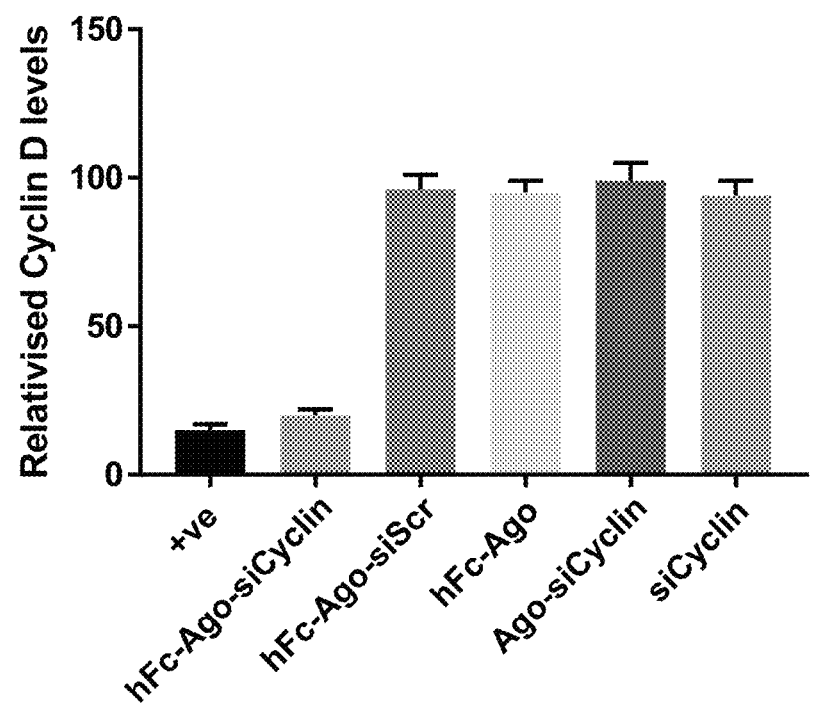
FIG. 11. Cyclin D levels following U2OS cell treatment with siRNA-loaded Ago2 attached to the surface of Lamp2b-ZZ domain EVs, resulting in significant target silencing.

EVs comprising fusion proteins between Lamp2b and the Fc binding polypeptide ZZ were generated and isolated from Hek293T cells using ultrafiltration and bead-elute chromatography. hFc-Ago2 fusion proteins were expressed in Hek293T cells and isolated by affinity chromatography, following which the fusion proteins were incubated in a molecular excess of siRNAs against cyclin D overnight. Excess siRNAs were removed by a second round of affinity purification. $5\times10^6$ loaded EVs were co-incubated with $10^5$ U2OS cells overnight, following which after 48 hours cells were harvested and cyclin D levels assessed. For the in vivo studies, $1\times10^6$ of A549 cells were mixed with 1:1 ratio of Matrigel and injected subcutaneously into NCRNU mice. Tumor-bearing mice were treated every other day with $10^7$ siRNA-loaded exosomes using tail-vein administration. Over the course of the study caliper measurements were used to calculate tumor volume. Cyclin D levels following U2OS cell treatment with siRNA-loaded Ago2 displayed on the surface of Lamp2b-ZZ domain EVs showed significant target silencing, as shown in FIG. 11. siCyclin D were directly transfected for the +ve control. hFc denotes exosome surface display; siCyclin—anti CyclinD siRNA; siScr—scrambled sequence. n=3.

The invention claimed is:

1. An exosome comprising at least one fusion protein, wherein the at least one fusion protein comprises at least one Fc binding polypeptide displayed on the outer surface of the exosome, wherein the at least one Fc binding polypeptide is fused to at least one human exosomal polypeptide;

wherein the at least one Fc binding polypeptide is selected from the group consisting of Protein A, Protein G, Protein A/G, Protein L, Protein LG, Z domain, ZZ domain, and a combination thereof; and wherein the at least one human exosomal polypeptide is selected from the group consisting of CD9, CD63, CD81, Lamp2b, TFNR, and a combination thereof.

2. The exosome according to claim 1, wherein the at least one Fc binding polypeptide comprises more than one Fc binding region.

3. The exosome according to claim 1, wherein the at least one Fc binding polypeptide is bound to at least one Fc containing protein.

4. The exosome according to claim 1, wherein the exosome has bound to it a plurality of Fc containing proteins through interaction between the Fc binding polypeptide and the Fc domains of the plurality of Fc containing proteins, wherein the plurality of Fc containing proteins are the same or different.

5. The exosome according to claim 3, wherein the at least one Fc containing protein is an antibody or a protein engineered to comprise an Fc domain.

6. The exosome according to claim 5, wherein the antibody is a targeting antibody, a therapeutic antibody, an antibody-drug conjugate (ADC), or an antibody for reducing opsonization or immune cell-mediated clearance.

7. The exosome according to claim 3, wherein the exosome having bound to it at least 10 Fc containing proteins.

8. The exosome according to claim 3, wherein the at least one Fc containing protein is attached to the outer surface of the exosome.

9. A non-covalent complex between (i) the fusion protein of the exosome of claim 1, and (ii) an Fc containing protein, wherein the Fc binding polypeptide binds to the Fc containing protein.

10. A composition comprising the exosome comprising at least one fusion protein of claim 1.

11. The exosome according to claim 3, wherein the exosome having bound to it at least 20 Fc containing proteins.

12. The exosome according to claim 3, wherein the exosome having bound to it at least 30 Fc containing proteins.

* * * * *